(12) United States Patent
van Boeckel et al.

(10) Patent No.: US 6,432,955 B1
(45) Date of Patent: Aug. 13, 2002

(54) HETEROCYCLIC DERIVATIVES AND THEIR USE AS ANTITHROMBOTIC AGENTS

(75) Inventors: Constant Adriaan Anton van Boeckel, Mercuriusstraat; Philippus Johannes Marie van Galen, Harnas; Johannes Bernardus Maria Rewinkel, Bram van de Bergstraat, all of (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/679,232

(22) Filed: Oct. 4, 2000

Related U.S. Application Data

(62) Division of application No. 09/403,327, filed as application No. PCT/EP98/02455 on Apr. 12, 1998, now Pat. No. 6,194,409.

(30) Foreign Application Priority Data

Apr. 24, 1997 (EP) .............................. 97201227

(51) Int. Cl.[7] .................... A61K 31/4709; A61K 31/53; C07D 217/22; C07D 253/04
(52) U.S. Cl. ....................... 514/243; 514/248; 514/258; 514/260; 514/301; 514/302; 514/310; 544/183; 544/184; 544/235; 544/237; 544/253; 544/293; 546/114; 546/115; 546/143

(58) Field of Search .................................. 544/183, 184, 544/235, 237, 253, 293; 546/114, 115, 143; 514/243, 248, 258, 260, 301, 302, 310

(56) References Cited

U.S. PATENT DOCUMENTS 5,519,036 A    5/1996   Himmelsbach ............. 514/310

FOREIGN PATENT DOCUMENTS

| EP | 0 555 824 A1 | 8/1993 |
| WO | WO 92/08709 | 5/1992 |
| WO | WO 92/16549 | 10/1992 |
| WO | WO 95/13274 | 5/1995 |

OTHER PUBLICATIONS

Ewing et al., Chemical Abstracts, vol. 134:163059, 2001.*
Ewing et al., Chemical Abstracts, vol. 133:30741, 2000.*
Ewing et al., Chemical Abstracts, vol. 131:130007, 1999.*

* cited by examiner

Primary Examiner—Richard L. Raymond
(74) Attorney, Agent, or Firm—Mark W. Milstead

(57) ABSTRACT

The present invention relates to therapeutically active antithrombotic compounds.

9 Claims, No Drawings

HETEROCYCLIC DERIVATIVES AND THEIR USE AS ANTITHROMBOTIC AGENTS

This application is a divisional application of U.S. Ser. No. 09/403,327 filed Oct. 19, 1999, now U.S. Pat. No. 6,194,409, which is the U.S. national stage of PCT/EP98/02455, filed Apr. 12, 1998.

The invention relates to new therapeutic compounds, in particular to antithrombotic agents, a process for their preparation, pharmaceutical compositions containing the compounds as active ingredients, as well as the use of said compounds for the manufacture of medicaments.

In therapy, a multiplicity of active compounds is used for the treatment and prophylaxis of all sorts of diseases. Drugs differ widely in their pharmacodynamic effects and clinical application, in penetrance, absorption and usual route of administration, in distribution among the body tissues and in disposition and mode of action. Apart from the type of patient and the type of disease to be treated or to be prevented, the physicochemical properties of therapeutically active compounds determine to a great extent the preferred route of their administration. In the development of drugs, the oral applicability thereof is usually an important selection criterium For the majority of patients this is obviously the most convenient route for access of the drug to the systemic circulation. In order for a drug—administered via oral route—to act, it must first be absorbed before it is transported to the appropriate tissue or organ, where it may penetrate to the responding subcellular structure and may subsequently be metabolized, or where it may be bound, stored, or whatever is necessary to elicit a response or to alter ongoing processes. However, not always compounds which have been found to possess an advantageous therapeutic activity are also sufficiently absorbed in the gastrointestinal tract to display effective oral bioavailability. Thus, one of the pivotal issues in drug design is to develop compounds which both show activity and good absorptive properties. An important area in which is actively sought for oral biavailability is the area of antithrombotic agents.

The present invention relates to antithrombotic compounds comprising the group Q, Q having the formula

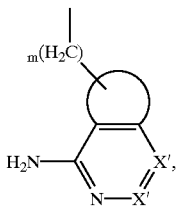

wherein the substructure

is a structure selected from

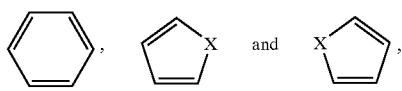

wherein
X is O or S;
X' being independently CH or N,
and m is 0, 1, 2 or 3;
wherein the group Q is bound through an oxygen atom or an optionally substituted nitrogen or carbon atom,
or a pharmaceutically acceptable salt thereof or a prodrug thereof The compounds of the invention are active antithrombotic agents having an improved pharmacological profile, in particular with regard to properties like their absorptive properties and their toxicity.

The term "antithrombotic compound" means any compound having antithrombotic activity. Examples of such compounds are inhibitors of serine proteases that play a role in the blood coagulation cascade or GpIIb/IIIa antagonists. The group Q is bound to the molecule through an oxygen atom or an optionally substituted nitrogen or carbon atom. "Optionally substituted" in this respect means any suitable substituent, such as, but not limited to, oxo, alkyl, alkenyl, alkoxy, aryl, halogen and the like. The term "prodrug" means a compound of the invention in which (an) amino group(s) is (are) protected, e.g. by (a) hydroxy or (1–6C) alkoxycarbonyl group(s), or a compound wherein—if present—(a) carboxylate group(s) is (are) esterified. The present invention relates to the surprising finding that the presence of the group Q in antithrombotic compounds gives rise to favourable properties of the compounds. Especially when Q is used to replace a basic moiety in compounds of which is known that they require such a moiety for their activity, an improvement of the pharmacological properties is realized, and in particular when that basic moiety is a (hetero)arylguanidino or (hetero)arylamidino moiety. In particular an improvement of the absorptive properties of those compounds is observed. Also a reduction of the toxicity of compounds of this invention is observed.

Preferably the group Q has the formula

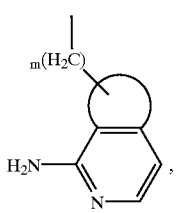

m being as previously defined.

An established in vitro model for the determination of the absorptive properties of drugs is the Caco-2 model (Artursson, P., S.T.P. Pharma Sciences 3(1), 5–10, 1993; Walter, E., et al. Pharmaceutical Research, 3, 360–365, 1995). In this in vitro model the transepithelial transport properties of a compound are determined in monolayers of a human intestinal cell-line (Caco-2) in terms of a permeability coefficient (apparent permeability). This model is useful for the prediction of in vivo absorption of compounds in the gastrointestinal tract. Preferably the antithrombotic compounds of the invention have a Caco-2 permeability of 8 nm/s or higher.

As noted above, amongst the compounds of the present invention are inhibitors of serine proteases of the blood coagulation cascade, and in particular inhibitors of thrombin and/or factor Xa. Preferred compounds inhibit thrombin more effectively than other serine proteases. More preferred compounds are thrombin inhibitors having, in addition, an $IC_{50}$ value of less than 1 $\mu$M. The compounds are useful for treating and preventing thrombin-mediated and thrombin-associated diseases. This includes a number of thrombotic and prothrombotic states in which the coagulation cascade is activated which include, but are not limited to, deep vein thrombosis, pulmonary embolism, thrombophlebitis, arterial occlusion from thrombosis or embolism, arterial reocclusion during or after angioplasty or thrombolysis, restenosis following arterial injury or invasive cardiological procedures, postoperative venous thrombosis or embolism, acute or chronic atherosclerosis, stroke, myocardial infarction, cancer and metastasis, and neurodegenerative diseases. Compounds of the invention may also be used as in vitro anticoagulants or as anticoagulants in extracorporeal blood circuits, such as those necessary in dialysis and surgery.

Serine proteases are enzymes which play an important role in the blood coagulation cascade. Apart from thrombin and factor Xa, other examples of this group of proteases comprise the factors VIIa, IXa, XIa, XIIa, and protein C. Thrombin is the final serine protease enzyme in the coagulation cascade. The prime function of thrombin is the cleavage of fibrinogen to generate fibrin monomers, which are cross-linked to form an insoluble gel. In addition, thrombin regulates its own production by activation of factors V and VIII earlier in the cascade. It also has important actions at cellular level, where it acts on specific receptors to cause platelet aggregation, endothelial cell activation and fibroblast proliferation. Thus thrombin has a central regulatory role in homeostasis and thrombus formation. Since inhibitors of thrombin may have a wide range of therapeutical applications, extensive research is done in this area. In the development of synthetic inhibitors of serine proteases, and more specifically of thrombin, the benzamidine moiety is one of the key structures. It mimics the protonated side-chain of the basic amino acids Arg and Lys of its natural substrates. Compounds with this moiety have been studied extensively and repeatedly. A very potent representative of this type of thrombin inhibitors is the amino acid derivative Nα-(2-naphthylsulfonyl)-glycyl-4-amidinophenylalanin-piperidide (NAPAP) (Stürzebecher, J. et al., Thromb. Res. 29, 635–642, 1983). However, the pharmacological profile of NAPAP is unattractive for therapeutical applications: the compound shows toxic effects after intravenous administration and, in addition, poor oral bioavailability after oral administration. Up until now, the NAPAP-like benzamidine derivatives which have been investigated for use as thrombin inhibitors show these unfavourable pharmacological and pharmacokinetic properties. It was assumed that these properties are due to the strong basicity of the amidino functionality of these compounds (Kaiser, et al., Pharmazie 42, 119–121, 1987; St ürzebecher, J. et al., Biol. Chem. Hoppe-Seyler, 373, 491–496, 1992). Several studies have been performed on variations of this basic structure (see for example St ürzebecher, J. et al., Pharmazie 43, 782–783, 1988; St ürzebecher, J. et al. (1993), DIC-Pathogenesis, Diagnosis and Therapy of Disseminated Intravascular Fibrin Formation [G. Müller-Berghaus et al., eds.] pp. 183–190, Amsterdam, London, New York, Tokyo: Exerpta Medica). However, modifications of the benzamidine moiety decreasing its basicity always resulted in a drastic loss of antithrombin activity (Stürzebecher, J. et al., J. Enzyme Inhibition 9, 87–99, 1995).

Oral bioavailability is a property of thrombin inhibitors which is urgently searched for. Potent intravenous thrombin inhibitors are clinically effective in acute care settings requiring the treatment of thrombin-related diseases. However, particularly the prevention of thrombin-related diseases such as myocardial infarct, thrombosis and stroke require long-term therapy, preferably by orally dosing an anticoagulant. Consequently, the search for active, orally bioavailable thrombin inhibitors continues unabated. Oral bioavailability is at least in part related to the ability of compounds to be absorbed in the gastrointestinal tract. The low oral bioavailability of NAPAP and its analogues may therefore be related to their deficient absorptive properties in the intestines.

The present invention provides a solution to the deficient pharmacological properties of the NAPAP-like compounds, in particular with respect to the toxicity and the deficient absorptive properties.

Preferred serine protease inhibitors of the invention have the formula (I), comprising the group Q; compounds of this type show improved transepithelial transport properties (increased apparent permeability) in comparison with prior art compounds:

$$R^1-Y-[NR^2-A-C(O)]_n-NR^3-CHR^4-C(O)-R^5 \quad (I),$$

wherein $R^1$ is (1–8C)alkyl, (6–14C)aryl-(1–8C)alkenyl, (6–14C)aryl-(1–8C)alkanoyl, (6–14C)aryl, (7–15C)aralkyl, bisaryl, heteroaryl, heteroaralkyl(1–8C)alkyl, heterocycloalkyl, cycloalkyl or cycloalkyl substituted alkyl; $R^2$ is H or (1–8C)alkyl; $R^3$ is Q when $R^4$ is H, or $R^3$ is H or (1–8C)alkyl when $R^4$ is Q; Q is as previously defined; $R^5$ is OH or $OR^6$, $R^6$ being (1–8C)alkyl, (3–12C)cycloalkyl or (7–15C)aralkyl, or $R^5$ is $NR^7R^8$, wherein $R^7$ and $R^8$ are the same or different being H, (1–8C)alkyl, (3–12C)cycloalkyl, (6–14C)aryl, (7–15C)aralkyl, optionally substituted with (1–8C)alkoxy, C(O)OH or $C(O)OR^6$, or $R^7$ and $R^8$ together with the nitrogen atom to which they are bonded are a nonaromatic (4–8)membered ring optionally containing another heteroatom, which ring may be condensed with another optionally aromatic ring and may be substituted with OH, an oxo group, (1–8C)alkyl, optionally substituted with one or more halogens or hydroxy groups, (2–8C)alkenyl, (1–8C)alkylidene, (2–8C)alkynyl, (1–8C)alkoxy, (1–8C) acyl, (6–14C)aryl, C(O)OH, $C(O)OR^6$, $C(O)NR^9R^{10}$, wherein $R^9$ and $R^{10}$ are the same or different being H or (1–8C)alkyl, or $SO_2R^{11}$ and $R^{11}$ is (1–8C)alkyl optionally substituted by one or more fluorine atoms; Y is $SO_2$ or C(O); A is $CHR^{12}$, $R^{12}$ being H, phenyl, benzyl, (1–8C)alkyl, optionally substituted with OH or $COR^{13}$ wherein $R^{13}$ is OH, (1–8C)alkoxy, morpholino, morpholino(1–8C)alkoxy, $NH_2$, $NHR^{14}$ or $NR^{14}R^{15}$, $R^{14}$ and $R^{15}$ being independently (1–8C)alkyl optionally substituted with $C(O)OR^2$ or $R^{14}$ and $R^{15}$ are a nonaromatic (4–8)membered ring together with the nitrogen atom to which they are bonded, or $R^{12}$ together with $R^3$ is —$(CH_2)_s$— when $R^4$ is Q, s being 2, 3 or 4, or A is $NR^2$;

and n is 0 or 1; or a pharmaceutically acceptable salt thereof.

Related thrombin inhibitors are disclosed in WO 92/16549 and WO 92/08709, wherein respectively para- and meta-substituted phenylalanine derivatives are described having an amidino, guanidino, oxamidino, aminomethyl or amino substituent. However, compounds with the amidino substituent show unfavourable pharmacological properties, whereas the other structures, with a modified amidino moiety, display a loss of activity (vide supra). Other modifications are described in EP 555824 where compounds are disclosed having a benzimidazolyl group, which compounds do not contain a primary amino functionality. Thrombin inhibitors having a benzamidine moiety have also been modified in other parts of the molecule, however, without improvement of the unfavourable pharmacological properties caused by the amidino substituent. Examples hereof are disclosed in EP 508220, wherein the compounds contain an azaglycyl group instead of the glycyl group of NAPAP, in DE 4115468, wherein that glycyl group is replaced e.g. by an aspartyl group; in WO 94/18185, wherein no glycyl group is present in the compounds and the piperidine group which is present in NAPAP is replaced by a piperazide group; in WO 95/13274, wherein the compounds also do not have a glycyl group and modifications are made—in comparison with NAPAP—in the arylsulfonyl part and the piperidine part of the molecule, and in EP 236163, wherein Nα-alkyl substituted amidinophenylalanin derivatives are described. Furthermore, Stürzebecher, J. et al. (Thrombosis Research 54, 245–252, 1989) suggest that the alkylene linkage connecting the benzamidine moiety to the rest of the molecule may have a length of 1–3 methylene groups. Therefore, there is a still need for serine protease inhibitors, especially thrombin inhibitors, with more favourable pharmacological properties, such as the inhibitors of the present invention which potentially have good oral bioavailability.

Preferred compounds of formula (I) are compounds wherein $R^1$ is phenyl, naphthyl, (iso)quinolinyl, tetrahydro(iso)quinolinyl, 3,4-dihydro-1H-isoquinolinyl, 2,3,4,5-tetrahydro-1H-benzo[d]azepinyl, 2,3-dihydro-5H-benzo[f][1,4]oxazepinyl, dibenzofuranyl, chromanyl, bisaryl, each aryl being a 5- or 6-membered ring and optionally containing a O, S or N-atom, which groups $R^1$ may optionally be substituted with one or more substituents selected from (1–8C)alkyl, (1–8C)alkoxy the alkyl group of which may be optionally substituted with an alkoxy group or an alkoxyalkyl group, phenyl-(1–8C)alkyl, tetrahydropyranyloxy, tetrahydropyranyloxy(1–8C)alkyl or $NR^{15}R^{16}$, in which $R^{15}$ and $R^{16}$ are independently selected from H and (1–8C)alkyl, or $R^1$ is (1–8C)alkyl substituted with a (5–8C)cycloalkyl, (7–10C)bicycloalkyl or (10–16C)polycycloalkyl, optionally substituted with a group selected from oxo or (1–8C)alkyl; $R^3$ is H or (1–8C)alkyl; $R^4$ is Q; $R^5$ is (1–8C)alkoxy, $NR^7R^8$, wherein $R^7$ and $R^8$ are the same or different being H, (1–8C)alkyl, (3–12C)cycloalkyl, optionally substituted with (1–8C)alkoxy or $COOR^6$, or $R^5$ is a group of the formula

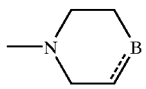

wherein the interrupted line represents an optional bond, B being $CR^{17}$ when the optional bond is present, or B is $CHR^{17}$, $R^{17}$ being H, (1–8C)alkyl, optionally substituted with one or more halogens or hydroxy groups, (2–8C)alkenyl, (2–8C)alkynyl, (1–8C)acyl, or (1–8C)alkoxy, or B is O, S, or $NR^{18}$, $R^{18}$ being (1–8C)alkyl, (1–8C)acyl, C(O)$NR^9R^{10}$ or $SO_2$-(1–8C)alkyl optionally substituted by one or more fluorine atoms.

More preferred compounds of formula (I) are compounds wherein $R^2$ and $R^3$ are H and Q is

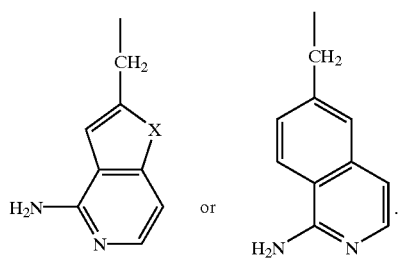

Also preferred are compounds wherein $R^5$ is

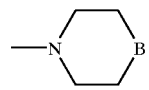

and B is $CH_2$ or CH(1–8C)alkyl.

Preferred groups $R^1$ are phenyl, naphthyl, tetrahydroisoquinolinyl, 3,4-dihydro-1H-isoquinolinyl, 2,3,4,5-tetrahydro-1H-benzo[d]azepinyl, 2,3-dihydro-5H-benzo[f][1,4]oxazepinyl, which groups $R^1$ may optionally be substituted with one or more substituents selected from (1–8C)alkyl, (1–8C)alkoxy the alkyl group of which may be optionally substituted with an alkoxy group or an alkoxyalkyl group, phenyl-(1–8C)alkyl, tetrahydropyranyloxy, tetrahydropyranyloxy(1–8C)alkyl or $NR^{15}R^{16}$. In compounds with these preferred $R^1$ groups, Y is preferably $SO_2$.

When $R^4$ is

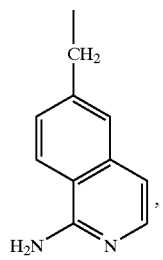

n preferably has the value 1. Preferably A is CH(1–8C)alkyl substituted with $COR^{13}$ wherein $R^{13}$ is OH, (1–8C)alkoxy, morpholino, morpholino(1–8C)alkoxy, $NHR^{14}$ or $NR^{14}R^{15}$, $R^{14}$ and $R^{15}$ being independently (1–8C)alkyl, or A is $CHR^{12}$, $R^{12}$ being —$(CH_2)_s$— together with $R^3$ when $R^4$ is Q, s being 2 or 3.

Other preferred compounds are compounds wherein n is 0 and $R^4$ is

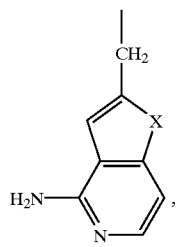

X being as previously defined.

Most preferred are the compounds according to formula (I) wherein $R^1$ is

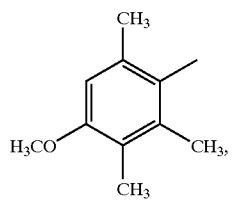

n is 1, $R^2$ is H, A is $CHCH_2C(O)OH$, $CHCH_2C(O)O(1-8C)$ alkyl, $CHCH_2C(O)$morpholine, $CHCH_2C(O)O(1-8C)$ alkylene-morpholine, $CHCH_2C(O)NHR^{14}$ or $CHCH_2C(O)NR^{14}R^{15}$, $R^{14}$ and $R^{15}$ being independently (1–8C)alkyl, $R^3$ is H, $R^4$ is

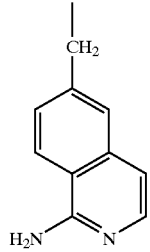

and $R^5$ is

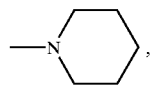

or the compounds according to formula (I) wherein $R^1$ is selected from

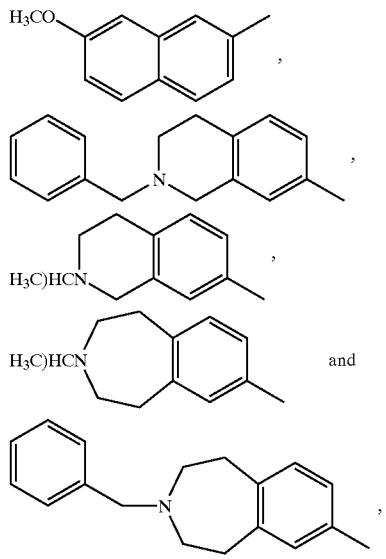

n is 0, $R^3$ is H, $R^4$ is

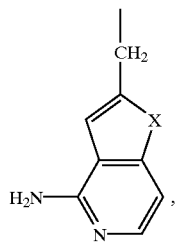

being as previously defined, and $R^5$ is

In the description of the compounds of formula (I) the following definitions are used. The term (1–8C)alkyl means a branched or unbranched alkyl group having 1–8 carbon atoms, for example methyl, ethyl, propyl, isopropyl, butyl, sec-butyl, tert-butyl, hexyl and octyl. The term (2–8C) alkenyl means a branched or unbranched alkenyl group having 2 to 8 carbon atoms, such as ethenyl, 2-butenyl, etc. The term (1–8C)alkylene means a branched or unbranched alkylene group having 1 to 8 carbon atoms, such as —$(CH_2)_a$— wherein a is 1 to 8, —$CH(CH_3)$—, —$CH(CH_3)$—$CH_2$—, etc. The term (1–8C)alkylidene means a branched or unbranched alkylidene group having 1–8 carbon atoms, such as methylene and ethylidene. The term (2–8C)alkynyl means a branched or unbranched alkynyl group having 2–8 carbon atoms, such as ethynyl and propynyl. The term (3–12C)cycloalkyl means a mono- or bicycloalkyl group having 3–12 carbon atoms, being cyclopropyl, cyclobutyl, cyclopentyl, cyclohexyl, cycloheptyl, cyclo-octyl, the camphor group, etc.. A preferred cycloalkyl group in the definition of $R^1$ is the camphor group. The term (1–8C)alkoxy means an alkoxy group having 1–8 carbon atoms, the alkyl moiety having the meaning as previously defined. The term (1–8C)acyl means an acyl group having 1–8 carbon atoms, the alkyl moiety having the meaning as previously defined. Formyl and acetyl are preferred acyl groups. The term (1–8)alkanoyl means an oxo-alkyl group, the alkyl moiety having the meaning as previously defined. The term (6–14C) aryl means an aromatic hydrocarbon group having 6 to 14 carbon atoms, such as phenyl, naphthyl, tetrahydronaphthyl, indenyl, which may optinally be substituted with one or more substituents such as—but not limited to—alkyl, alkoxy, the alkyl group of which may be optionally substituted with an alkoxy group or an alkoxyalkyl group (e.g the substituent groups —O—$(CH_2)_2$—$OCH_3$ or —O—CH$(CH_2OCH_3)_2$), tetrahydropyranyloxy, tetrahydropyranyloxymethyl, acyl, alkylthio, hydroxyalkyl, haloalkyl, carboxy, carboxyalkyl, carboalkoxy, hydroxy, halogen, trifluoromethyl, trifluoromethylcarbonyl, nitro, cyano, amino, dialkylamino, alkylsulfinyl and/or alkylsulfonyl (in the relevant cases alkyl is meant to be (1–8C) alkyl). Preferred aryl groups are

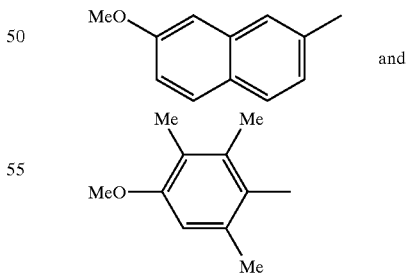

The term (7–15C)aralkyl means an aralkyl group having 7 to 15 carbon atoms, wherein the alkyl group is a (1–8C) alkyl group and the aryl group is a (6–14C)aryl as previously defined. Phenyl-(1–8C)alkyl groups are preferred aralkyl groups, such as benzyl. The term heteroaryl means a substituted or unsubstituted aromatic group having 4 to 12 carbon atoms, at least including one heteroatom selected from N, O, and S, like imidazolyl, thienyl, benzthienyl, quinolinyl, isoquinolinyl, tetrahydroquinolinyl, tetrahydroisoquinolinyl, indolyl, dibenzofuranyl, chromanyl,

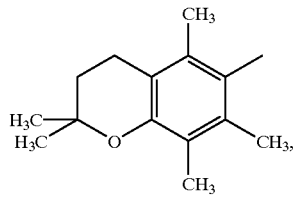

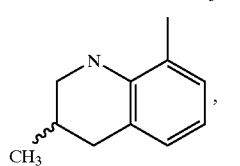

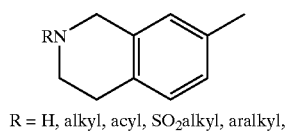

R = H, alkyl, acyl, SO₂alkyl, aralkyl,

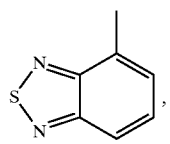
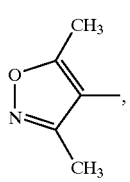

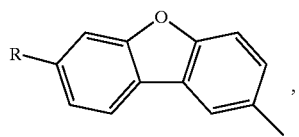

R = F, NO₂, CN

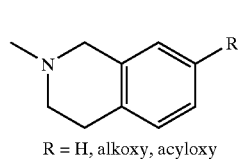
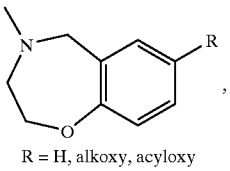

R = H, alkoxy, acyloxy     R = H, alkoxy, acyloxy and

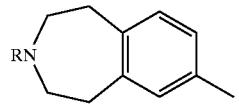

R = H, alkyl, acyl, SO₂alkyl, aralkyl.

The substituents on the heteroaryl group may be selected from the group of substituents listed for the aryl group. Heteroaralkyl groups are analogs of the (7–15C)aralkyl groups, at least including one heteroatom selected from N, O, and S. The term bisaryl in the definition of $R^1$ means two independently chosen aryl or heteroaryl groups according to the definitions of the term aryl and heteroaryl, connected to each other by a bond or by a short bridge, having a length of one or two atoms, such as $CH_2$, $N_2$ or $SO_2$, optionally substituted with a substituent as listed for the aryl group. Examples of bisaryls are biphenyl,

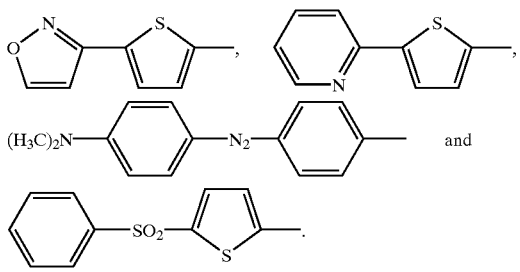

The term cycloalkyl substituted alkyl in the definition of $R^1$ means an alkyl group, preferably having 1–8 carbon atoms, carrying a mono-, bi- or polycycloalkyl group, preferably having 5–8, 7–10 and 10–16 carbon atoms, respectively, which cycloalkyl group may optionally be substituted with an oxo group and/or a substituent as listed for the aryl group. The term heterocycloalkyl means an optionally substituted cycloalkyl group, preferably having 4 or 5 carbon atoms, further containing one heteroatom selected from O, S or N, such as tetrahydrofuran and tetrahydropyran. The substituents on the hetercycloalkyl group may be selected from the group of substituents listed for the aryl group. The term nonaromatic (4–8)membered ring in the definition of $NR^7R^8$, where $R^7$ and $R^8$ together with the nitrogen atom to which they are bonded are a ring, means a ring containing the nitrogen atom and further having at most 3–7 carbon atoms, which ring may contain unsaturated bonds. Examples of such (4–8)membered rings are azetidine, pyrrolidine, piperidine, piperazine morpholine and thiomorpholine.

In the development of synthetic inhibitors of serine proteases, and more specifically of thrombin, the interest in small synthetic peptides that are recognized by proteolytic enzymes in a manner similar to that of natural substrates, has increased. As a result, new peptide-like inhibitors have been prepared, such as the transition state inhibitors of thrombin and the low molecular weight thrombin inhibitor Inogatran (Thromb. Haemostas. 1995, 73:1325 (Abs. 1633); WO 93/11152 (Example 67)), which has been disclosed to be a potent and selective thrombin inhibitor. Related compounds are described in WO 95/23609; in comparison with Inogatran and its analogs, compounds disclosed in this patent application have an aromatic group in the agmatine-like group. Although these developments already have lead to new and meaningful insights, the search for more effective and more selective, and in particular orally applicable, thrombin inhibitors still proceeds.

Thus, other preferred serine protease inhibitors of the invention are small synthetic peptides comprising the group Q, and have the formula (XX)

$$J—D—E—N(R')^1—Q \qquad (XX)$$

in which formula Q is as previously defined; $(R')^1$ is H or (1–4C)alkyl; J is H, optionally substituted D,L α-hydroxyacetyl, $(R')^2$, $(R')^2—O—C(O)—$, $(R')^2—C(O)—$, $(R')^2—SO_2—$, $(R')^7OOC—(CH(R')^3)_p—SO_2—$, $(R')^7OOC—(CH(R')^3)_p—$, $(R')^3{}_2NCO—(CH(R')^3)_p—$, Het-CO—$(CH(R')^3)_p—$, or an N-protecting group, wherein $(R')^2$ is selected from (1–12C)alkyl, (2–12C)alkenyl, (2–12C)alkynyl and (3–12C)cycloalkyl, which groups may optionally be substituted with (3–12C)cycloalkyl, (1–6C)alkoxy, oxo, OH, COOH, $CF_3$ or halogen, and from (6–14C)aryl, (7–15C)aralkyl and (8–16)aralkenyl, the aryl groups of which may optionally be substituted with (1–6C)alkyl, (3–12C)cycloalkyl, (1–6C)alkoxy, OH, COOH, CF$_3$ or halogen; each group (R')$^3$ is independently H or has the same meaning as (R')$^2$; (R')$^7$ has the same meaning as (R')$^3$ or is Het-(1–6C)alkyl or Het-(2–6C)alkynyl; and Het is a 4-, 5- or 6-membered heterocycle containing one or more heteroatoms selected from O, N or S; p is 1, 2 or 3; D is a bond, an amino-acid of the formula —NH—CH[(CH$_2$)$_q$C(O)OH]—C(O)— or an ester derivative thereof and q being 0, 1, 2 or 3, —N((1–12C)alkyl)-CH$_2$—CO—, —N((2–12C)alkenyl)-CH$_2$—CO—, —N((2–12C)alkynyl)-CH$_2$—C—, —N(benzyl)-CH$_2$—CO—, D-1-Tiq, D-3-Tiq, D-Atc, Aic, D-1-Piq, D-3-Piq or a L- or D-amino acid having a hydrophobic, basic or neutral side chain, which amino acid may optionally be N-(1–6C)alkyl substituted; or J and D together are the residue (R')$^4$(R')$^5$N—CH(R')$^6$—C(O)—, wherein (R')$^4$ and (R')$^5$ independently are (R')$^2$, (R')$^2$—O—C(O)—, (R')$^2$—C(O)—, (R')$^2$—SO$_2$—, (R')$^7$OOC—(CH(R')$^3$)$_p$—SO$_2$—, (R')$^7$OOC—(CH(R')$^3$)$_p$—, H$_2$NCO—(CH(R')$^3$)$_p$—, or an N-protecting group, or one of (R')$^4$ and (R')$^5$ is connected with (R')$^6$ to form a 5- or 6-membered ring together with "N—C" to which they are bound, which ring may be fused with an aliphatic or aromatic 6-membered ring; and (R')$^6$ is a hydrophobic, basic or neutral side chain; E is an L-amino acid with a hydrophobic side chain, serine, threonine, a cyclic amino acid optionally containing an additional heteroatom selected from N, O or S, and optionally substituted with (1–6C)alkyl, (1–6C)alkoxy, benzyloxy or oxo, or E is —N(R')$^3$—CH$_2$—C(O)— or the fragment

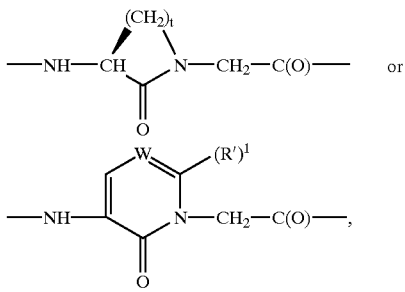

wherein t is 2, 3, or 4, and W is CH or N, or E—N(R')$^1$ taken together form the fragment

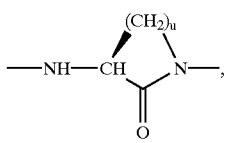

wherein u is 1, 2 or 3; or a prodrug thereof.

Preferred compounds of formula (XX) are those wherein E is an L-amino acid with a hydrophobic side chain, serine, threonine or —N(R')$^3$—CH$_2$—C(O)— or wherein E—N(R')$^1$ taken together form the fragment

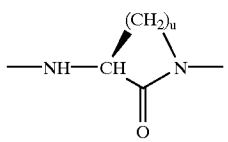

Other preferred compounds have the formula (XX), wherein J is as previously defined; D is a bond, an amino-acid of the formula —NH—CH[(CH$_2$)$_q$C(O)OH]—C(O)— or an ester derivative thereof and q being 0, 1, 2 or 3, —N((1–6C)alkyl)-CH$_2$—CO—, —N((2–6C)alkenyl)-CH$_2$—CO—, —N(benzyl)-CH$_2$—CO—, D-1-Tiq, D-3-Tiq, D-Atc, Aic, D-1-Piq, D-3-Piq or a D-amino acid having a hydrophobic side chain, which amino acid may optionally be N-(1–6C)alkyl substituted; or J and D together are the residue (R')$^4$(R')$^5$N—CH(R')$^6$—C(O)—; and E is a cyclic amino acid optionally containing an additional heteroatom selected from N, O or S, and optionally substituted with (1–6C)alkyl, (1–6C)alkoxy, benzyloxy or oxo, or E is —N(R')$^3$—CH$_2$—C(O)— or the fragment

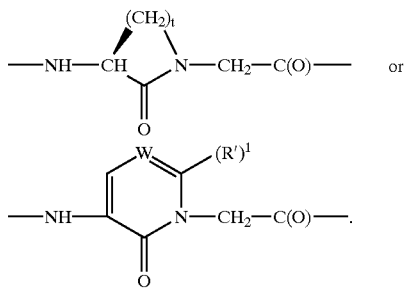

More preferred compounds of formula (XX) are those wherein J is H, 2-hydroxy-3-cyclohexyl-propionyl-, 9-hydroxy-fluorene-9-carboxyl, (R')$^2$, (R')$^2$—SO$_2$—, (R')$^7$OOC—(CH(R')$^3$)$_p$—SO$_2$—, (R')$^7$OOC—(CH(R')$^3$)$_p$—, (R')$^3$$_2$N—CO—(CH(R')$^3$)$_p$—, Het-CO—(CH(R')$^3$)$_p$— wherein Het contains as a heteroatom at least a nitrogen atom which is bound to CO, or an N-protecting group, wherein (R')$^2$ is selected from (1–12C)alkyl, (2–12C)alkenyl, (6–14C)aryl, (7–15C)aralkyl and (8–16C)aralkenyl which groups may optionally be substituted (1–6C)alkoxy; each group (R')$^3$ is independently H or has the same meaning as (R')$^2$; (R')$^7$ has the same meaning as (R')$^3$ or is morpholino-(1–6C)alkyl or morpholino-(2–6C)alkynyl; D is a bond, D-1-Tiq, D-3-Tiq, D-Atc, Aic, D-1-Piq, D-3-Piq or a D-amino acid having a hydrophobic side chain, which amino acid may optionally be N-(1–6C)alkyl substituted; or J and D together are the residue (R')$^4$(R')$^5$N—CH(R')$^6$—C(O)—.

Most preferred are the compounds of formula (XX) wherein J is H, (R')$^2$—SO$_2$—, (R')$^7$OOC—(CH(R')$^3$)$_p$—, (R')$^1$$_2$N—CO—(CH(R')$^3$)$_p$—,

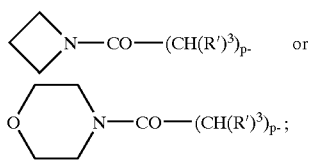

D is a bond, D-1-Tiq, D-3-Tiq, D-Atc, Aic, D-1-Piq, D-3-Piq or a D-amino acid having hydrophobic side chain; or J and D together are the residue (R')$^4$(R')$^5$N—CH(R')$^6$—C(O)—, wherein at least one of (R')$^4$ and (R')$^5$ is (R')$^7$OOC—(CH(R')$^3$)$_p$— or (R')$^2$—SO$_2$— and the other independently is (1–12C)alkyl, (2–12C)alkenyl, (2–12C)alkynyl, (3–12C)cycloalkyl, (7–15C)aralkyl, (R')$^2$—SO$_2$— or (R')$^7$OOC—(CH(R')$^3$)$_p$—, and (R')$^6$ is a hydrophobic side chain.

Preferably, the group Q in the compounds of formula (XX) has one of the structures:

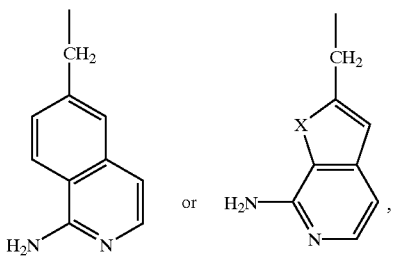

wherein X is O or S.

Like the compounds of formula (I), the compounds of formula (XX) have an anticoagulant effect and are useful for treating and preventing thrombin-mediated and thrombin-associated diseases, applicable as herein before described.

In the description of the compounds of the formula (XX), the following definitions are used. The term optionally substituted D,L α-hydroxyacetyl means a group of the formula HO—$CR^aR^b$—C(O)—, wherein $R^a$ and $R^b$ independently are H, a hydrophobic side chain, or $R^a$ and $R^b$ together form a 5- or 6-membered ring, which is optionally fused with one or two aliphatic or aromatic 6-membered rings, and which 5- or 6-membered ring consists of carbon atoms and optionally one heteroatom selected from N, O and S. Preferred D,L α-hydroxyacetyl groups are 2-hydroxy-3-cyclohexyl-propionyl- and 9-hydroxy-fluorene-9-carboxyl. The term (1–12C)alkyl means a branched or unbranched alkyl group having 1 to 12 carbon atoms, such as methyl, ethyl, t-butyl, isopentyl, heptyl, dodecyl, and the like. Preferred alkyl groups are (1–6C)alkyl groups, having 1–6 carbon atoms. A (2–12C)alkenyl group is a branched or unbranched unsaturated hydrocarbon group having 2 to 12 carbon atoms. Preferred are (2–6C)alkenyl groups. Examples are ethenyl, propenyl, allyl, and the like. The term (1–6C)alkylene means a branched or unbranched alkylene group having 1 to 6 carbon atoms, such as —$(CH_2)_b$— and b is 1 to 6, —CH($CH_3$)—, —CH($CH_3$)—($CH_2$)—, etc. A (2–12C)alkynyl group is a branched or unbranched hydrocarbon group containing a triple bond and having 2 to 12 carbon atoms. Preferred are (2–6C)alkynyl groups, such as ethynyl and propynyl. A (6–14C)aryl group is an aromatic moiety of 6 to 14 carbon atoms. The aryl group may further contain one or more hetero atoms, such as N, S, or O, also referred to as heteroaryl groups. Examples of aryl groups are phenyl, naphthyl, (iso)quinolyl, indanyl, and the like. Most preferred is the phenyl group. (7–15C)Aralkyl and (8–16C) aralkenyl groups are alkyl and alkenyl groups respectively, substituted by one or more aryl groups, the total number of carbon atoms being 7 to 15 and 8 to 16, respectively. The term (1–6C)alkoxy means an alkoxy group having 1–6 carbon atoms, the alkyl moiety of which having the meaning as previously defined. The term (3–12C)cycloalkyl means a mono- or bicycloalkyl group having 3–12 carbon atoms, being cyclopropyl, cyclobutyl, cyclopentyl, cyclohexyl, cycloheptyl, cyclo-octyl, the camphor group, etc. Cyclopentyl and cyclohexyl are preferred cycloalkyl groups. The term halogen means fluorine, chlorine, bromine or iodine. The term ester derivative means any appropriate ester derivative, preferably (1–4C)alkyl-esters, such as methyl-, ethyl- or t-butyl-esters. The terms 1- and 3-Tiq mean 1,2,3,4-tetrahydroisoquinoline-1- and -3-carboxylic acid, respectively, 1- and 3-Piq are perhydroisoquinoline-1- and -3-carboxylic acid, respectively; Atc is 2-aminotetralin-2-carboxylic acid; Aic is amino indane carboxylic acid; Phe is phenylalanine; Cha is cyclohexylalanine; Dpa is diphenyla-lanine; Coa is cyclooctylalanine; Chg is cyclohexylglycine; Nle is norleucine; Asp is aspartic acid. The term hydrophobic side chain means a (1–12C)alkyl, optionally substituted with one or more (3–12C)cycloalkyl groups or (6–14C)aryl groups (which may contain a heteroatom, e.g. nitrogen) such as cyclohexyl, cyclo-octyl, phenyl, pyridinyl, naphthyl, tetrahydronaphthyl, and the like, which hydrophobic side chain may optionally be substituted with substituents such as halogen, trifluoromethyl, lower alkyl (for instance methyl or ethyl), lower alkoxy (for instance methoxy), phenyloxy, benzyloxy, and the like. In the definitions, the term substituted in general means: substituted by one or more substituent. Amino acids having a basic side chain are for example, but not limited to, arginine and lysine, preferably arginine. The term amino acids having a neutral side chain refers to amino acids such as methionine sulphon and the like. Cyclic amino acids are for example 2-azetidine carboxylic acid, proline, pipecolic acid, 1-amino-1-carboxy-(3–8C) cycloalkane (preferably 4C, 5C or 6C), 4-piperidine carboxylic acid, 4-thiazolidine carboxylic acid, 3,4-dehydroproline, azaproline, 2-octahydroindole carboxylic acid, and the like. Preferred are 2-azetidine carboxylic acid, proline, pipecolic acid, 4-thiazolidine carboxylic acid, 3,4-dehydroproline and 2-octahydroindole carboxylic acid.

Also preferred serine protease inhibitors of the present invention are compounds of the formula (XXX):

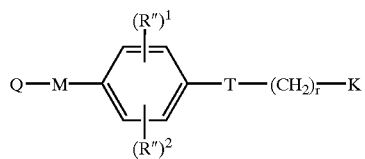

(XXX)

in which formula Q is as previously defined; r is an integer of 0 to 4; $(R'')^1$ is a hydrogen atom, a carboxyl group, an alkoxycarbonyl group, a carboxyalkyl group, an alkoxycarbonylalkyl group, a carboxyalkoxy group or an alkoxycarbonylalkoxy group, $(R'')^2$ is a hydrogen atom, a hydroxyl group, a lower alkyl group or a lower alkoxy group; M is an alkylene group having a carbon number of 1 to 4, which may have 1 or 2 substituents selected from the group consisting of hydroxyalkyl, carboxyl, alkoxycarbonyl, carboxyalkyl and alkoxycarbonylalkyl; T is a single bond, an oxygen atom, a sulfur atom or a carbonyl group; K is a saturated or unsaturated 5- or 6-membered heterocyclic moiety or cyclic hydrocarbon moiety optionally having a substituent group, an amino group optionally having a substituent group or an aminoalkyl group optionally having a substituent group.

Related compounds are known for instance from EP 0,540,051. According to the present invention the compounds of EP 0,540,051 are altered by replacing the aromatic group carrying the amidine substituent by the group Q, thus improving in particular the absorptive properties of the compounds, such as examples having the structure:

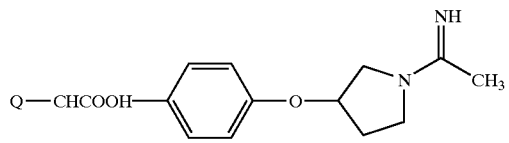

Like the compounds of the structures (I) and (XX), the compounds of structure (XXX) show a strong anticoagulant effect and are applicable as herein described.

In the compounds of the present invention represented by general formula (XXX), any straight chain, branched chain or cyclic alkyl group having I to 6 carbon atoms may be used as the lower alkyl group. Illustrative examples include methyl, ethyl, propyl, isopropyl, butyl, sec- or tert-butyl, pentyl, hexyl, cyclopropyl, cyclobutyl, cyclopentyl, cyclohexyl and the like. The lower alkoxy group may have 1 to 6 carbon atoms. Illustrative examples include methoxy, ethoxy, propoxy, isopropoxy, butoxy, sec- or tert-butoxy and the like. The alkoxycarbonyl, carboxyalkyl, alkoxycarbonylkalkyl, carboxyalkoxy, alkoxycarbonylalkoxy and hydroxyalkyl groups preferably have 1 to 6 carbon atoms, more preferably 1 to 4 carbon atoms, respectively. Illustrative examples of the alkoxycarbonyl group include methoxycarbonyl, ethoxycarbonyl, propoxycarbonyl, butoxycarbonyl and the like. Illustrative examples of the carboxyalkyl group include carboxymethyl, carboxyethyl, carboxypropyl and the like. Illustrative examples of the alkoxycarbonylalkyl group include methoxycarbonylmethyl, ethoxycarbonylmethyl, propoxycarbonylmethyl, methoxycarbonylethyl, ethoxycarbonylethyl, methoxycarbonylpropyl, ethoxycarbonylpropyl and the like. Illustrative examples of the carboxylalkoxy group include carboxymethoxy, carboxyethoxy, carboxypropoxy and the like. Illustrative examples of the alkoxycarbonylalkoxy group include methoxycarbonylmethoxy, ethoxycarbonylmethoxy, propoxycarbonylmethoxy, methoxycarbonylethoxy, ethoxycarbonylethoxy and the like. Illustrative examples of the hydroxyalkyl group include hydroxymethyl, hydroxyethyl, hydroxypropyl, hydroxybutyl and the like. The saturated or unsaturated 5- or 6-membered heterocyclic moiety may contain preferably one or two hetero-atom(s) selected from nitrogen and oxygen atoms. Illustrative examples of such a preferred type of heterocyclic rings include pyrrolidine, piperidine, imidazoline, piperazine, tetrahydrofuran, hexahydropyrimidine, pyrrole, imidazole, pyrazine, pyrrolidinone, piperidinone, morpholine and the like. More preferable are pyrrolidine and piperidine which contain one nitrogen atom as the hetero-atom. Illustrative examples of the saturated or unsaturated cyclic hydrocarbon moiety include cyclopentyl, cyclohexyl and the like. Illustrative examples of the aminoalkyl group include aminomethyl, aminoethyl, aminopropyl and the like. Illustrative examples of the substituents applicable to these heterocyclic moieties and cyclic hydrocarbon moieties include preferably lower alkyl, lower alkanoyl, carbamoyl, mono- or dialkylcarbamoyl, formimidoyl, alkanoimidoyl, benzimidoyl, carboxyl, alkoxycarbonylimino and the like, more preferably formimidoyl and alkanoimidoyl groups. Illustrative examples of the substituents applicable to these amino groups and amino moieties of aminoalkyl groups include preferably lower alkyl, pyradinyl, pyrrolidinyl, carbamoyl, mono- or dialkylcarbamoyl, lower alkanoyl, formimidoyl, alkanoimidoyl, benzimidoyl, alkoxycarbonyl and the like, more preferably pyrazinyi, pyrrolidinyl, formimidoyl, alkanoimidoyl groups. In this instance, each of the alkyl, alkoxy, alkanoyl and the like listed above may preferably have a carbon number of from 1 to 6.

Other preferred serine protease inhibitors of the present invention are compounds of the formula (XL):

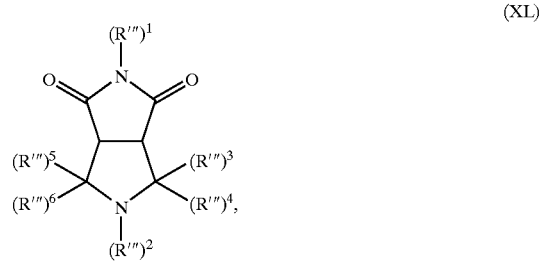

(XL)

in which formula $(R'')^1$ and $(R''')^2$ are independently H, lower alkyl, aryl, heteroaryl, cycloalkyl or lower alkyl substituted by one or more substituents selected from $CONH_2$, COO-(lower alkyl), aryl, heteroaryl and cycloalkyl; or $(R''')^2$ is lower alkanoyl; $(R''')^3$ is H, COOH, $CONH_2$, COO-(lower alkyl), CONH-(lower alkyl) or CON (lower alkyl)$_2$; $(R''')^4$, $(R''')^5$ and $(R''')^6$ are independently H, lower alkyl, aryl, aralkyl or cycloalkyl; or $(R''')^4$ and/or one of $(R''')^5$ and $(R''')^6$ is heteroaryl or lower alkyl substituted with OH, $SO_2H$, $SO_3H$, guanidino, aryl-(lower alkoxy), lower alkoxy or lower alkylthio; or $(R''')^2$ together with $(R''')^4$ forms a tri- or tetramethylene group, in which (a) a methylene group may be replaced by S, SO or $SO_2$ or may be substituted with OH, lower alkyl, lower alkenyl or carboxy-(lower alkyl) or (b) one of the methylene groups may be substituted with lower alkenyl and the other with (lower alkyl)-COOH; and at least one of $(R''')^1$, $(R''')^2$, $(R''')^4$, $(R''')^5$ and $(R''')^6$ is the group of formula Q, Q having the previously defined meaning. Related compounds are known from EP 0,728,758. The present invention is an improvement in the art when compared to these known compounds because of the presence of the specific group Q for introducing the favourable properties as herein before described.

Like the compounds of the structures (I), (XX) and (XXX), the compounds of structure (XL) show anticoagulant activity and are applicable as herein described. The compounds of structure (XL) display this effect in particular through their specific thrombin- and FXa-inhibiting activity.

In the description of compounds of formula (XL) the term "lower" means a branched or unbranched group having 1–6 C-atoms. Preferred lower alkyl or lower alkanoyl groups contain up to 4 C-atoms, e.g. methyl, isopropyl, butyl, isobutyl, sec-butyl, tert.-butyl, and acetyl, respectively. "Aryl" alone or in combination means groups like phenyl, which may be substituted, for instance with amidino, guanidino, hydroxyamidino, nitro, amino or methylenedioxy. "Aralkyl" means an aryl bound to a lower alkyl, e.g. a benzyl group, substituted in the phenyl ring, or phenylethyl. "Cycloalkyl" means saturated groups having 3–7 C-atoms, like cyclohexyl. "Heteroaryl" means 5- to 10 membered aromatic groups, which may consist of two rings, and contain one (or more) N-atom(s) and may be substituted, e.g. by one or more $NH_2$-groups. An example is chinazolinyl, such as 2,4-diaminochinazolin-6- or 7-yl. Examples of groups having amino, guanidino or N-hydroxyamidino substituents are amino-substituted chinazolinyl and (amino, amidino, guanidino or N-hydroxyamidino)-substituted phenyl, benzyl and lower alkyl groups.

Further preferred compounds according to the invention are the GpIIb/IIIa antagonists of the formula (L):

Q-[spacer]-COOH  (L), wherein Q has the previously defined meaning; the distance between the amino substituted carbon atom of the group Q and the carbon atom of the carboxylate moiety has a length of 12–18 Å; the spacer is any suitable chemical moiety; and the carboxylate group may be esterified. The compounds of structure (L) show anticoagulant effect and are applicable as herein described.

From literature it is known, that a large group of spacers are suitable for the above purpose, provided that the length thereof is restricted (see Bioorg. & Med. Chemistry Letters, 7(2), 209–212, (1997), and references cited therein). Examples of compounds of formula (L) are derived from the following known compounds, in which the benzamidine moiety has been replaced by the group Q (but not limited to these examples): the compounds Ro 43-8857 (J. Med. Chem. 35, 4393 (1992)), Ro 44-9883, Ro 48-3657, Fradafiban, BIBL 12, FK-633, GR 144053, EMD 76 334, SR 121566, SB 208651, SC 54684, SC 54701, SC 52012, DMP 754, GPI 562 and compounds described in EP 529, 858, WO 96/20172, EP 496,378, EP 530,505, Bioorg. & Med. Chem. 3, 539 (1995), WO 93/08174 and J.Am.Chem-.Soc. 115, 8861 (1993). This replacement by the group Q in the above compounds results in an improvement of the pharmacological properties of the compounds, in particular of the absorptive properties in the intestines, as herein described.

Preferred compounds of formula (L) have the formula (La):

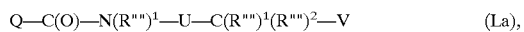

wherein Q has the previously defined meaning; $(R'''')^1$ is independently H or (1–4C)alkyl; U is a bond, $CH(R'''')^1$; $(R'''')^2$ is (1–12C)alkyl, (2–12C)alkenyl, (2–12C)alkynyl, (3–8C)cycloalkyl (6–14C)aryl, (7–15C)aralkyl or (8–16) aralkenyl, which may optionally be substituted with (1–6C) alkyl, (3–8C)cycloalkyl, (1–6C)alkoxy, OH, COOH, $CF_3$ or halogen; V is a 5-, 6-, or 7 -membered saturated, unsaturated or aromatic ring which may optionally contain one or more heteroatoms selected from O, N or S and which ring is substituted with one or two substituents selected from —$(CH_2)_v$—$COO(R'''')$ and —O—$(CH_2)_v$—$COO(R'''')^1$, v being 1, 2, 3 or 4. More preferred compounds of formula (La) are those wherein m is 0; U is a bond; $(R'''')^2$ is (1–4C)alkyl, phenyl or benzyl, which may optionally be substituted with OH or halogen and V is phenyl, piperidinyl, piperazinyl or thiazolyl, substituted with one substituent selected from —$CH_2$—$COO(R'''')^1$ and —O—$CH_2$—COO $(R'''')^1$.

Other preferred compounds of the formula (L) have the formula (Lb)

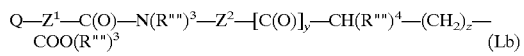

wherein Q has the previously defined meaning; $Z^1$ is a bond, C=C or C≡C; $(R'''')^3$ is H or (1–4C)alkyl; $Z^2$ is selected from

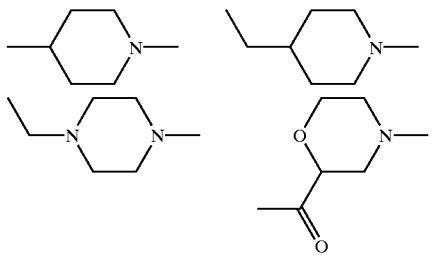

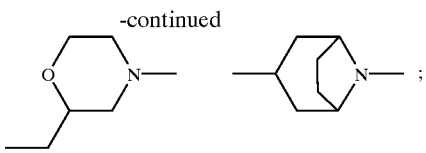

$(R'''')^4$ is H, (1–12C)alkyl, (2–12C)alkenyl, (2–12C)alkynyl, (3–8C)cycloalkyl, (6–14C)aryl, (7–15C)aralkyl or (8–16) aralkenyl, which may optionally be substituted with (1–6C) alkyl, (3–8C)cycloalkyl, (1–6C)alkoxy, OH, COOH, $CF_3$ or halogen; y is 0 or 1 and z is 0 or 1.

More preferred are the compounds of formula (Lb) wherein $Z^1$ is C=C; $Z^2$ is

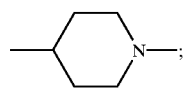

$(R'''')^4$ is H; y is 1 and z is 0.

Other preferred compounds of the formula (L) have the formula (Lc)

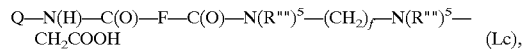

wherein

Q has the previously defined meaning;

$(R'''')^5$ is independently H, (1–4C)alkyl or benzyl or both $(R'''')^5$ groups are an ethylene bridge to form a 6- or 7-membered ring together with N—$(CH_2)_u$—N to which they are bound;

F is C=C, or 1,2-, 1,3- or 1,4-phenylene, or 1,2-(4–5C) heteroarylene, 2,3-naphthylene or 1,2-(5–7C) cycloalkylene, which groups may optionally be substituted with (1–4C)alkyl; and f is 2 or 3.

The terms used in the definitions of the compounds of formula (L), (La), (Lb) and (Lc) have the same meaning as those used for the compounds of formula (XX).

The present invention further relates to the finding that also in other therapeutic compounds the presence of the group Q gives rise to an improved pharmacological profile. Especially when Q is used to replace a basic moiety in compounds of which is known that they require such a moiety for their therapeutic activity, an improvement of the absorptive properties is observed, in particular when that basic moiety is a (hetero)arylguanidino or (hetero) arylamidino moiety. Preferred therapeutic compounds of the invention have an apparent Caco-2 permeability of 8 nm/s or higher. Preferably the group Q has the formula

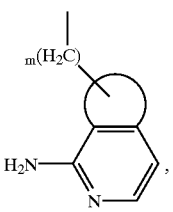

m being as previously defined.

The compounds of the invention may be used in a broad range of therapeutic applications which require oral administration of a drug or wherein oral administration thereof is considered favourable, such as in particular (but not limited to) CNS-active compounds, compounds useful for treating immunological disorders, antithrombotic agents, and the like. Preferred compounds of the present invention are antithrombotic agents.

The term "therapeutic compound" as used herein means any compound which can be used in therapy, which implies the curing of a disease or malfunction of the body and which covers prophylactic treatment.

Compounds of the present invention wherein Q has the formula

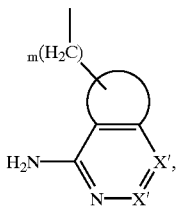

wherein the substructure

is a structure selected from

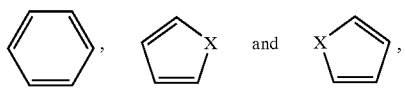

wherein

X is O or S;

X' being independently CH or N; and m is 0, 1, 2 or 3, can be prepared using suitable starting compounds and methods as described in the literature e.g. 4-amino-6-chloroquinazoline and 4-amino-7-chloroquinazoline as described by A. Rosowsky and N. Papathanasopoulos in J. Heterocycl. Chem. 9, 1235 (1972); 4-aminothieno[2,3d] pyridazine or 7-aminothieno[2,3d]pyridazine by M. Robba, B. Roques and Y. Le Guen in Bull. Soc. Chim. France 4220, (1967); 4-aminothieno[2,3d]pyrimidine by M. Robba, J.-M. Lecompte and M. Cugnon de Sevricourt in Bull. Soc. Chim. France 592, (1975); 4-aminothieno[3,2d]pyrimidine by M. Robba, J.-M. Lecompte and M. Cugnon de Sevricourt in Tetrahedron 27, 487, (1971); 4-amino-6-bromothieno[2,3d] pyrimidine by M. Robba, J.-M. Lecompte and M. Cugnon de Sevricourt in Bull. Soc. Chim. France 761, (1976); 4-amino-6-bromoquinazoline by M. F. G. Stevens and A. Kreutzberger in Angew. Chem. 81, 84, (1969).

The compounds of the present invention wherein Q has the formula

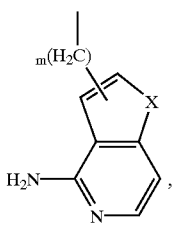

wherein m is 0, 1, 2 or 3 and X is CH=CH, O or S, can be prepared using compounds of formula (II).

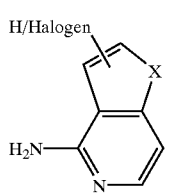
(II)

A suitable method starts from a compound of formula (III) (wherein the halogen atom, if present, preferably is Br), the hydroxy group of which is chlorinated, e.g. by treatment with $POCl_3$, to give the compound of formula (IV), followed by conversion into the amino analogue of formula (II), for example by first converting the chloro-substituent into a phenoxy-substituent by reaction with phenol under alkaline conditions, and subsequently treatment with ammonium acetate, or by direct conversion of the chloro-compound into the corresponding amino-compound by heating the former with ammonia under pressure.

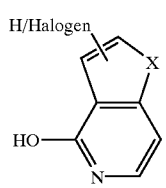
(III)

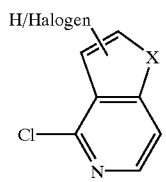
(IV)

The compound of formula (IV) in this sequence, wherein X is CH=CH and Lhe halogen is Br, may also be prepared by converting the corresponding unsubstituted compound into the N-oxide salt, e.g. with a peracid, such as m-chloroperbenzoic acid, followed by HCl treatment, and subsequently reacting this N-oxide salt with a chlorinating reagent, like $POCl_3$.

Compounds according to formula (I) can be prepared by deprotection of the following compound (e.g. by saponification)

wherein G e.g. is an alkyl or benzyl group, followed by coupling with $R^5$—H, or they can be prepared by deprotection of the compound

wherein Pg is an N-protecting group, followed by coupling with one of the groups $R^1$—Y—$NR^2$—A—C(O)—OH, $R^1$—Y—Lg or $R^1$—C(O)—OH, wherein Lg is a leaving group.

Compounds of formula (I) wherein $R^4$ is Q may be prepared starting with a compound of formula (V),

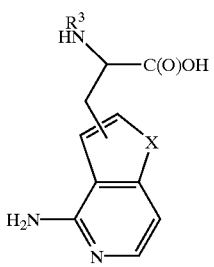

or a derivative thereof wherein the amino group at the aromatic group (arylamino) is protected, wherein X and $R^3$ have the previously defined meanings. The carboxylic acid group of a compound of formula (V) is esterified, e.g. by treatment with $R^6OH$ and thionyl chloride, wherein $R^6$ has the previously defined meaning, to form a compound of formula (VI), or an arylamino protected derivative thereof.

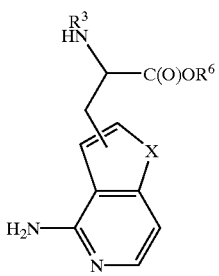

A compound of formula (VI) is converted into a compound of formula (Ia), being the compound of formula (I) wherein $R^5$ is $OR^6$, or an arylamino protected derivative thereof, either by coupling to $R^1YLg$ (Lg is a leaving group) (n=0), for example by reaction with $R^1YCl$ under basic conditions, e.g. by using triethylamine, or by peptide coupling with $R^1YNR^2AC(O)OH$ (n=1) or $R^1C(O)OH$ (n=0) using as a coupling reagent for example N,N-dicyclohexylcarbodiimide (DCCI) and 1-hydroxybenzotriazole (HOBT) or 2-(1H-benzotriazol-1-yl)-1,1,3,3-tetramethyluronium tetrafluoroborate (TBTU), wherein $R^1$, $R^2$, Y, n and A have the previously defined meanings. The protective group, if present, may optionally be removed.

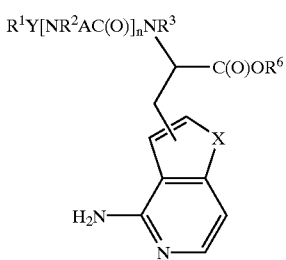

The ester group of a compound of formula (Ia) or an arylamino protected derivative thereof may be saponified to form the corresponding acid, after which the protective group, if present, may optionally be removed. The acid formed from a compound of formula (Ia) may be coupled to an amine of formula $HNR^7R^8$, wherein $R^7$ and $R^8$ have the previously defined meanings, for example by using DCCI/HOBT or TBTU, followed by removal of the optionally present protective group, to give a compound of formula (Ib), which is the compound of formula (I), wherein $R^5$ is $NR^7R^8$.

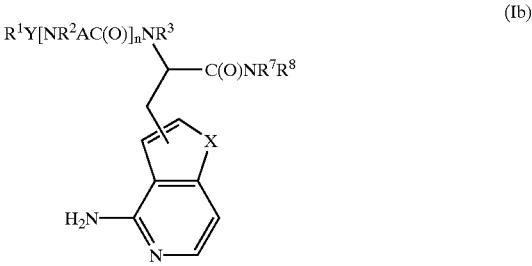

An alternative procedure for the preparation of a compound, of formula (Ib) starts with the protection of the N-terminus of a compound of formula (V) with an N-protecting group Pg, such as Boc (tert-butoxycarbonyl), forming a compound of formula (VII), where also the arylamino group may be protected.

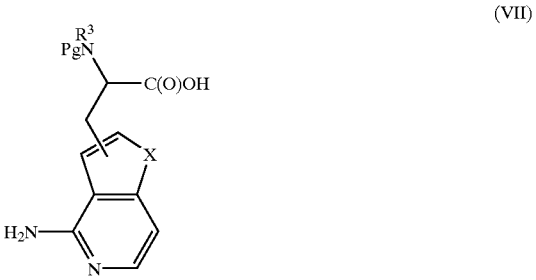

Subsequently, a compound of formula (VII) is coupled to an amine of formula $HNR^7R^8$ according to the procedure as described above for the conversion of a compound of formula (Ia) into (Ib), after which the N-terminus is deprotected, followed by a coupling to $R^1YLg$ (n=0), or by peptide coupling with $R^1YNR^2AC(O)OH$ (n=1) or $R^1C(O)OH$ (n=0) according to the procedures as described above for the conversion of a compound of formula (VI) into a compound of formula (Ia), followed by removal of the optionally present protective group, giving the compound of formula (Ib).

A suitable process for the preparation of the compound of formula (V) is the conversion of a compound of formula (VIII), wherein Pg is an N-protecting group and Lg is a leaving group, such as the mesyl group, into a compound of formula (IX), for example by reaction with an appropriate amino acid derivative of the general formula $PgR^3N$—CH$[C(O)OR]_2$ in the presence of a base, e.g. [[(1,1-dimethylethoxy)carbonyl]amino] propanedioic acid diethyl ester in the presence of sodium ethoxide, wherein Pg and $R^3$ have the previously defined meanings and both Pg-groups may be the same or different, and R is a branched or unbranched (1–8C)alkyl group, such as ethyl. (If here $R^3$ is H, the amino group may be alkylated later in the procedure according to methods well known in the art to form compounds wherein $R^3$ is alkyl.) Hydrolysis and decarboxylation of a compound of formula (IX) gives a compound of formula (V).

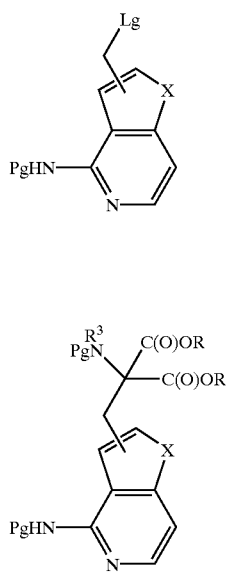

(VIII)

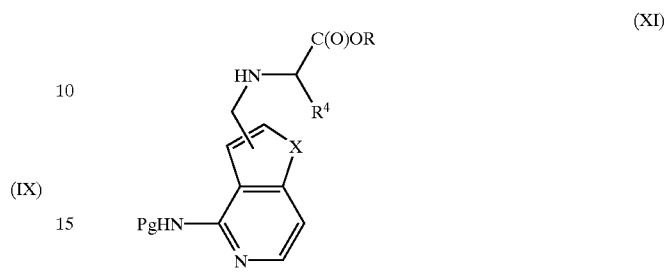

(XI). An alternative procedure for the preparation of a compound of formula (XI) starts from a compound of formula (VIII) by substitution of Lg by an appropriate amino acid derivative of the general formula $NH_2$—$CHR^4$—$C(O)OR$.

(XI)

(IX)

The compound according to formula (VIII) may be prepared by methods known in the art. The arylamino group of a compound of formula (II) is protected with an N-protecting group, after which the ring wherein X is located is provided with a formyl substituent either by treatment with a base, like lithium diisopropylamide, or with an organometallic reagent, like n-butyllithium, followed by addition of N,N-dimethylformamide, forming a compound of formula (X). (For compounds wherein m is 2 or 3, appropriate analogues of a compound of formula (X) may be prepared by this method which subsequently may be converted according the procedures as described for the conversion of a compound of formula (X).)

Compounds of formula (XI) are then converted into compounds of formula (Ic), the compounds of formula (I) wherein $R^3$ is Q and $R^5$ is $OR^6$, by a procedure analogous to the preparation of compounds of formula (Ia) from compounds of formula (VI) followed by removal of the protective group.

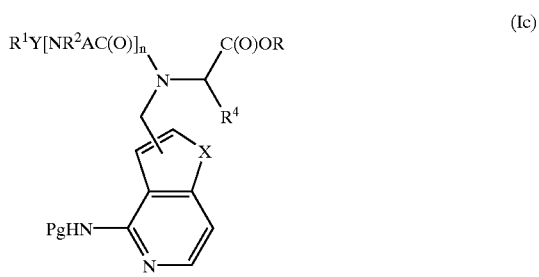

(Ic)

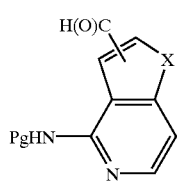

(X)

The compound of formula (X) is reduced, e.g. using sodium borohydride, into the corresponding alcohol, which then is converted into a leaving group, e.g. an appropriate sulfonate group, thereby forming a compound of formula (VIII).

Compounds of formula (X) are suitable intermediates for the preparation of compounds of formula (I) wherein $R^3$ is Q. In those preparations a compound of formula (X) is reacted with an appropriate amino acid derivative of the general formula $NH_2$—$C^4$—$C(O)OR$, $R^4$ and R having the previously defined meanings. The resulting imine is either directly converted into a compound of formula (XI) by reduction, using e.g. sodium cyanoborohydride, or isolated and subsequently reduced with an suitable reducing agent like sodium borohydride to form a compound of formula From compounds of formula (Ic) compounds of formula (Id) are prepared, which are the compounds of formula (I), wherein $R^3$ is Q and $R^5$ is $NR^7R^8$, following the procedure as described for the conversion of (Ia) into (Ib).

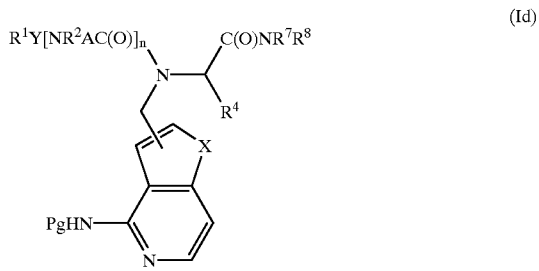

(Id)

Alternatively, a compound of formula (Id) may be obtained after protection of the N-terminus of (XI) with an N-protecting group Pg, such as Boc, both protecting groups in the molecule being the same or different, and saponification of the ester group to give intermediate (XII), and further derivatization as described for the conversion of a compound of formula (VII) into a compound of formula (Ib).

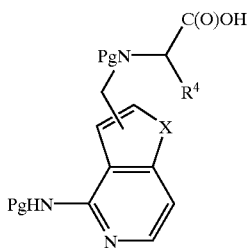
(XII)

Compounds of formula (I) wherein $R^{12}$ together with $R^3$ is —$(CH_2)_s$— can be prepared from amines of formula (VI) wherein $R^3$ is hydrogen and the arylamino is optionally protected. Reaction of these amines with aldehydes of formula $Pg(R^2)NCH((CH_2)_{(s-1)}CHO)COOG$, wherein Pg is a N-protecting group and $R^2$, s and G have the previously defined meanings, gives imides which are reduced using e.g. sodium cyanoborohydride to give cyclic compounds of formula (XIII). After removal of the N-protecting group Pg the moiety, $R^1Y$ can be introduced as described for the conversion of compounds of formula (VI) into compounds of formula (Ia). The group $OR^6$ can be modified in the same way as described for the conversion of compounds of formula (Ia) into compounds of formula (Ib) and removal of protecting groups if present gives compounds of formula (Ie). Furthermore, compounds of formula (Ie) and (XIII) can be prepared using the methods described by H. Mack et al. in J. Enzyme Inhibition 9, 73 (1995), wherein instead of the cyanophenyl building blocks used in the literature, building blocks containing moiety Q or a arylamino protected derivative thereof (e.g. compounds of formula (VI)) can be used.

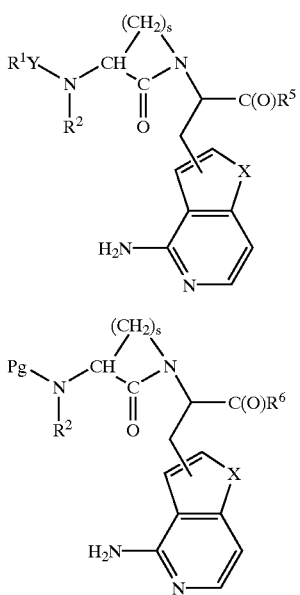
(Ie)

(XIII)

Compounds of formula (XX) can be prepared from compounds of formula (X). Reaction of a compound of formula (X) with an amine of formula $(R')^1NH_2$ gives an imide, which is either directly converted into a compound of formula (XXI) by reduction, using e.g. sodium cyano borohydride, or is isolated and subsequently reduced with a suitable agent like sodium borohydride to form a compound of formula (XXI), wherein $(R')^1$ has the previously defined meanings.

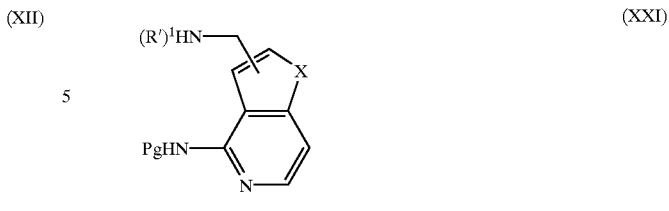
(XXI)

Alternatively a compound of formula (X) is reduced, using e.g. sodium borohydride, into the coresponding alcohol which then is converted into an azide using the method described by A. S. Thompson et al. in J. Org. Chem. 58, 5886 (1993). This azide can be reduced into an amine using reagents known in the art such as Pd/CaCO$_3$ catalyzed hydrogenation to yield a compound of formula (XXI) in which $(R')^1$ is hydrogen.

A compound of formula (XXI), or a derivative thereof wherein the arylamino is not protected, can be coupled with carboxylate compounds of formula J—D—E—OH, in which J, D and E have the previously defined meanings, or a protected derivative thereof, using peptide coupling methods. Subsequent removal of the optionally present protective groups gives compounds of formula (XX).

Compounds of formula (XXa) can be prepared by reaction of amines of formula (XXI), wherein $(R')^1$ is hydrogen with aldehydes of formula $PgHNCH((CH_2)_{(u-1)}CHO)COOG$, wherein Pg is a N-protecting group and u and G have the previously defined meanings, using the method described for compounds of formula (Ie).

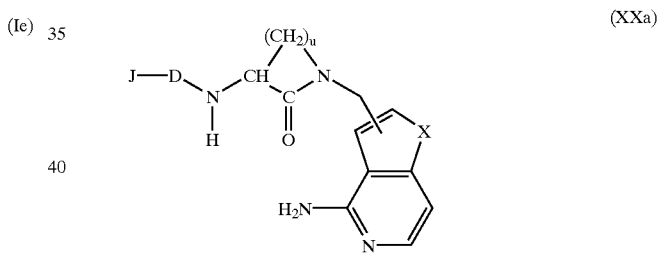
(XXa)

Compounds of formula (XXX) may be prepared in several ways in which the synthetic connection of moiety Q and the substituted phenyl part is made in moiety M. The method described in EP 0540051 may be used to prepare componds of formula (XXX) starting with compounds cf formula (VIII).

Compounds of formula (XL) can be prepared by reaction of a compound of formula (XLI) with a compound of formula (XLII) and a compound of formula (XLIII), wherein $(R''')^1$, $(R''')^2$, $(R''')^5$, and $(R''')^6$ have the previously defined meanings according to the methods described in EP 0728758. When $(R''')^1$ or $(R''')^2$ is the group of formula Q, compounds of formula (II), (VIII) or (X) or an arylamino protected derivative thereof can be used to prepare compounds of formula (XLI) or (XLII). When $(R''')^4$ is the group of formula Q amino acids of formula (VI) or an arylamino protected derivative thereof can be used as starting materials. When $(R''')^5$ or $(R''')^6$ is the group of formula Q, compounds of formula (X) or an arylamino protected derivative thereof can be used as a starting material, being aldehydes of formula (XLIII), or used to-prepare ketones of formula (XLIII).

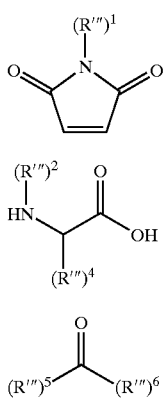

(XLI)

(XLII)

(XLIII)

Compounds of formula (L) can be prepared using methods known in the art described for Gp IIb/IIIa receptor antagonists containing a (hetero)arylamidine moiety instead of moiety Q. Compounds of formula (La) can conveniently be prepared from compounds of formula (X). An aldehyde of formula (X) is oxidized, using e.g. sodium chlorite, into the corresponding carboxylic acid. This carboxylic acid, or a derivative thereof wherein at the arylamino is not protected, can be coupled with an amine linker of formula $HN(R'''')^1$—U—$(R''')^1(R''')^2$—V or a N-protected derivative thereof, wherein $(R''')^1$, U, $(R''')^2$-and V have the previously defined meanings, using peptide coupling methods (e.g. using the amines and methods described in J. Med. Chem. 35, 4393 (1992), EP 0,505,868 or J. Med. Chem. 39, 3193 (1996)). Subsequent removal of the optionally present protective groups gives compounds of formula (La). Using a similar peptide coupling conditions a linker molecule having one free carboxylate can also be coupled with compound of formula (XXI), or a derivative thereof wherein the arylamino is not protected. Subsequent removal of the optionally present protective groups gives compounds of formula (L). Also halogen containing compounds of formula (II) can be used as starting material. The linker molecule can be attached using Pd mediated reactions such as Suzuki coupling, Heck reaction, or first transmetalation, using e.g. n-BuLi, and secondly reaction with a linker molecule containing an electrophilic function. Subsequent removal of the optionally present protective groups gives compounds of formula (L). For instance, Heck reaction of a halogen containing compound of formula (H) and an acrylic acid derivative leads to compounds,of formula (Lb). An alternative method for the preparation of compounds of formula (Lb) is a condensation reaction of aldehydes of formula (X) with a malonic acid derivative. Modification of this malonic acid derivative using methods known in the art and subsequent removal of optionally present protecting groups yields compounds of formula (Lb).

Compounds of the invention can also be prepared using a solid phase synthesis strategy. To prepare compounds of formula (Ia) the carboxylic acid of the compounds of formula (VII) can be covalently attached to a polymeric support such as a polystyrene-resin using a ester or amide bond as anchoring bond. In this case protection of the arylamino function is preferred. For example anchoring using a ester bond to the Kaiser oxime resin, Boc-protection of the N-terminus and acetyl amide protection of the arylamino group. The N-terminus protecting group can be removed selectively followed by coupling to $R^1YLg$ (n=0), or by peptide coupling with $R^1C(O)OH$ (n=0), $Pg^2NR^2AC(O)OH$ (n=1) or $R^1YNR^2AC(O)OH$ (n=1) according to the procedures described above for the conversion of compounds of formula (VI) into compounds of formula (Ia). Protecting group $Pg^2$ is a protecting group that can be removed selectively. Removal of $Pg^2$ liberates the N-terminus which can be coupled with $R^1YLg$ (n=0), or with $R^1C(O)OH$ (n=0) by peptide coupling methods according to the procedures described above for the conversion of compounds of formula (VI) into compounds of formula (Ia). Cleavage of the anchoring bond and removal of protecting groups, if present, gives compounds of formula (Ia) or (Ib) depending on the type of anchoring bond and way of cleavage used. For example cleavage of the anchoring ester bond to the Kaiser oxime resin with amines of type $HNNR^7R^8$ followed by removal of the optionally present protective groups yields compounds of formula (Ib). The solid phase synthesis strategy outlined above starting from compounds of formula (VII) can also be applied using the carboxylic acid of compounds of formula (XII) to yield compounds of formula (Ic) or (Id). Further, this strategy can be applied to carboxylic acids of formula J—D—E—OH— in which J, D, and E have the previously defined meanings—, a synthetic precursor thereof or a protected derivative thereof. Cleavage of the anchoring bond to the Kaiser oxime resin using amines of formula (XXI) yields compounds of formula (XX) after removal of the optionally present protecting group. Alternatively, the arylamino functionality of moiety Q can be used to be covalently attached to a polymeric support using e.g. a carbamate functionality as method of anchoring and used in a solid phase synthesis.

Several solid-phase synthesis strategies especially in the solid-phase synthesis of peptides are known in the art. An overview of solid-phase peptide synthesis is given by P. Lloyd-Williams, F. Albericio and E. Giralt in Tetrahedron 48, 11065–11133 (1993).

The peptide coupling, as mentioned as a procedural step in the above described method to prepare the compounds of the invention, can be carried out by methods commonly known in the art for the coupling—or condensation—of peptide fragments such as by the azide method, mixed anhydride method, activated ester method, or, preferably, by the carbodiimide method, especially with the addition of catalytic and racemisation suppressing compounds like N-hydroxy-succinimide and N-hydroxybenzotriazole. An overview is given in *The Peptides, Analysis, Synthesis, Biology,* Vol 3, E. Gross and J. Meienhofer, eds. (Academic Press, New York, 1981).

The term N-protecting group as used in this whole document means a group commonly used in peptide chemistry for the protection of an a-amino group, like the tert-butyloxycarbonyl (Boc) group, the benzyloxycarbonyl (Z) group, the 9-fluorenylmethyloxycarbonyl (Fmoc) group or the phthaloyl (Phth) group. Removal of the protecting groups can take place in different ways, depending on the nature of those protecting groups. Usually deprotection takes place under acidic conditions and in the presence of scavengers. An overview of amino protecting groups and methods for their removal is given in the above mentioned *The Peptides, Analysis, Synthesis, Biology,* Vol 3.

Suitable leaving groups (Lg) are known in the art, for example from A. L. Ternay: Contemporary Organic Chemistry ($2^{nd}$ ed., W. B. Saunders Company, 1979, see pages 158 and 170–172). Preferred leaving groups are chloride, mesylate and tosylate.

The compounds of the invention, which can occur in the form of a free base, may be isolated from the reaction mixture in the form of a pharmaceutically acceptable salt. The pharmaceutically acceptable salts may also be obtained by treating the free base of formula I with an organic or inorganic acid such as HCl, HBr, HI, $H_2SO_4$, $H_3PO_4$, acetic acid, propionic acid, glycolic acid, maleic acid, malonic acid, methanesulphonic acid, fumaric acid, succinic acid, tartaric acid, citric acid, benzoic acid, ascorbic acid and the like.

The compounds of this invention may possess one or more chiral carbon atoms, and may therefore be obtained as a pure enantiomer, or as a mixture of enantiomers, or as a mixture containing diastereomers. Methods for obtaining the pure enantiomers are well known in the art, e.g. crystallization of salts which are obtained from optically active acids and the racemic mixture, or chromatography using chiral columns.

The compounds of the invention may be administered enterally or parenterally. The exact dose and regimen of these compounds and compositions thereof will neccessarily be dependent upon the needs of the individual subject to whom the medicament is being administered, the degree of affliction or need and the judgment of the medical practitioner. In general parenteral administration requires lower dosages than other methods of administration which are more dependent upon absorption. However, the daily dosages are for humans preferably 0.001–100 mg per kg body weight, more preferably 0.01–10 mg per kg body weight. The medicament manufactured with the compounds of this invention may also be used as adjuvant in acute anticoagulant therapy. In such a case, the medicament is administered with other compounds useful in treating such disease states. The compounds may also be used with implantable pharmaceutical devices such as those described in U.S. Pat. No. 4,767,628, the contents of which are incorporated by this reference. Then the device will contain sufficient amounts of compound to slowly release the compound (e.g. for more than a month). Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation, or as a spray, e.g. for use as a nasal spray. For making dosage units, e.g. tablets, the use of conventional additives such as fillers, colorants, polymeric binders and the like is contemplated. In general any pharmaceutically acceptable additive which does not interfere with the function of the active compounds can be used. Suitable carriers with which the compositions can be administered include lactose, starch, cellulose derivatives and the like, or mixtures thereof, used in suitable amounts.

The invention is further illustrated by the following examples.

EXAMPLES

Melting points were measured on a Büchi 535 and are uncorrected. The $^1$H NMR measurements were performed on BRUKER AC 200, BRUKER AM 360 and BRUKER DRX 400 spectrophotometers operating at a $^1$H frequency of 200, 360 and 400 MHz respectively. The $^{19}$F measurements were performed on a BRUKER AC 200 spectrophotometer operating at a $^{19}$F frequency of 188 MHz.

6-Aiq: [[(1-amino-6-isoquinolinyl)methyl]amino]
Atp: [[(4-aminothieno[3,2c]pyridin-2-yl)methyl]amino]
Azt: azetidine-2-carboxylate
Boc: t-butyloxycarbonyl
Cha: cyclohexylalanyl
Gly: glycyl
Phe: phenylalanyl
Pro: prolyl
TFA: trifluoroacetic acid Example 1

3-(1-amino-6-isoquinolinyl)-2-[[2-[(2-naphthalenylsulfonyl)amino]acetyl]amino]propionic acid methyl ester hydrochloride (1k)

1a. 6-Bromoisoquinoline N-oxide hydrochloride

To a stirred solution of 13.2 g of 6-bromoisoquinoline (Tyson, F. L., J. Am. Chem. Soc. 61, 183 (1939)) in 250 mL of dichloromethane at room temperature was added in portions 16.2 g of m-chloroperbenzoic acid (purity 70%). After stirring the mixture for one hour 200 mL of methanol was added and the bulk was reduced to 150 mL. A hydrogen chloride solution in methanol (100 mL, 0.75 M) was added and after slightly heating a clear solution was obtained. Diethylether (250 mL) was added to this solution and cooled in an ice bath. The hydrochloride salt precipitated and was isolated by filtration to give 15 g of 1a. M.p. 194–196° C.

1b. 6-Bromo-1-chloroisoquinoline 70 mL of phosphorylchloride were added to 14.9 g of 1a and the mixture was heated at 90° C. for 2 hours. Excess of phosphorylchloride was evaporated, water was added, followed by aqueous 2N NaOH until pH 9 and the mixture was extracted with dichloromethane. The dichloromethane extract was washed with brine, dried ($MgSO_4$) and concentrated. The residue was chromatographed on silica gel (toluene/ethyl acetate 4/1) giving 10.1 g of 1b. M.p.= 102.7–103.7° C.

1c. 6-Bromo-1-phenoxyisoquinoline

A mixture of 10 g of 1b, 31 g of phenol and 4 g of KOH was heated at 140° C. for 2 hours. After cooling to room temperature aqueous 3N NaOH was added and the mixture was extracted with dichloromethane. The dichloromethane extract was washed with aqueous 2N NaOH, washed with water, dried ($MgSO_4$) and concentrated to yield 12.2 g of 1c. $^1$H-NMR 200 MHz ($CDCl_3$) δ: 7.1–7.6 (6H, m), 7.70 (1H, dd, J=9 Hz and J=2 Hz), 7.95–8.10 (2H, m), 8.31 (1H, d, J=9 Hz).

1d. 1-Amino-6-bromoisoquinoline

A mixture of 12 g of 1c and 27 g of ammonium acetate was heated at 150° C. for 14 hours. After cooling to room temperature aqueous 3N NaOH was added and the mixture was extracted with ethyl acetate. The ethyl acetate extract was washed with brine and aqueous 2N hydrochloric acid was added until pH2–3. The acid aqueous layer was separated, made basic (pH10) with aqueous 2N NaOH and extracted with ethyl acetate. The ethyl acetate layer was washed with brine, dried ($MgSO_4$) and concentrated to give 6.4 g of 1d. $^1$H-NMR 200 MHz ($CDCl_3$) δ: 5.1 (2H, br s), 6.96 (1H, dd, J=6 Hz and J=1 Hz), 7.54–7.70 (2H, m), 7.88 (1H, d, J=2 Hz), 7.98 (1H, d, J=6 Hz).

1e. N-(6-bromo-1-isoquinolinyl)benzamide 7.0 g of benzoic anhydride was added to a solution of 6.38 g of 1d in 70 mL of pyridine at room temperature and the solution was heated at 125° C. for 1 hour. The pyridine was evaporated and water and dichloromethane were added. The organic layer was separated, washed with water, dried (MgSO$_4$) and concentrated. The crude product was dissolved in dichloromethane and diethyl ether was added to give an amorphous solid that was isolated by filtration (yield 7.84 g). The filtrate was chromatographed on a silica gel column (dichloromethane/methanol:95/5) giving an additional 1.0 g of 1e. $^1$H-NMR 200 MHz (CDCl$_3$) δ: 6.90 (1H,d, J=6 Hz), 7.35 –8.48 (9H, m), 8.87 (1H, d, J=9 Hz).

1f. N-(6-formyl-1-isoquinolinyl)benzamide

To a stirred solution of 29 mL of n-BuLi (1.6 M in hexane) in 40 mL of dry tetrahydrofuran under a nitrogen atmosphere at −78° C. was added dropwise a solution of 2.5 g of 1e in 60 mL of dry tetrahydrofuran over a period of 15 min. After stirring for 30 min a mixture of 34 mL of N,N-dimethylformamide and 20 mL of tetrahydrofuran was added fast. The cooling bath was removed, the reaction mixture was allowed to come to 0° C. and was poured into ice cold aqueous hydrochloric acid (60 mL, 0.5 N). The mixture was adjusted to pH 6, brine was added and the mixture was extracted with ethyl acetate. The ethyl acetate extract was dried (MgSO$_4$) and concentrated under reduced pressure. Purification on silica gel (toluene/ethyl acetate:3/1) gave 1.3 g of aldehyde 1f. $^1$H-NMR 200 MHz (CDCl$_3$) δ: 7.12 (1H, d, J=7 Hz). 7.40–8.51 (9H, m), 9.26 (1H, d, J=8 Hz), 10.23 (1H, s).

1g. N-[6-(hydroxymethyl)-1-isoquinolinyl] benzamide

To a stirred suspension of 1.23 g of 1f in 40 mL of tetrahydrofuran and 15 mL of methanol was added 217 mg sodium borohydride in small portions. After stirring the mixture at ambient temperature for 5 min, 50 mL of water was added and tetrahydrofuran and methanol were removed in vacuo. Brine was added and the mixture was extracted with ethyl acetate. The ethyl acetate extract was dried (MgSO$_4$) and concentrated under reduced pressure giving 1.27 g of 1g. $^1$H-NMR 200 MHz (CDCl$_3$) δ: 4.75 (2H, s), 6.95 (1H, br.s), 730–7.55 (7H, m), 8.25–8.38 (2H, m), 8.69 (1H, br.s).

1h. [[1l-(benzoylamino)-6-isoquinolinyl]methyl][[(1, 1-dimethylethoxy)carbonyl]amino]propanedioic acid diethyl ester To a stirred suspension of 1.27 g of 1g in 30 mL of dichloromethane at 0° C. was added 1.23 mL of triethylamine and 0.69 mL of methane sulfonylchloride and the mixture was allowed to warm to room temperature. After stirring for 2 hours, 40 mL of tetrahydrofuran and 1.22 g of lithium chloride were added and the suspension was stirred for 16 hours at room temperature. Brine was added and the organic layer was separated. The aqueous layer was extracted with dichloromethane. The combined organic layers were dried over magnesium sulfate and concentrated under reduced pressure keeping the temperature below 30° C. The residue was coevaporated with toluene under reduced pressure again keeping the temperature below 30° C. The residue (chloride) was immediately dissolved in 20 mL of dioxane and added to sodium malonate reaction mixture A. [This sodium malonate reaction mixture A was obtained by addition of 3 g of [[(1,1-dimethylethoxy)carbonyl]amino] propanedioic acid diethyl ester (Paik, Y. H., Dowd, P., J. Org. Chem. 51, 2910 –2913 (1986)) in 10 mL of dioxane to a solution of sodium ethoxide (10 mmol) in 10 mL of dioxane and 30 mL of ethanol, stirring for 10 min at room temperature and subsequently addition of 0.5 g of sodium iodide.] After addition of the crude chloride the reaction mixture was stirred at 80° C. for two hours. After cooling to room temperature water was added, the mixture was neutralized with aqueous 1N hydrochloric acid and extracted with ethyl acetate. The organic layer was dried (MgSO$_4$) and concentrated under reduced pressure. The residue was chromatographed on silica gel (toluene/ethyl acetate:5/1) giving 1.45 g of 1h. 1H-NMR 200 MHz (CDCl$_3$) δ: 1.31 (6H, t), 1.51 (9H, s), 3.83 (2H, s), 4.18–4.39 (4H, m), 5.77 (1H, s), 6.92 (1H, d, J=7 Hz), 7.30–7.56 (6H, m), 8.41–8.49 (2H, m), 8.92 (1H, d, J=9 Hz).

1i. 2-Amino-3-(1-amino-6-isoquinolinyl)propionic acid dihydrochloride 15 mL of acetic acid and 30 mL of a solution of 6N hydrochloric acid were added to 1.34 g of 1h and heated at 100° C. for 16 h. After cooling to room temperature the aqueous solution was extracted twice with diethyl ether. The aqueous phase was concentrated under reduced pressure giving 0.79 g of amino acid 1i. $^1$H-NMR 200 MHz (D$_2$O) δ: 3.33–3.56 (2H, m), 4.36 (1H, dd, J=6.5 Hz and J=7.5 Hz), 7.12 (1H, d, J=7 Hz), 7.46 (1H, d, J=7 Hz), 7.62 (1H, dd, J=8 Hz and J=2 Hz), 7.73 (1H, d, J=2 Hz), 8.18 (1H, d, J=8 Hz).

1j. 2-Amino-3-(1-amino-6-isoquinolinyl)propionic acid methyl ester dihydrochloride 1.1 mL of thionyl chloride was added to a cooled solution (ice bath) of 65 mg of amino acid 1i in 4 mL of methanol. After stirring at 50° C. for 3 hours the mixture was concentrated under reduced pressure to give 66 mg of methyl ester 1j. The crude product was used without further purification. $^1$H-NMR 200 MHz (CD$_3$OD) δ: 3.36–3.59 (2H, m), 3.81 (3H, s), 4.53 (1H, t, J=7 Hz), 7.23 (1H, d, J=7 Hz), 7.60 (1H, d, J=7 Hz), 7.73 (1H, dd, J=9 Hz and J=2 Hz), 7.87 (1H, d, J=2 Hz), 8.47 (1H, d, J=9 Hz).

1k. 3-(1-amino-6-isoquinolinyl)-2-[[2-[(2-naphthalenylsulfonyl)amino]acetyl]amino]propionic acid methyl ester hydrochloride 62 mg of 1j was coevaporated with N,N-dimethylformamide and 3 mL of N,N-dimethylformamide, 58 mg of 2-[(2-naphthalenylsulfonyl)amino]acetic acid (WO 92/16549), and 0.1 mL of N-ethylmorpholine (pH of the mixture was 8) were added. The mixture was cooled at 0° C. and 47 mg of 1-hydroxybenzotriazole (HOBt) and 48 mg of N,N-dicyclohexylcarbodiimide (DCC) were added. After stirring for 16 hours at room temperature the mixture was concentrated in vacuo. Water was added, the pH was adjusted to 8–9 and extracted with ethyl acetate. The ethyl acetate extract was dried (MgSO$_4$), concentrated and chromatographed on silica gel (ethyl acetate/pyridine/acetic acid/water:81/31/18/7). The product was dissolved in ethyl acetate, washed with water (adjusted to pH 8–9), dried (MgSO$_4$) and concentrated to give 43 mg of free base. One equivalent hydrochloric acid was added and lyophilisation (t-butanol/water) afforded 1k. $^1$H-NMR 200 MHz (CD$_3$OD) δ: 3.09–3.41 (2H, m), 3.55 (2H, s), 3.69 (3H, s), 4.77 (1H, dd J=9 Hz and J=5 Hz), 7.16 (1H, d, J=7 Hz), 7.48–7.83 (6H, m), 7.91–8.03 (3H, m), 8.31 (1H, d, J=9 Hz), 8.38 (1H, d, J=2 Hz).

Example 2

N-[1-[(1-amino-6-isoquinolinyl)methyl]-2-oxo-2-(1-piperidinyl)ethyl]-2-[(2-naphthalenylsulfonyl)amino] acetamide hydrochloride (2b)

2a. 3-(1-amino-6-isoquinolinyl)-2-[[2-[(2-naphthalenylsulfonyl)amino]acetyl]amino]propionic acid hydrochloride 0.16 mL of aqueous 2N NaOH was added to a solution of 47 mg of 1k in 1.0 mL of dioxane and 0.5 mL water. After stirring at room temperature for one hour, the reaction mixture was made acidic (pH 2) and extracted with a mixture of n-butanol and dichloromethane. Evaporation of the organic solvents yielded 47 mg of acid 2a. $^1$H-NMR 200 MHz (CDCl$_3$/CD$_3$ OD=3/1) δ: 3.20–3.65 (4H, m), 4.87 (1H, dd, J=7 Hz and J=5 Hz), 7.10 (1H, d, J=7 Hz), 7.41 (1H, d, J=7 Hz), 7.58–8.03 (8H, m), 8.29 (1H, d, 7 Hz), 8.41 (1H, d, 2 Hz)

2b. N-[1-[(1-amino-6-isoquinolinyl)methyl]-2-oxo-2-(1-piperdinyl)ethyl]-2-[(2-naphthalenylsulfonyl)amino]acetamide hydrochloride 47 mg of 2a was suspended in 3 mL of N,N-dimethylformamide and concentrated in vacuo. The residue was dissolved in 3 mL of N,N-dimethylformamide and 0.11 mL of piperidine and 33 mg of 2-(1H-benzotriazol-1-yl)-1,1,3,3-tetramethyluronium tetrafluoroborate was added. When the pH of the reaction mixture was not 8–9, the pH was adjusted to 8–9 with N,N-diisopropylethylamine. After stirring 16 hours at room temperature the reaction mixture was concentrated in vacuo and chromatographed on silica gel (ethyl acetate/pyridine/acetic acid/water:81/31/18/7 v/v/v/v). The product was dissolved in dichloromethane, washed with water (adjusted to pH 8–9), dried (magnesium sulfate) and concentrated to give 43 mg of free base. The free base was dissolved in a t-butanol/water mixture, one equivalent hydrochloric acid was added and lyophilisation gave the title compound 2b. $^1$H-NMR 200 MHz (CD$_3$OD) δ: 1.20–1.65 (6H, m), 2.92–3.52 (6H, m), 3.54 (2H, s), 5.12 (1H, t, J=7 Hz), 7.17 (1H, d, J=7 Hz), 7.51–8.08 (9H, m), 8.31 (1H, d, J=9 Hz), 8.41 (1H, d, J=2 Hz).

Example 3

3-(4-aminothieno[3,2c]pyridin-2-yl)-2-[[2-[(2-naphthalenylsulfonyl)amino]acetyl]amino]-propionic acid methyl ester hydrochloride (3i)

3a. 4-Phenoxythieno[3,2c]pyridine

Compound 3a was prepared from 4-chlorothieno[3,2c]pyridine (New, J. S. et al., J. Med. Chem. 32, 1147–1156, (1989)) using the procedure described for 1c. $^1$H-NMR 200 MHz (CDCl$_3$) δ: 7.18–7.28 (3H, m), 7.38–7.50 (4H, m), 7.64 (1H, d, J=6 Hz), 8.97 (1H, d, J=6 Hz).

3b. 4-Aminothieno[3,2c]pyridine

The procedure described for 1d was used to prepare 3b from 3a but the reaction was performed at 155° C. for 3 days. $^1$H-NMR 200 MHz (CD$_3$OD) δ: 7.16 (1H, d, J=6 Hz), 7.48 (1H, d, J=6 Hz), 7.55 (1H, d, J=6 Hz), 7.71 (1H, d, J=6 Hz).

3c. N-(thieno[3.2c]pyridin-4-yl)benzamide

The procedure described for 1e was used to prepare 3c from 3b. $^1$H-NMR 200 MHz (CDCl$_3$) δ: 7.42–7.77 (6H, m), 7.97–8.22 (3H, m), 9.12–9.22 (1H, m).

3d. N-(2-formylthieno[3,2c]pyridin-4-yl)benzamide 5.2 mL of nBuLi (1.6 N in hexane) was added to a stirred solution of 0.96 mL of diisopropylamine in 8 mL of tetrahydrofuran under a nitrogen atmosphere at −25° C. After stirring for 20 min the solution was cooled to −78° C., a solution of 0.88 g of 3c in 14 mL of tetrahydrofuran was added dropwise and the reaction mixture was stirred for 45 min. Then a mixture of 0.6 mL of N,N-dimethylformamide and 7 mL of tetrahydrofuran was added. The cooling bath was removed, the reaction mixture was allowed to come to room temperature and was poured into an ice cold aqueous hydrochloric acid solution (20 mL, 0.5 N). The mixture was adjusted to pH 7 and the organic solvents were evaporated. The precipitate formed was isolated by filtration and dried. The yield was 0.98 g of aldehyde 3d. $^1$H-NMR 200 MHz (CDCl$_3$) δ: 7.48–7.80 (5H, m), 8.02–8.14 (2H, m), 8.30–8.38 (2H, m), 10.11 (1H, s).

3e. N-[2-(hydroxymethyl)thieno[3.2c]pyridin4-yl]benzamide

This compound was prepared from 3d using the procedure described for 1g. $^1$H-NMR 200 MHz (CDCl$_3$) δ: 4.88 (2H, s), 7.28 (1H, br.s). 7.48–7.76(5H, m), 7.99–8.22 (3H, m).

3f. [[4-(benzoylamino)thieno[3,2c]pyridin-2-yl]methyl][[(1,1-dimethylethoxy)carbonyl]amino]-propanedioic acid diethyl ester This compound was prepared from 3e using the procedure described for 1h. $^1$H-NMR 200 MHz (CDCl$_3$) δ: 1.28 (6H, t), 1.46 (9H, s), 3.98 (2H, s), 4.18–4.3.8 (4H, m), 7.05–8.17 (7H,m), 8.75 (1H, br.s).

3g. 2-Amino-3-(4-aminothieno[3,2c]pyridin-2-yl) propionic acid dihydrochloride

This compound was prepared from 3f using the procedure described for 1i. $^1$H-NMR 200 MHz D$_2$O) δ: 3.57–3.80 (2H, m), 4.44 (1H, dd, J=6 Hz and J=7 Hz), 7.45 (1H, d, J=7 Hz), 7.66 (1H, d, J=7 Hz), 7.85 (1H, s).

3h. 2-Amino-3-(4-aminothieno[3,2c]pyridin-2-yl) propionic acid methyl ester dihydrochloride This compound was prepared from 3g using the procedure described for 1j. $^1$H-NMR 200 MHz (CD$_3$OD) δ: 3.65–3.72 (2H, mn), 3.90 (3H, s), 4.53 (1H, t, J=6 Hz), 7.47 (1H, dd, J=7 Hz and J=2 Hz), 7.66 (1H, d, J=7 Hz), 7.82 (1H, br.s).

3i. 3-(4-Aminothieno[3,2c]pyridin-2-yl)-2-[[2-[(2-naphthalenylsulfonyl)amino]acetyl]amino]-propionic acid methyl ester hydrochloride This compound was prepared from 3h using the procedure described for 1k. $^1$H-NMR 360 MHz (CD$_3$OD) δ: 3.32–3.56 (2H, m), 3.61 (2H, s), 3.73 (3H, s), 4.75 (1H, dd, J=8 Hz and J=5 Hz), 7.37 (1H, dd, J=1Hz and J=7 Hz), 7.58–7.70 (4H, m), 7.83 (1H, dd, J=8 Hz and J=2 Hz, 7.95–8.05 (3H, m), 8.42 (1H, d, J=2 Hz).

Example 4

N-[1-[(4-Aminothieno[3,2c]pyridin-2-yl)methyl]-2-oxo-2-(1-piperidinyl)ethyl]-2-[(2-naphthalenylsulfonyl)amino]acetamide hydrochloride 0.06 mL of aqueous 2N NaOH was added to a solution of 20 mg of 3i in 0.25 mL of tetrahydrofuran, 0.1 mL of methanol and 0.25 mL of water. After stirring at room temperature for one hour the reaction mixture was neutralized and concentrated under reduced pressure. Tituration of the residue with a small amount of water, acidified to pH 2 with hydrochloric acid, gave 3-(4-aminothieno[3,2c]pyridin-2-yl)-2-[[2-[(2-naphthalenylsulfonyl)amino]acetyl]amino]-propionic acid hydrochloride. This acid was coupled with piperidine using the procedure described for 2b. Purification on silica gel (dichloromethane/methanol:9/1), addition of one equivalent hydrochloric acid, and lyophilisation (t-butanol/water) gave the title compound 4. $^1$H-NMR 360 MHz (CD$_3$OD) δ: 1.32–1.64 (6H, m),3.10–3.53 (6H, m), 3.61 and 3.64 (2H, ABq, J=17 Hz), 5.08 (1H, t, J=6 Hz), 7.35 (1H, dd, J=1Hz and J=7 Hz), 7.56–7.70 (4H,m), 7.84 (1H, dd, J=9 Hz and J=2 Hz), 7.96–8.06 (3H, m), 8.43 (1H, d, J=2 Hz).

Example 5

N-[1-[(1-Amino-6-isoquinolinyl)methyl]-2-oxo-2-(1-piperidinyl)ethyl]-2-[[(3,4-dihydro-2,5,7,8-pentamethyl-2H-1-benzopyran-6-yl)sulfonyl]amino] acetamide hydrochloride (5c)

5a. 1,1-Dimethylethyl 1-[(1-amino-6-isoquinolinyl) methyl]-2-oxo-2-(1-piperidinyl)ethyl-carbamate 144 mg of di-t-butyl dicarbonate in 1 mL of methanol was added to a solution of 100 mg of amino acid 1i in 4.5 mL of methanol and 0.5 mL of triethylamine. After stirring for 10 min the mixture was concentrated under reduced pressure and coevaporated with toluene, Addition of methanol gave a precipitate which was collected by filtration. The residue (132 mg) was suspended in N,N-dimethylformamide and 0.04 mL of piperidine, 133 mg of 2-(lH-benzotriazol-1-yl)-1,1,3,3-tetramethyluronium tetrafluoroborate was added. After stirring for one hour the reaction mixture was concentrated under reduced pressure. Purification by column chromatography (silica gel, dichloromethane/methanol:9/1) gave 77 mg of 5a. $^1$H-NMR 200 MHz (CDCl$_3$) δ: 0.93–1.59 (15H, m), 2.95–3.55 (6H, m), 4.93, (1H, t, J=7 Hz), 6.95 (1H, dd J=6 Hz and J=2 Hz), 7.37 (1H, dd, J=8 Hz and J=2 Hz), 7.41 (1H, d, J=2 Hz), 7,78–7.84 (2H, m).

5b. [(3,4-dihydro-2,2,5,7,8-pentamethyl-2H-1-benzopyran-6-yl)sulfonyl]amino]acetic acid 0.33 g of glycine was dissolved in 8.8 mL of aqueous 1N sodium hydroxide, a solution of 1.2 g of (3,4-dihydro-2,2, 5,7,8-pentamethyl-2H-1-benzopyran-6-yl)sulfonylchloride in 4 mL dioxane and 4 mL ether was added and stirred for 16 h. The aqueous solution was acidified to pH 3 with hydrochloric acid and extracted twice with ether. The combined organic layers were dried over magnesium sulfate and concentrated to give 1.15 g of 5b. $^1$H-NMR 200 MHz (CDCl$_3$) δ: 1.32 (6H, s), 1.82 (2H, t, J=7 Hz), 2.12 (3H, s ), 2.53 (3H, s), 2.55 (3H, s), 2.64 (2H, t, J=7 Hz), 3.77 (2H, s).

5c. N-[1-[(1-Amino-6-isoquinolinyl)methyl]-2-oxo-2-(1-piperidinyl)ethyl]-2-[[(3,4-dihydro-2,2,5,7,8-pentamethyl-2H-1-benzopyran-6-yl)sulfonyl]amino] acetamide hydrochloride To 70 mg of 5a in 2 mL of dichloromethane was added 0.01 mL of thioanisol and 0.5 mL of trifluoroacetic acid. After stirring for 2 hours at room temperature the reaction mixture was concentrated and coevaporated with water and subsequently with N,N-dimethylformamide. The residue and 72 mg of 5b was suspended in 3 mL of N,N-dimethylformamide and N-ethylmorpholine was added until pH 8. The mixture was cooled at 0° C. and 45 mg of 1-hydroxybenzotriazole and 45 mg of N,N-dicyclohexylcarbodiimide were added. After stirring for 16 hours at room temperature the mixture was concentrated in vacuo. Dichloromethane was added to the residue and filtered. The filtrate was purified on silica gel (dichloromethane/methanol: 95/5) to give the free base. To this free base was added one equivalent hydrochloric acid and lyophylisation (t-butanol/water) gave 75 mg of the title compound 5c. $^1$H-NMR 200 MHz (CDCl$_3$) δ1.32 (6H, s), 1.60–187 (8H, m), 2.13 (3H, s), 2.56–3.78 (16H,m), 5.28–5.38 (1H, m), 7.15–7.21 (2H, m), 7.59 (1H, d, J=7 Hz), 7.75–7.86 (2H, m).

Example 6

N-[1-[(1-Amino-6-isoquinolinyl)methyl]-2-oxo-2-(1-piperidinyl)ethyl]-2-[[(4-methylphenyl)sulfonyl] amino]acetamide hydrochloride The procedure described for 5c was used. Deprotection of 5a and subsequently coupling with [[(4-methylphenyl) sulfonyl]amino]acetic acid (McChesney, E. W. and Swann, W. K., J. Am. Chem. Soc. 59, 1116 (1937)) yielded the title compound 6. $^1$H-NMR 200 MHz (CD$_3$OD) δ: 1.22–1.68 (6H, m), 2.42 (3H, s), 3.03–3.68 (8H, m), 5.21 (1H, dd, J=6 Hz and J=7 Hz), 7.19 (1H, d, J=7 Hz), 7.35–7.80 (7H, m), 8.32 (1H, d, J=9 Hz).

Example 7

(2S)-N-[1-[(1-amino-6-isoquinolinyl)methyl]-2-oxo-2-(1-piperidinyl)ethyl]-3-hydroxy-2-[(2-naphthalenylsulfonyl)amino]propanamide hydrochloride The procedure described for 5c was used. Deprotection of 5a and coupling with (2S)-3-hydroxy-2-[(2-naphthalenylsulfonyl)amino]propanoic acid (prepared from L-serine and 2-naphthalenylsulfonylchloride using the procedure described for 5b) yielded 7. $^1$H-NMR 200 MHz (CD$_3$OD) δ: 1.12–1.58 (6H, m), 2.57–2.69 (1H, m) 2.95–3.95 (8H, m), 4.9–5.1 (1H, m), 7.11–7.22 (1H, m), 7.43–8.16 (9H, m), 8.24–8.34 (1H, m), 8.41–8.45 (1H, m).

Example 8

(3S)-4-[[-1-[(1-amino-6-isoquinolinyl)methyl]-2-oxo-2-(1-piperidinyl)ethyl]amino]-3-[[(4-methoxy-2,3,6-trimethylphenyl)sulfonyl]amino]4-oxo-butanoic acid 1,1-dimethylethylester hydrochloride The procedure described for 5c was used. Deprotection of 5a and coupling with 121 mg of (2S)-2-[[(4-methoxy-2,3, 6-trimethylphenyl)sulfonyl]amino]butanedioic acid 4-(1,1-dimethyl-ethyl)ester (prepared from Asp(OtBu)-OH and (4-methoxy-2,3,6-trimethylphenyl)-sulfonylchloride using the procedure described for 5b) yielded after purification 8 as a mixture of diastereomers (1:1). $^1$H-NMR 200 MHz (CD$_3$OD) δ: 1.30 and 1.35 (9H, 2×s), 1.38–1.70 (6H, m), 2.12 and 2.14 (3H, 2× s) 2.18–2.51 (2H, m), 2.53 and 2.54, (3H, 2×s), 285–3.54 (6H, m), 3.81 and 3.86 (3H, 2×s), 3.95–4.11 (1H, m), 5.03–5.21 (1H, m), 6.73 and 6.75 (1H, 2×s), 7.17–7.24 (1H, m), 7.52–7.78 (3H, m), 8.30–8.38 (1H, m).

Example 9

(3S)-4-[[1-[(1-amino-6-isoquinolinyl)methyl]-2-oxo-2-(1-piperidinyl)ethyl]amino]-3-[[(4-methoxy-2,3,6-trimethylphenyl)sulfonyl]amino]4-oxo-butanoic acid hydrochloride 10 mL of aqueous 1N hydrochloric acid was added to 45 mg of 8. After stirring for 6 h at 50° C. the reaction mixture was concentrated in vacuo. The residue was purified (silica gel, ethyl acetate/pyridine/acetic acid/water 81/31/18/7 and LH20, methanol/dichloromethane:1/1) to yield the free base.

Addition of one equivalent hydrogen chloride and lyophilisation (t-butanol/water) yielded 32 mg of 9 as a mixture of diastereoisomers. $^1$H-NMR 200 MHz (CD$_3$OD) δ: 1.3–1.7 (6H, m), 2.14 (3H, s) 2.20–2.38 (1H, m), 2.53 and 2.55, (3H, 2×s), 2.62 and 2.64 (3H, 2×s), 2.71–3.98 (8H, m), 3.85 and 3.87 (3H, 2×s), 5.08–5.21 (1H, m), 6.61 (1H, br.s), 7.07 (1H, d, J=7 Hz), 7.42–7.64 (3H, m), 8.21–8.28 (1H, m).

Example 10

3,4-dihydro-2,2,5,7,8-pentamethyl-2H-1-benzopyran-6-ylsulfonic acid 2-[[[1-[(1-amino-6-isoquinolinyl)methyl]-2-oxo-2-(1-piperidinyl)ethyl]amino]carbonyl]hydrazide hydrochloride To 100 mg of 5a in 2 mL of dichloromethane was added 2 ml of trifluoroacetic acid. After stirring for 15 minutes at room temperature the reaction mixture was concentrated and coevaporated with toluene. The residue was suspended in 3 mL N,N-dimethylformamide and 0.14 mL of N,N-diisopropylethylamine and 76 mg of Boc Azagly 4-nitrophenylester (Gante, J. And Weitzel.,R., Liebigs Ann. Chem. 349 (1990)) were added. After stirring for 2 hours at room temperature the reaction mixture was concentrated under reduced pressure and crystallized from diethylether/dichloromethane to give 89 mg of the coupled product. To 50 mg of this product were added 1.8 mL of acetic acid and 0.2 mL of aqueous 1N hydrochloric acid. After stirring for 45 minutes at room temperature the reaction mixture was concentrated under reduced pressure and coevaporated with toluene. The residue was suspended in 2 mL of N,N-dimethylformamide and 0.06 mL of N,N-diisopropylethyiamine and a solution of 38 mg of (3,4-dihydro-2,2,5,7,8-pentamethyl-2H-1-benzopyran-6-yl)sulfonylchloride in 1 mL of N,N-dimethylformamide was added. After stirring for 3 hours at room temperature the reaction mixture was concentrated under reduced pressure and purification yielded 38 mg of 10. $^1$H-NMR 200 MHz (CD$_3$OD) δ: 0.95–1.65 (6H, m), 1.24 (3H, s), 1.28 (3H, s), 1.80 (2H, t, J=7 Hz), 2.33 (3H, s), 2.53 (3H, s), 2.55 (3H, s), 2.64–3.48 (8H, m), 5.00 (1H, t, J=7 Hz)), 7.44 (1H, dd, J=2 Hz and J=9 Hz), 7.59 (1H, d, J=7 Hz), 7.64 (1H, d, J=2 Hz), 8.22 (1H, d, J=9 Hz).

Example 11

1-[3-(1-amino-6-isoquinolinyl)-2-[(2-naphthalenylsulfonyl)amino]-1-oxopropyl]-4-methylpiperidine hydrochloride (11b)

11a. 3-(1-amino-6-isoquinolinyl)-2-[(2-naphthalenylsulfonyl)amino]propionic acid methyl ester hydrochloride 0.10 g of 2-naphthalenylsulfonylchloride dissolved in 0.8 mL of dichloromethane and 0.2 mL of dioxane was added to a solution of 0.13 g of 1j in 6 mL dichloromethane and 0.17 mL of triethylamine at 0° C. After stirring at room temperature for 1 hour water was added, sodium hydroxide was added until pH 8–9 and the mixture was extracted with dichloromethane. The dichloromethane extract was dried (MgSO$_4$) and concentrated. Purification (silica gel, dichloromethane/methanol 95/5), addition of one equivalent of hydrochloric acid and lyophilisation (t-butanol/water) gave 69 mg of 11a. $^1$H-NMR 200 MHz (CDCl$_3$) δ: 3.00–3.34 (2H, m), 3.49 (3H, s), 4.34 (1H, dd, J=5 Hz and J=9 Hz), 6.72 (1H, d, J=7 Hz), 7.25–7.87 (9H, m), 8.04 (1H, d, J=8 Hz), 8.16 (1H, d, J=2 Hz).

11b. 1-[3-(1-amino-6-isoquinolinyl)-2-[(2-naphthalenylsulfonyl)amino]-1-oxopropyl]-4-methylpiperidine hydrochloride Compound 11a was saponified and subsequently coupled with 4-methylpiperidine using the procedure described for 4 to give 11b. $^1$H-NMR 200 MHz (CD$_3$OD) δ: 0.15–3.24 (12H, m), 3.75–4.24 (2H, m), 4.57–4.72 (1H, m), 6.71–7.91 (10H, m), 8.11–8.19 (2H, m).

Example 12

1-[3-(1-amino-6-isoquinolinyl)-2-[[(7-methoxy-2-naphthalenyl)sulfonyl]amino]-1-oxopropyl]-4-methylpiperidine hydrochloride (12b)

12a. (7-methoxy-2-naphthalenyl)sulfonyl chloride 2-(7-hydroxynaphthalenyl)sulfonic acid was methylated (J.Org. Chem. 57 2631 (1992)) and subsequently treated with thionyl chloride (Hel. Chim. Acta 176, 1653 (1959) using the procedures described in the indicated literature to give the title compound 12a. M.p.: 81–85° C.

12b. 1-[3-(-amino-6-isoquinolinyl)-2-[[(7-methoxy-2-naphthalenyl)sulfonyl]amino]-1-oxopropyl]-4-methylpiperidine hydrochloride Using the procedure described for 11a, the reaction of methyl ester 1j and sulfonyl chloride 12a gave 3-(1-amino-6-isoquinoinyl)-2-[[(7-methoxy-2-naphthalenyl)sulfonyl)amino]propionic acid methyl ester. This ester was saponified and subsequently coupled with 4-methylpiperidine using the procedure described for the previous example to give the title compound 12b. $^1$H-NMR 200 MHz (CD$_3$OD) δ: 0.18–0.85 (5H, m), 1.22–1.58 (3H, m), 1.78–3.18 (4H, m), 3.80–4.26 (2H, m), 3.88 (3H, s), 4.57–4.72 (1H, m), 6.97–7.04 (1H, m), 7.20–7.79 (8H, m), 8.01–8.14 (2H, m).

Example 13

1-[3-(4-aminothieno[3,2c]pyridin-2-yl)-2-[(2-naphthalenylsulfonyl)amino]-1-oxopropyl]-4-methylpiperidine hydrochloride Using the procedure described for 11a, the reaction of compound 3h and 2-naphthalenylsulfonylchloride gave 3-(4-aminothieno[3,2c]pyridin-2-yl)-2-[(2-naphthalenyl-sulfonyl)amino]propionic acid methyl ester hydrochloride. This compound was saponified and coupled with 4-methylpiperidine according to the procedure described for 11b giving the title compound 13. $^1$H-NMR 200 MHz (CD$_3$OD) δ: 0.1–3.3 (12H, m), 3.72–4.18 (2H, m), 4.54–4.68 (1H, mn), 7.16–7.23 (1H, m), 7.38–8.01 (8H, m), 8.27–8.32 (1H, m).

Example 14

1-[3-(4-aminothieno[3,2c]pyridin-2-yl)-2-[[(7-methoxy-2-naphthalenyl)sulfonyl]amino]-1-oxopropyl]-4-(methylsulfonyl)piperazine hydrochloride (14c)

14a. 3-(4-aminothieno[3,2c]pyridin-2-yl)-2-[[(7-methoxy-2-naphthalenyl)sulfonyl]-amino]propionic acid hydrochloride The procedure described for 11a was used to prepare 3-(4-aminothieno[3,2c]pyridin-2-yl)-2-[[(7-methoxy-2-naphthalenyl)sulfonyl]amino]propionic acid methyl ester from 3h and 12a. This sulfonamide (130 mg) was dissolved in 3 mL of dioxane and 1.1 mL of water and 0.4 mL of aqueous 2N NaOH was added. After stirring at room temperature for 2 hours the reaction mixture was neutralized and concentrated under reduced pressure. The residue was subsequently titurated with dichloromethane and with a small amount of water acidified to pH 3 with hydrochloric acid to give 114 mg of compound 14a. TLC (silica gel, ethyl acetate/pyridine/acetic acid/water 81/31/18/7) rf=0.29.

14b. 1-Methylsulfonylpiperazine 3.5 mL of methane sulfonylchloride in 50 mL of dichloromethane was added slowly to a solution of 4.9 g of 1-formylpiperazine and 6.1 mL of triethylamine in 100 mL of dichloromethane at 0° C. After stirring for 1 hour water was added and the organic layer was separated. The aqueous layer was extracted several times with dichloromethane. The combined organic layers were dried (MgSO$_4$) and concentrated to yield 5.8 g of 1-formyl-4-(methylsulfonyl) piperazine. The crude product was dissolved in 15ml of ethanol and 15 mL of aqueous 2N NaOH and stirred for 1.5 hours at 80° C. After cooling to room temperature water was added and extracted several times with dichloromethane. The combine organic layers were dried (MgSO$_4$) and concentrated to give 2.9 g of the title compound 14b. $^1$H-NMR 200 MHz (DMSOd6) δ: 2.70–2.77 (4H, m), 2.83 (3H, s), 2.95–3.02 (4H, m).

14c. 1-[3-(4-aminothieno[3,2c]pyridin-2-[[(7-methoxy-2-naphthalenyl)sulfonyl]amino]-1-osopropyl]-4-(methylsulfonyl)piperazine hydrochloride Using the procedure described for 2b, 14a was coupled with 14b to give the title compound 14c. $^1$H-NMR 400 MHz (CD$_3$OD) δ: 2.66 (3H, s), 2.62–3.69 (10H, m), 3.97 (3H, s), 4.6–4.7 (1H, m), 7.14 (1H, d, J=7 Hz), 7.29–7.35 (3H, m), 7.46–7.60 (2H, m), 7.81–7.86 (2H, m), 8.18 (1H, bs.s).

Example 15

1-[3-(4-aminothieno[3,2c]pyridin-2-yl)-2-[[(7-methoxy-2-naphthalenyl)sulfonyl]amino]-1-oxopropyl]morpholine hydrochloride Using the procedure described for 2b, 14a was coupled with morpholine to give 15. $^1$H-NMR 200 MHz (CD$_3$OD) δ: 3.07–3.52 (10H, m), 3.94 (3H, s), 4.62 (1H, dd, J=9 Hz and J=5 Hz), 7.19–7.58 (6H, m), 7.76–7.82 (2H, m), 8.13 (1H, d, J=2 Hz).

Example 16

1-[3-(4-aminothieno[3,2c]pyridin-2-yl)-2-[[[(5-dimethylamino)naphthalenyl]sulfonyl]-amino]-1-oxopropyl]-4-methylpiperidine hydrochloride (16b)

16a. 3-(4-aminothieno[3,2c]pyridin-2-yl)-2-[[[(5-dimethylamino)naphthalenyl]sulfonyl]amino]-propionic acid hydrochloride Using the procedure described for 14a, coupling of 3h and (5-dimethylaminonaphthalenyl)-sulfonyl chloride gave title compound 16a. TLC (silica gel, ethyl acetate/pyridine/acetic acid/water: 81/31/18/7)rf=0.3.

16b. 1-[3-(4-aminothieno[3,2c]pyridin-2-yl)-2-[[[(5-dimethylamino)naphthalenyl]sulfonyl]-amino]-1-oxopropyl]-4-methylpiperidine hydrochloride Using the procedure described for 2b, 16a was coupled with 4-methylpiperidine to give the title compound 16b. $^1$H-NMR 200 MHz (CD$_3$OD) δ: 0.1–3.3 (12H, m), 2.82 (3H, s), 3.53–4.28 (2H, m), 4.41–4.52 (1H, m), 7.02–7.58 (6H, m), 8.12-8.24 (2H, m), 8.40–8.24 (1H, m)

Example 17

1-[3-(4-aminothieno[3,2c]pyridin-2-yl)-2-[[[(5-dimethylamino)nalphthalenyl]sulfonyl]-amino]-1-oxopropyl]-4-(methylsulfonyl)piperazine hydrochloride Using the procedure described for 2b, 16a was coupled with 1-methylsulfonylpiperazine to give the title compound 17. $^1$H-NMR 200 MHz (CD$_3$OD) δ: 2.64 (3H, s), 2.83 (6H, s), 2.76–3.46 (10H, m), 4.50 (1H, dd, J=8 Hz and J=7 Hz), ), 7.03–7.15 (2H, m), 7.25 (1H, br.s), 7.43–7.57 (3H, m), 8.14–8.20 (2H m), 8.41–8.48 (1H, m)

Example 18

1-[3-(4-aminothieno[3,2c]pyridin-2-yl)-2-[[(7-methoxy-2-naphthalenyl)sulfonyl]amino]-1-oxopropyl]-4-methylpiperidine hydrochloride Using the procedure described for 2b, 14a was coupled with 4-methylpiperidine to give the title compound 18. $^1$H-NNMR 200 MHz (CD$_3$OD) δ: 0.1–3.3 (12H, m), 3.93 (3H, s), 3.65–4.17 (2H, m), 4.52–4.65 (1H, m), 7.09–7.87 (8H, m), 8.18–8.23 (1H, m).

Example 19

1-[3-(4-aminothieno[3,2c]pyridin-2-yl)-2-[[(7-methoxy-2-naphthalenyl)sulfonyl]oxopropyl]-4-ethylpiperidine hydrochloride Using the procedure described for 2b, 14a was coupled with 4-ethylpiperidine to give the title compound 19. $^1$H-NMR 200 MHz (CD$_3$OD) δ: 0.1–3.3 (14H, m), 3.72–3.83 (1H, m), 3.93 and 3.94 (3H, 2×s), 3.94–4.16 (1H, m), 4.52–4.63 (1H, m), 7.12–7.61 (6H, m), 7.76–7.85 (2H, m), 8.17–8.24 (1H, m).

Example 20

1-[3-(4-aminothieno[3,2c]pyridin-2yl)-2-[[[(5-dimethylamino)naphthalenyl]sulfonyl]-amino]-1-oxopropyl]morpholine hydrochloride Using the procedure described for 2b, 16a was coupled with morpholine to give the title compound 20. $^1$H-NMR 200 MHz (CD$_3$OD) δ: 2.82 (6H, s), 2.99–3.46 (10H, m), 4.45 (1H, dd, J=8 Hz and J=7 Hz), ), 7.01–7.13 (2H, m), 7.24 (1H, br.s), 7.41–7.57 (3H, m), 8.14–8.19 (2H, m), 8.40–8.47 (1H, m)

Example 21

1-[3-(4-aminothieno[3,2c]pyridin-2yl)-2-[[(7-methoxy-2-naphthalenyl)sulfonyl]amino]-1-oxopropyl]-4-formylpiperazine hydrochloride Using the procedure described for 2b, 14a was coupled with 1-formylpiperazine to give the title compound 21. $^1$H-NMR 400 MHz (CD$_3$OD) δ: 2.81–3.68 (10H, m), 3.72 (3H, s), 4.66 (1H, dd, J=6 Hz and J=8 Hz)), 7.08–7.10 (1H, m), 7.25–7.32 (3H, m), 7.49 (1H, d, J=7 Hz), 7.58 (1H, dd, J=2 Hz and J=9 Hz), 7.77–7.81 (2H, m), 7.92 and 7.98 (1H, 2×s), 8.17 (1H, bs.s).

Example 22

1-[3-(4-aminothieno[3,2c]pyridin-2-yl)-2-[[(7-methoxy-2-naphthalenyl)sulfonyl]amino]-1-oxopropyl]-4-methoxypiperidine hydrochloride (22b)

22a. 4-Methoxypiperidine hydrochloride 5.8 g of di-t-butyl dicarbonate was added to a solution of 3.13 g of 4-hydroxypiperidine in 29 ml of tetrahydrofuran and 7 mL of pyridine. After 16 hours at room temperature the mixture was concentrated and coevaporated with toluene. The residue was dissolved in 23 mL of tetrahydrofuran and 3.3 mL of methyl iodide was added. To this solution 1.2 g of sodium hydride (60% dispersion) was added in small potions. After stirring for 2 hours at room temperature methanol was added carefully to destroy the excess sodium hydride. The reaction mixture was concentrated in vacuo. Water was added, the pH adjusted to 4 and extracted with ethyl acetate. The ethyl acetate extract was dried (MgSO$_4$) and concentrated. Column chromatography (silica gel, toluene/ethyl acetate: 4/1) yielded 2.7 g of 1-Boc-4-methoxypiperidine. This compound was cooled at 0° C. and 30 mL of 3N hydrochloric acid in methanol was added. After stirring for 19 hours at room temperature the reaction mixture was concentrated to give 2.4 g of 4-methoxypiperidine hydrochloride. $^1$H-NMR 200 MHz (CD$_3$OD) δ: 1.76–2.12 (4H, m), 3.03–3.61 (5H, m), 3.36 (3H, s).

22b. 1-[3-(4-aminothieno[3.2c]pyridin-2-yl)-2-[[(7-methoxy-2-naphthalenyl)sulfonyl]amino]-1-oxopropyl]-4-methoxypiperidine hydrochloride Using the procedure described for 2b, 14a was coupled with 22a to give the title compound 22b. $^1$H-NMR 400 MHz (CD$_3$OD) δ: 1.82–1.62 (4H, m), 2.90–3.64 (7H, m), 3.21 and 3.22 (3H, 2×s), 3.94 (3H, s), 4.59–4.64 (1H, m), 7.11 (1H, d, J=7Hz), 7.25–7.34 (3H, m), 7.49–7.58 (2H, m), 7.77–7.82 (2H, m), 8.18 (1H, br.s).

Example 23

1-[3-(4-aminothieno[3,2c]pyridin-2-yl)-2-[[(7-methoxy-2-naphthalenyl)sulfonyl]amino]-1-oxopropyl]-4-[(trifluormethyl)sulfonyl]piperazine hydrochloride (23b)

23a. 1-(trifluormethyl)sulfonyl]piperazine hydrochloride 2.0 mL of trifluormethanesulfonic anhydride in 10 mL of dichloromethane was slowly added to a stirred solution of 2.0 g of Boc-piperazine and 1.65 mL of triethylamine in 31 mL of dichloromethane at −78° C. After 1 hour the reaction mixture was allowed to warm to 0° C., poured into water, neutralized and extracted with dichloromethane. The dichloromethane extract was washed with 5% NaHCO$_3$, dried (MgSO$_4$) and concentrated. Column chromatography (silica gel, toluene/ethyl acetate: 9/1) yielded 1.6 g of 1-Boc-4-[(trifuormethyl)sulfonyl]piperazine.

0.2 g of this compound was cooled at 0° C. and 3 mL of 3N hydrochloric acid in methanol was added. After stirring for 19 hours at room temperature the reaction mixture was concentrated to give 0.1 g of 1-(trifluormethyl)sulfonyl] piperazine hydrochloride. $^{19}$F-NMR 188 MHz (CD$_3$OD) δ: −76.6.

23b. 1-[3-(4-aminothieno[3.2c]pyridin-2-yl)-2-[[(7-methoxy-2-naphthalenyl)sulfonyl]amino]-1-oxopropyl]-4-[(trifluormethyl)sulfonyl]piperazine hydrochloride Using the procedure described for 2b, 14a was coupled with 23a to give the title compound 23b. $^{19}$F-NMR 188 MHz (CD$_3$OD) δ: −78.3.

Example 24

1-[3-(4-aminothieno[3,2c]pyridin-2-yl)-2-[[(7-methoxy-2-naphthalenyl)sulfonyl]amino]-1-oxopropyl]-4-methylpinerazine dihydrochloride Using the procedure described for 2b, 14a was coupled with 1-methylpiperazine to give the title compound 24. $^1$H-NMR 400 MHz (CD$_3$OD) δ: 1.99–2.51 (4H, m), 2.23 (3H, s), 3.12–3.72 (6H, m), 3.94 (3H, s), 4.63 (1H, dd, J=5 Hz and J=9 Hz), 7.18 (1H, d, J=7 Hz), 7.26–7.31 (2H, m), 7.39 (1H, s), 7.46 (1H, d, J=7 Hz), 7.56 (1H, dd, J=2 Hz and J=9 Hz), 7.78–7.82 (2H, m), 8.15 (1H, d, J=2 Hz).

Example 25

1-[3-(4-aminothieno[3,2c]pyridin-2-yl)-2-[[(7-methoxy-2-naphthalenyl)sulfonyl]amino]-1-oxopropyl]thiomorpholine hydrochloride Using the procedure described for 2b, 14a was coupled with thiomorpholine to give the title compound 25. $^1$H-NMR 400 MHz (CDCl$_3$) δ: 1.87–2.41 (4H, m), 3.03–3.75 (6H, m), 3.95 (3H, s), 4.56 (1H, dd, J=5 Hz and J=8 Hz)), 6.94 (1H, d, J=7 Hz), 7.21 (1H, d, J=3 Hz), 7.28–7.35 (2H, m), 7.57 (1H, d, J=6 Hz), 7.63 (1H, dd, J=2 Hz and J=9 Hz), 7.76–7.84 (2H, m), 8.25 (1H, bs.s).

Example 26

3-(4-aminothieno[3,2c]pyridin-2-yl)-N-(2-methoxyethyl)-2-[[(7-methoxy-2-naphthalenyl)-sulfonyl]amino]-N-methyl-propanamide hydrochloride Using the procedure described for 2b, 14a was coupled with N-methyl-2-methoxyethylamine to give the title compound 26. $^1$H-NMR 400 MHz (CD$_3$OD) δ: 2.73 and 2.98 (3H, 2×s), 3.08 and 3.28 (3H, 2×s), 2.85–3.48 (5H, m), 3.91 (3H, s), 4.01–4.27 (1H, m), 4.56–4.76 (1H, m), 6.89–7.02 (1H, m), 7.16–7.78 (7H, m), 8.04–8.19 (1H, m).

Example 27

1-[3-(4-aminothieno[3,2c]pyridin-2-yl)-2-[[(7-methoxy-2-naphthalenyl)sulfonyl]amino]-1-oxopropyl]-4-(1-oxoethyl)piperidine hydrochloride Using the procedure described for 2b, 14a was coupled with 4-(1-oxoethyl)piperidine to give the title compound 27. $^1$H-NMR 400 MHz (CD$_3$OD) δ: 0.52–0.72 (1H, m), 0.97–1.18 (1H, m), 1.53–1.71 (2H, m), 1.92 and 1.98 (3H, 2×s), 2.04–2.56 (2H, m), 2.76–2.9 (1H, m), 3.08–3.28 (2H, m), 3.73–4.05 (2H, m), 3.94 (3H, s), 4.57–4.63 (1H, m), 7.09 (1H, d, J=7 Hz), 7.23–7.35 (3H, m), 7.53–7.60 (2H, m), 7.75–7.86 (2H, m), 8.17 and 8.22 (1H, 2×br.s).

Example 28

1-[3-(4-aminothieno[3,2c]pyridin-2-yl)-2-[[(7-methoxy-2-naphthalenyl)sulfonyl]amino]-1-oxopropyl]-4-methylenepiperidine hydrochloride (28b)

28a. 4-methylenepiperidine hydrochloride 6 g of di-t-butyldicarbonate, 2 g of 4-piperidone monohydrate hydrochloride and 6.3 mL of pyridine were dissolved in 25 mL of tetrahydrofuran. After stirring for 4 days at room temperature the reaction mixture was concentrated, water was added, the pH adjusted to 3 and extracted with ethyl acetate. The ethyl acetate extracts were dried (magnesium sulfate) and concentrated. This residue (0.6 g) was transformed into Boc-4-methylenepiperidine using the procedure described in J. Am. Chem. Soc. 101, 7032 (1979). Boc-4-methylenepiperidine was dissolved in 3N hydrochloric acid in methanol and stirred for 19 hours at room temperature. Evaporation yielded 0.24 g of the title compound 28a. ¹H-NMR 200 MHz (CDCl₃) δ: 2.57 (4H, br.s), 3.22 (4H, br.s), 4.88 (2H, s).

28b. 1-[3-(4-aminothieno[3,2c]pyridin-2-yl)-2-[[(7-methoxy-2-naphthalenyl)sulfonyl]amino]-1-oxopropyl]-4-methylenepiperidine hydrochloride Using the procedure described for 2b, 14a was coupled with 28a to give the title compound 28b. ¹H-NMR 400 MHz (DMSOd6) δ: 1.55–2.04 (4H, m), 2.89–3.5 (6H, m), 3.88 (3H, s), 4.49–4.67 (3H, m), 7.43–7.78 (8H, m), 8.09 (1H, 2×br.s).

Example 29

2-[[3-(4-aminothieno[3,2c]pyridin-2-yl)-2-[[(7-methoxy-2-naphthalenyl)sulfonyl]amino]-1-oxopropyl](cyclopropyl)amino]acetic acid ethyl ester hydrochloride The procedure described for 2b was used to couple 14a with [(cyclopropyl)amino]acetic acid ethyl ester giving the title compound 29. [(Cyclopropyl)amino]acetic acid ethyl ester was prepared cyclopropylbromide and glycine ethyl ester using the procedure described by J. T. Suh et al. (J. Med. Chem. 28, 57–66 (1985)). ¹H-NMR 400 MHz (CD₃OD) δ: 0.76–1.12 (4H, m), 1.24 (3H, t, J=7 Hz), 2.93–3.02 (2H, m), 3.28–3.36 (1H, m), 3.84 and 4.20 (2H, ABq, J=17 Hz), 3.93 (3H, s), 4.14 (2H, q, J=7 Hz), 5.10 (1H, dd, J=4 Hz and J=10 Hz), 6.86 (1H, d, J=6 Hz), 7.15–7.70 (7H, m), 8.05 (1H, s), Example 30

1-[3-(4-aminothieno[3,2c]pyridin-2-yl)-2-[[[1-(1R,4S)-(7,7-dimethyl-2-oxobicyclo[2.2.1]hept-1-yl)methyl]sulfonyl]amino]-1-oxopropyl]-4-methylpiperidine hydrochloride (30b)

30a. 1,1-Dimethylethyl 1-[(4-aminothieno[3,2c]pyridin-2-yl)methyl]-2-oxo-2-[1-(4-methylpiperidinyl)]ethyl carbamate The procedure described for 5a was used. Amino acid 3g was protected with the t-butyloxy carbamate group and subsequently coupled with 4-methylpiperidine to give the title compound 30a. ¹H-NMR 200 MHz (CDCl₃) δ: 0.1–3.4 (12H, m), 1.40 (9H, s), 3.78–3.95 (1H, m), 4.42–4.56 (1H, m), 4.87–4.97 (1H, m), 7.04–7.11 (2H, m), 7.78 (1H, d, J=7 Hz).

30b. 1-[3-(4-aminothieno[3,2c]pyridin-2-yl)-2-[[[1-(1R,4S)-(7,7-dimethyl-2-oxobicyclo[2.2.1]hept-1-yl)methyl]sulfonyl]amino]-1-oxopropyl]-4-methylpiperidine hydrochloride To 82 mg of 30a in 2.2 mL of dichloromethane was added 2.2 mL of trifluoroacetic acid. After stirring for 1 hour at room temperature the reaction mixture was concentrated and coevaporated with toluene. The residue was dissolved in 3 mL of dichloromethane and 0.12 mL of triethylamine, cooled at 0° C. and 55 mg of (−)camphor-10-sulfonylchloride was added. After stirring for 16 hours at room temperature water was added, the pH was adjusted to 8–9 and the mixture was extracted with dichloromethane. The extract was dried (magnesium sulfate) and concentrated. Purification on silica gel (dichloromethane/methanol: 9/1) afforded the free base. Addition of one equivalent hydrochloric acid and lyophilisation gave 58 mg of the title compound 30b. ¹H-NMR 200 MHz (CD₃OD) δ: 0.1–3.5 (28H, m), 3.93–4.16 (1H, m), 4.37–4.58 (1H, m), 7.39–7.48 (1H, m), 7.58–7.73 (2H, m).

Example 31

1-[3-(4-aminothieno[3.2c]pyridin-2-yl)-2-[[(3,4-dihydro-2,2,5,7,8-pentamethyl-2H-1-benzopyran-6-yl)sulfonyl]amino]-1-oxopropyl]-4-methylpiperidine hydrochloride The procedure described for 30b was used to couple 30a with (3,4-dihydro-2,2,5,7,8-pentamethyl-2H-1-benzopyran-6-yl)sulfonyl chloride giving the title compound 31. ¹H-NMR 200 MHz (CD₃OD) δ: 0.1–1.6 (14H, m), 1.82 (2H, t, J=7 Hz), 2.02–3.3 (15H, m), 3.45–3.75 (1H, m), 4.11–4.48 (2H, m), 7.25–7.32 (1H, m), 7.44–7.63 (2H, m).

Example 32

1-[3-(4-aminothieno[3,2c]pyridin-2-yl)-2-[[(2-dibenzofuranyl)sulfonyl]amino]-1-oxopropyl]-4-methylpiperidine hydrochloride The procedure described for 30b was used to couple 30a with (2-dibenzofuranyl)sulfonyl chloride giving the title compound 32. ¹H-NMR 200 MHz (CD₃OD) δ: 0.1–0.75 (5H, m), 1.25–1.56 (3H, m), 1.92–2.50 (1H, m), 2.71–3.3 (3H, m), 3.75–4.23 (2H, m), 4.54–4.69 (1H, m), 6.99–7.05 (1H, m), 7.29–7.48 (6H, m), 7.86–8.09 (2H, m), 8.37–8.42 (1H, m).

Example 33

1-[3-(4-aminothieno[3,2c]pyridin-2-yl)-2-[[2-[5-(2-pyridinyl)thienyl]sulfonyl]amino]-1-oxopropyl]-4-methylpiperidine hydrochloride The procedure described for 30b was used to couple 30a with [5-(2-pyridinyl)thienyl]sulfonyl chloride giving the title compound 33. ¹H-NMR 200 MHz (CD₃OD) δ: 0.05–1.69 (8H, m), 2.25–2.60 (1H, m), 2.85–3.41 (3H, m), 3.78–4.00 (1H, m), 4.17–4.37 (1H, m), 4.59–4.72 (1H, m), 7.13–7.22 (1H, m), 7.29–7.60 (5H, m), 7.82–7.88 (2H, m), 8.47–8.55 (1H, m).

Example 34

1-[3-(4-aminothieno[3,2c]pyridin-2-yl)-2-[[(6,7-dimethoxy-2-naphthalenyl)sulfonyl]-amino]-1-oxopropyl]-4-methylpiperidine hydrochloride (34b)

34a. 2-(6,7-Dimethoxynaphthalenyl)sulfonyl chloride 2-(6,7-dihydroxynaphthalenyl)sulfonic acid was methylated (J. Org. Chem. 57, 2631 (1992)) and subsequently treated with thionyl chloride (Hel. Chim. Acta 176, 1653 (1959)) using the procedures described in the indicated literature to give the title compound 34a. M.p.: 111–115° C.

34b. 1-[3-(4-aminothieno[3,2c]pyridin-2-yl)-2-[[(6,7-dimethoxy-2-naphthalenyl)sulfonyl]amino]-1-oxopropyl]-4-methylpiperidine hydrochloride The procedure described for 30b was used to couple 30a with 34a giving the title compound 34b. ¹H-NMR 200 MHz (CD₃OD) δ: 0.05–1.58 (8H, m), 1.88–3.3 (4H, m), 3.72–4.19 (2H, m), 3.97 (3H, s), 3.98 and 3.99 (3H, 2×s), 4.48–4.64 (1H, m), 7.26–7.32 (3H, m), 7.46–7.79 (4H, m), 8.12 (1H, d, J=2 Hz).

Example 35

1-[3-(4-aminothieno[3,2c]pyridin-2-yl)-2-[[2-[5-(3-isoxazolyl)thienyl]sulfonyl]amino]-1-oxopropyl]-4-methylpiperidine hydrochloride The procedure described for 30b was used to couple 30a with [5-(3-isoxazolyl)thienyl]sulfonyl chloride giving the title compound 35. $^1$H-NMR 200 MHz (CD$_3$OD) δ: 0.05–1.75 (8H, m), 2.25–2.64 (1H, m), 2.84–3.40 (3H, m), 3.79–4.02 (1H, m), 4.18–4.39 (1H, m), 4.61–4.74 (1H, m), 6.75–6.79 (1H, m), 7.14–7.20 (1H, m), 7.38–7.61 (4H, m), 8.46 (1H, d, J=2 Hz).

Example 36

1-[3-(4-aminothieno[3,2c]pyridin-2-yl)-2-[[(4,6-dimethoxy-2-naphthalenyl)sulfonyl]amino]-1-oxopropyl]-4-methylpiperidine hydrochloride (36b)

36a. (4,6-Dimethoxy-2-naphthalenyl)sulfonyl chloride (4,6-dihydroxy-2-naphthalenyl)sulfonic acid was methylated (J. Org. Chem. 57, 2631 (1992)) and subsequently treated with phosphorous oxychloride (J. Am. Chem. Soc. 74, 2006 (1952)) using the procedures described in the indicated literature to give the title compound 36a. M.p.: 133.9–134.5° C.

36b. 1-[3-(4-aminothieno[3,2c]pyridin-2-yl)-2-[[(4,6-dimethoxy-2-naphthalenyl)sulfonyl]amino]-1-oxopropyl]-4-methylpiperidine hydrochloride The procedure described for 30b was used to couple 30a with 36a giving the title compound 36b. $^1$H-NMR 200 MHz (CD$_3$OD) δ: 0.0–3.3 (12H, m), 3.60–3.76 (1H, m), 3.93 and 3.94 (3H, 2×s), 4.04 (3H, s), 3.97–4.18 (1H, m), 4.44–4.60 (1H, m), 7.04–7.57 (6H, m), 7.78–7.87 (2H, m).

Example 37

1-[3-(1-Amino-7-isoquinolinyl)-2-[[(7-methoxy-2-naphthalenyl)sulfonyl]amino]-1-oxopropyl]-4-methylpiperidine hydrochloride (37j)

37a. 7-Bromoisoquinoline N-oxide hydrochloride

Compound 37a was prepared from 7-bromoisoquinoline (Tyson, F. L., J. Am. Chem. Soc. 61, 183 (1939), this procedure gave a mixture of 7-bromoisoquinoline and 5-bromoisoquinoline) using the procedure described for 1a. The title compound was contaminated with the 5-bromoisoquinoline N-oxide hydrochloride. M.p. 107.0–112.5° C.

37b. 7-Bromo-1-chloroisoquinoline

Compound 37b was prepared from 37a using the procedure described for 1b. $^1$H-NMR 200 MHz (CDCl$_3$) δ: 7.57–7.88 (3H, m), 8.32 (1H, d, J=6 Hz), 8.51–8.54 (1H, m).

37c. 7-Bromo-1-phenoxyisoquinoline

Compound 37c was prepared from 37b using the procedure described for 1c. $^1$H-NMR 200 MHz (CDCl$_3$) δ: 6.76–6.97 (2H, m), 7.18–8.09 (7H, m), 8.60–8.64 (1H, m).

37d. 1-Amino-7-bromoisoquinoline

Compound 37d was prepared from 37c using the procedure described for Id. $^1$H-NMR 200 MHz (CDCl$_3$) δ: 5.1 (2H, br. s), 7.03 (1H, dd, J=6 Hz and J=1 Hz), 7.59 (1H, d, J=9 Hz), 7.70 (1H, dd, J=9 Hz and J=2 Hz), 7.95–8.00 (2H, m).

37e. N-(7-bromo-1-isoquinolinyl)benzamide

Compound 37e was prepared from 37d using the procedure described for 1e, $^1$H-NMR 200 MHz (CDCl$_3$) δ: 6.98 (1H, d, J=6 Hz), 7.37–7.57 (6H, m), 8.41–8.48 (2H, m), 9.14 (1H, d, J=2 Hz).

37f. N-[7-(hydroxymethyl)-1-isoquinolinyl]benzamide

N-(7-Formylisoquinolinyl)benzamide was prepared from 37e using the procedure described for 1f but was not purified using column chromatography. The crude aldehyde was transformed into the title compound using the procedure described for 1g followed by purification using column chromatography on silica gel (toluene/ethyl acetate: 2/1). M.p. 137.5–139.0° C.

37g. [[1-(benzoylamino)-7-isoquinolinyl]methyl] [[(1,1-dimethylethoxy)carbonylamino]propanedioic acid diethyl ester Compound 37g was prepared from 37f using the procedure described for 1h. M.p. 190.5–193.0° C.

37h. 2-Amino-3-(1-amino-7-isoquinolinyl)propionic acid dihydrochloride

Compound 37h was prepared from 37g using the procedure described for 1i. $^1$H-NMR 200 MHz (D$_2$O) δ: 3.34–3.52 (2H, m), 4.29 (1H, dd, J=6 Hz and J=7 Hz), 7.13 (1H, dd, J=7 Hz and J=1 Hz), 7.43 (1H, d, J=7 Hz), 7.82 (2H, br.s), 8.05 (1H, br.s).

37i. 2-Amino-3-(1-amino-7-isoquinolinyl)propionic acid methyl ester dihydrochloride Compound 37i was prepared from 37h using the procedure described for 1j. $^1$H-NMR 200 MHz (CD$_3$OD) δ: 3.38–3.60 (2H, m), 3.80 (3H, s), 4.52 (1H, t, J=7 Hz), 7.25 (1H, dd, J=7 Hz and J=1 Hz), 7.59 (1H, d, J=7 Hz), 7.87–7.99 (2H, m), 8.48 (1H, br.s).

37j. 1-[3-(1-amino-7-isoquinolinyl)-2-[[(7-methoxy-2-naphthalenyl) sulfonyl]amino]-1-oxopropyl]-4-methylpiperidine hydrochloride Using the procedure described for 11a, methyl ester 37i and compound 12a gave 3-(1-amino-7-isoquinolinyl)-2-[[(7-methoxy-2-naphthalenyl)sulfonyl)amino]propionic acid methyl ester. This ester was saponified and subsequently coupled with 4-methylpiperidine using the procedure described for 4 to give 37. $^1$H-NMR 200 MHz (CD$_3$OD) δ: −0.20–0.77 (5H, m), 1.22–1.58 (3H, m), 1.73–3.20 (4H, m), 3.65–4.19 (2H, m), 3,93 (3H, s), 4.53–4.68 (1H, m), 7.00–7.06 (1H, m), 7.23–7.31 (2H, m), 7.43–7.51 (2H, m), 7.56–8.15 (6H, m).

Example 38

(3S)-4-[[1-(1-amino-7-isoquinolinyl)methyl]-2-oxo-2-(1-piperidinyl)ethyl]amino]-3-[[(4-methoxy-2,3,6-trimethylphenyl)sulfonyl]amino]-4-oxo-butanoic acid 1,1-dimethylethyl-ester hydrochloride Using the procedure described for 5a aminoacid 37h gave 1,1-dimethylethyl [1-[(]-amino-7-isoquinolinyl)methyl]-2- oxo-2-(]-piperidinyl)ethylcarbamate. This compound was deprotected and coupled with (2S)-2-[(4-methoxy-2,3,6-trimethylphenyl)sulfonyl]butanedioic acid 4-(1,1-dimethylethyl)ester using the procedure described for example 8 to give the title compound as a mixture of diastereoisomers (1:1). $^1$H-NMR 200 MHz (CD$_3$OD) δ: 1.30 and 1.33 (9H, 2×s), 1.38–1.68 (6H, m), 2.12 and 2.14 (3H, 2×s), 2.25–2.43 (2H, m), 2.52 (3H, s), 2.61 (3H, s), 2.90–3.56 (6H, m), 3.81 and 3.86 (3H, 2×s), 3.92–4.10 (1H, m), 5.16–5.23 (1H, m), 6.72 and 6.75 (1H, 2×s), 7.18–7.24 (1H, m), 7.51–7.56 (1H, m), 7.74–7.88 (2H, m), 8.23 and 8.26 (1H, 2×s).

Example 39

Solid-phase Synthesis of Compounds of Formula (Id) with n=0. X=S, R$^1$Y=R$^1$C(O), R$^4$=H (Table 39)

39a. N-(4-thieno[3,2c]pyridinyl)acetylamide 4.1 g of acetic anhydride was added to a solution of 5.0 g of 3b in 100 mL of pyridine at room temperature and the solution was heated at 125° C. for 2.5 hours. The pyridine was evaporated, and the crude product was coevaporated four times with toluene. The residue was chromatographed on a silica gel column (dichloromethane/methanol 95:5) to give 4.7 g of 39a. $^1$H NMR 200 MHZ (CD$_3$OD) δ: 2.26 (3H,s), 7.49 (1H,d,J=6 Hz), 7.70 (1H,d,J=6 Hz), 7.86 (1H, d,J=6 Hz), 8.21(1H,d,J=6 Hz).

39b. N-(2-formylthieno[3,2c]pyridin-4-yl)acetylamide

The procedure described for 3d was used to prepare 39b from 39a. $^1$H NMR 200 MHz (CD$_3$OD/CDCl$_3$ 9:1) δ: 2.33 (3H,s), 7.72 (1H,d), 8.30 (1H,s), 8.32 (1H,d), 10.10 (1H,s).

39c. N-[(4-(acetylamino)thieno[3,2c]pyridin-2-yl)methyl]-glycine methyl ester 1.7 g of 39b was dissolved in 80 mL of dioxane/methanol (1:1 v/v). To this solution was added a solution of 1.0 g of glycine methyl ester hydrochloride and 1.1 g of N,N-diisopropylethylamine in methanol. The reaction mixture was heated at 60° C. for 1 hour, and then coevaporated three times with methanol. Conversion of the aldehyde was checked with NMR of the formed imine. $^1$H NMR 200 MHZ (CD$_3$OD) δ: 2.30 (3H,s), 3.79 (3H,s), 4.48 (2H,s), 7.75 (1H,d), 7.85 (1H,s), 8.25 (1H,d), 8.60 (1H,s). The imine was dissolved in 40 mL of methanol and reduced to the amine with sodium borohydride, added in small portions to an amount of 1.4 g. The reaction mixture was neutralized with acetic acid, the solvents were evaporated, and the residue was coevaporated with toluene. The crude product was chromatographed on silica gel (toluene/ethanol 9:1) giving 0.55 g of 39c. $^1$H NMR 200 MHz (CD$_3$OD) δ: 2.26 (3H,s), 3.47 (2H,s), 3.70 (3H,s), 4.14 (2H,s), 7.32 (1H,s), 7.79 (1H,d), 8.19 (1H,d).

39d. N,N-[tert.-butyloxycarbonyl][((4-(acetylamino)thieno[3,2c]pyridin-2-yl)methyl]-glycine methyl ester The procedure described for 5a was used for the preparation of 39d from 39c. $^1$H NMR 200 MHZ (CD$_3$OD) δ: 1.47 (9H,s), 2.25 (3H,s), 3.69 (3H,s), 4.02 (2H,m), 4.78 (2H,m), 7.37 (1H,m), 7.79 (1H,m), 8.20 (1H,m).

39e. N,N-[tert.-butyloxycarbonyl][(4-(acetylamino)thieno[3,2c]pyridin-2-yl)methyl]-glycine Compound 39d was saponified as described for 2a but the reaction was performed for 3 hours. Compound 39e was isolated by silica gel chromatography (dichloromethane/methanol 7:3). $^1$H NMR 200 MHZ (CD$_3$OD) δ: 1.48 (9H,s), 2.25 (3H,s), 3.84 (2H,m), 4.76 (2H,m), 7.33 (1H,m), 7.77 (1H,m), 8.16 (1H,m).

39f. Derivatization of Kaiser oxime resin with acid 39e 2.36 g of 39e was coevaporated twice with dry N,N-dimethylformamide and subsequently dissolved in 25 mL of dichloromethane/N,N-dimethylformamide (3:2 v/v). 1.06 g of N-hydroxybenzotriazole was added and the resulting solution was added to 1.42 g of Kaiser oxime resin (1.1 mmol/g). After the addition of 1.22 mL of diisopropylcarbodiimide, the suspension was shaken overnight at room temperature. The resin was filtered off and washed with dichloromethane/N,N-dimethylformamide (3:2 v/v) and N,N-dimethylformamide. Further washings were performed by alternate addition of 2-propanol and dichloromethane (three times each). Unreacted oxime functions were capped by treatment of the resin with 35 mL of a mixture of acetic anhydride/N,N-diisopropylethylamine/N,N-dimethylformamide (3:1:12 v/v/v) for 30 minutes at room temperature. The resin was filtered off and washed with N,N-dimethylformamide, 2-propanol and dichloromethane (three times each). The resin was dried in vacuo to give 1.9 g of 39f.

39g. 1-[2-[[(4-aminothieno[3,2c]pyridin-2-yl)methyl][benzoyl]amino]-1-oxoethyl]-4-methylpiperidine (compound of formula (Id) with n=0, X=S, R$^1$Y=benzoyl, R$^4$=H, NR$^7$R$^8$=4-methylpiperidinyl)

290 mg of 39f was treated with 6 mL of 25 vol % trifluoroacetic acid in dichloromethane for 30 minutes at room temperature. The resin was filtered off and washed with dichloromethane, 2-propanol and dichloromethane. The resin was washed three times with 6 mL dichloromethane/N,N-dimethylformamide (3:2 v/v) containing 150 μl N,N-diisopropylethylamine and immediately reacted with 105 mg benzoic acid in 6ml dichloromethane/N,N-dimethylformamide (3:2 v/v) containing 150 μl of N,N-diisopropylethylamine and 400 mg of bromotripyrrolidinophosphonium hexafluorophosphate (PyBrop). The suspension was shaken for 90 minutes at room temperature. The resin was filtered off and washed with dichloromethane/1-methyl-2-pyrrolidinone (3:2 v/v), followed by washings with 1-methyl-2-pyrrolidinone, 2-propanol and 1-methyl-2-pyrrolidinone. The reaction turned out to be not complete (chloranil test). The resin was reacted with 105 mg benzoic acid in 6 mL dichloromethane/N,N-dimethylformamide (3:2 v/v) containing 150 μl of N,N-diisopropylethylamine and 400 mg of PyBrop. The suspension was shaken for 60 minutes at room temperature. The resin was filtered off and washed with dichloromethane/1-methyl-2-pyrrolidinone (3:2 v/v), followed by washings with 1-methyl-2-pyrrolidinone, 2-propanol and 1-methyl-2-pyrrolidinone. The chloranil test revealed complete conversion. 34 mg of the resin was suspended in 1 mL of a 0.5 M solution of 4-methylpiperidine in distilled tetrahydrofuran and shaken for 16 hours at room temperature. The resin was filtered off and washed with dichloromethane and methanol. The filtrates were collected and concentrated to dryness. The residue was dissolved in 1 mL ethylenediamine/ethanol (1:1 v/v) and shaken for 16 hours at room temperature. The reaction mixture was evaporated to dryness. The residue was dissolved in dichloromethane, applied to a silica gel column, and eluted with a gradient dichloromethane/methanol 95/5 v/v→dichloromethane/methanol=9/1 v/v. The UV positive fractions were pooled and evaporated to dryness yielding 7 mg of 39g.

Table 39
Solid-phase Synthesis of Compounds of Formula (Id) with n=0, X=S, $R^1Y=R^1C(O)$, $R^4=H$ Using the procedure described for example 39g the carboxylic acids of structure $R^1C(O)OH$ corresponding to $R^1C(O)$ in Table 39 were coupled to derivatized resin 39f. 34 mg portions of the resulting resins were treated with amines of structure $NHR^7R^8$ as depicted in Table 39. When 3,4-dimethoxyaniline, 5-aminoindane or 4-aminobiphenyl was used as amine, the resin was suspended in 1 mL of a 0.5 M solution of amine in distilled tetrahydrofuran containing 2% acetic acid and was shaken for 3 days. Work-up of the samples was performed as described for 39g.

All compounds were characterised by reversed phase liquid chromatography on a Supelcosil LC-18-DB column using following conditions: Flow: 1.0 ml/min; Buffers A: water, B: acetonitrile/water (9:1 v/v), C: 0.5M phosphate buffer pH=2.1; Gradient: 0→45 min 75%A–5%B–20%C→15%A–65%B–20%C. UV-detection at 210 nm. Retention times are given in minutes in Table 39.

TABLE 39

RP-HPLC retention times for example 39

| $R^7R^8N$ | $R^1C(O)$ (benzoyl) | (indol-3-yl-acetyl) | (cinnamoyl) | (2-propylcyclopropanecarbonyl) | (furan-2-yl-acryloyl) |
|---|---|---|---|---|---|
| propylamine | 23.2 | 25.8 | 28.6 | 32.9 | 18.4 | 24.6 |
| tetrahydropyridine | 25.5 | 27.6 | 30.2 | 34.7 | 20.9 | 26.5 |
| 2-(pyridin-2-yl)ethylamine | 15.6 | 18.0 | 21.1 | 24.4 | 11.3 | 16.7 |
| 4-methylpiperidine | 29.5 | 31.3 | 33.5 | 38.4 | 25.2 | 30.2 |
| tetrahydroisoquinoline | 31.0 | 32.7 | 35.1 | 39.4 | 27.3 | 31.9 |
| 3,4-dimethoxyaniline | 26.2 | 28.2 | 30.9 | 34.6 | 22.2 | 27.3 |

TABLE 39-continued

RP-HPLC retention times for example 39

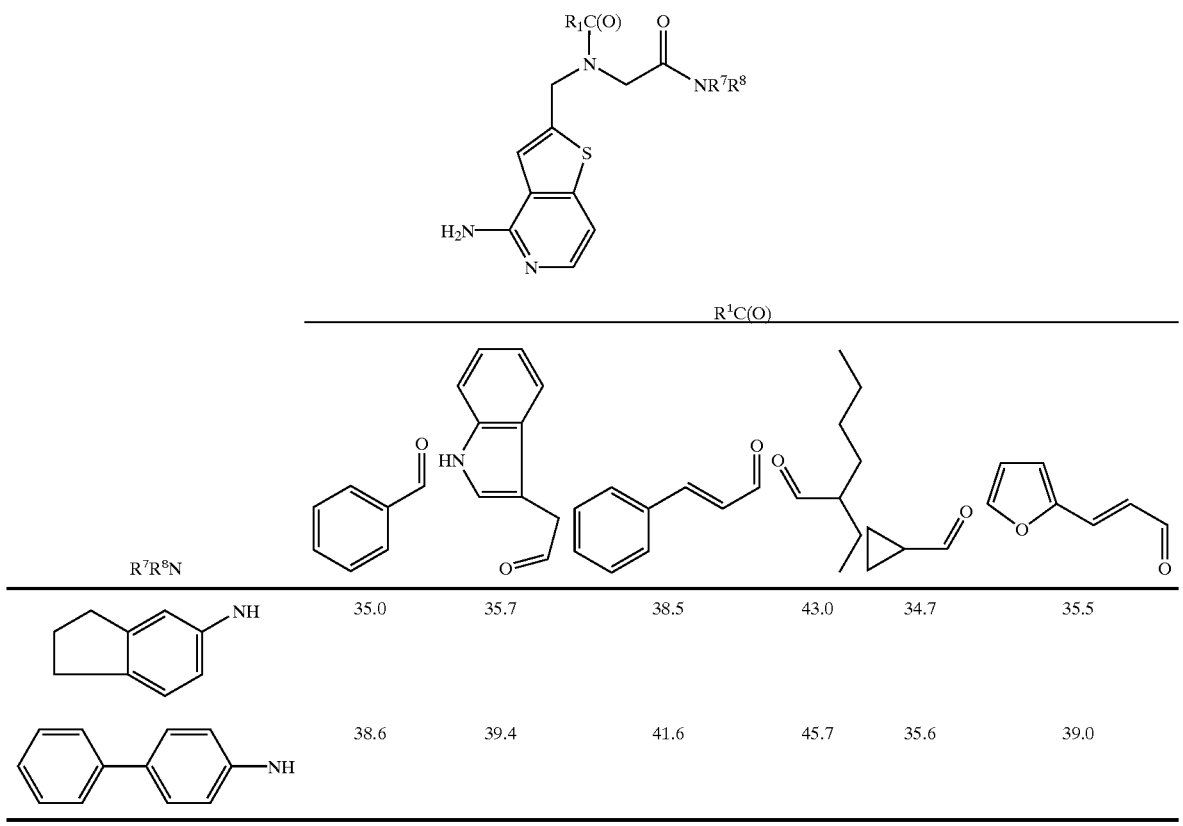

Example 40

(S)-[[1-(2-[[(1-amino-6-isoquinolinyl)carbonyl]amino]-1-oxopropyl)piperidin-4-yl]oxy]acetic acid hydrochloride

40a. [1 Benzoylamino)-6-isoquinolinyl]carboxylic acid

To a stirred solution of 400 mg sodium chlorite and 80 mg sodium dihydrogen phosphate in 2.5 mL of water and 2.5 mL of dimethylsulfoxide in a cooling bath at room temperature was added dropwise a solution of 510 mg N-(6-formyl-1-isoquinolinyl)benzamide (1f) in 2.5 mL of dimethylsulfoxide. After 16 hours at room temperature a solution of 170 mg sodium chlorite in 0.5 mL of water and 1.0 mL of dimethylsulfoxide was added and stirred at room temperature for an additional 6 hours. Then 100 mL water was added, the pH adjusted to three using 2N hydrochloric acid and the resulting suspension was kept at 5° C. for 16 hours. The precipitate was collected to afford 450 mg of the title compound.

TLC: Rf=0.8, silica gel, ethyl acetate/pyridine/acetic acid/water 63/20/6/11 v/v/v/v.

40b. (1-Amino-6-isoquinolinyl)carboxylic acid hydrochloride

A mixture of 445 mg [1-(benzoylamino)-6-isoquinolinyl] carboxylic acid, 10 mL of acetic acid and 20 mL of 4N hydrochloric acid was heated at 100° C. for one day. The reaction mixture was concentrated and coevaporated with 0.5N hydrochloric acid. The resulting residue was triturated with diethyl ether to yield 341 mg of the title compound.

$^1$H-NMR 200 MHz (CD$_3$OD) δ: 7.35 (1H, dd, J=1 Hz and J=7 Hz), 7.63 (1H, d, J=7 Hz), 8.30 (1H, dd, J=2 Hz and J=8 Hz), 8.49–8.57 (2H, m).

40c. tert-Butyl (S)-[[1-(2-amino-1-oxopropyl) piperidin-4-yl]oxy]acetic acid hydrochloride To a solution of 4.7 g of benzyl (S)-[2-[4-[(tert-butyloxycarbonyl)methoxy]piperidin-1-yl]-1-methyl-2-oxoethyl]carbamate (prepared from Z—L-Ala-OH as described in J. Med. Chem. 35, 4393 (1992) and EP0505868) in 80 mL of methanol were added 5 mL of 2N hydrochloric acid and 0.5 g of palladium on carbon (10%) and the mixture was hydrogenated at atmospheric pressure. After two hours the mixture was filtered and the filtrate was concentrated to give 3.3 g of the title compound.

TLC: Rf=0.3, silica gel, ethyl acetate/pyridine/acetic acid/water: 63/20/6/11 v/v/v/v.

40d. tert-Butyl (S)-[[1-(2-[[(1-amino-6-isoquinolinyl)carbonyl]amino]-1-oxopropyl) piperidin-4-yl]oxy]acetic acid To a solution of 0.33 g (1-amino-6-isoquinolinyl) carboxylic acid hydrochloride in 20 mL of N,N-dimethylformamide were added 0.34 g hydroxybenztriazole, 0.504 mL N-methylmorpholine, 0.525 g tert-butyl (S)-[[1-(2-amino-1-oxopropyl)piperidin-4-yl]oxy]acetic acid hydrochloride and 0.425 g 1-(3-dimethylaminopropyl)-3- ethylcarbodiimide. After stirring at room temperature for three days the mixture was concentrated. Dichloromethane and 1% aqueous sodium hydrogencarbonate were added to the residue and the organic layer was separated. The aqueous layer was washed four times with dichloromethane, the combined organic layers dried (sodium sulfate) and concentrated. The residue was purified by chromatography (silica gel, dichloromethane/methanol: 10/1 v/v followed by a purification using silica gel, ethyl acetate/methanol: 10/1 v/v) to give 0.619 g of the title compound.

TLC: Rf=0.4, silica gel, dichloromethane/methanol: 10/1/ v/v.

40e. (S)-[[1-(2-[[(1-amino-6-isoquinolinyl)carbonyl] amino]-1-oxopropyl)piperidin-4-yl]oxy]acetic acid hydrochloride To a solution of 594 mg of tert-butyl (S)-[[1-(2-[[(1-amino-6-isoquinolinyl)carbonyl]amino]-1-oxopropyl) piperidin-4-yl]oxy]acetic acid in 8 mL of dioxane was added 3 mL 36% hydrochloric acid and stirred at room temperature for two hours. The solution was concentrated and trituration of the residue with diethyl ether yielded 560 mg of the title compound. HPLC Supelcosil LC-18-DB column using a gradient elution system of 20% A/80% B to 20% A/20% B/60% C over 40 min at a flow of 0.25 ml/min(A: 0.5M phosphate buffer pH 2.1, B: water, C acetonitril/water 3/2 v/v). Rt=22.4 min.

Example 41

Ethyl (S)-[[1-(2-[[(1-amino-6-isoquinolinyl) carbonyl]amino]-1-oxopropyyl)piperidin-4-yl]oxy] acetic acid hydrochloride To a stirred solution of 394 mg of (S)-[[1-(2-[[(1-amino-6-isoquinolinyl)carbonyl]amino]-1-oxopropyl)piperidin-4-yl]oxy]acetic acid hydrochloride in 10 mL of ethanol at 0° C. was added 0.55 mL of sulfuric acid (95–98%). The reaction mixture was allowed to warm to room temperature and after 2 hours 5 mL of 2N aqueous sodium hydroxide, 20 mL of brine, 20 mL of 5% aqueous sodium hydrogencarbonate and 40 mL of dichloromethane was added. The organic layer was separated and the aqueous layer was extracted three times with dichloromethane. The combined organic layers were dried (sodium sulfate) and concentrated. Purification using column chromatography (silica gel, dichloromethane:ethanol=9:1) and lyophilisation (t-butanol/hydrochloric acid) yielded 265 mg of the title compound.

Rt=27.1 min on HPLC Supelcosil LC-18-DB column using a gradient elution system of 20% A/80% B to 20% A/20% B/60% C over 40 min at a flow of 0.25 ml/min (A: 0.5M phosphate buffer pH 2.1, B: water, C acetonitril/water 3/2 v/v).

Example 42

1-[3-(4-Aminofuro[3,2c]pyridin-2-yl)-2-[[(7-methoxy-2-naphthalenyl)sulfonyl]amino]-1-oxopropyl]-4-methylpiperidine hydrochloride (42h)

42a. 4-Aminofuro[3,2c]pyridine

Liquid ammonia (150 mL) was added to a solution of 15.3 g (100 mmol) 4-chlorofuro[3,2c]pyridine (J. S. New et al., J.Med. Chem. 32, 1147 (1989)) in 550 mL of ethanol in a steel vessel. Nitrogen was pressed upon until an initial pressure of 4 atm was obtained. This reaction mixture was heated for 2 days at 200° C. The solvent was removed in vacuo and the residue dissolved in water. The pH value was adjusted to pH 10 by adding aqueous sodium carbonate solution, followed by extraction with ethyl acetate. The organic extract was washed with brine and dried (sodium sulfate). Evaporation of the solvent in vacuo gave pure 4-aminofuro[3,2c]pyridine. Yield: 12.2 g (91%); m.p. 120–122° C.; EI-MS: 134 ($M^+$).

42b. N-(furo[3,2c]pyridin-4-yl)benzamide

The procedure described for 1e was used to prepare 42c from 42b. $^1$H-NMR 200 MHz (CDCl$_3$) δ: 7.20–7.69 (6H, m), 8.17–8.87 (3H, m).

42c. N-[2-(hydroxymethyl)furo[3,2c]pyridin-4-yl] benzamide

To a stirred solution of 1.27 mL of n-butyl lithium (1.6 M in hexane) in 4 mL of tetrahydrofuran under a nitrogen atmosphere at −78° C. was added dropwise a solution of 81mg of N-(4-furo[3,2c]pyridinyl)benzamide in 10 mL of tetrahydrofuran over a period of 15 minutes. After stirring for 20 min a mixture of 0.5 mL of N,N-dimethylformamide and 2 mL of tetrahydrofuran was added fast. The cooling bath was removed, the reaction mixture was allowed to come to 0° C. and poured into a cold mixture of 1 mL of 2 N hydrochloric acid and 50 mL of brine. The mixture was adjusted to pH 6 and extracted with ethyl acetate. The ethyl acetate extract was dried (magnesium sulfate) and concentrated under reduced pressure. The residue was dissolved in 1 mL of tetrahydrofuran and 4 mL of methanol and 10 mg of sodium borohydride was added in small portions. After stirring the mixture at ambient temperature for 10 min, 10 mL of water was added, the pH adjusted to 8 using 1N hydrochloric acid and tetrahydrofuran and methanol were removed in vacuo. Brine was added and the mixture was extracted with ethyl acetate. The ethyl acetate extract was dried (magnesium sulfate) and concentrated under reduced pressure. The crude product chromatographed on a silica gel column (toluene/ethyl acetate: 1/2) yielding 45 mg of title compound 42c. $^1$H-NMR 200 MHz (CDCl$_3$) δ: 4.74 (2H, s), 6.92–6.95 (1H, m), 7.30–7.68 (4H, m), 7.99–8.18 (3H, m).

42d. [[4-(benzoylamino)furo[3,2c]pyridin-2-yl] methyl][[(1-dimethylethoxy)carbonyl]amino] propanedioic acid diethyl ester The procedure described for 1h was used to prepare 42d from 42c. Purification using column chromatography on silica gel (toluene:ethyl acetate=4:1) afforded 16% of title compound 42d. $^1$H-NMR 200 MHz (CDCl$_3$) δ: 1.31 (6H, t, J=7 Hz), 1.46 (9H, s), 3.89 (2H, s), 4.25–4.38 (4H, m), 6.90 (1H, br.s), 7.10–7.63 (4H, m), 7.96–8.10 (3H, m), Elution of the column with ethyl acetate yielded a mixture which was rechromatographed on silica gel (ethyl acetate) giving 6% of [(4-aminothieno[3,2c]pyridin-2-yl)-methyl][[(1,1-dimethylethoxy)carbonyl]amino]propanedioic acid diethyl ester. $^1$H-NMR 200 MHz (CDCl$_3$) δ: 1.30 (6H, t, J=7 Hz), 1.46 (9H, s), 3.85 (2H, s), 4.23–4.38 (4H, m), 6.35 (1H, d, J=1 Hz), 6.75 (1H, dd, J=1 Hz and J=6 Hz), 7.87 (1H, d, J=6 Hz).

42e. 2-Amino-3-(4-aminofuro[3,2c]pyridin-2-yl) propionic acid dihydrochloride This compound was prepared from [2-[4-(benzoylamino) furo[3,2c]pyridinyl]methyl][[(1,1-dimethylethoxy) carbonyl]amino]propanedioic acid diethyl ester and [(4-aminothieno[3,2c]pyridin-2-yl)-methyl][[(1,1- dimethylethoxy)carbonyl]amino]propanedioic acid diethyl ester using the procedure described for 1i. NMR 200 MHz (D$_2$O) δ: 3.55 (2H, d, J=6 Hz), 4.44 (1H, t, J=6 Hz), 7.00 (1H, d, J=1 Hz), 7.11 (1H, dd, J=1 Hz and J=7 Hz), 7.66 (1H,d, J=7 Hz).

42f. 2-Amino-3-(4-aminofuro[3,2c]pyridin-2-yl) propionic acid methyl ester dihydrochloride This compound was prepared from 42e using the procedure described for 1j. $^1$H-NMR 200 MHz (CD$_3$OD) δ: 3.59 (2H, d, J=6 Hz), 3.90 (3H, s), 4.57 (1H, t, J=6 Hz), 7.21 (1H, d, J=7 Hz), 7.22 (1H, s), 7.79 (1H, d, J=7 Hz).

42g. 3-(4-Aminofuro[3,2c]pyridin-2-yl)-2-[[(7-methoxy-2-naphthalenyl)sulfonyl]amino]propionic acid methyl ester Using the procedure described for 11a, the reaction of methyl ester 42f and sulfonyl chloride 12a gave the tile compound. $^1$H-NMR 200 MHz (CDCl$_3$ and 20% MeOD) δ: 3.02–3.26 (2H, m), 3.49 (3H, s), 3.94 (3H, s), 4.35 (1H, dd, J=5 Hz and J=9 Hz), 6.46–6.51 (2H, m), 7.16 (1H, d, J=2.5 Hz), 7.25 (1H, dd, J=2.5 Hz and J=9 Hz), 7.45–7.74 (4H, m), 8.17 (1H, d, J=2 Hz).

42h. 1-[3-(4-Aminofuro[3,2c]pyridin-2-yl)-2-[[(7-methoxy-2-naphthalenyl)sulfonyl]amino]-1-oxopropyl]-4-methylpiperidine hydrochloride Compound 42g was saponified and subsequently coupled with 4-methylpiperidine using the procedure described for 4 to give 42h. $^1$H-NMR 400 MHz (CD$_3$OD) δ: 0.30–0.41 (0.6H, m), 0.61–0.84 (1.4H, m), 0.66 (1.8H, d, J=6 Hz), 0.81 (1.2H, d, J=1.2Hz), 1.37–1.68 (3H, m), 2.15–2.23 (0.4H, m), 2.41–2.50 (0.6H, m), 2.88–3.14 (3H, m), 3.86–3.95 (1H, m), 3.96 (3H, s), 4.07–4.22 (1H, m), 4.68–4.78 (1H, m), 6.80 (0.4H, s), 6.85 (0.6H, s), 6.93 (0.4H, d, J=7 Hz), 6.97 (0.6H, d, J=7 Hz), 7.27–7.31 (2H, m), 7.49–7.58 (2H, m), 7.77–7.82 (2H, m), 8.13 (0.4H, d, J=2 Hz), 8.15 (1H, d, J=2 Hz).

Example 43

1-[3-(4-aminothieno[3,2c]pyridin-2-yl)-2-[[(2-trifluoroacetyl-1,2,3,4-tetrahydro-7-isoquinolinyl) sulfonyl]amino]-1-oxopropyl]-4-methylpiperidine (43c)

43a. 2-Trifluoroacetyl-1,2,3,4-tetrahydroisoquinoline

This intermediate was prepared using the experimental procedure described for 30-trifluoroacetyl-2,3,4,5-tetrahydro-1H-3-benzazepine (preparation 3b) in WO 95/13274. The crude product was distilled at reduced pressure (p=1.2 mbar, T=95–110° C.) yielding 77% of title compound 43a.

43b. (2-trifluoroacetyl-1,2,3.4-tetrahydro-7-isoquinolinyl)sulfonyl chloride This compound was obtained by the method described in J.Med.Chem. 23, 837 (1980). Crystallization from ether yielded 65% of title compound 43b (rf=0.34; silica gel: heptane/ether=4/6).

43c. 1-[3-(4-aminothieno[3,2c]pyridin-2-yl)-2-[[(2-trifluoroacetyl-1,2,3,4-tetrahydro-7-isoquinolinyl) sulfonyl]amino]-1-oxopropyl]-4-methylpiperidine To 0.56 g of 1,1-dimethylethyl [1-[(4-aminothieno[3,2c] pyridin-2-yl)methyl]-2-oxo-2-[1-(4-methylpiperidinyl) ethylcarbamate (30a) in 16 mL of dichloromethane was added 16 mL of trifluoroacetic acid. After stirring for 1.5 hours at room temperature the reaction mixture was concentrated and coevaporated with toluene. The residue was dissolved in 20 mL of dichloromethane and 0.56 mL of triethylamine, cooled at 0° C. and 0.49 g of (2-trifluoroacetyl-1,2,3,4-tetrahydro-7-isoquinolinyl) sulfonyl chloride in 8 mL of dichloromethane was added dropwise. The pH of the reaction mixture was adjusted to 8–9 with triethylamine (an additional 0.22 mL was required). After stirring for 0.5 hours at room temperature water was added, the pH was adjusted to 8–9 and the mixture was extracted with dichloromethane. The extract was dried (magnesium sulfate) and concentrated. Purification on silica gel (dichloromethane/methanol: 95/5 v/v) yielded 0.69 g of title compound 43c. $^1$H-NMR 200 MHz (CDCl$_3$) δ: 0.62–0.93 (4H, m), 1.35–1.68 (3H, m), 2.18–3.30 (11H, m), 3.60–3.92 (3H, m), 4.18–4.62 (2H, m), 4.70–4.77 (2H, m), 6.98–7.30 (3H, m), 7.52–7.62 (2H, m), 7.72–7.80 (1H, m).

Example 44

1-[3-(4-aminothieno[3,2c]pyridin-2-yl)-2-[[(1,2,3,4-tetrahydro-7-isoquinolinyl)sulfonyl]amino]-1-oxopropyl]-4-methylpiperidine Using the experimental procedure described in "preparation 23" of patent WO 95/13274 (Pfizer) 0.64 g of 43c yielded 0.43 g of 44 after crystallization from ethanol. $^1$H-NMR 200 MHz (CDCl$_3$, 10% CD$_3$OD) δ: 0.05–0.98 (4H, m), 1.34–1.68 (3H, m), 2.15–2.58 (1H, m), 2.64–3.77 (12H, m), 3.91–3.99 (2H, m), 4.19–4.38 (1H, m), 4.45–4.57 (1H, m), 7.01–7.17 (3H, m), 7.39–7.53 (2H, m), 7.74 and 7.78 (1H, 2×s).

Example 45

1-[3-(4-aminothieno[3,2c]pyridin-2-yl)-2-[[[2-(2-propyl)-1,2,3,4-tetrahydro-7-isoquinolinyl)sulfonyl] amino]-1-oxopropyl]-4-methylpiperidine dihydrochloride To 91 mg of 44 dissolved in 5 mL of tetrahydrofuran under a nitrogen atmosphere was added 127 mg of potassium carbonate and 90 μl of 2-iodopropane. After stirring at 65° C. for one day an additional 120 mg of potassium carbonate and 90 μl of 2-iodopropane were added and the reaction mixture stirred at 65° C. for an additional day. The solvent was evaporated and dichloromethane and water were added. The organic layer was separated, dried (magnesium sulfate) and concentrated. Purification by chromatography on silica gel using dichloromethane:methanol=85:15 (v/v) yielded 41 mg of free base. Treatment of this free base with 2 equivalents hydrogen chloride and lyophilisation yielded the title compound. $^1$H-NM 400 MHz (CD$_3$OD) δ: 0.68 and 0.94 (3H, 2×t, J=6 Hz), 1.46 (6H, d, J=7 Hz), 4.62 (1H, t, J=7 hz), 7.30–7.39 (2H, m), 7.54–7.72 (4H, m), 0.21–4.52 (remaining protons, m).

Example 46

1-[3-(4-aminothieno[3,2c]pyridin-2-yl)-2-[[(2-methylsulfonyl-1,2,3,4-tetrahydro-7-isoquinolinyl) sulfonyl]amino]-1-oxopropyl]-4-methylpiperidine hydrochloride A mixture of 99 mg of 44, 4 mL of dichloromethane and 0.98 mL of triethylamine was cooled at 0° C. A total of 0.43 mL of methanesulfonylchloride was added in small quantities and the reaction mixture was stirred 8 hours at 0° C. The reaction mixture was diluted with dichloromethane and washed with water, dried (magnesium sulfate) and concentrated. Purification by chromatography on silica gel using dichloromethane:methanol=9:1 yielded free base. Treatment of this free base with one equivalent hydrogen chloride and lyophilisation yielded 88 mg of title compound 46. 1H-NMR 400 MHz (CD$_3$OD) δ: 0.30–0.94(2H, m), 0.71and 0.91 (3H, 2×t, J=6 Hz), 1.45–1.66 (3H, m), 2.23–3.20 (6H, m), 2.91 and 2.93 (3H, 2×s), 3.47–3.58 (2H, m), 3.75–3.93 (1H, m), 4.11–4.32 (1H, m), 4.38 and 4.42 (2H, 2×s), 7.24–7.40 (2H, m), 7.51–7.61 (4H, m)

Example 47

1-[3-(4-aminothieno[3,2c]pyridin-2-yl)-2-[[(2-trifluoroacetyl-1,2,3,4-tetrahydro-6-isoquinolinyl)sulfonyl]amino]-1-oxopropyl]-4-methylpiperidine hydrochloride (47b)

47a. (2-trifluoroacetyl-1,2,3,4-tetrahydro-6-isoquinolinyl)sulfonyl chloride

The mother liquor obtained in the synthesis of 43b was subjected to column chromatography on silica gel (heptane/ether=4/6) affording title compound 47a (rf=0.46; SiO$_2$: heptane/ether=4/6).

47b. 1-[3-(4-aminothieno[3,2c]pyridin-2-yl)-2-[[(2-trifluoroacetyl-1,2,3,4-tetrahydro-6-isoquinolinyl)sulfonyl]amino]-1-oxopropyl]-4-methylpiperidine hydrochloride Using the experimental procedure described for 43c, 30a was deprotected and coupled with 47a to yield compound 47b. $^{19}$F-NMR 188 MHz (CD$_3$OD) δ: −71.7.

Example 48

1-[3-(4-aminothieno[3,2c]pyridin-2-yl)-2-[[(4-methoxy-2,3,6-trimethylphenyl)sulfonyl]amino]-1-oxopropyl]-4-methylpiperidine hydrochloride The procedure described for 30b was used to couple 30a with 4-methoxy-2,3,6-trimethylphenylsulfonylchloride to give the title compound. $^1$H-NMR 400 MHz (CD$_3$OD) δ: 0.38–0.97 (2H, m), 0.74 and 0.88 (3H, 2×t, J=7 Hz), 1.29–1.62 (3H, m), 1.99 and 2.01 (3H, 2×s), 2.27–3.3 (4H, m), 2.46 (3H, s), 2.50 (3H, s),3.65–3.81 (1H, m), 3.81 and 3.82 (3H, 2×s), 4.19–4.47 (2H, m), 6.61 (1H, s), 7.31–7.34 (1H, m), 7.48–7.50 (1H, m), 7.56–7.60 (1H, m)

Example 49

4-[3-(4-aminothieno[3,2c]pyridin-2-yl)-2-[[(7-methoxy-2-naphthalenyl)sulfonyl]amino]-1-oxopropyl]-N,N-dimethylamino-1-piperazinecarboxamide hydrochloride (49b)

49a. N,N-dimethylamino-1-piperazinecarboxamide hydrochloride

To a solution of 1.92 g 1-(1,1-dimethylethyloxycarbonyl) piperazine in 11 mL of dichloromethane and 1.5 mL of triethylamine at room temperature was added dropwise 1 mL of dimethylcarbamylchloride. After 16 hours 5% aqueous sodium hydrogencarbonate and dichloromethane were added, the organic layer separated, dried over magnesium sulfate and concentrated. Column chromatography on silica gel (dichloromethane/methanol=95/5 v/v) yielded 1.34 g 1-(1,1-dimethylethyloxycarbonyl)-4-(dimethylaminocarbonyl)piperazine. This compound was dissolved in a 3N hydrogen chloride solution in methanol at 0° C. After 15 min the reaction mixture was allowed to warm to room temperature and After stirring for 3 days at room temperature the reaction mixture was concentrated to give 1.06 g of 1-(dimethylaminocarbonyl)piperazine hydrochloride. rf=0.29, SiO$_2$:dichloromethane/methanol=4/1 v/v.

49b. 4-[3-(4-aminothieno[3,2c]pyridin-2-yl)-2-[[(7-methoxy-2-naphthalenyl)sulfonyl]amino]-1-oxopropyl]-N,N-dimethylamino-1-piperazinecarboxamide hydrochloride Using the procedure described for 2b, 49a was coupled with 14a to give compound 49b. $^1$H-NMR 200 MHz (CD$_3$OD) δ: 2.55–3.64 (6H, m), 2.78 (6H, s), 3.94 (3H, s), 4.63 (1H, dd, J=9 Hz and J=5 Hz), 7.20–7.59 (6H, m), 7.76–7.84 (2H, m), 8.15–8.18 (1H, m).

Example 50

1-[3-(4-aminothieno[3,2c]pyridin-2-yl)-2-[[(7-nitrodibenzofuran-2-yl)sulfonyl]amino]-1-oxopropyl]-4-methylpiperidine hydrochloride (50b)

50a. (7-Nitrodibenzofuran-2-yl)sulfonylchloride

To a stirred solution of 100 mg of 3-nitrodibenzofuran in 1.7 mL of dichloromethane at −20° C. under a nitrogen atmosphere was added 0.44 mL chlorosulfonic acid in small portions. The reaction mixture was allowed to slowly warm to room temperature and stirred for 66 hours at room temperature. The reaction mixture was poured into ice-cold water, extracted four times with dichloromethane, dried (magnesium sulfate) and concentrated. Purification on silica gel (dichloromethane) yielded 129 mg of 50a: rf=0.73.

50b. 1-[3-(4-aminothieno[3,2c]pyridin-2-yl)-2-[[(7-nitrodibenzofuran-2-yl)sulfonyl]amino]-1-oxopropyl]-4-methylpiperidine hydrochloride The procedure described for 30b was used to couple 30a with 50a giving title compound 50b. $^1$H-NMR 400 MHz (CDCl$_3$) δ: 0.39 and 0.81 (3H, 2×d, J=6 Hz), 0.06–3.34 (9H, m), 3.88–4.19 (m, 2H), 4.71–4.79(1H, m), 6.82–8.86 (12H, m).

Example 51

(2S)-N-[1-[(1-amino-6-isoquinolinyl)methyl]-2-oxo-2-(1-piperidinyl)ethyl]-4-(4-morpholinyl)-4-oxo-2-[(4-methoxy-2,3,6-trimethylphenylsulfonyl)amino] butanamide hydrochloride 51a. (2S)-4-(4-Morpholinyl)-4-oxo-2-[(4-methoxy-2,3,6-trimethylphenylsulfonyl)amino]butanoic acid 2.45 g of Fmoc-Asp-OtBu was dissolved in 10 mL of dichloromethane and 0.63 mL of morpholine and 2.05 g of 2-(1H-benzotriazol-1-yl)-1,1,3,3-tetramethyluronium tetrafluoroborate were added. The pH of the reaction mixture was kept at 8 using triethylamine. After stirring 1 hour at room temperature aqueous 5% sodium hydrogencarbonate was added to the reaction mixture. The organic layer was separated, washed with water, dried over magnesium sulfate and concentrated. The residue was dissolved in 20 mL of N,N-dimethylformamide and 5 mL of piperidine was added. After stirring 1 hour at room temperature the reaction mixture was concentrated, the residue was dissolved in ethyl acetate and extracted several times with ice-cold water adjusted to pH 3 with 1N hydrochloric acid. The combined water layers were saturated with sodium chloride, made basic (pH 9) using 2N sodium hydroxide and extracted with dichloromethane. The combined dichloromethane layers were dried over magnesium sulfate and concentrated. The residue was dissolved in 30 mL of dichloromethane and 1.4 mL of triethylamine and 2.5 g of 4-methoxy-2,3,6-trimethylphenylsulfonylchloride (Mtr-chloride) were added. After stirring 2 hours at room temperature aqueous 5% sodium hydrogencarbonate was added to the reaction mixture and extracted three times with dichloromethane. The combined dichloromethane layers were dried over magnesiumsulfate and concentrated. The residue was dissolved in 40 mL of dichloromethane, 10 mL of trifluoroacetic acid was added and stirred at room temperature for one hour. The reaction mixture was concentrated and coevaporated twice with toluene. Dichloromethane and water were added to the residue and the mixture was made basic (pH 9) using aqueous 2N sodium hydroxide. The aqueous layer was separated and washed with dichloromethane. The dichloromethane layers were washed with aqueous 5% sodium hydrogencarbonate. The combined basic aqueous layers w,ere made acid (pH 2) using 2 N hydrochloric acid and three times extracted with dichloromethane. The combined dichloromethane layers were dried over magnesium sulfate and concentrated to give 1.94 g of compound 51a, $^1$H-NMR 200 MH (CDCl$_3$) δ: 2.14 (3H, s), 2.60 (3H, s), 2.65 (3H, s), 2.83–3.98 (11H, m), 3.85 (3H, s), 6.05 (1H, d), 6.57 (1H, s).

51b. (2S)-N-[1-[(1-amino-6-isoquinolinyl)methyl]-2-oxo-2-(1-piperidinyl)ethyl]-4-(4-morpholinyl)-4-oxo-2-[(4-methoxy-2,3,6-trimethylphenylsulfonyl) amino]butanamide hydrochloride The procedure described for 5c was used. Deprotection of 5a and coupling with 51a yielded after purification the title compound (79%) as a mixture of diastereomers (1:1). $^1$H-NMR 200 MHz (CD$_3$OD) δ: 1.30–1.51 (6H, m), 2.14 (3H, s), 2.51 and 2.53 (3H, 2×s), 2.63 (3H, s), 2.31–3.62 (16H, m), 3.84 and 3.86 (3H, 2×s), 3.99–4.15 (1H, m), 5.08–5.21 (1H, m), 6.75 and 6.76 (1H, 2×s), 7.18–7.25 (1H, m), 7.52–7.81 (3H, m), 8.25–8.37 (1H, m).

Example 52

(4S)-5-[[1-[(1-amino-6-isoquinolinyl)methyl]-2-oxo-2-(1-piperidinyl)ethyl]amino]-4-[[(4-methoxy-2,3,6-trimethylphenyl)sulfonyl]amino]-5-oxo-pentanoic acid ethylester hydrochloride The procedure described for 5c was used. Deprotection of 5a and coupling with Mtr-Glu(OEt)-OH (prepared from Fmoc-Glu-OtBu, ethanol and Mtr-chloride according to the procedure described for 51a) yielded after purification the title compound (76%) as a mixture of diastereomers (1:1). $^1$H-NMR 400 MHz (CD$_3$OD) δ: 1.15–2.32 (11H, m), 2.13 (3H, s), 2.40 and 2.42 (3H, 2×s), 2.44 and 2.47 (3H, 2×s), 2.75–4.08 (11H, m), 4.99–5.19 (1H, m), 6.71 and 6.72 (1H, 2×s), 7.16–7.20 (1H, m), 7.51–7.76 (3H, m), 8.30–8.36 (1H, m).

Example 53

(3S)-4-[[4-[[1-[[(1-amino-6-isoquinolinyl)methyl]-2-oxo-2-(1-piperidinyl)ethyl]amino]-3-[[(4-methoxy-2,3,6-trimethylphenyl)sulfonyl]amino]-1,4-dioxobutyl] amino]butanoic acid ethyl ester hydrochloride The procedure described for 5c was used. Deprotection of 150 mg of 5a and coupling with 189 mg of Mtr-Asp(NH—(CH$_2$)$_3$COOEt)-OH (prepared from Fmoc-Asp-OtBu and 4-aminobutanoic acid ethyl ester using the procedure described for 51a) yielded after purification compound 53 (155 mg) as a mixture of diastereomers (1:1). $^1$H-NMR 400 MHz (CD$_3$OD) δ: 1.22 (3H, t, J=7 Hz), 1.05–1.74 (8H, m), 2.12 (3H, s), 2.24–2.48 (4H, m), 2.53 (3H, s), 2.62 (3H, s), 2.89–3.56 (8H, m), 3.81 (3H, s), 3.85 (3H, s), 3.99–4.13 (3H, m), 5.02–5.16 (1H, m), 6.72 and 6.73 (1H, 2×s), 7.11–7.15 (1H, m), 7.53–7.70(3H, rm), 8.21–8.26 (1H, m).

Example 54

(2S)-N-[1-[(1-amino-6-isoquinolinyl)methyl]-2-oxo-2-(1-piperidinyl)ethyl]-2[[(4-methoxy-2,3,6-trimethylphenyl)sulfonyl]amino]-4-methylpentanamide hydrochloride The procedure described for 5c was used. Deprotection of 75 mg of 5a and coupling with 72 mg of (2S)-2-[[(4-methoxy-2,3,6-trimethylphenyl)sulfonyl]amino]-4-methylpentanoic acid (prepared from L-leucine and 4-methoxy-2,3,6-trimethylphenylsulfonylchloride using the procedure described for 5b) yielded after purification the title compound (65 mg) as a mixture of diastereomers (1:1). $^1$H-NMR 400 MHz (CD$_3$OD) δ: 0.50 and 0.68 (3H, 2×d, J=7 Hz), 0.61 and 0.79 (3H, 2×d, J=7 Hz), 0.97–1.65 (9H, m), 2.13 (3H, s), 2.54 and 2.56 (3H, 2×s), 2.61 and 2.62 (3H, 2×s), 2.76–3.68 (7H, m), 3.78 and 3.84 (3H, 2×s), 4.98–5.02 and 5.18–5.22 (1H, 2×m), 6.71 (1H, s), 7.16–7.19(1H, m), 7.53–7.78 (4H, m), 8.29–8.34 (1H, m).

Example 55

(2S)-N-[1-[(1-amino-6-isoquinolinyl)methyl]-2-oxo-2-(1-piperidinyl)ethyl]-3-phenyl-2-[[(4-methoxy-2,3,6-trimethylphenyl)sulfonyl]amino]propanamide hydrochloride To a solution of 0.5 g of L-phenylalanine t-butyl ester hydrochloride in 4 mL of N,N-dimethylformamide were added 0.67 g of 4-methoxy-2,3,6-trimethylphenylsulfonylchloride and 0.96 mL of N,N-diisopropylethylamine. After stirring for 2 hours at room temperature the reaction mixture was concentrated and the residue dissolved in ethyl acetate. The ethyl acetate solution was washed with aqueous potassium hydrogensulfate (5%), water, aqueous sodium hydrogencarbonate (5%) and brine, dried over magnesium sulfate and concentrated. The residue was dissolved in 16 mL of dichloromethane and 4 mL of trifluoroacetic acid was added. After stirring for 2h at room temperature the reaction mixture was concentrated. Dichloromethane and aqueous sodium hydrogencarbonate (5%) were added to the residue (the mixture was basic), the aqueous layer separated and washed with dichloromethane. The aqueous layer was made acid (pH 2) using 2 N hydrochloric acid and several times extracted with dichloromethane. The combined dichloromethane layers were washed with brine, dried over magnesium sulfate and concentrated to give 0.65 g of (2S)-2-[[(4-methoxy-2,3,6-trimethylphenyl)sulfonyl]amino]-3-phenylpropane acid. This acid (80 mg) was coupled with deprotected 5a (75 mg) according to the procedure described for 5c to afford compound 55 (55 mg) as a mixture of diastereomers (1:1). $^1$H-NMR 400 MHz (CD$_3$OD) δ: 1.25–1.67 (6H, m), 1.97 and 1.99 (3H, 2×s), 2.12 and 2.17 (3H, 2×s), 2.45–3.54 (8H, m), 2.49 (3H, s), 3.81 and 3.85 (3H, 2×s), 3.82–3.92 (1H, m), 5.13–5.28 (1H, m), 6.61 (1H, s), 6.84–7.07 (5H, m), 7.17–7.21 (1H, m), 7.50–7.56 (1H, m), 7.65–7.69 (1H, m), 7.76–7.82 (1H, m), 8.30–8.35 (1H, m).

Example 56

(3S)-4-[[1-[(1-amino-6-isoquinolinyl)methyl]-2-oxo-2-(1-piperidinyl)ethyl]amino]-3-[[(phenylmethyl)sulfonyl]amino]-4-oxo-butanoic acid 1,1-dimethylethylester hydrochloride The procedure described for 5c was used. Deprotection of 100 mg of 5a and coupling with 95 mg of (2S)-[[(phenylmethyl)sulfonyl]amino]butanedioic acid 4-(1,1-dimethylethyl)ester (prepared from Asp(OtBu)-OH and phenylmethylsulfonylchloride using the procedure described for 5b) yielded the title compound (133 mg) as a mixture of diastereomers (1:1). $^1$H-NMR 400 MHz (CD$_3$OD) δ: 0.83–1.69 (6H, m), 1.41 and 1.42 (9H, 2xs), 2.42–2.63 (2H, m), 3.09–3.61 (6H, m), 4.01–4.38 (3H, m) 5.22–5.31 (1H, m), 7.13–7.80 (9H, m), 8.25–8.30 (1H, m).

Example 57

(3S)-4-[[1-[(1-amino-6-isoquinolinyl)methyl]-2-oxo-2-(1-piperidinyl)ethyl]amino]-3-[[4-methoxyphenyl)sulfonyl]amino]-4-oxo-butanoic acid 1,1-dimethylethylester hydrochloride The procedure described for 5c was used. Deprotection of 100 mg of 5a and coupling with 99 mg of (2S)-[[(4-methoxyphenyl)sulfonyl]amino]butanedioic acid 4-(1,1-dimethylethyl)ester (prepared from Asp(OtBu)-OH and 4-methoxyphenylsulfonylchloride using the procedure described for 5b) yielded the title compound (85 mg) as a mixture of diastereomers (1:1). $^1$H-NMR 400 MHz (CD$_3$OD) δ: 1.25–1.67 (6H, m), 1;32 and 1.35 (9H, 2xs), 2.18–2.48 (2H, m), 3.96–3.55 (6H, m), 3.83 and 3.86 (3H, 2xs), 4.04–4.14 (1H, m), 5.05–5.17 (1H, m), 6.99–7.05 (2H, m), 7.19–7.23 (1H, m), 7.51–7.79 (5H, m), 8.30–8.36 (1H, m).

Example 58

N-[1-(4-Amino-thieno[3,2-c]pyridin-2-ylmethyl)-2-(4-methyl-piperidin-1-yl)-2-oxo-ethyl]-4-(tetrahydropyran-4-yloxy)-benzenesulfonamide (58c)

58a. 4-(4-Bromo-phenoxy)-tetrahydropyran

A mixture of 4.0 mL of diethyl-azodicarboxylate in 20 mL of dry tetrahydrofuran was added at 5° C. to a stirred solution of 3.5 g of 4-bromo-phenol, 2.4 mL of 4-hydroxy-tetrahydropyran and 6.6 g triphenylphosphine in 75 mL of tetrahydrofuran within 30 minutes. Stirring was continued at room temperature for 72 hours. The solvent was evaporated in vacuo and the residue chromatographed on silica gel (ethyl acetate) yielding 5.6 g of 4-(4-bromo-phenoxy)-tetrahydropyran as a white solid. M.p. 53–55° C., EI-MS: 256 (M$^+$).

58b. 4-(Tetrahydropyran-4-yloxy)-benzenesulfonyl chloride

To a solution of 2.8 g of 4-(4-Bromo-phenoxy)-tetrahydropyran in 75 mL of dry tetrahydrofuran was added 7.5 mL of n-butyllithium (1.6 N in hexane) at −78° C. After stirring at −78° C. for 2 hours the reaction mixture was allowed to warm to −40° C. and a solution of 4.1 mL of sulfuryl chloride in 75 mL of dry hexane was added within 15 minutes. Stirring was continued for 1 hour at −30° C. and subsequently for another hour at 5° C. The mixture was poured on ice, extracted with diethyl ether and the ether extract washed with cold water and brine, dried (sodium sulfate), and concentrated. The residue was purified by silica chromatography (isohexane/ethyl acetate=4/1) yielding 0.62 g of 4-(tetrahydropyran-4-yloxy)-benzenesulfonyl chloride as a colorless oil. EI-MS: 276 (M$^+$).

58c. N-[1-(4-Amino-thieno[3,2-c]pyridin-2-ylmethyl)-2-(4-methyl-piperidin-1-yl)-2-oxo-ethyl]-4-(tetrahydropyran-4-yloxy)-benzenesulfonamide 10 mL of a saturated solution of hydrogen chloride in diethyl ether were added dropwise to a mixture of 210 mg of 30a in 15 mL of dry dichloromethane and the reaction mixture was stirred for one hour at room temperature. The solvent was removed in vacuo. 20 mL of dichloromethane were added and subsequently removed in vacuo in order to get rid of traces of moisture. This procedure was repeated twice. The residue was dissolved in 15 mL of dichloromethane and 0.7 mL of triethylamine and 207 mg of 4-(tetrahydropyran-4-yloxy)-benzenesulfonyl chloride in 15 mL of dry dioxane were added dropwise. After stirring at room temperature for 48 hours the solvents were evaporated in vacuo, the residue redissolved in ethyl acetate, washed with water and brine, dried (sodium sulfate), and concentrated. Purification by silica chromatography (ethyl acetate/methanol=98/2, 96/4, 94/6, 92/8 v/v) gave 100 mg of 58c. M.p. 127–129° C., EI-MS: 558 (M$^+$).

Example 59

N-[1-(4-Amino-thieno[3,2-c]pyridin-2-ylmethyl)-2-(4-methyl-piperidin-1-yl)-2-oxo-ethyl]-4-(tetrahydropyran-4-yloxymethyl)-benzenesulfonamide (59c)

59a. 4-(4-Bromo-benzyloxy)-tetrahydropyran

A mixture of 2.90 mL of 4-hydroxy-tetrahydropyran in 30 mL of dry N,N-dimethylformamide was added dropwise to a stirred suspension of 0.84 g of sodium hydride (95%, dispersion in mineral oil) in 30 mL of dry N,N-dimethylformamide at 5° C. The resulting clear solution was allowed to come to room temperature and stirring was continued for 24 hours, followed by dropwise addition of 9.40 g of 4-bromo-benzylbromide in 50 mL of dry N,N-dimethylformamide at 5° C. and stirring at room temperature for 24 hours. The mixture was poured into water and extracted with ethyl acetate. The combined extracts were washed with water and brine, dried (sodium sulfate), and concentrated. The residue was purified by silica chromatography (isohexane/ethyl acetate=9/1, 8/2, 7/3, 6/4 v/v) yielding 5.40 g of 4-(4-bromo-benzyloxy)-tetrahydropyran as an oil. EI-MS: 270 (M$^+$).

59b. 4-(Tetrahydropyran-4-yloxymethyl)-benzenesulfonyl chloride

This compound was prepared from 0.68 g of 4-(4-bromo-benzyloxy)-tetrahydropyran, 2 mL of n-butyllithium (1.6 N in hexane) and 0.81 mL of sulfuryl chloride using the procedure described for 58b. Yield: 0.70 g (oil), $^1$H-NMR (D$_6$-DMSO): δ=1.41 (m, 2H), 1.86 (m, 2H), 3.32 (m, 2H), 3.54 (m, 1H), 3.79 (m, 2H), 4.53 (s, 2H), 7.30 (d, 2H), 7.61 (d, 2H).

59c. N-[1-(4-Amino-thieno[3,2-c]pyridin-2-ylmethyl)-2-(4-methyl-piperidin-1-yl)-2-oxo-ethyl]-4-(tetrahydropyran-4-yloxymethyl)-benzenesulfonamide This compound was prepared from 218 mg of 4-(tetrahydropyran-4-yloxymethyl)-benzenesulfonyl chlo-

Example 60

N-[1-(4-Amino-thieno[3,2-c]pyridin-2-ylmethyl)-2-(4-methyl-piperidin-1-yl)-2-oxo-ethyl]-4-(2-methoxy-ethoxy)-benzenesulfonamide (60c)

60a. (2-Methoxy-ethoxy)-benzene

A mixture of 4.70 g of phenol and 35 mL of dry N,N-dimethylformamide was added dropwise to a stirred suspension of 1.30 g of sodium hydride (95%, dispersion in mineral oil) in 15 mL of dry N,N-dimethylformamide at 5° C. Stirring was continued for 2 hours at 5° C., followed by dropwise addition of 5.20 mL of 2-bromoethyl methyl ether (technical grade, 90%) at 5° C. The mixture was allowed to come to room temperature and stirring was continued for 72 hours. The mixture was poured into water and extracted with diethyl ether. The combined extracts were washed with water and brine, dried (sodium sulfate) and concentrated to give 5.90 g of (2-methoxy-ethoxy)-benzene as an oil. EI-MS: 159 ($M^+$).

60b. 4-(2-Methoxy-ethoxy)-benzenesulfonyl chloride (2-Methoxy-ethoxy)-benzene (4.78 g) was dissolved in 50 mL of chloroform and the solution was cooled to −10° C. Chlorosulfonic acid (4 mL) was added dropwise while maintaining the temperature of the mixture at −10° C. Stirring was continued for an additional hour at −10° C. The precipitated sulfonic acid was isolated by filtration and washed with cold chloroform and with cold isohexane (EI-MS: 232 ($M^+$), m.p. 130–133° C.). 139 mg of the acid were dissolved in 5 mL of dichloromethane and 125 mg of phosphorous pentachloride was added at 5° C. After stirring for one hour at 5° C. complete reaction was indicated by TLC. The volatile components were removed in vacuo and the crude 4-(2-methoxy-ethoxy)-benzenesulfonyl chloride was used in the next step without further purification.

60c. N-[1-(4-Amino-thieno[3,2-c]pyridin-2-ylmethyl)-2-(4-methyl-piperidin-1-yl)-2-oxo-ethyl]-4-(2-methoxy-ethoxy)-benzenesulfonamide This compound was prepared from 0.6 mmol 4-(2-methoxy-ethoxy)-benzenesulfonyl chloride and 210 mg (0.5 mmol) of 30a using the procedure described for 58c. Yield: 30 mg (white crystals), m.p. 210° C. (decomp.), EI-MS: 532 ($M^+$).

Example 61

N-[1-(4-Amino-thieno]3,2-c]pyridin-2-ylmethyl)-2-(4-methyl-piperidin-1-yl)-2-oxo-ethyl]-4-(2-methoxy-1-methoxymethyl-ethoxy)-benzenesulfonamide (61 f)

61a. 2-Methoxymethyl-oxirane 8.1 mL of methanol and 1.3 g of tetrabutylammonium bromide were dissolved in 20 mL of 10 N sodium hydroxide, and 15.7 mL of 2-chloromethyl-oxirane were added under vigorous stirring at such a rate that the internal temperature did not exceed 30° C. Stirring was continued at room temperature for 24 hours, followed by extraction with diethyl ether. The combined organic extracts were dried (sodium sulfate) and the solvents were removed. Distillation afforded 14.0 g of 2-methoxymethyl-oxirane as a liquid. B.p. 20–25° C./12 Torr (reference: Dayles, Alwyn G.; Hawari, Jalal A.-A.; Muggleton, Brenda; Tse, Man-Wing; J.Chem-.Soc.Perkin Trans.2; 35, 1981; 1132–1137: b.p. 35° C./20 Torr).

61b. 1,3-Dimethoxy-propan-2-ol

To a stirred solution of 13.2 g of 2-methoxymethyl-oxirane in 75 mL of methanol was added 0.1 mL of boron trifluoride etherate while stirring at 5° C. Stirring was continued for 24 hours at room temperature, followed by removal of the solvent. Distillation afforded 7.0 g of 1,3-dimethoxy-propan-2-ol as a liquid. B.p. 75–80° C./12 Torr (reference: Gilchrist, Purves, J.Chem.Soc. 1925, 127, 2739, 2743: b.p. 69.5–70.5/15 Torr); (+)-FAB-MS: 121 ($MH^+$).

61c. Methanesulfonic acid 2-methoxy-1-methoxymethyl-ethyl ester 4.3 mL of methanesulfonyl chloride was added dropwise at 5° C. to a stirred solution of 6.0 g of 1,3-dimethoxy-propan-2-ol and 9.0 mL of triethylamine in 60 mL of dichloromethane. Stirring was continued for 72 hours at room temperature, followed by extraction with water. The combined organic extracts were dried (sodium sulfate) and concentrated and the residue purified by silica chromatography (isohexane/ethyl acetate=9/1, 8/2, 7/3, 6/4 v/v) yielding 2.5 g of methanesulfonic acid 2-methoxy-1-methoxymethyl-ethyl ester as an oil. EI-MS: 198 ($M^+$).

61d. (2-Methoxy-1-methoxymethyl-ethoxy)-benzene

A stirred mixture of 2.0 g of methanesulfonic acid 2-methoxy-1-methoxymethyl-ethyl ester, 1.4 g of phenol and 2.8 g of powdered potassium carbonate in 50 mL of dry N,N-dimethylformamide was heated at 90° C. for 24 hours. After cooling, water was added at room temperature and the mixture extracted with diethyl ether. The combined ether extracts were washed with aqueous sodium hydroxide (2 N) and water, dried (sodium sulfate) and concentrated. The crude product (1.0 g) was used in the next step without further purification. EI-MS: 198 ($M^+$).

61e. 4-(2-Methoxy-1-methoxymethyl-ethoxy)-benzenesulfonyl chloride (2-Methoxy-1-methoxymethyl-ethoxy)-benzene (1.0 g) was dissolved in 10 mL of chloroform and the solution was cooled to −30° C. Chlorosulfonic acid (1 ml) was added dropwise while maintaining the temperature of the mixture below −20° C. Stirring was continued in succession for one hour at −20° C., for one hour at 5oC and for 30 minutes at room temperature. The mixture was poured on ice, the organic layer washed with cold water, dried (sodium sulfate) and concentrated yielding 0.8 g of 4-(2-methoxy-1-methoxymethyl-ethoxy)-benzenesulfonyl chloride as an oil. EI-MS: 294 ($M^+$).

61f. N-[1-(4-Amino-thieno[3,2-c]pyridin-2-ylmethyl)-2-(4-methyl-piperidin-1-yl)-2-oxo-ethyl]-4-(2-methoxy-1-methoxymethyl-ethoxy)-benzenesulfonamide This compound was prepared from 0.75 mmol of 4-(2-methoxy-1-methoxymethyl-ethoxy)-benzenesulfonyl chloride and 210 mg (0.5 mmol) of 30a using the procedure described for 58c. Yield: 120 mg (oil), EI-MS: 576 ($M^+$).

Example 62

Octane-1-sulfonic acid [1-(4-amino-thieno[3,2-c]pyridin-2-ylmethyl)-2-(4-methyl-piperidin-1-yl)-2-oxo-ethyl]-amide This compound was prepared from 0.15 mL of octane sulfonyl chloride and 210 mg of 30a using the procedure

--- ride and 210 mg (0.5 mmol) 30a using the procedure described for 58c. Yield: 100 mg, m.p. 124–128° C., (+)-FAB-MS: 573 ($MH^+$).

Example 63

7-Methoxy-3,4-dihydro-1H-isoquinoline-2-sulfonic acid [1-(4-amino-thieno[3,2-c]pyridin-2-ylmethyl)-2-(4-methyl-piperidin-1-yl)-2-oxo-ethyl]-amide (63g)

63a. Isoquinolin-7-ol

Aminoacetaldehyde dimethyl acetal (79 g) was added to a solution of 106 g of 3-benzyloxy-benzaldehyde in 1100 mL of toluene. The mixture was refluxed for 6 hours using a Dean-Stark trap and subsequently cooled to 5° C. In a nitrogen atmosphere trichloroacetic acid anhydride (212 mL) and borontrifluoride etherate (185 mL) were added in succession at such a rate, that the temperature of the mixture was kept below 10° C. After stirring for 5 days at room temperature the precipitated material was separated by filtration, washed with diethyl ether and dissolved in 750 mL of water The pH value was adjusted to 9 by adding concentrated aqueous ammonia. The precipitated product was separated by filtration, followed by washing with diethyl ether and drying in vacuo Yield: 53.2 g; m.p. 210–218° C.; EI-MS: 145 (M$^+$).

63b. 1,2,3,4-Tetrahydro-isoquinolin-7-ol (hydroacetate)

53.2 g of isoquinolin-7-ol were dissolved in 1000 mL of glacial acetic acid and hydrogenated for 48 hours at room temperature using pre-hydrogenated platinum dioxide (3.5 g) as catalyst. Filtration followed by concentration and addition of 50 mL of acetone gave a clear solution. Addition of diethyl ether resulted in precipitation of pure 1,2,3,4-tetrahydro-isoquinolin-7-ol-hydroacetate. Yield: 44.9 g; m.p.179–182° C.; EI-MS: 149 (M$^+$).

63c. 7-Hydroxy-3,4-dihydro-1H-isoquinoline-2-carboxylic acid tert-butyl ester A mixture of 17.1 g of di-tert-butyl-dicarbonate in 170 mL of dichloromethane was added dropwise to a stirred suspension of 16.4 g of 1,2,3,4-tetrahydro-isoquinolin-7-ol-hydroacetate and 32.6 mL of triethylamine in 164 mL of dichloromethane at 5° C. Stirring was continued at 5° C. for one hour, followed by evaporation of the volatiles. The residue was redissolved in ethyl acetate and this solution was washed in succession with aqueous acetic acid (1 N), saturated sodium hydrogen carbonate solution and brine and dried (sodium sulfate). Removal of the solvent in vacuo gave pure 7-hydroxy-3,4-dihydro-1H-isoquinoline-2-carboxylic acid tert-butyl ester as a solid. Yield: 17.5 g; m.p.140–142.5° C.; EI-MS: 249 (M$^+$).

63d. 7-Methoxy-3,4-dihydro-1H-isoquinoline-2-carboxylic acid tert-butyl ester To a stirred mixture of 2.5 g of 7-hydroxy-3,4-dihydro-1H-isoquinoline-2-carboxylic acid tert-butyl ester and 2.8 g of powdered potassium carbonate in 25 mL of dry N,N-dimethylformamide was added methyl iodide (0.94 mL) at 5° C. Stirring was continued for 24 hours at room temperature. Water was added and the mixture was extracted with ethyl acetate. The combined organic extracts were washed with water and brine, dried (sodium sulfate) and the solvent was removed in vacuo. The crude product (2.7 g; oil) was used in the next step without further purification. EI-MS: 263 (M$^+$).

63e. 7-Methoxy-1,2,3,4-tetrahydro-isoquinoline

At 5° C., 50 mL of a saturated solution of hydrogen chloride in diethyl ether were added dropwise to a mixture of 2.3 g of 7-methoxy-3,4-dihydro-1H-isoquinoline-2-carboxylic acid tert-butyl ester in 50 mL of diethyl ether and the reaction mixture stirred for 2 hours at room temperature. The precipitated product (hydrochloride) was separated by filtration, washed with diethyl ether and dried in vacuo. Yield: 1.5 g (7.5 mmol); m.p. 215–218° C., EI-MS: 163 (M$^+$).

63f. 7-Methoxy-3,4-dihydro-1H-isoquinoline-2-sulfonyl chloride

To a stirred, precooled solution (−40° C.) of 0.41 mL of sulfuryl chloride in 10 mL of chloroform was added a mixture of 1.0 g of 7-methoxy-1,2,3,4-tetrahydro-isoquinoline-hydrochloride and 2.1 mL of triethylamine in 25 mL of chloroform at 40° C. Stirring was continued at −30° C. for one hour and additionally at 5° C. for one hour. The mixture was poured on ice, the organic layer extracted with cold water, dried (sodium sulfate) and concentrated. The residue was redissolved in diethyl ether and chromatographed on silica gel (isohexane/ethyl acetate=8/2 v/v) yielding 0.62 g of 7-methoxy-3,4-dihydro-1H-isoquinoline-2-sulfonyl chloride as an oil.

EI-MS: 261 (M$^+$).

63g. 7-Methoxy-3,4-dihydro-1H-isoquinoline-2-sulfonic acid [1-(4-amino-thieno[3,2-c]pyridin-2-ylmethyl)-2-(4-methyl-piperidin-1-yl)-2-oxo-ethyl]-amide This compound was prepared from 200 mg of 7-methoxy-3,4-dihydro-1H-isoquinoline-2-sulfonyl chloride and 210 mg of 30a using the procedure described for 58c. Yield: 110 mg; m.p. 175–176° C., (+)-FAB-MS: 544 (MH$^+$).

Example 64

2,3-Dihydro-5H-benzo[f][4]oxazepine-4-sulfonic acid [1-(4-amino-thieno[3,2-c]pyridin-2-ylmethyl)-2-(4-methyl-piperidin-1-yl)-2-oxo-ethyl]-amide (64g)

64a. 2-(Benzylimino-methyl)-phenol

A mixture of 5.0 mL of 2-hydroxy-benzaldehyde, 6.3 mL of benzylamine and 0.05 g of p-toluenesulphonic acid was refluxed in toluene for 2 hours using a Dean-Stark trap to remove liberated water. The volatiles were removed in vacuo yielding 10.1 g of crude 2-(benzylimino-methyl)-phenol.

64b. 2-(Benzylamino-methyl)-phenol

Sodium borohydride (0.2 g) was added in small portions to 3 mL of dry 2-propanol in a nitrogen atmosphere. To this mixture was added dropwise a solution of 1.0 g of 2-(benzylimino-methyl)-phenol in 3 mL of 2-propanol. After complete addition, stirring was continued for 1 h. Then water was added in order to decompose excess borohydride, and the volatiles were removed in vacuo. The residue was redissolved in ethyl acetate, washed with water, dried (sodium sulfate) and concentrated yielding 0.9 g of 2-(benzylamino-methyl)-phenol as an oil. EI-MS. 213 (M$^+$).

64c. 4-Benzyl-4,5-dihydro-benzo[f][1,4]oxazepin-3-one

A mixture of 19.0 g of 2-(benzylamino-methyl)-phenol and 75 mL of toluene was cooled to 0° C., and a solution of chloroacetyl chloride (7.8 mL) in 75 mL of toluene was slowly added while stirring. Stirring was continued for 16 h. Dry N,N-dimethylformamide (60 mL) was added and the solution was cooled to 0° C. In a nitrogen atmosphere 3.4 g of sodium hydride (95%; dispersion in mineral oil) were added in small portions and the mixture was allowed to stir at room temperature for 2 h. Water was added and the aqueous layer was extracted with ethyl acetate. The combined organic extracts were dried (sodium sulfate) and the solvent was removed in vacuo yielding 12.4 g of 4-benzyl-4,5-dihydro-benzo[f][1,4]oxazepin-3-one. M.p. 95–97° C., EI-MS: 253 (M$^+$).

64d. 4-Benzyl-2,3,4,5-tetrahydro-benzo[f][1,4] oxazepine

A solution of 2.5 g of 4-benzyl-4,5-dihydro-benzo[f][1,4]oxazepin-3-one in 50 mL of tetrahydrofuran was added dropwise to a suspension of 1.14 g of lithium aluminum hydride in 50 mL of tetrahydrofuran. The mixture was refluxed for 5 hours and then allowed to cool down to room temperature. 2.2 mL of saturated aqueous sodium chloride solution was added in order to decompose excess lithium aluminum hydride. The precipitated solid was removed by filtration, and the filtrate was concentrated to give 2.2 g of pure 4-benzyl-2,3,4,5-tetrahydro-benzo[f][1,4]oxazepine as an oil. EI-MS: 239 (M$^+$).

64e. 2,3,4,5-Tetrahydro-benzo[f][1,4]oxazepine 10.2 g of 4-benzyl-2,3,4,5-tetrahydro-benzo[f][1,4]oxazepine were dissolved in 100 mL of ethanol and hydrogenated for 5 hours at room temperature using 1.2 g of palladium (10% on carbon) as catalyst. Filtration followed by removal of the solvent in vacuo gave 6.1g of 2,3,4,5-tetrahydro-benzo[f][1,4j]oxazepine as an oil. EI-MS: 149 (M$^+$).

64f. 2,3-Dihydro-5H-benzo[f][1,4]oxazepine-4-sulfonyl chloride

This compound was prepared from 1.5 g of 2,3,4,5-tetrahydro-benzo[f][1,4]oxazepine, 0.81 mL of sulfuryl chloride and 1.8 mL of ethyl diisopropyl amine using the procedure described for 63f. Yield: 0.3 g (oil), EI-MS: 247 (M$^+$).

64g. 2,3-Dihydro-5H-benzo[f][1,4]oxazepine-4-sulfonic acid [1-(4-amino-thieno[3,2-c]pyridin-2-ylmethyl)-2-(4-methyl-piperidin-1-yl)-2-oxo-ethyl]-amide This compound was prepared from 200 mg of 2,3-dihydro-5H-benzo[f][1,4]oxazepine-4-sulfonyl chloride and 210 mg of 30a using the procedure described for 58c. Yield: 80 mg (oil), (+)-FAB-MS: 530 (MH$^+$).

Example 65

7-Methoxy-2,3-dihydro-5H-benzo[f][1,4]oxazepine-4-sulfonic acid [1-(4-amino-thieno[3,2-c]pyridin-2-ylmethyl)-2-(4-methyl-piperidin-1-yl)-2-oxo-ethyl]-amide (65g)

65a. 2-(Benzylimino-methyl)-4-methoxy-phenol

This compound was prepared from 2.7 g of 2-hydroxy-5-methoxy-benzaldehyde, 2.3 mL of benzylamine and 0.03 g of p-toluenesulphonic acid using the procedure described for 64a. Yield: 4.3 g (oil).

65b. 2-(Benzylamino-methyl)-4-methoxy-phenol

This compound was prepared from 1.0 g of 2-(benzylimino-methyl)-4-methoxy-phenol and 0.18 g of sodium borohydride using the procedure described 64b. Yield: 1.0 g (oil), EI-MS: 243 (M$^+$).

65c. 4-Benzyl-7-methoxy-4,5-dihydro-benzo[f][1,4] oxazepin-3-one

A mixture of 2.43 g of 2-(benzylamino-methyl)-4-methoxy-phenol and 20 mL of toluene was cooled to 5° C. and a solution of chloroacetyl chloride (0.88 ml) in 5 mL of toluene slowly added while stirring. Stirring was continued for 2 hours at room temperature. Dry tetrahydrofuran (25 mL) was added and 3.4 g of sodium hydride (95%; dispersion in mineral oil) were added in small portions under a nitrogen atmosphere. The mixture was allowed to stir at room temperature for 24 h. Water was added and the aqueous layer was extracted with ethyl acetate. The combined organic extracts were dried (sodium sulfate) and the solvent removed in vacuo yielding 2.0 g of 4-benzyl-7-methoxy-4,5-dihydro-benzo[f][1,4]oxazepin-3-one as an oil. EI-MS: 283 (M$^+$).

65d. 4-Benzyl-7-methoxy-2,3,4,5-tetrahydro-benzo [f][1,4]oxazepine

This compound was prepared from 5.7 g of 4-benzyl-7-methoxy-4,5-dihydro-benzo[f][1,4]-oxazepin-3-one and 2.3 g of lithium aluminum hydride using the procedure described for 64d. Yield: 6.1 g (oil), EI-MS: 269 (M$^+$).

65e. 7-Methoxy-2,3,4,5-tetrahydro-benzo[f][1,4] oxazepine

This compound was prepared from 6.1 g of 4-benzyl-7-methoxy-4,5-dihydro-benzo[f][1,4]oxazepine and 1.0 g of palladium (10% on carbon) as catalyst using the procedure described for 64e Yield: 2.7 g; m.p. 96–97° C., EI-MS: 179 (M$^+$).

65f. 7-Methoxy-2,3-dihydro-5H-benzo[f][1,4] oxazepine-4-sulfonyl chloride

This compound was prepared from 1.4 g of 7-methoxy-2,3,4,5-tetrahydro-benzo[f]l[1,4]oxazepine, 0.91 mL of sulfuryl chloride and 4.7 mL of triethylamine using the procedure described for 63f. Yield: 0.23 g (oil), EI-MS: 277 (M$^+$).

65g. 7-Methoxy-2,3-dihydro-5H-benzo[f][1,4] oxazepine-4-sulfonic acid [1-(4-amino-thieno[3,2-c] pyridin-2-ylmethyl)-2-(4-methyl-piperidin-1-yl)-2-oxo-ethyl]-amide This compound was prepared from 210 mg of 7-methoxy-2,3-dihydro-5H-benzo[f][1,4]oxazepine-4-sulfonyl chloride and 210 mg of 30a using the procedure described for 58c. Yield: 70 mg (oil), (+)-FAB-MS: 560 (MH$^+$).

Example 66

(3S)-4-[[1-(1-amino-6-isoquinolinyl)methyl]-2-oxo-2-(1-piperidinyl)ethyl]amino]3-[[4-(3,5-dimethylisoxazolyl)sulfonyl]amino]-4-oxo-butanoic acid 1,1-dimethylethylester hydrochloride The procedure described for 5c was used. Deprotection of 100 mg of 5a and coupling with 96 mg of (2S)-2-[[4-(3,5- dimethylisoxazolyl)sulfonyl]amino]butanedioic acid 4-(1,1-dimethylethyl)ester (prepared from Asp(OtBu)-OH and 3,5-dimethylisoxazole-4-sulfonyl chloride using the procedure described for 5b) yielded the title compound (66 mg) as a mixture of diastereomers (1:1). $^1$H-NMR 400 MHz (CD$_3$OD) δ: 1.15–1.68 (6H, m), 1.40 (9H, s), 2.20–2.62 (2H, m), 2.31 (3H, s), 2.33 and 2.37 (3H, 2×s), 2.96–3.56 (6H, m), 4.10–4.14 (1H, m), 5.04–5.14 (1H, m), 7.16–7.23 (1H, m), 7.53–7.78 (3H, m), 8.32–8.38 (1H, m).

Example 67

(2S)-N'-[1-[(1-amino-6-isoquinolinyl)methyl]-2-oxo-2-(1-piperidinyl)ethyl]-2-[[(4-methoxy-2,3,6-trimethylphenyl)sulfonyl]amino]-butanediamide hydrochloride The procedure described for 5c was used. Deprotection of 100 mg of 5a and coupling with 105 mg of (2S)-4-amino-2-[[(4-methoxy-2,3,6-trimethylphenyl)sulfonyl]amino]-4-oxobutanoic acid (prepared from Asn-OH and 4-methoxy-2,3,6-trimethylsulfonylchloride (Mtr-chloride)using the procedure described for 5b) yielded the title compound (66 mg) as a mixture of diastereomers (1:1). $^1$H-NMR 400 MHz (CD$_3$OD) δ: 1.20–1.68 (6H, m), 2.15 and 2.16 (3H, 2×s), 2.27–2.58 (2H, m), 2.57 (3H,s), 2.64 (3H, s), 2.93–3.57 (6H, m), 3.83 and 3.87 (3H, 2×s), 3.98–4.09 (1H, m), 5.07–5.19 (1H, m), 6.75 and 6.76 (1H, 2×s), 7.22–7.27 (1H, m), 7.55–7.79 (3H, m), 8.33–8.38 (1H, m).

Example 68

(3S)-4-[[1-[(1-amino-6-isoquinolinyl)methyl]-2-oxo-2-(4-morpholinyl)ethyl]amino]-3-[[(4-methoxy-2,3,6-trimethylphenyl)sulfonyl]amino]-4-oxo-butanoic acid 1,1-dimethylethylester hydrochloride Protection of 0.23 g of amino acid 1i and subsequently coupling with morpholine according to the procedure described for 5a yielded 1,1-dimethylethyl [1-[(1-amino-6-isoquinolinyl)methyl]-2-oxo-2-(4-morpholinyl)ethylcarbamate. The procedure described for 5c was used for the deprotection of 90 mg of 1,1-dimethylethyl [1-[(1-amino-6-isoquinolinyl)methyl]-2-oxo-2-(4-morpholinyl)ethylcarbamate and coupling with 96 mg of (2S)-2-[[(4-methoxy-2,3,6-trimethylphenyl)sulfonyl]amino]butanedioic acid 4-(1,1-dimethylethyl)ester (prepared from Asp(OtBu)-OH and (4-methoxy-2,3,6-trimethylphenyl)sulfonylchloride using the procedure described for 5b) to yield the title compound (56 mg) as a mixture of diastereomers (1:1). $^1$H-NMR 400 MHz (CD$_3$OD) δ: 1.29 and 1.33 (9H, 2×s), 2.12 and 2.13 (3H, 2×s), 2.19–2.47 (2H, m), 2.52 and 2.53 (3H, 2×s), 2.62 (3H, s), 2.95–3.65 (10H, m), 3.81 and 3.86 (3H, 2×s), 3.95–4.08 (1H, m), 5.03–5.18 (1H, m), 6.73 and 6.75 (1H, 2×s), 7.18–7.23 (1H, m), 7.53–7.78 (3H, m), 8.31–8.38 (1H, m).

Example 69

1-[3-(4-Aminothieno[3,2c]pyridin-2-yl)-2-[(1-oxo-2-propylpentyl)amino]-1-oxopropyl]-4-methylpiperidine hydrochloride Compound 30a (53 mg) was dissolved in 1.5 mL of dichloromethane and 1.5 mL of trifluoroacetic acid was added. After stirring at room temperature for 1.5 hours the reaction mixture was concentrated and coevaporated with toluene. The residue was dissolved in 2 mL of dichloromethane and 0.053 mL of triethylamine, cooled at 0° C. and 23 mg of 2-propylpentanoyl chloride was added. After stirring at room temperature for 1.5 h, dichloromethane and water were added. The organic layer was separated, dried (magnesium sulfate) and concentrated. Purification by chromatography on silica gel (dichloromethane:methanol=95:5 (v/v)) yielded the free base. Treatment of this free base with one equivalent hydrochloric acid and lyophilisation yielded compound 69 (22 mg). $^1$H-NMR 400 MHz (CD$_3$OD) δ: 0.61–1.74 (22H, m), 2.18 2.27 (1H, m), 2.59–2.70 (1H, m), 2.99–3.10 (1H, m), 3.25–3.49 (2H, m), 3.99–4.16 (1H, m), 4.41–4.51 (1H, m), 5.22–5.35 (1H, m), 7.37–7.42 (1H, m), 7.58–7.61 (2H, m).

Example 70

1-[3-(4-Aminothieno[3,2c]pyridin-2-yl)-2-[[3-(4-chlorophenyl)-1-oxopropyl]amino]1-oxopropyl]-4-methylpiperidine hydrochloride Compound 30a (60 mg) was dissolved in 1.5 mL of dichloromethane and 1.5 mL of trifluoroacetic acid was added. After stirring at room temperature for 1.5 h, the reaction mixture was concentrated and coevaporated with toluene. The residue was dissolved in 2 mL of dichloromethane and adjusted to pH 8 using N,N-diisopropylethylamine. This solution was added to an active ester solution that was prepared by dissolving 29 mg of 3-(4-chlorophenyl)propanoic acid, 21 mg of hydroxybenztriazole and 33 mg of dicyclohexylcarbodiimide in 2.5 mL of dichloromethane and stirring at room temperature for 15 min. After the addition of the active ester solution the pH of the reaction mixture was adjusted to 8 using N,N-diisopropylamine and stirred for 16 h at room temperature. The reaction mixture was filtered, water was added, and the organic layer was separated. The aqueous layer was extracted with dichloromethane, the combined organic layers were dried (magnesium sulfate) and concentrated. Purification by chromatography on silica gel (dichloromethane:methanol=9:1(v/v)) yielded the free base. Treatment of this free base with one equivalent hydrochloric acid and lyophilisation yielded the title compound (66 mg). $^1$H-NNR 400 MHz (CDCl$_3$) δ: 0.88 and 0.92 (3H, 2×d, J=6 Hz), 0.74–1.72 (5H, m), 2.54–3.44 (8H, m), 3.81–3.92 (1H, m), 4.39–4.46 (1H, m), 5.17–5.23 (1H, m), 6.99–7.45 (7H, m), 7.82 (1H, br. s), 8.36 (2H, br.s).

Example 71

Solid-phase Synthesis of Compounds of Formula (Ib) with n=0, X=S, R$^1$Y=R$^1$SO$_2$, R$^3$=H (Table 71)

71a. 3-[4-aminothieno[3,2c]pyridin-2-yl]-2-[N-tert.butyloxycarbonyl]amino propionic acid methyl ester 9.3 g of compound 3h was coevaporated twice with dry methanol and subsequently dissolved in 300 mL of methanol/triethylamine (9:1 v/v). 7.5 g of di-tert.butyl carbonate was added and the reaction mixture was stirred for 2 hours at room temperature. Three additional portions of 1.5 g of di-tert.butyl carbonate were added over the next 5 hours.

The reaction mixture was evaporated and coevaporated twice with methanol. The residue was purified with silica gel chromatography with a gradient of methanol (0→8%) in dichloromethane containing 2 vol % of triethylamine. This afforded 6.9 g of 71a. $^1$H NMR 200 MHz (CD$_3$OD) δ: 1.41 (9H,s), 3.34 (2H,dd), 3.75 (3H,s), 4.46 (1H,dd), 7.07 (1H,d), 7.29 (1H,s), 7.67 (1H,d).

71b. 3-[4-(acetylamino)thieno[3,2c]pyridin-2-yl]-2-[N-tert.butyloxycarbonyl]amino propionic acid methyl ester 6.9 g of 71a was dissolved in 67 mL of pyridine and 1.8 mL of acetic anhydride was added. After 2 hours at room temperature another 1.8 mL of acetic anhydride was added and the solution was stirred overnight at room temperature. The pyridine was evaporated, and the crude product was coevaporated three times with toluene. The residue was chromatographed on a silica gel column (ethyl acetate/methanol 98:2) to give 5.7 g of 71b. $^1$H NMR 400 MHZ (CDCl$_3$) δ: 1.45 (9H,s), 2.32 (3H,s), 3.45 (2H,dd), 3.80 (3H,s), 4.68 (1H,dd), 7.18 (1H,s), 7.52 (1H,d), 8.11(1H, d).

71c. 3-[4-(acetylamino)thieno[3,2c]pyridin-2-yl]-2-[N-tert.butyloxycarbonyl]amino propionic acid 5.7 g of 711b was dissolved in 90 mL of dioxane/water (1:1v/v) and 2N NaOH was added until pH 12. During the saponification was pH continuously adjusted to maintain pH 12. After 2 hours TLC (dichloromethane/methanol 9:1 v/v containing 0.5% triethylamine) showed complete conversion into the acid. The solution was neutralized with acetic acid and the mixture was concentrated to a small volume. The solution was acidified until pH 4 with acetic acid and extracted with ethyl acetate. Between both layers a solid (sodium salt) appeared which was collected by filtration. The salt was added to a dichloromethane/water mixture and acetic acid was added until pH 4. Again a solid (free acid) appeared between both layers. Filtration gave 4.0 g of free acid 71c. $^1$H NMR 200 MHz (CD$_3$OD) δ: 1.40 (9H,s), 2.28 (3H,s), 3.43 (2H,dd), 4.44 (1H,dd), 7.34 (1H,s), 7.79 (1H,d), 8.13(1H,d).

71d. Derivatization of Kaiser oxime resin with acid 71c 2.0 g of 71c was coevaporated twice with dry N,N-dimethylformamide and subsequently dissolved in 50 mL of dichloromethane/N,N-dimethylformamide (3:2 v/v). 0.88 g of N-hydroxybenzotriazole was added and the resulting solution was added to 3.5 g of Kaiser oxime resin (0.4 mmol/g). After the addition of 1.0 mL of diisopropylcarbodiimide, the suspension was shaken overnight at room temperature. The resin was filtered off and washed with dichloromethane/N,N-dimethylformamide (3:2 v/v) and N,N-dimethylformamide. Further washings were performed by alternate addition of 2-propanol and dichloromethane (three times each). Unreacted oxime functions were capped by treatment of the resin with 35 mL acetic anhydride/N,N-diisopropylethylamine/N,N-dimethylformamide (3:1:12 v/v/v) for 30 minutes at room temperature. The resin was filtered off and washed with N,N-dimethylformamide, 2-propanol and dichloromethane (three times each). The resin was dried in vacuo to give 4.2 g of 71d.

71e. 3-(4-aminothieno[3,2c]pyridin-2-yl)-2-[[(4-chlorophenyl)sulfonyl]amino]-N-[2-(3-fluorophenyl)ethyl)]-propanamide (compound of formula (Ib) with n=0, X=S, R$^1$Y=4-chlorophenylsulfonyl R$^3$=H, R$^7$=3-fluorophenylethyl, R$^8$=H 50 mg (20 μmol) of 71d was treated with 2 mL of 25 vol% trifluoroacetic acid in dichloromethane for 30 minutes at room temperature. The resin was filtered off and washed with dichloromethane, 2-propanol and dichloromethane. The resin was washed three times with 1 mL dichloromethane/N,N-dimethylformamide (3:2 v/v) containing 80 μmol N,N-diisopropylethylamine and immediately reacted with 80 μmol p-chlorobenzenesulfonyl chloride in 1 mL dichloromethane/N,N-dimethylformamide (3:2 v/v) containing 80 μmol N,N-diisopropylethylamine. The suspension was shaken for 45 minutes at room temperature. The resin was filtered off and washed with dichloromethane/N,N-dimethylformamide (3:2 v/v), followed by washings with dichloromethane, 2-propanol and dichloromethane. The ninhydrin test revealed complete conversion of the amine. The resin was suspended in 1 mL of a 0.5 M solution of 3-fluorophenethylamine in distilled tetrahydrofuran and shaken for 16 hours at room temperature. The resin was filtered off and washed with tetrahydrofuran and methanol. The filtrates were collected and concentrated to dryness. The residue was dissolved in 1 mL ethylenediamine/ethanol (1:1 v/v) and shaken for 16 hours at room temperature. The reaction mixture was evaporated to dryness, dissolved in methanol/water (1:1 v/v) and applied to a DOWEX-NH$_4^+$ column (4.5 mL) to remove excess of amine. The column was eluted with methanol/water (1:1 v/v). The UV positive fractions were pooled and evaporated to dryness yielding 9.5 mg of 71e.

Table 71

Solid-phase Synthesis of Compounds of Formula (Ib) with n=0, X=S, R$^1$Y=R$^1$SO$_2$, R$^3$=H.

Using the procedure described for example 71e the sulfonyl chlorides (R$^1$SO$_2$Cl) corresponding to R$^1$ in Table 71 were coupled to derivatized resin 71d. 50 mg portions of the resulting resins were treated with amines of structure NHR$^7$R$^8$ as depicted in Table 71. Work-up of the samples was performed as described for 71e.

All compounds were characterized by reversed phase liquid chromatography on a Supelcosil LC-18-DB column using following conditions: Flow: 1.0 ml/min; Buffers A: water, B: acetonitrile/water (9:1 v/v), C: 0.5M phosphate buffer pH=2.1; Gradient 1: 0→30 min 65%A-15%B-20%C→25%A-55%B-20%C. UV-detection at 210 nm. Retention times are given in minutes in Table 71.

TABLE 71
RP-HPLC retention times for compounds of example 71
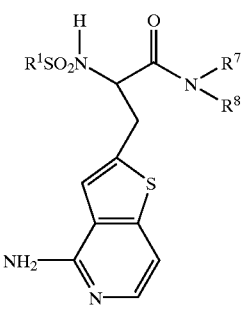
| R⁷NR⁸ | R¹SO₂ dibenzofuran-SO₂ | phenyl-SO₂ | 4-Cl-phenyl-SO₂ | benzothiadiazole-SO₂ | 6-OMe-naphthyl-SO₂ |
|---|---|---|---|---|---|
| tetrahydroisoquinoline | 30.6 | 23.0 | 26.7 | 23.1 | 28.9 |
| N-methyl-N-benzyl | 29.9 | 23.9 | 26.6 | 22.4 | 28.3 |
| 4-Cl-benzyl-NH | 30.4 | 24.3 | 27.1 | 24.2 | 29.0 |
| 3-F-phenethyl-NH | 29.2 | 23.9 | 26.2 | 22.8 | 28.0 |
| 3-methoxyphenyl-methylpiperazine | 32.2 |  | 28.9 | 24.4 | 30.5 |
| tetrahydropyridine | 26.6 | 19.1 | 22.8 | 18.0 | 24.7 |
| 2-pyridyl-ethyl-NH | 13.6 | 6.3 | 8.5 | 3.5 | 11.8 |
| indanyl-NH | 33.8 | 28.1 | 30.7 | 27.3 | 32.1 |

Example 72

Solid-phase Synthesis of Compounds of Formula (Ib) with n=0, X=S, R$^1$Y=R$^1$C(O), R$^3$=H (Table 72)

72a 3-(4-aminothieno[3,2c]pyridin-2-yl)-N-[methyl]-N-[phenylmethyl)]-2-[[(2-pyridinyl)-carbonyl]amino]-propanamide (compound of formula (Ib) with n=0, X=S, R$^1$Y=2-pyridine-carboxyl, R$^3$=H, R$^7$=benzyl, R$^8$=methyl)

50 mg (20 μmol) of 71d was treated with 2 mL of 25 vol % trifluoroacetic acid in dichloromethane for 30 minutes at room temperature. The resin was filtered off and washed with dichloromethane, 2-propanol and dichloromethane. The resin was washed three times with 1 mL dichloromethane/N,N-dimethylformamide (3:2 v/v) containing 80 μmol N,N-diisopropylethylamine and immediately reacted with 80 μmol 2-pyridinecarboxylic acid in 1 ml dichloromethane/N,N-dimethylformamide (3:2 v/v) containing 80 μmol of N,N-diisopropylethylamine and 80 μmol of (O-(benzotriazol-1-yl))-1,1,3,3-tetramethyl uronium tetrafluoroborate. The suspension was shaken for 45 minutes at room temperature. The resin was filtered off and washed with dichloromethane/N,N-dimethylformamide (3:2 v/v), followed by washings with dichloromethane, 2-propanol and dichloromethane. The ninhydrin test revealed complete conversion of the amine. The resin was suspended in 1 mL of a 0.5 M solution of methylbenzylamine in distilled tetrahydrofuran and shaken for 16 hours at room temperature. The resin was filtered off and washed with tetrahydrofuran and methanol. The filtrates were collected and concentrated to dryness. Further processing of the sample was performed as described for 71e, yielding 8.0 mg of compound 72a.

Table 72
Solid-phase Synthesis of Compounds of Formula (Ib) with n=0, X=S, R$^1$Y=R$^1$C(O), R$^3$=H.

Using the procedure described for example 72a the carboxylic acids (R$^1$C(O)OH) corresponding to R$^1$ in Table 72 were coupled to derivatized resin 71d. 50 mg portions of the resulting resins were treated with amines of structure NHR$^7$R$^8$ as depicted in Table 72. Work-up of the samples was performed as described for 71e.

All compounds were characterized by reversed phase liquid chromatograpy using the conditions described for compounds 71f. Retention times are given in minutes in Table 72. Standard gradient 1 was run, times marked with an asterisk were determined after applying the following gradient: 0→30 min 75%A-5%B-20%C→35%A-45%B-20%C.

TABLE 72

RP-HPLC retention times for example 72

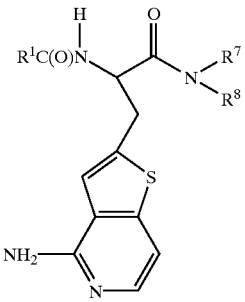

| R$^7$NR$^8$ \ R$^1$C(O) | pyridinyl | adamantyl-CH | adamantyl-CH₂ | methoxyphenyl | cyclohexyl | cyclopropyl |
|---|---|---|---|---|---|---|
| tetrahydroisoquinoline | 21.0 | 31.9 | 23.4 | 28.3/29.0 | 24.6 | 16.6 |
| N-methylbenzylamine | 22.4 | 32.0 | 23.0 | 28.6/29.5 | 24.7 | 17.1 |

TABLE 72-continued
RP-HPLC retention times for example 72
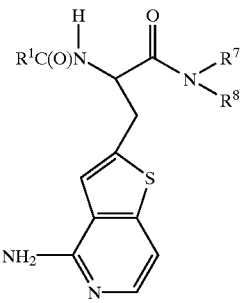
| $R^7NR^8$ | $R^1C(O)$ 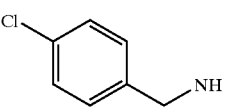 | 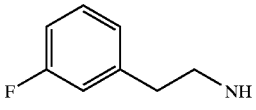 | 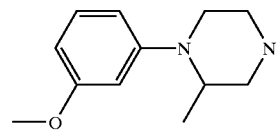 | 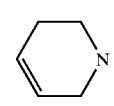 | 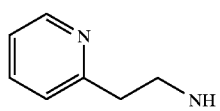 | 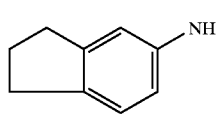 |
|---|---|---|---|---|---|---|
| 4-chlorobenzyl-NH | 22.9 | 31.8 | 24.2 | 28.9/29.7 | | 18.3 |
| 3-fluorophenethyl-NH | 22.3 | 30.8 | 23.4 | 28.5/29.6 | | 18.9 |
| 3-methoxyphenyl-methylpiperazine | | | 24.3 | 30.2/31.2 | 25.9 | 19.3 |
| tetrahydropyridine | 17.3 | 28.3 | 18.7 | 24.1/25.3 | 20.7 | 12.4 |
| 2-pyridylethyl-NH | 14.3* | 22.7* | 15.9* | 20.5/21.3* | 18.4* | 10.7* |
| indanyl-NH | 27.9 | 36.9 | 28.2 | 33.6/34.6 | 30.3 | 24.1 |

Example 73

N-(carboxymethyl)-D-cyclohexylalanyl-N-[(4-aminothieno[3,2c]pyridin-2-yl)methyl]-(N-cyclopentyl-glycin)amide (N—(HOOCCH₂)-D-Cha-N-cyclopentyl-Gly-Atp) (73j)

73a. N-[2-(azidomethyl)thieno[3,2c]pyridin-4-yl]benzamide

The experimental procedure described in J. Org. Chem. 58, 5886 (1993) was slightly modified. To 1.0 g of N-[2-(hydroxymethyl)thieno[3,2c]pyridin-4-yl]benzamide (3e) was added toluene and evaporated under reduced pressure to remove traces of moisture. To the residue was added 5 mL of toluene and 5 mL of dioxane, the solution was cooled at 0° C. and 1.14 mL of diphenylphosphoryl azide (DDPA) and 0.79 mL 1,8-diazabicyclo(5.4.0)undec-7ene (DBU) were added. After stirring this suspension for 68 hours at room temperature the reaction was not completed and an additional 0.38 mL of DPPA and 0.27 mL of DBU were added. After 24 hours the reaction mixture was poured into water (pH 7) and extracted with ethyl acetate. The organic layer was dried (magnesium sulfate) and concentrated. Purification on silica gel (toluene/ethyl acetate: 3/1 (v/v)) gave 0.98 g azide. $^1$H-NMR 200 MHz (CDCl$_3$) δ: 4.59 (2H, s), 7.38–7.59 (5H, m), 8.01–8.09 (3H, m).

73b N-[2-(aminomethyl)thieno[3,2c]pyridin-4-yl]benzamide

Through a solution of 1.07 g of N-[2-(azidomethyl)thieno[3,2c)pyridin-4-yl]benzamide in 50 mL of ethanol containing 0.6 g of 5% palladium/calcium carbonate was bubbled hydrogen for 40 hours. Filtration and column chromatography on silica gel (dichloromethane/methanol=9/1 (v/v)) yielded 0.79 g of the title compound. $^1$H-NMR 200 MHz (CDCl$_3$) δ: 4.18 (2H, s), 7.35–7.63 (5H, m), 7.99–8.12 (3H, m).

73c. 4-amino-2-(aminomethyl)thieno[3,2c]pyridine hydrochloride

A solution of 0.33 g of N-[2-(aminomethyl)thieno[3,2c]pyridin-4-yl]benzamide in 40 mL of 4N hydrochloric acid and 20 mL of acetic acid was refluxed for 16 hours. The reaction mixture was washed with diethylether to remove benzoic acid and the aqueous solution was concentrated under reduced pressure to give 0.256 g of 4-amino-2-(aminomethyl)thieno[3,2c]pyridine hydrochloride. $^1$H-NMR 200 MHz (D$_2$O) δ: 4.57 (2H, s), 7.43 (1H, d, J=7 Hz), 7.63 (1H, d, J=7 Hz), 7.83 (1H, s).

73d. N-Cyclopentyl-Gly-OMe

Cyclopentanone (15.6 g) was added to a solution of H-Gly-OMe HCl (23.2 g) in 200 mL of methanol. The mixture was stirred for 15 minutes and sodium cyanoborohydride (7 g) was added. The pH was adjusted to 6. The reaction mixture was stirred for 16 hours at room temperature. To complete the reaction cyclopentanone (1 g) was added and stirring was continued. The reaction was monitored on TLC. When all the starting material had disappeared, the mixture was acidified to pH 2 and was stirred for 30 minutes. The solvent was removed and the residue was diluted with water. The solution was washed with ether, the pH adjusted to 12 with 6N sodium hydroxide and extracted with dichloromethane. The combined organic layers were washed with a saturated sodium chloride solution, dried on sodium sulfate and evaporated in vacuo to yield 16 g of an oil.

Rf=0.46 in ethyl acetate/pyridine/acetic acid/water 63/20/6/11 (v/v/v/v) on silica.

73e. N-(t-butyloxycarbonylmethyl)-D-Cha-OMe t-Butyl bromo acetate (17 g) was added to a stirred solution H-D-Cha-OMe HCl (26 g) in 300 mL of acetonitrile. The pH of the mixture was adjusted to 8.5 with N,N-diisopropylethylamine. The mixture was stirred for 16 hours at room temperature and evaporated in vacuo. The residue was dissolved in dichloromethane and the solution was washed with water, dried on sodium sulfate and evaporated in vacuo. Chromatography over silica gel in hexane/ethyl acetate 9/1 (v/v) gave 20 g of N-(t-butyloxycarbonylmethyl)-D-Cha-OMe.

Rf=0.46 in ethyl acetate/pyridine/acetic acid/water 63/20/6/11 (v/v/v/v) on silica.

73f. N-Boc-N-(t-butyloxycarbonylmethyl)-D-Cha-OMe

The pH of a solution of N-(t-butyloxycarbonylmethyl)-D-Cha-OMe (20 g) and di-t-butyl dicarbonate (17 g) was adjusted to 8.5 with N,N-diisopropylethylamine. The mixture was stirred for 16 hours at room temperature. The solvent was removed in vacuo. Dichloromethane and water were added to the residue. The organic layer was separated, washed with cold 1N hydrochloric acid, water, 5% sodium hydrogen carbonate and water. The organic layer was dried on sodium sulfate and the filtrate was evaporated to an amorphous solid of N-Boc-N-(t-butyloxycarbonylmethyl)-D-Cha-OMe with a yield of 28 g.

Rf=0.60 in ethyl acetate/pyridine/acetic acid/water 252/20/6/11 (v/v/v/v) on silica.

73g. N-Boc-N-(t-butyloxycarbonylmethyl)-D-Cha-OH

A solution of N-Boc-N-(t-butyloxycarbonylmethyl)-D-Cha-OMe (28 g) in 420 mL of dioxane:water 9/1 (v/v) was treated with sufficient 1N sodium hydroxide to keep the pH at 13 for 90 minutes at room temperature. After acidification, the mixture was poured into water and was extracted with dichloromethane. The organic layer was washed with water and was dried on sodium sulfate. The filtrate was evaporated and yielded 24 g of N-Boc-N-(t-butyloxycarbonylmethyl)-D-Cha-OH.

Rf=0.23 in dichloromethane/methanol 9/1 (v/v) on silica.

73h. N-Boc-N-(t-butyloxycarbonylmethyl)-D-Cha-N-cyclopentyl-Gly-OMe

N-cyclopentyl-Gly-OMe (10.2 g) and 2-(1H-benzotriazol-1-yl)-1,1,3,3-tetramethyluronium tetrafluoroborate (TBTU; 21.2 g) were added to a solution of N-Boc-N-(t-butyloxy-carbonylmethyl)-D-Cha-OH (24 g) in 300 mL of N,N-dimethyl formamide. The pH of the mixture was adjusted to 8.5. The mixture was stirred overnight at room temperature and was concentrated by evaporation. Water and ethyl acetate were added to the residue. The organic layer was separated and washed with 1N hydrochloric acid, water, 5% sodium hydrogen carbonate and water and dried over sodium sulfate. The filtrate was evaporated and the residue was chromatographed on silica gel in hexane/ethyl acetate 8/2 (v/v) as eluent. The fractions containing N-Boc-N-(t-butyloxycarbonylmethyl)-D-Cha-N-cyclopentyl-Gly-OMe were pooled and evaporated. Yield: 17 g.

Rf=0.57 in hexane/ethyl acetate 7/3 (v/v) on silica.

73i. N-Boc-N-(t-butyloxycarbonylmethyl)-D-Cha-N-cyclopentyl-Gly-OH

N-Boc-N-(t-butyloxycarbonylmethyl)-D-Cha-N-cyclopentyl-Gly-OMe (17 g) was saponified in a mixture of dioxane/water 1/1 (v/v, 150 mL) and diluted sodium hydroxide and yielded 15 g of an amorphous solid. Chromatography over silica gel with dichloromethane/methanol 95/5 (v/v) as eluent gave 13 g of N-Boc-N-(t-butyloxycarbonylmethyl)-D-Cha-N-cyclopentyl-Gly-OH.

Rf=0.30 in dichloromethane/methanol 9/1 (v/v) on silica.

73j. N—(HOOCCH2)-D-Cha-N-cyclopentyl-Gly-Atp

To a solution of 91 mg of 4-amino-2-(aminomethyl)thieno[3,2c]pyridine hydrochloride and 182 mg of N-Boc-N-(t-butyloxycarbonylmethyl)-D-Cha-N-cyclopentyl-Gly-OH in 2.5 mL of N,N-dimethylformamide was added 125 mg 2-(1H-benzotriazol-1-yl)-1,1,3,3-tetramethyluronium tetrafluoroborate (TBTU) and the pH was adjusted to 8 using N,N-diisopropylethylamine. The pH was maintained at 8 during the reaction. After 16 hours the reaction mixture was concentrated under reduced pressure. Dichloromethane was added, washed with an aqueous 5% sodium hydrogencarbonate solution, dried (magnesium sulfate) and concentrated. Purification on silica gel (dichloromethane/methanol: 95/5 (v/v)) gave 164 mg of N-Boc-N-(t-butyloxycarbonylmethyl)-D-Cha-N-cyclopentyl-Gly-Atp as an oil. 142 mg of this oil was dissolved in 2.5 mL of dichloromethane and 2.5 mL of trifluoroacetic acid and stirred at room temperature. After 16 hours the reaction mixture was concentrated, dissolved in 0.2 M hydrochloric acid and washed with ether. The aqueous solution was concentrated under reduced pressure. HPLC purification on a preparative Delta-pack C-18 column using a gradient elution system of 20% A/70% B/10% C to 20% A/20% B/60% C (A=0.5M sodium dihydrogen phosphate+ phosphoric acid (pH=2.1); B=water; C=cyanomethane/water 3/2 (v/v) over 45 min, at a flow rate of 80 mL/min. Yield: 100 mg. $^{1}$H-NMR 400 MHz (D$_2$O) δ: 0.43–1.84 (21H, m), 3.40–3.67 (2H, m), 3.84–4.13 (3H, m), 4.46–4.7 (3H, m), 7.21–7.26 (1H, m), 7.39–7.48 (2H, m).

Example 74

N-(carboxymethyl)-D-cyclohexylalanyl-[N-(1-amino-6-isoquinolinyl)methyl]-L-azetidin-2-carboxamide trifluoroacetate (N—(HOOCCH$_2$)-D-Cha-L-Azt-6-Aiq TFA)(74f)

74a. N-[6-(azidomethyl)-1-isoquinolinyl]-benzamide

To 6.3 g of N-[6-(hydroxymethyl)-1-isoquinolinyl] benzamide (1g) in 40 mL of toluene and 40 mL of dioxane at 0° C. 7.8 mL of diphenylphosphoryl azide (DDPA) and 5.4 mL of 1,8-diazabicyclo(5.4.0)undec-7ene (DBU) were added. After 24 hours the reaction mixture was poured into water (pH 7) and extracted with ethyl acetate. The organic layer was dried (sodium sulfate) and concentrated. Trituration with diethyl ether gave 6.4 g of the title compound. Mp. 125–129° C. MS (m/e)=303.

74b. N-[6-(aminomethyl)-1-isoquinolinyl] benzamide

A solution of 6.4 g of N-[6-(azidomethyl)-1-isoquinolinyl]benzamide in 300 mL of ethanol and 60 mL of N,N-dimethylformamide containing 3.8 g of 5% palladium/calcium carbonate was hydrogenated for 20 hours. Filtration and concentration i. vac. yielded the title compound as an oil. MS (m/e)=277.

74c. 1-amino-6-(aminomethyl)isoquinoline hydrochloride

A solution of 5.8 g of N-[6-(aminomethyl)-1-isoquinolinyl]benzamide in 300 mL of 4N hydrochloric acid and 150 mL of acetic acid was refluxed for 6 hours. The reaction mixture was washed with diethylether to remove benzoic acid and the aqueous solution was concentrated under reduced pressure to give 3.0 g of the title compound. MS (m/e)=173.

74d. (N-Boc-N-(t-butyloxycarbonylmethyl)-D-Cha-(L)-azetidine-2-carboxylic acid 0.71 mL (5.43 mmol) Isobutyl chloroformate was added dropwise to a cooled (−15−−20° C.) solution of 1.90 g (4.94 mmol) N-Boc-N-(t-butyloxycarbonylmethyl)-D-Cha-OH and 0.6 mL (5.43 mmol) N-methyl morpholine in 15 mL dichloromethane. After 45 min, 0.50 g (4.94 mmol) (L)-azetidine-2-carboxylic acid (L-H-Azt-OH) was added. After 1 h, the organic phase was extracted with water, the organic layer was dried (sodium sulfate), filtered, and the solvent was removed i.vac. to yield 2.3 g (quant.) of the title compound as a nearly colorless oil. FAB-MS: m/e=469 (M+H$^+$).

74e. N-Boc-N-(t-butyloxycarbonylmethyl)-D-Cha-L-Azt-6-Aiq 0.45 g (1.28 mmol) Chloro-N,N,N',N'-bis (pentamethylene)-formamidinium hexafluorophosphate was added to a cooled (ice bath) solution of 0.60 g (1.28 mmol) N-Boc-N-(t-butyloxycarbonylmethyl)-D-Cha-L-Azt-OH (74d) and 0.23 g (1.28 mmol) 1-amino-6-(aminomethyl) isoquinoline hydrochloride (74c) in 5 mL dichloromethane, followed by the addtion of 0.68 mL (3.83 mmol) N,N-diisopropylethylamine. After 2 h at room temperature, the solution was extracted with water, the organic layer was dried (sodium sulfate), filtered, and the solvent was removed i. vac. The residue was filtered over silica gel using ethyl acetate:methanol (15:1) as an eluent. The solvent was removed i. vac. to yield N-Boc-N-(t-butyloxycarbonylmethyl)-D-Cha-L-Azt-6-Aiq as an amorphous solid. FAB-MS m/e=623.

74f. N—(HOOCCH$_2$)-D-Cha-L-Azt-6-Aiq TFA 3.0 mL Trifluoroacetic acid was added to a solution of 200 mg (0.32 mmol) N-Boc-N-(t-butyloxycarbonylmethyl)-D-

Cha-L-Azt-6-Aiq in 3 mL dichloromethane. After 3 h, the solvent was removed i. vac., the residue was dissolved in methanol, filtered, and the solvent was removed i. vac. to yield 90 mg of an amorphous residue. The residue was purified by column chromatography (reversed phase RP18 select B; methanol:water 55:45) to yield the title compound as an amorphous solid. FAB-MS: m/e=467.

Example 75

N-(carboxymethyl)-D-cyclohexylalanyl-N-[(4-amino-thieno [3,2c]pyridin-2-yl)-methyl]-L-azetidin-2-carboxamide trifluoroacetate (N—(HOOCCH$_2$)-D-Cha-L-Azt-Atp TFA)(75b)

75a. N-Boc-N-(t-butyloxycarbonylmethyl)-D-Cha-L-Azt-Atp 0.45 g (1.28 mmol) Chloro-N,N,N',N'-bis (pentamethylene)-formamidinium hexafluorophosphate was added to a cooled (ice bath) solution of 0.60 g (1.28 mmol) N-Boc-N-(t-butyloxycarbonylmethyl)-D-Cha-L-Azt-OH (74d) and 0.28 g (1.28 mmol) 4-amino-2-(aminomethyl) thieno[3,2c]pyridine hydrochloride (73c) in 5 mL dichloromethane, followed by the addition of 0.68 mL (3.83 mmol) N,N-diisopropylethylamine. After 15 min at 0° C. and 2 h at room temperature, the solution was filtered, the filtrate was extracted with water, the organic layer was dried (sodium sulfate), filtered, and the solvent was removed i. vac. The residue was filtered over silica gel using ethyl acetate:methanol (15:1) as an eluent. The solvent was removed in vacuo to yield N-Boc-N-(t-butyloxycarbonylmethyl)-D-Cha-L-Azt-Atp as an amorphous solid. FAB-MS m/e=629.

75b. N—(HOOCCH$_2$)-D-Cha-L-Azt-Atp TFA)

2.0 mL Trifluoroacetic acid was added to a solution of 85 mg (0.13 mmol) N-Boc-N-(t-butyloxycarbonylmethyl)-D-Cha-L-Azt-Atp in 2 mL dichloromethane. After 3 h, the solvent was removed in vacuo, the residue was dissolved in methanol, filtered, and the solvent was removed in vacuo to yield 100 mg of an amorphous residue. The residue was purified by column chromatography (reversed phase RP18 select B; methanol:water=60:40). The solvent was removed in vacuo, the residue was dissolved in methanol, toluene was added, the solvent was removed in vacuo, the residue was triturated with methanol, filtered, and the solvent was removed in vacuo to yield the title compound as an amorphous solid, FAB-MS: m/e=473.

Example 76

N-Methyl-D-phenylalanyl-N-[(1-amino-6-isoquinolinyl)methyl]-L-prolinamide trifluoroacetate (N-Me-D-Phe-Pro-6-Aiq TFA) (76b)

76a. N-Boc-N-Me-D-Phe-Pro-6-Aiq

In the manner described in example 74e N-Boc-N-methyl-D-phenylalanyl-N-[(1-amino-6isoquinolinyl)-methyl] L-prolineamide (N-Boc-N-Me-D-Phe-Pro-6-Aiq) was obtained by the reaction of N-Boc-N-methyl-D-phenylalanyl-L-proline (N-Boc-N-Me-D-Phe-Pro-OH) with 1-amino-6-(aminomethyl)isoquinoline hydrochloride (74c). Amorphous solid. FAB-MS: m/e=531.

76b. N-Me-D-Phe-Pro-6-Aiq TFA

The Boc-group of N-Boc-N-Me-D-Phe-Pro-6-Aiq was removed as described in example 74f, and the title compound was obtained as a solid, which decomposed on melting at 72° C. FAB-MS: m/e=431.

Example 77

N-(carboxymethyl)-D-phenylalanyl-N-[(1-amino-6-isoquinolinyl)methyl]-L-prolinamide trifluoroacetate (N—(HOOCCH$_2$)-D-Phe-Pro-6-Aiq TFA) (77f)

77a. N-(t-butyloxycarbonylmethyl)-D-Phe-OMe 15 mL Hünig-base was added to a suspension of 10.0 g D-phenylalanine-methylester (D-H-Phe-OMe) and 5 mL t-butyl bromoacetate in 100 mL dichloromethane (pH=8). The suspension slowly converted into a solution, and after 20 hours at room temperature, it was extracted with water, the organic layer was separated, dried (sodium sulfate), filtered, and concentrated i. vac. The residue was filtered (silica gel, elution with heptane/ethyl acetate=2:1). Concentration in vacuo yielded 6.4 g of the tilte compound as an oil. MS (m/e)=293.

77b. N-Boc-N-(t-butyloxycarbonylmethyl)-D-Phe-OMe 25 mL Hünig-base was added to a solution of 16.7 g N-(t-butyloxycarbonylmethyl)-D-Phe-OMe and 14.8 g di-t-butyl dicarbonate in 150 mL N,N-dimethylformamide (pH=8). After 60 h at room temperature, the N,N-dimethylformamide was removed, the residue dissolved in ethyl acetate, extracted with water, dried (sodium sulfate), filtered, and concentrated in vacuo to yield the title compound as a yellow oil. MS (m/e)=393.

77c. N-Boc-N-(t-butyloxycarbonylmethyl)-D-Phe-OH 22.4 g N-Boc-N-(t-butyloxycarbonylmethyl)-D-Phe-OMe and 2.3 g sodium hydroxide were dissolved in 180 mL dioxane and 35 mL water. After 26 hours at room temperature, the solvent was removed in vacuo, the residue was dissolved in diethyl ether and extracted with water, the aqueous layer was acidified with conc hydrochloric acid and extracted with ether. The organic layer was dried (sodium sulfate), filtered, and concentrated in vacuo to yield 18.4 g of the title compound as a yellow oil. MS (m/e)=379.

77d. N-Boc-N-(t-butyloxycarbonylmethyl)-D-Phe-Pro-OH was prepared analogously to 74d using N-Boc-N-(t-butyloxycarbonylmethyl)-D-Phe-OH and proline and isolated in 79% yield as a yellow oil. MS (m/z)=476.

77e. N-Boc-N-(t-butyloxycarbonylmethyl)-D-Phe-Pro-6-Aiq

In the manner described in example 74e, N-Boc-N-(t-butyloxycarbonylmethyl)-D-Phe-Pro-6-Aiq was obtained by the reaction of N-Boc-N-(t-butyloxycarbonylmethyl)-D-Phe-Pro-OH with 1-amino-6-(aminomethyl)isoquinoline hydrochloride (74c). Amorphous solid. FAB-MS: m/e=631.

77f. N—(HOOCCH$_2$)-D-Phe-Pro-6-Aiq TFA

The Boc-group and t-butyl ester of N-Boc-N-(t-butyloxycarbonylmethyl)-D-Phe-Pro-6-Aiq were removed as described in example 74f, and the title compound was obtained as an amorphous solid. FAB-MS: m/e=475.

Example 78

N-(carboxymethyl)-D-cyclohexylalanyl-N-[(1-amino-6-isoquinolinyl)methyl]-(N-cyclopentyl-glycin)-amide trifluoroacetate (N—(HOOCCH$_2$)-D-Cha-N-cyclopentyl-Gly6-Aiq TFA) (78b)

78a. N-Boc-N-(t-butyloxycarbonylmethyl)-D-Cha-N-cyclopentyl-Gly-6-Aiq

In the manner described in example 74e, N-Boc-N-(t-butyloxycarbonylmethyl)-D-Cha-N-cyclopentyl-Gly-6-Aiq was obtained by the reaction of N-Boc-N-(t-butyloxycarbonylmethyl)-D-Cha-N-cyclopentyl-Gly-OH (73i) with 1-amino-6-(aminomethyl)isoquinoline hydrochloride (74c). Amorphous solid. FAB-MS: m/e=665.

78b. N—(HOOCCH$_2$)-D-Cha-N-cyclopentyl-Gly-6-Aiq TFA

The Boc-group and the t-butyl group were removed as described in example 74f, and the title compound was obtained as an amorphous solid. FAB-MS: m/e=509.

Example 79

N-(carboxymethyl)-D-cyclohexylalanyl-N-[(1-amino-6-isoquinolinyl)methyl]-(N-cyclohexyl-glycin)-amide trifluoroacetate (N—(HOOCCH$_2$)-D-Cha-N-cyclohexyl-Gly-6-Aiq TFA)(79e)

79a. N-Cyclohexyl-Gly-OMe was prepared from cyclohexanone (36.9 g) and H-Gly-OMe HCl (46.4 g) in 400 mL of methanol analogously to 73d to give 23.4 g of an oil. MS (m/e)=171 [M+].

79b. N-Boc-N-(t-butyloxycarbonylmethyl)-D-Cha-N-cyclohexyl-Gly-OMe was prepared from N-cyclohexyl-Gly-OMe and N-Boc-N-(t-butyloxycarbonylmethyl)-D-Cha-OH analogously to 73h.

79c. N-Boc-N-(t-butyloxycarbonylmethyl)-D-Cha-N-cyclohexyl-Gly-OH was prepared from N-Boc-N-(t-butyloxycarbonylmethyl)-D-Cha-(N-cyclohexyl)-Gly-OMe analogously to 73l.

79d. N-Boc-N-(t-butyloxycarbonylmethyl)-D-Cha-N-cyclohexyl-Gly-6-Aiq

In the manner described in example 74e, N-Boc-N-(t-butyloxycarbonylmethyl)-D-Cha-N-cyclohexyl-Gly-6-Aiq was obtained by the reaction of N-Boc-N-(t-butyloxycarbonylmethyl)-D-Cha-N-cyclohexyl-Gly-OH with 1-amino-6-(aminomethyl)isoquinoline hydrochloride (74c). Amorphous solid. FAB-MS: m/e=679.

79e. N—(HOOCCH$_2$)-D-Cha-(N-cyclohexyl)Gly-6-Aiq TFA

The Boc-group and the t-butyl group were removed as described in example 74f, and the title compound was obtained as an amorphous solid. Mp. 99° C. (dec.); FAB-MS: m/e=523.

Example 80

N-(carboxymethyl)-D-cyclohexylalanyl)-N-[(4-aminothieno[3,2c]pyridin-2-yl)-methyl]-L-prolinamide.hydrochloride (N—(HOOCCH$_2$)-D-Cha-Pro-Atp.HCl)

(step 1; coupling of the fist amino acid to Kaiser oxim resin). N-Boc-Pro-OH, (1.7 g, 8.0 mmol) and N,N'-dicyclohexylcarbodiimide (0.83 g, 4.0 mmol) in dichloromethane (20 mL) were stirred for 1 hour at 0 deg., the precipitate was removed and the solution was added to Kaiser oxim resin (1.0 g, 1.0 mmol, swollen in dichloromethane for 2 hours prior to the addition of the activated proline derivative). The resin was shaken for 16 h, the solvent was removed, the resin was washed with dichoromethane and diethyl ether (3 times each) and air dried.

(step 2; deprotection). 200 mg of the N-Boc-Pro-coupled resin was swollen for 2 hours in dichloromethane (2 ml). 4 mL of 25% trifluoroacetic acid in dichloromethane was added and shaken for 2 hours at room temperature. The solvent was removed, the resin was washed with dichloromethane, methanol, and diethylether, and air dried.

(step 3; coupling to the second amino acid) 134 mg of the resin from step 2 was swollen in N,N-dimethylformamide for 30 min. The solvent was removed, and a solution of 142 mg N-Boc-N-t-butyloxycarbonylmethyl)-D-Cha-OH, 118 mg TBTU and 0,04 mL N-methyl morpholine were added to the resin. The mixture was shaken for 16 h, the solvent was removed and the resin was washed with N,N-dimethylformamide, methanol, and diethylether.

(step 4; cleavage of the product from the resin using an amine). 150 mg (0.1 mmol) of the resin from step 3 was swollen in dichloromethane for 2 h. The solvent was removed, a mixture of 4-amino-2-(aminomethyl)thieno[3,2c]pyridine hydrochloride (73c.) (67 mg, 0.3 mmol) and N,N-diisopropylethylamine (0.3 mL) in dichloromethane (2–7 mL) was added to the resin. The mixture was shaken for 16 hours the solvent was removed and collected, the resin was washed with dichloromethane (1 mL). The solutions were combined, the solvent was removed i.vac., the residue was dissolved in ethyl acetate and extracted with phosphated buffer (pH=7.0). The organic phase was collected, dried (magnesium sulfate), filtered, and the solvent was removed to give N-Boc-N-(t-butyloxycarbonylmethyl)-D-Cha-Pro-Atp (11 mg, 17%), FAB-MS, m/e=643 [M+].

(step 5; deprotection). The product from step 4 was dissolved in 0.5 mL 4 M HCl in dioxane and kept at 5 deg for 16 h. The solvent was removed i.vac., and the product triturated with diethylether to give 5 mg (62%) of the target compound. Mp 170 deg (dec); FAB-MS (m/e) 487 [M+].

Example 81

3-[4-[[3-(4-Aminothieno[3,2c]pyridin-2-yl)acryloyl](methyl)amino]piperidin-1-yl]-3-oxopropionic acid methyl ester 81a. 3-[4-(Benzoylamino)thieno[3,2c]pyridin-2-yl] acrylic acid A mixture of N-(2-formylthieno[3,2c]pyridin-4-yl) benzamide (3d 5.2 g, 18.5 mmol), malonic acid (3.83 g, 36.8 mmol), and piperidine (0.73 mL, 7.4 mmol) in 57 mL of pyridine was heated at 105° C. during 5.5 hours. After evaporation of pyridine, water was added and 0.1 N hydrochloric acid until pH=3. The precipitate formed was collected by filtration, washed with water and acetone to yield a yellow compound (3.9 g).

81b. 3-(4-Aminothieno[3.2c]pyridin-2-yl)acrylic acid

A solution of 3-[4-(benzoylamino)thieno[3,2c]pyridin-2-yl]acrylic acid (3.9 g, 12 mmol) in 4 N hydrochloric acid (760 mL) and acetic acid (240 mL) was heated at reflux during 20 hours. The reaction mixture was cooled, then the precipitate formed was filtered off and washed with diethyl ether, and dried under vacuum to yield the title compound (2.3 g).

81c. 3-Oxo-3-(4-oxopiperidin-1-yl)pronionic acid methyl ester

To a solution of 4-piperidone monohydrate, hydrochloride (30.7 g; 0.2 mol), sodium carbonate (42 g; 0.4 mol) in water (160 mL) was added dichloromethane (500 mL). The mixture was stirred at room temperature and a solution of methyl malonylchloride (26 ml; 1.2 eq) in dichloromethane (100 mL) was added dropwise at room temperature, keeping the temperature of the reaction mixture below 30° C. The pH was maintained at 8 at the end of the addition. The mixture was stirred 4 hours at room temperature. The residue was extracted twice with dichloromethane, dried over magnesium sulfate and evaporate to yield the title compound (37.4 g).

81d. 3-(4-(Methylamino)piperidin-1-yl)-3-oxopropionic acid methyl ester hydrochloride To a solution of methylamine hydrochloride (67.5 g, 10 eq) in methanol (520 mL) was added a solution of 3-oxo-3-(4-oxopiperidin-1-yl)propionic acid methyl ester (20 g; 0.1 mol) in methanol (170 mL) and stepwise sodium cyanoborohydride (powder; 5.03 g, 0.08 mol). The reaction mixture was stirred 24 hours at room temperature. After addition of a saturated water solution of sodium carbonate, the residue was evaporated and extracted with dichloromethane. The organic phase was dried and evaporated to yield the crude 3-(4-(methylamino)piperidin-1-yl)-3-oxopropionic acid methyl ester (11.6 g) which was converted to the hydrochloride with hydrogen chloride in ethyl acetate/methanol.

81e. 3-[4-[[3-(4-Aminothieno[3,2c]pyridin-2-yl)acryloyl](methyl)amino]piperidin-1-yl]-3-oxopropionic acid methyl ester To a solution of 3-(4-aminothieno[3,2c]pyridin-2-yl)acrylic acid (1 g, 3.9 mmol) in 110 mL of N,N-dimethylformamide, under nitrogen, was added N-ethylmorpholine (1.5 mL, 11.7 mmol), hydroxybenzotriazole (0.53 g, 3.9 mmol) followed by 3-(4-(methylamino) piperidin-1-yl)-3-oxopropionic acid methyl ester hydrochloride (0.98, g, 3.9 mmol) and N'-(3-dimethylaminopropyl)-N-ethyl carbodiimide hydrochloride (EDC). The reaction mixture was stirred at room temperature during 4 hours. After evaporation of N,N-dimethylformamide under reduced pressure, the residue was dissolved in 200 mL of dichloromethane. The organic phase was washed water, saturated sodium hydrogencarbonate and water, dried with magnesium sulfate, and evaporated to yield the pure the title compound after several washing with diethyl ether, and drying under vacuum (600 mg). m.p.=130° C.

Calculated % C, 57.58; H, 5.81; N, 13.44;
Found % C, 55.78; H, 5.84; N, 13.05.

Example 82

3-[4-[[3-(4-Aminothieno[3,2c]pyridin-2-yl)acryloyl](methyl)amino]piperidin-1-yl]-3-oxopropionic acid dihydrochloride A solution of 3-[4-[[3-(4-aminothieno[3,2c]pyridin-2-yl) acryloyl](methyl)amino]piperidin-1-yl]-3-oxopropionic acid methyl ester (0.1 g, 2.4 mmol) in 3N hydrochloric acid (10 mL) was stirred during 24 hours at room temperature. Hydrochloric phase was evaporated under pressure. The residue was triturated with acetone, to yield the title compound as crystals, which were dried under vacuum with $P_2O_5$. (80 mg). m.p.=200° C.

Calculated % C, 48.00; H, 5.09; N, 11.79;
Found % C, 47.73; H, 5.12; N, 11.59.

Example 83

3-(4-{[3-(1-amino-6-isoquinolinyl)-acryloyl](methyl)amino]piperidin-1-yl)-3-oxo-propionic acid methyl ester Using the method described in example 81a N-(6-formyl-1-isoquinolinyl)benzamide (1f) was transformed into 3-(1-(benzylamino)-6-isoquinolinyl)acrylic acid. This compound was used to prepare 3-(1-amino-6-isoquinolinyl)acrylic acid according to the procedure described in example 81b. Reaction of 3-(1-amino-6-isoquinolinyl)acrylic acid with 3-(4-(methylamino)piperidin-1-yl)-3-oxopropionic acid methyl ester hydrochloride according to the procedures described in example 81e yielded the title compound. NMR (CDCl$_3$) δ: 1.8 (4H, m), 2.7 (1H, m), 3.0 (3H, s), 3.2 (1H, m), 3.5 (2H, d), 3.7 (3H, s), 3.9 (1H, br d), 4.8 (2H, m), 4.9 (2H, br s), 7.0 (1H, d), 7.5 (1H, d), 7.65 (1H, d), 7.8 (3H, m), 8.0 (1H, d).

Example 84

3-(4-{[3-(1-amino-6-isoquinolinyl)acryloyl](methyl) amino]piperidin-1-yl}-3-oxo-propionic acid hydrochloride The method is the same as in example 82 but starting from 3-(4-{[3-(1-amino-6-isoquinolinyl)-acryloyl](methyl) amino]piperidin-1-yl)-3-oxo-propionic acid methyl ester (Example 83) NMR (DMSO) δ: 1.8 (4 H, m), 2.7–3.4 (5H, m+2s), 3.5 (2H, s), 3.9 (1H, br d), 4.3–4.9 (2H, m+br d), 7.1–8.9 (7H, m), 9.4 (2H, br s), 13.4 (1H, br s)

Example 85

(7-Methoxynaphthalen-2-yl)sulfonic acid {1-[1-amino-7-isoquinolinylmethyl]-2-oxopyrrolidin-3-(S)-yl}amide hydrochloride (85j.)

85a. 7-Methoxy-isoquinoline

Aminoacetaldehyde dimethyl acetal (81.9 mL) was added to a solution of 60.8 mL of 3-methoxy-benzaldehyde in 600 mL of toluene. The mixture was refluxed for 5 h using a Dean-Stark trap and subsequently cooled to 5° C. In a nitrogene atmosphere trifluoroacetic acid anhydride (209 mL) and borontrifluoride etherate (185 mL) were added in succession at such a rate, that the internal temperature was kept below 1° C. After stirring for 3 days at room temperature the the reaction mixture was poured on ice, 250 mL 2 N hydrochloric acid added and the organic layer extracted with 1 N hydrochloric acid. The pH value of the combined aqueous extracts was adjusted to pH 9 by adding concentrated aqueous ammonia. Extraction with ethyl acetate, followed by drying and removal of the solvent in vacuo gave 66.9 g (84%) of the title compound as a light brownish oil. EI-MS: 159 ($M^+$).

85b. 7-Methoxy-isoquinoline-N-oxide hydrochloride

At room temperature 58 g of m-chloroperoxybenzoic acid (purity 75%) were added in portions to a stirred solution of 7-methoxy-isoquinoline (35.9 g) in 500 mL of dichloromethane. Stirring was continued for 3 hours and subsequently methanol (400 mL) was added. The bulk was reduced to 300 mL and 325 mL of a saturated solution of hydrogen chloride in diethyl ether were added. Dilution with 600 mL of diethyl ether afforded precipitation of yellow crystals, which were separated by filtration, washed with chilled diethyl ether and dried in vacuo. Yield: 41.3 g (87%); m.p. 185–187° C.; (+)-FAB-MS: 176 ($MH^+$-HCl).

85c. 1-Chloro-7-methoxy-isoquinoline

7-Methoxy-isoquinoline-N-oxide hydrochloride (38.2 g) was added in portions to phosphoryl chloride (275 mL) and the mixture heated at 90° C. for 6 h. Excess of phosphoryl chloride was removed in vacuo. The remaining white solid was washed with water, filtered and dried in vacuo.

Yield: 28.3 g (81%), m.p. 77–78° C.

85d. 7-Methoxy-isoquinolin-1-ylamine

Liquid ammonia (220 mL) was added to a solution of 32.8 g of 1-chloro-7-methoxy-isoquinoline in 420 mL of ethanol in a steel vessel. Nitrogen was pressed upon until an initial pressure of 20 atm. was obtained. This reaction mixture was heated for 2 days at 170° C. The solvent was removed in vacuo and the residue dissolved in water. The pH value was adjusted to pH 10 by adding aqueous sodium carbonate solution, followed by extraction with ethyl acetate. The organic extract was washed with brine and dried ($Na_2SO_4$). Evaporation of the solvent in vacuo gave pure 7-methoxy-isoquinolin-1-ylamine as a white solid. Yield 24.0 g (81%); m.p. 128–130° C.

85e. 1-Amino-isoquinolin-7-ol

Boron tribromide (3 5 mL) in 50 mL of dichloromethane was added dropwise to a stirred solution of 7-methoxy-isoquinolin-1-ylamine (21.6 g) in 70 mL of dichloromethane at 10° C. After stirring for 4 d at ambient temperature the reaction mixture was poured on ice and the pH adjusted to pH 9 by adding concentrated aqueous ammonia. The precipitated material was collected by filtration and dried in vacuo to give 19.3 g (97%) of the title compound as a light brownish solid. M.p. 260° C. (decomp.); EI-MS: 160 ($M^+$).

85f. Trifluoro-methanesulfonic acid 1-amino-isoquinolin-7-yl ester

A mixture of 20.0 g of 1-amino-isoquinolin-7-ol and 67.2 g of N-phenyl-bis(trifluoromethane-sulfonimid) in 300 mL of dichloromethane and 300 mL of dioxane was cooled in an ice bath and 26.9 mL of N,N-diisopropylethylamine added dropwise. The resulting mixture was heated for 24 h at 70° C., after which the volatiles were removed in vacuo. The remaining residue was dissolved in ethyl acetate, washed with successive portions of 2N NaOH, water and brine and dried ($Na_2SO_4$). Filtration and concentration afforded a colourless oil, which was purified by silica chromatography (ethyl acetate/isohexane=3/7, 4/6, 5/5, 6/4, 7/3) yielding 35.4 g (92%) of the title compound as yellow crystals. M.p. 115–118° C.; EI-MS: 292 ($M^+$).

85g. 1-Amino-isoquinoline-7-carbonitrile

Palladium acetate (0.9 g) was added to a heated mixture of trifluoromethanesulfonic acid 1-amino-isoquinolin-7-yl ester (5.8 g), zinc cyanide (2.3 g) and triphenylphosphine (1.0 g) in 75 mL of N-methyl-pyrrolidone at 190° C. (exothermic!). Stirring was continued at 190° C. for 2 h. Precipitated material was removed by filtration and discarded. Ethyl acetate was added and the organic mixture washed with 2N aqueous ammonia, water and brine and dried ($Na_2SO_4$). Filtration and concentration afforded a brownish oil, which was purified by silica chromatography (ethyl acetate/isohexane=3/7, 4/6, 5/5, 6/4, 7/3, 8/2) to give 3.2 g (94%) of the title compound as yellow crystals. M.p. 183–186° C.

85h. 1-amino-7-(aminomethyl)isoquinoline

Liquid ammonia (210 mL) was added to a mixture of 4.2 g of 1-amino-isoquinoline-7-carbonitrile and 4.0 g of Raney-Ni in 210 mL of methanol in a steel vessel Hydrogen was pressed upon until an initial pressure of 100 atm. was obtained. This mixture was reacted for 16 hours at ambient temperature, the catalyst subsequently removed by filtration and the solvent pumped off. The residue was purified by silica chromatography (methanol/ammonia saturated methanol=85:15, 8:2) yielding 1.1 g (25%) of the title compound as a light yellow solid. M.p. 114–117° C.

85i. [1-(1-amino-7-isoquinolinylmethyl)-2-oxopryrrolidin-3-(S)yl]carbamic acid tert-butyl ester To a solution of 0.3 g of Boc-L-Asp(H)-OBn (WO 96/40679) dissolved in 2 mL methanol was added 176 mg of 1-amino-7-(aminomethyl)isoquinoline. After stirring for 30 minutes, a solution of 80 mg sodium cyanoborohydride and 90 mg zinc chloride in 2 mL methanol was added. The mixture was stirred for an additional two hours. After this time, 7 mL of an aqueous 0.2 N sodium hydroxide solution was added and the resulting mixture was concentrated. The residue was treated with 100 mL dichloromethane and 10 mL water, filtered and an additional 100 mL water was added to the filtrate. The organic layer was separated and washed with aqueous 5% sodium hydrogencarbonate and brine. All aqueous layers were washed twice with dichloromethane. The combined organic layers were dried over sodium sulfate and concentrated. The residue was purified by column chromatography on silica gel eluting with a gradient of ethyl acetate/dichloromethane/methanol=10/10/1 to dichloromethane/methanol 10/1 to give 146 mg of the title compound.

Rf=0.3 in ethyl acetate/dichloromethane/methanol=10/10/2 (v/v) on silica.

85j. (7-Methoxynaphthalen-2-yl)sulfonic acid {1-[1-amino-7-isoquinolinylmethyl]-2-oxopyrrolidin-3-(S)-yl}amide hydrochloride To a stirred solution of 146 mg of [1-(1-amino-7-isoquinolinylmethyl)-2-oxopyrrolidin-3-(S)yl]carbamic acid tert-butyl ester in 2 mL dichloromethane and 0.1 mL methanol was added 5 mL of a 3M hydrogenchloride solution in dioxane. After stirring for 50 minutes at room temperature the mixture was concentrated. To the residue was added 10 mL dichloromethane, 0.285 mL N,N-diisopropylethylamine and 118 mg 7-methoxynaphthalen-2-ylsulfonyl chloride and stirred at room temperature for 16 hours. Dichloromethane was added and the mixture was extracted with aqueous 5% sodium hydrogencarbonate and brine. Both aqueous extracts were washed with dichloromethane and the combined dichloromethane extracts were dried over sodium sulfate and concentrated. The residue was purified by column chromatography on silica gel eluting with ethyl acetate/dichloromethane/methanol=10/10/2 to give the free base. This free base was dissolved in tert-butanol, one equivalent hydrochloric acid was added and lyophilisation gave 90 mg of the title compound.

MS ESI+: 477 (M+H).

Example 86

(7-Methoxynaphthalen-2-yl)sulfonic acid {1-[(4-amino-furo[3,2-c]pyridin-2-yl)methyl]-2-oxopyrrolidin-3-(S)-yl}amide hydrochloride (86f.)

86a. Furo[3,2-c]pyridin-4-ylamine

The procedure described to prepare 7-methoxyisoquinolin-1-ylamine was used to convert 15.3 g of 4-chloro-furo[3,2-c]pyridine into 12.2 g of the title compound as a brownish solid. m.p. 122–124° C.; EI-MS: 134 (M+).

86b. 2-Iodo-furo[3,2-c]pyridin-4-ylamine

Furo[3,2-c]pyridin-4-ylamine (7.8 g) was dissolved in 175 mL of glacial acetic acid and sodium acetate (14.3 g) added in portions (exothermic!). Subsequently a solution of iodine (44.2 g) in 150 mL of tetrahydrofuran was added dropwise and the resulting mixture allowed to stir for 4 d at ambient temperature. The mixture was poured on ice and the pH value adjusted to pH 10 by adding 10 N sodium hydroxide solution, followed by extraction with ethyl acetate. The organic extract was washed several times with sodium thiosulfate solution and brine, dried (Na$_2$SO$_4$) and concentrated. The crude product was purified by silica chromatography (ethyl acetate/isohexane=5/5, 7.5/2.5, 10/0) to give 10.3 g (68%) of the title compound as a brownish solid. M.p. 170–173° C.; EI-MS: 260 (M+).

86c. 4-Amino-furo[3,2-c]pyridine-2-carbonitrile

This compound was prepared from 2-iodo-furo[3,2-c]pyridin-4-ylamine (5.2 g), zinc cyanide (3.6 g), triphenylphosphine (2.1 g) and palladium acetate (1.8 g) in 75 mL of N-methyl-pyrrolidone using the procedure described for 1-amino-isoquinoline-7-carbonitrile. Yield: 2.0 g (64%); yellow solid; m.p. 280° C. (decomp.).

86d. 4-Amino-2-(aminomethyl)furo[3,2-c]pyridine

This compound was prepared from 4-amino-furo[3,2-c]pyridine-2-carbonitrile (5.7 g), using the procedure described for 1-amino-7-(aminomethyl)isoquinoline. Yield: 3.5 g (60%); yellow crystals; m.p. 142–144° C., EI-MS: 163 (M+).

86e. [1-((4-amino-furo[3,2-c]pyridin-2-yl)methylamino)-2-oxopyrrolidin-3-(S)yl]carbamic acid tert-butyl ester Using the procedure described in example 85i 166 mg of 4-amino-2-(aminomethyl)furo[3,2-c]pyridine was transformed into 150 mg of the title compound. MS ESI+: 347 (M+H).

86f. (7-Methoxynaphthalen-2-yl)sulfonic acid {1-[(4-amino-furo[3,2-c]pyridin-2-yl)methyl]-2-oxopyrrolidin-3-(S)-yl}amide hydrochloride Using the procedure described in example 85j 150 mg of [1-((4-amino-furo[3,2-c]pyridin-2-yl)methylamino)-2-oxopyrrolidin-3-(S)yl]carbamic acid tert-butyl ester was transformed into 110 mg of the title compound. MS ESI+: 467 (M+H).

Example 87

(7-Methoxynaphthalen-2-yl)sulfonic acid {1-[1-amino-6-isoquinolinylmethyl]-2-oxopyrrolidin-3-(S)-yl}amide hydrochloride Using the procedure described in example 85 176 mg of 1-amino-6-(aminomethyl)isoquinoline as transformed into 81 mg of the title compound. MS ESI+: 477 (M+H).

Example 88

(7-Methoxynaphthalen-2-yl)sulfonic acid {1-[(4-amino-thieno[3,2-c]pyridin-2-yl)methyl]-2-oxopyrrolidin-3-(S)-yl}amide hydrochloride Using the procedure described in example 85 184 mg of 4-amino-2-(aminomethyl)thieno[3,2-c]pyridine was transformed into 222 mg of the title compound. MS ESI+: 483 (M+H).

Example 89

1-Amino-6-[(2-(3-(cyclohexylmethylsulfonylamino)-6-methyl2-oxo-1,2-dihydropyridinyl)-1-oxo-ethyl)aminomethyl]isoquinoline hydrochloride (89b.)

89a. [3-(cyclohexylmethylsulfonylamino)-6-methyl-2-oxo-1,2-dihydropyridinyl]-acetic acid To a stirred solution of 0.71 g of tert-butyl [3-amino-6-methyl-2-oxo-1,2-dihydropyridinyl]-acetate (WO 97/01338) at 0° C. under a nitrogen atmosphere was added 0.60 mL cyclohexyl-methanesulfonyl chloride (J. F. King et al J. Am. Chem. Soc. 114, 1743 (1992)). After stirring at room temperature for 3 hours the reaction mixture was concentrated. The residue was dissolved in ethyl acetate, washed successively with 0.1 N hydrochloric acid, water and brine, dried over sodium sulphate and concentrated. The residue was dissolved in a mixture of 0.2 mL water and 1.8 mL trifluoroacetic acid. After stirring at room temperature for 4 h, water and ethyl acetate were added. The organic layer was separated, washed twice with 0.1 N hydrochloric acid, dried over sodium sulphate and concentrated. The solid residue was washed with a cold dichloromethane/diethyl ether mixture to give 0.72 g of the title compound.

TLC: Rf=0.25, dichloromethane/methanol=9/1 v/v on silica.

89b. 1-Amino-6-[(2-(3-(cyclohexylmethylsulfonylamino)-6-methyl-2-oxo-1,2-dihydropyridinyl)-1-oxo-ethyl)aminomethyl]isoquinoline hydrochloride To a stirred solution of 0.14 g of [3-(cyclohexylmethylsulfonylamino)-6-methyl-2-oxo-1,2-dihydropyridinyl]-acetic acid and 0.07 g of 1-amino-6-(aminomethyl)isoquinoline in 5 mL dichloromethane and 2 mL N,N-dimethylformamide was added 0.19 g 2-(1H-benzotriazol-1-yl)-1,1,3,3-tetramethyluronium tetrafluoroborate (TBTU). After 16 h at room temperature additional 50 mg TBTU and 0.10 mL N-methylmorpholine were added and the mixture was stirred at room temperature for an additional 16 h. Dichloromethane was added and the reaction mixture was washed with aqueous saturated sodium hydrogencarbonate and water. Both aqueous washes were extracted three times with dichloromethane. The combined organic phases were dried over sodium sulphate and concentrated. The residue was purified by chromatography on silica gel (eluent: dichloromethane/methanol=9/1 v/v) to yield the free base. This free base was dissolved in a mixture of t-butanol/water=1/1 (v/v) and one equivalent hydrochloric acid was added. Lyophilisation yielded 135 mg of the title compound. MS ESI+: 498 (M+H).

Example 90

1-Amino-6-[(2-(3-(benzylsulfonylamino)-6-methyl-2-oxo-1,2-dihydropyridinyl)-1-oxo-ethyl)aminomethyl]isoquinoline hydrochloride (89b.)

The procedure described in example 89 was used to convert 168mg of [3-(benzylsulfonylamino)-6-methyl-2-oxo-1,2-dihydropyridinyl]-acetic acid (WO 97/01338) into 99 mg of the title compound. MS ESI+: 492 (M+H).

Example 91

(2-{2-(S)-[(1-Amino-isoquinolin-6-ylmethyl)-carbamoyl]-pyrrolidine-1-yl}-2-oxo-1-(R)- phenyl-ethyl)-carbamic acid isopropyl ester hydroacetate (91d)

91a. (R)-Isopropoxy-carbonylamino-phenyl-acetic acid

A mixture of (D)-phenylglycine (5.0 g) in 66 mL of 1 N NaOH was cooled in an ice bath, 33 mL of isopropyl chloroformate (1 M solution in toluene) added dropwise and the resulting mixture was stirred for 16 h at ambient temperature. After adding aqueous NaOH (pH 11) the organic layer was discarded. $KHSO_4$ was added and the acidified aqueous solution extracted with ethyl acetate several times. Evaporation of the solvent in vacuo gave pure (R)-isopropoxy-carbonylamino-phenyl-acetic acid. Yield: 6.3 g (81%); white solid; m.p. 123–127° C.; (−)-APCI-MS: 236 ([M-H]−).

91b. 1-[(R)-Isopropoxycarbonylamino-phenyl-acetyl]-pyrrolidine-2-(S)-carboxylic acid methyl ester A mixture of (R)-Isopropoxycarbonylamino-phenyl-acetic acid (0.74 g), (L)-proline methyl ester hydrochloride (0.51 g), N-methyl morpholine (1.00 mL) and 1.00 g of 2-(1H-benzotriazole-1-yl)-1,1,3,3-tetramethyluronium tetrafluoroborate (TBTU) in 10 mL of dry N,N-dimethyl formamide was stirred for 3 h at ambient temperature. The volatiles were pumped off and water was added followed by extraction with ethyl acetate and concentration of the organic layer. The remaining residue was purified by silica chromatography (ethyl acetate:isohexane=3/1) to give 0.95 g (91%) of the title compound as a colorless oil. (+)-APCI-MS: 349 (MH+).

91c. 1-[(R)-Isopropoxycarbonylamino-phenyl-acetyl]-pyrrolidine-2-(S)-carboxylic acid A mixture of 1-[(R)-isopropoxycarbonylamino-phenyl-acetyl]-pyrrolidine-2-(S)-carboxylic acid methyl ester (0.95 g) and 0.13 g of LiOH in 20 mL of methanol and 5 mL of water was stirred for 16 h at ambient temperature. $KHSO_4$ was added, the volatiles were pumped off followed by addition of water, extraction with ethyl acetate and concentration of the organic layer to give 0.76 g (83%) of the title compound as a white solid. (+)-APCI-MS: 335 (MH+).

91d. (2-{2-(S)-[(1-Amino-isoquinolin-6-ylmethyl)-carbamoyl]-pyrrolidine-1-yl}-2-oxo-1-(R)-phenyl-ethyl)-carbamic acid isopropyl ester hydroacetate A mixture of 1-[(R)-isopropoxycarbonylamino-phenyl-acetyl]-pyrrolidine-2-(S)-carboxylic acid (0.20 g), 6-aminomethyl-isoquinolin-1-ylamine (0.6 mmol), N-methyl morpholine (0.2 mL) and 0.19 g of 2-(1H-benzotriazole-1-yl)-1,1,3,3-tetramethyluronium tetrafluoroborate (TBTU) in 3 mL of dry N,N-dimethyl formamide was stirred for 3 h at ambient temperature. 0.120 mL $CH_3COOH$ were added, the mixture was concentrated and the remaining residue was purified by HPLC (RP-18; $H_2O$/$CH_3OH$ 95/5→0/100) to give 0.10 g (35%) of the title compound as a colorless oil. (+)-APCI-MS: 490 (MH+).

Example 92

(1-(R)-{2-(S)-[(1-Amino-isoquinolin-6-ylmethyl)-carbamoyl]-pyrrolidine-1-carbonyl}-2-isopropyl-sulfanyl-2-methyl-propyl)-carbamic acid ethyl ester hydroacetate (92e)

92a. 2-(R)-Amino-3-isopropylsulfanyl-3-methyl-butyric acid

NaH (1.3 g) was added in portions to 70 mL ethanol while cooling. Subsequently D-penicillamine (4.0 g) was added. The mixture kept stirring for 5 minutes at 5° C., after which isopropyl iodide (2.8 mL) was added. The mixture was allowed to stir 16 h at ambient temperature. 2 N HCl was added followed by evaporation of the volatiles to give 11.9 g crude 2-(R)-amino-3-isopropylsulfanyl-3-methyl-butyric acid, which was used in the next step without further purification.

92b. 2-(R)-Ethoxycarbonylamino-3-isopropylsulfanyl-3-methyl-butyric acid 2-(R)-Amino-3-isopropylsulfanyl-3-methyl-butyric acid (approx. 27 mmol; crude material from the previous step) was dissolved in 40 mL of water and 40 mL of dioxane and pH 9.5 was adjusted by adding aqueous NaOH. Ethyl chloroformate (3.3 mL) was slowly added at 5° C. while maintaining pH 9.5 by addition of the appropriate amount of aqueous NaOH. Stirring was continued for 6 h at room temperature. Aqueous NaOH was added (pH 11) and the dioxane removed in vacuo followed by extraction of the remaining aqueous solution with ethyl acetate. $KHSO_4$ was added and the acidified aqueous solution extracted with ethyl acetate several times. Evaporation of the solvent in vacuo gave a yellow oil, which was purified by HPLC (RP-18; pH 2.3; $H_2O/CH_3OH$ 3/7) to give 1.50 g (21%) of the title compound as a colorless oil. (+)-APCI-MS: 264 (MH$^-$).

92c. 1-[2-(R)-Ethoxycarbonylamino-3-isopropylsulfanyl-3-methyl-butyryl-]-pyrrolidine-2-(S)-carboxylic acid methyl ester A mixture of (L)-proline methyl ester hydrochloride (0.28 g), 2-(R)-ethoxycarbonylamino-3-isopropylsulfanyl-3-methyl-butyric acid (0.44 g), N-methyl morpholine (0.73 mL) and 0.54 g of 2-(1H-benzotriazole-1-yl)-1,1,3,3-tetramethyluronium tetrafluoroborate (TBTU) in 10 mL of dry N,N-dimethylformamide was stirred for 16 h at ambient temperature. The volatiles were pumped off and water was added followed by extraction with ethyl acetate and concentration of the organic layer. The remaining residue was purified by silica chromatography (ethyl acetate/isohexane= 1/1) to give 0.45 g (72%) of the title compound as a colorless oil. (+)-APCI-MS: 375 (MH$^+$).

92d. 1-[2-(R)-Ethoxycarbonylamino-3-isopropylsulfanyl-3-methyl-butyryl]-pyrroidine-2-(S)-carboxylic acid A mixture of 1-[2-(R)-ethoxycarbonylamino-3-isopropylsulfanyl-3-methyl-butyryl-]-pyrrolidine-2-(S)-carboxylic acid methyl ester (0.45 g) and 0.06 g of LiOH in 6 mL of methanol and 1 mL of water was stirred for 16 h at ambient temperature. $KHSO_4$ was added, the volatiles were pumped off followed by addition of water, extraction with ethyl acetate and concentration of the organic layer to give 0.34 g (79%) of the title compound as a colorless oil. (+)-APCI-MS: 361 (MH$^+$).

92e. (1-(R)-{2-(S)-[(1-Amino-isoquinolin-6-ylmethyl)-carbamoyl]-pyrrolidine-1-carbonyl}2-isopropylsulfanyl-2-methyl-propyl)-carbamic acid ethyl ester hydroacetate A mixture of 1-[2-(R)-ethoxycarbonylamino-3-isopropylsulfanyl-3-methyl-butyryl]-pyrrolidine-2-(S)-carboxylic acid (0.160 g), 6-aminomethyl-isoquinolin-1-ylamine (0.078 g), N-methyl morpholine (0.14 mL) and 0.14 g of 2-(1H-benzotriazole-1-yl)-1,1,3,3-tetramethyluronium tetrafluoroborate (TBTU) in 3 mL of dry N,N-dimethyl formamide was stirred for 3 h at ambient temperature. 0.100 mL $CH_3COOH$ were added, the mixture was concentrated and the remaining residue was purified by HPLC (RP-18; $H_2O/CH_3OH$ 95/5→0/100) to give 0.17 g (66%) of the title compound as a colorless oil. (+)-APCI-MS: 516 (MH$^+$).

Example 93

(2-{2-(S-)-[(1-Amino-isoquinolin-6-ylmethyl)-carbamoyl]-pyrrolidine-1-yl}-2-oxo-1-(R)-phenyl-ethyl)-carbamic acid isobutylester hydroacetate (93d)

93a. (R)-Isobutoxy-carbonylamino-phenyl-acetic acid

The procedure described for example 91a was used. Reaction of 2.0 g of (D)-phenylglycine and 2.0 mL of isobutyl chloroformate gave 0.4 g (12%) of the title compound as a colorless oil. (−)-APCI-MS: 250 ([M-H]$^-$).

93b. 1-[(R)-Isobutoxycarbonylamino-phenyl-acetyl]-pyrrolidine-2-(S)-carboxylic acid methyl ester The procedure described for example 91b was used. From 0.40 g of (R)-isobutoxycarbonylamino-phenyl-acetic acid and 0.26 g of (L)-proline methyl ester hydrochloride 0.45 g (78%) of the title compound was obtained as a colorless oil. (+)-APCI-MS: 363 (MH$^+$).

93c. 1-[(R)-Isobutoxycarbonylamino-phenyl-acetyl]-pyrrolidine-2-(S)-carboxylic acid Starting with 0.45 g of 1-[(R)-isobutoxycarbonylamino-phenyl-acetyl]-pyrrolidine-2-(S)-carboxylic acid methyl ester using the procedure described for example 91c gave 0.38 g (88%) of the title compound as a white solid. (+)-APCI-MS: 349 (MH$^+$).

93d. (2-{2-(S)-[(1-Amino-isoquinolin-6-ylmethyl)-carbamoyl]-pyrrolidine-1-yl}2-oxo-1-(R)-phenyl-ethyl)-carbamic acid isobutylester hydroacetate The procedure described in example 91d was used to transform 0.100 g of 1-[-(R)-isobutoxycarbonylamino-phenyl-acetyl)-pyrrolidine-2-(S)-carboxylic acid into 0.045 g (32%) of the title compound. (+)-APCI-MS: 504 (MH$^+$).

Example 94

(2-{2-(S)-(1-Amino-isoquinolin-6-ylmethyl)-carbamoyl]-pyrrolidine-1-yl}-2-oxo-1-(R)-phenyl-ethyl)-carbamic acid ethyl ester hydroacetate (94d)

94a. (R)-Ethoxy-carbonylamino-phenyl-acetic acid

The procedure described for example 91a was used. 2.0 g of (D)-phenylglycine as starting material gave 2.1 g (71%) of the title compound as a white solid, M.p. 143–150° C.; (−)-APCI-MS: 222 ([M-H]$^-$).

94b. 1-[(R)-Ethoxy carbonylamino-phenyl-acetyl]-pyrrolidine-2-(S)-carboxylic acid methyl ester Reaction of 2.0 g of (R)-ethoxycarbonylamino-phenyl-acetic acid and 1.50 g of (L)-proline methyl ester hydrochloride according to the procedure described for example 91b gave 1.70 g (57%) of the title compound as a colorless oil. (+)-APCI-MS: 335 (MH$^+$).

94c. 1-[(R)-Ethoxycarbonylamino-phenyl-acetyl]-pyrrolidine-2-(S)-carboxylic acid Saponification of 1.70 g of 1-[(R)-ethoxycarbonylamino-phenyl-acetyl]-pyrrolidine-2-(S)-carboxylic acid methyl ester according to the procedure described in example 91c gave 1.44 g (88%) of the title compound as a white solid. (m.p. 163–166° C.). (+)-APCI-MS: 321 (MH$^+$).

94d. (2-{2-(S)-[(1-Amino-isoquinolin-6-ylmethyl)-carbamoyl]-pyrrolidine-1-yl}2-oxo-1-(R)-phenyl-ethyl)-carbamic acid ethyl ester hydroacetate The procedure described for example 91d. was used to convert 0.35 g of 1-[(R)-ethoxycarbonylamino-phenyl-acetyl]-pyrrolidine-2-(S)-carboxylic acid into 0.31 g (53%) of the title compound. (+)-APCI-MS: 476 (MH$^+$).

Example 95

(1-(R)-{2-(S)-[(1-Amino-isoquinolin-6-ylmethyl)-carbamoyl]-pyrrolidine-1-carbonyl}-2-isopropylsulfanyl-2-methyl-propyl)-carbamic acid isopropyl ester hydroacetate (95d)

95a. 2-(R)-Isopropoxycarbonylamino-3-isopropylsulfanyl-3-methyl-butyric acid 2-(R)-Amino-3-isopropylsulfanyl-3-methyl-butyric acid (17 mmol; crude material obtained from D-penicillamine and isopropyl iodide) was dissolved in 40 mL of water and 40 mL of dioxane and pH 9.5 was adjusted by adding aqueous NaOH. Isopropyl chloroformate (22 mL; 1 M solution in toluene) was slowly added at 5° C. while maintaining pH 9.5 by addition of the appropriate amount of aqueous NaOH. Stirring was continued for 6 h at room temperature. Aqueous NaOH was added (pH 11) and the dioxane removed in vacuo followed by extraction of the remaining aqueous solution with ethyl acetate. KHSO$_4$ was added and the acidified aqueous solution extracted with ethyl acetate several times. Evaporation of the solvent in vacuo gave a yellow oil, which was purified by HPLC (RP-18; pH 2.3; H$_2$O/CH$_3$OH 3/7) to give 3.0 g (64%) of the title compound as a colorless oil. (−)-APCI-MS: 276 ([M-H]$^-$).

95b. 1-[2-(R)-Isopropoxycarbonylamino-3-isopropylsulfanyl-3-methyl-butyryl-]-pyrrolidine-2-(S)-carboxylic acid methyl ester Reaction of 0.54 g of (L)-proline methyl ester hydrochloride and 0.89 g of 2-(R)-isopropoxy-carbonylamino-3-isopropylsulfanyl-3-methyl-butyric acid according to the procedure described for example 91b afforded 1.10 g (88%) of the title compound as a colorless oil. (+)-APCI-MS: 389 (MH$^+$).

95c. 1-[2-(R)-Isopropoxycarbonylamino-3-isopropylsulfanyl-3-methyl-butyryl]-pyrrolidine-2-(S)-carboxylic acid Saponification of 1.10 g of 1-[2-(R)-isopropoxycarbonylamino-3-isopropylsulfanyl-3-methyl-butyryl-]-pyrrolidine-2-(S)-carboxylic acid methyl ester according to the procedure described in example 91c gave 0.59 g (79%) of the title compound as a white solid. M.p. 128–130° C.; (−)-APCI-MS: 373 ([M-H]$^-$).

95d. (1-(R)-{2-(S)-[(1-Amino-isoquinolin-6-ylmethyl)-carbamoyl]-pyrrolidine-1-carbonyl}-2-iso-propylsulfanyl-2-methyl-propyl)-carbamic acid ethyl ester hydroacetate The procedure described for example 91d was used to convert 0.13 g of 1-[2-(R)-isopropoxycarbonylamino-3-isopropylsulfanyl-3-methyl-butyryl]-pyrrolidine-2-(S)-carboxylic acid into 0.13 g of the title compound. (+)-APCI-MS: 530 (MH$^+$).

Example 96

(3-{2-(S)-[1-Amino-isoquinoline-6-ylmethyl)-carbamoyl]-pyrrolidine-1-yl}-2-(R)-ethoxy-carbonylamino-1,1-dimethyl-3-oxo-propylsulfanyl)-acetic acid tert.-butyl ester hydroacetate (96d)

96a. 3-tert.-Butoxycarbonylmethylsulfanyl-2-(R)-ethoxycarbonylamino-3-methyl-butyric acid NaH (0.81 g; 35.2 mmol) was added in portions to 40 mL ethanol while cooling. Subsequently D-penicillamine (2.50 g) was added. The mixture kept stirring for 5 minutes at 5° C., after which bromoacetic acid tert.-butyl ester (2.55 mL) was added. The mixture was allowed to stir 16 h at ambient temperature and subsequently hydrolyzed with 2 N HCl. The solvents were distilled off, the residue was redissolved in 50 mL of water and 50 mL of dioxane and pH 9.5 was adjusted by adding aqueous NaOH. Ethyl chloroformate (2.1 mL) was slowly added at 5° C. while maintaining pH 9.5 by addition of the appropriate amount of aqueous NaOH. Stirring was continued for 6 h at room temperature. Aqueous NaOH was added (pH 10) and the dioxane removed in vacuo followed by extraction of the remaining aqueous solution with ethyl acetate. KHSO$_4$ was added and the acidified aqueous solution extracted with ethyl acetate several times. Evaporation of the solvent in vacuo gave a colorless oil, which was purified by HPLC (RP-18; pH 2.3; H$_2$O/CH$_3$OH 3/7) to give 0.86 g (15%) of the title compound as a colorless oil. (+)-APCI-MS: 358 (MNa$^+$).

96b. 1-[3-tert.-Butoxycarbonylmethylsulfanyl-2-(R)-ethoxycarbonylamino-3-methyl-butyryl]-pyrrolidine-2-(S)-carboxylic acid methyl ester Reaction of 0.44 g of (L)-proline methyl ester hydrochloride and 0.86 g of 3-tert.-butoxycarbonylmethylsulfanyl-2-(R)-ethoxycarbonylamino-3-methyl-butyric acid according to the procedure described in example 91b yielded 0.60 g (52%) of the title compound as a colorless oil. (+)-APCI-MS: 474 (MH$^+$).

96c. 1-[3-tert-Butoxycarbonylmethylsulfanyl-2-(R)-ethoxycarbonylamino-3-methyl-butyryl]-pyrrolidine-2-(S)-carboxylic acid Saponification of 0.60 g of 1-[3-tert.-butoxycarbonylmethylsulfanyl-2-(R)-ethoxycarbonylamino-3-methyl-butyryl]-pyrrolidine-2-(S)-carboxylic acid methyl ester according to the procedure

96d. (3-{2-(S)-[(1-Amino-isoquinolin-6-ylmethyl)-carbamoyl]-pyrrolidine-1-yl}-2-(R)-ethoxy-carbonylamino-1,1-dimethyl-3-oxo-propylsulfanyl)-acetic acid tert.-butyl ester hydroacetate The procedure described for example 91d. was used to convert 0.080 g of 1-[3-tert.-Butoxycarbonylmethylsulfanyl-2-(R)-ethoxycarbonylamino-3-methyl-butyryl]-pyrrolidine-2-(S)-carboxylic acid into 0.071 g (61%) of the title compound. (+)-APCI-MS: 588 (MH$^+$).

Example 97

1-(2-(R)-Acetylamino-3-biphenyl-4yl-propionyl)-pyrrolidine-2-(S)-carboxylic acid (1-amino-isoquinolin-6-ylmethyl)-amide (97f)

97a. (D)-N-Acetyl-4-bromo-phenylalanine ethyl ester (D,L)-N-Acetyl-4-bromo-phenylalanine ethyl ester (14.1 g) was dissolved in a mixture of 200 mL dimethyl sulfoxide, 150 mL of water and 40 mL of 1 M aqueous KCl (pH 4). At 39° C. a solution of subtilisine (0.13 g) in 10 mL of water was added and the reaction mixture was allowed to stirr for one hour while maintaining pH 7 by continous addition of the appropriate amount of 1 N NaOH. The mixture was poured into a mixture of 2000 mL of water and 23 mL of 1 N NaOH. Extraction with ethyl acetate followed by evaporation of the solvent in vacuo gave 5.6 g (80%) of the title compound as a white solid. M.p. 106–110° C.; (+)-APCI-MS: 315 (MH$^+$).

97b. (D)-N-Acetyl-4-phenyl-phenylalanine ethyl ester

A mixture of (D)-N-acetyl-4-bromo-phenylalanine ethyl ester (3.14 g), (1.80 g) phenyl boronic acid, sodium carbonate (2.12 g), Pd(OAc)$_2$ (0.11 g), tri-o-tolylphosphine (0.300 g) in 60 mL of dimethoxyethane and 10 mL of water was heated for 3 h at 90° C. Extraction with ethyl ester followed by removal of the solvent in vacuo gave 2.5 g (80%) of the title compound as a white solid. M.p. 161–164° C., (+)-APCI-MS: 312 (MH$^+$).

97c. (D)-N-Acetyl-4-phenyl-phenylalanine

A mixture of (D)-N-acetyl-4-phenyl-phenylalanine ethyl ester (1.55 g) and 0.16 g of LiOH in 20 mL of methanol and 5 mL of water was stirred for 2 h at ambient temperature. KHSO$_4$ was added, the volatiles were pumped off followed by addition of water, extraction with ethyl acetate and removal of the solvent. Yield: 1.14 g (81%) of the title compound as a white solid. M.p. 219–223° C.; (–)-APCI-MS: 282 ([M-H]$^-$).

97d. 1-(2-(R)-Acetylamino-3-biphenyl-4yl-propionyl)-pyrrolidine-2-(S)-carboxylic acid benzyl ester Reaction of 0.41 g of (L)-proline benzyl ester and 0.57 g of (D)-N-acetyl-4-phenyl-phenylalanine according to the procedure described in example 91b yielded 0.54 g (57%) of the title compound as a white solid. (+)-APCI-MS: 471 (MH$^+$).

97e. 1-(2-(R)-Acetylamino-3-biphenyl-4yl-propionyl)-pyrrolidine-2-(S)-carboxylic acid 1-(2-(R)-Acetylamino-3-biphenyl-4yl-propionyl)-pyrrolidine-2-(S)-carboxylic acid benzyl ester (0.50 g) were dissolved in 30 mL of methanol and hydrogenated for 4 h at room temperature using 0.3 g palladium on charcoal (10%) as catalyst. Filtration followed by concentration in vacuo affords 0.37 g (91%) of the title compound as a white solid. (+)-APCI-MS: 381 (MH$^+$).

97f 1-(2-(R)-Acetylamino-3-biphenyl-4yl-propionyl)-pyrrolidine-2-(S)-carboxylic acid (1-amino-isoquinolin-6-ylmethyl)-amide A mixture of 1-(2-(R)-acetylamino-3-biphenyl-4yl-propionyl)-pyrrolidine-2-(S)-carboxylic acid (0.120 g), 6-aminomethyl-isoquinolin-1-ylamine (0.058 g), N-methyl morpholine (0.11 mL) and 0.100 g of 2-(1H-benzotriazole-1-yl)-1,1,3,3-tetramethyluronium tetrafluoroborate (TBTU) in 4.5 mL of dry N,N-dimethyl formamide was stirred for 3 h at ambient temperature. The mixture was concentrated and the remaining residue was purified by silica chromatography (dichloro-methane/methanol 8/2) to give 0.120 g (70%) of the title compound as a light yellow solid. (+)-APCI-MS: 536 (MH$^+$).

Example 98

(2-{2-(S)-[(1-Amino-isoquinolin-6-ylmethyl)-carbamoyl]-pyrrolidine-1yl}-1-(R)-(4methoxybenzyl)-2-oxo-ethyl)-carbamic acid ethyl ester (98d)

98a. (D)-N-Ethoxycarbonyl-4-methoxy-phenylalanine

A mixture of (D)-4-methoxyphenylalanine hydrochloride (1.16 g) in 15 mL of 1 N NaOH and 10 mL of dichloromethane was cooled in an ice bath, 0.48 mL of ethyl chloroformate were added dropwise and the resulting mixture was stirred for 2 h at room temperature. After adding aqueous NaOH (pH 10) the organic layer was discarded. KHSO$_4$ was added (pH 3) and the aqueous solution was extracted with dichloromethane acetate. Evaporation of the solvent in vacuo gave 1.00 g (76%) of the title compound as a colorless oil. (–)-APCI-MS: 266 ([M-H]$^-$).

98b. 1-(2-(R)-Ethoxycarbonylamino-3-(4-methoxyphenyl)-propionyl)-pyrrolidine-2-(S)-carboxylic acid benzyl ester Reaction of 0.63 g of (L)-proline benzyl ester hydrochloride and 0.70 g of (D)-N-ethoxycarbonyl-4-methoxy-phenylalanine according to the procedure described in example 91b yielded 0.98 g (81%) of the title compound as a colorless oil. (+)-APCI-MS: 455 (MH$^+$).

98c. 1-(2-(R)-Ethoxycarbonylamino-3-(4-methoxyphenyl)-propionyl)-pyrrolidine-2-(S)-carboxylic acid Hydrogenation of 0.82 g of 1-(2-(R)-ethoxycarbonylamino-3-(4-methoxyphenyl)-propionyl)- pyrrolidine-2-(S)-carboxylic acid benzyl ester according to the procedure described in example 97e afforded 0.61 g (93%) of the title compound as a white solid. (+)-APCI-MS: 365 (MH$^+$).

98d. (2-{2-(S )-[(1-Amino-isoquinolin-6-ylmethyl)-carbamoyl]-pyrrolidine 1-yl}-1-(R)-(4-methoxybenzyl)-2-oxo-ethyl)-carbamic acid ethyl ester Using the procedure described in example 97f 0.115 g of 1-(2-(R)-ethoxycarbonylamino-3-(4-methoxyphenyl)-propionyl)-pyrrolidine-2-(S)-carboxylic acid was converted into 0.130 g (79%) of the title compound. (+)-APCI-MS: 520 (MH$^+$).

Example 99

(3-{2-(S)-[(1-Amino-isoquinolin-6-ylmethyl)-carbamoyl]-pyrrolidine-1-yl}-2-(R)-ethoxy-carbonylamino-1,1-dimethyl-3-oxo-propylsulfanyl)-acetic acid hydrotrifluoroacetate A mixture of (3-{2-(S)-[(1-amino-isoquinolin-6-ylmethyl)-carbamoyl]-pyrrolidine-1-yl}-2-(R)-ethoxycarbonylamino-1,1-dimethyl-3-oxo-propylsulfanyl)-acetic acid tert.-butyl ester hydroacetate (0.031 g; 0.048 mmol) and 1 mL trifluoroacetic acid in 1 mL of dichloromethane was stirred for 3 h at ambient temperature. The volatiles were pumped off followed by lyophilization to give 0.016 g (52%) of the title compound as a white solid. (+)-APCI-MS: 532 (MH$^+$).

Example 100

(2-{2-(S)-[(1-Amino-isoquinolin-6-ylmethyl)-carbamoyl]-pyrrolidine-1-yl}-1-(R)-cyclohexyl-2-oxo-ethyl)-carbamic acid ethyl ester hydroacetate (100d)

100a. (R)-Ethoxy-carbonylamino-cyclohexyl-acetic acid

Using to the procedure described in example 91d, 2.85 g of (D)-cyclohexylglycine gave 1.1 g (33%) of the title compound as a colorless oil. (−)-APCI-MS: 228 ([M-H]$^-$).

100b. 1-[(R)-Ethoxycarbonylamino-cyclohexyl-acetyl]-pyrrolidine-2-(S)-carboxylic acid benzyl ester Reaction of 1.1 g of (R)-ethoxycarbonylamino-cyclohexyl-acetic acid and 1.16 g of (L)-proline benzyl ester hydrochloride according to the procedure described in example 91b gave 1.50 g (75%) of the title compound as a colorless oil. (+)-APCI-MS: 417 (MH$^+$).

100c. 1-[(R)-Ethoxycarbonylamino-cyclohexyl-acetyl]-pyrrolidine-2-(S)-carboxylic acid Hydrogenation of 1.5 g of 1-[(R)-ethoxycarbonylamino-cyclohexyl-acetyl]-pyrrolidine-2-(S)-carboxylic acid benzyl ester according to the procedure described for example 97e afforded 1.13 g (96%) of the title compound as a white solid. (+)-APCI-MS: 327 (MH$^+$).

100d. (2-{2-(S)-[(1-Amino-isoquinolin-6-ylmethyl)-carbamoyl]-pyrrolidine-1-yl}-2-oxo-1-(R)-cyclohexyl-ethyl)-carbamic acid ethyl ester hydroacetate Using the procedure described in example 91d 0.350 g of 1-[(R)-ethoxycarbonylamino-cyclohexyl-acetyl]-pyrrolidine-2-(S)-carboxylic acid was converted into 0.430 g (83%) of the title compound. (+)-APCI-MS: 482 (MH$^+$).

Example 101

1-[2-(R)-Acetylamino-3-(4-methoxyphenyl)-propionyl)-pyrrolidine-2-(S)-carboxylic acid (1-amino-isoquinolin-6-ylmethyl)-amide (101c)

101a. 1-(2-(R)-Acetylamino-3-(4-methoxyphenyl)-propionyl)-pyrrolidine-2-(S)-carboxylic acid benzyl ester Reaction of 0.48 g of (D)-N-acetyl-4-methoxy-phenylalanine (; 2.0 mmol) and 0.41 g of (L)-proline benzyl ester according to the procedure described in example 91b afforded 0.35 g (41%) of the title compound as a colorless oil. (+)-APCI-MS: 425 (MH$^+$).

101b. 1-(2-(R)-Acetylamino-3-(4-methoxyphenyl)-propionyl)-pyrrolidine-2-(S)-carboxylic acid Hydrogenation 0.35 g of 1-(2-(R)-acetylamino-3-(4-methoxyphenyl)-propionyl)-pyrrolidine-2-(S)-carboxylic acid benzyl ester using to the procedure described for example 97e gave 0.27 g (100%) of the title compound as a colorless oil. (+)-APCI-MS: 335 (MH$^+$).

101c. 1-[2-(R)-Acetylamino-3-(4-methoxyphenyl)-propionyl)-pyrrolidine-2-(S)-carboxylic acid (1-amino-isoquinolin-6-ylmethyl)-amide Using the procedure described for example 97f 0.140 g of 1-(2-(R)-acetylamino-3-(4-methoxyphenyl)-propionyl)-pyrrolidine-2-(S)-carboxylic acid was converted into 0.160 g (80%) of the title compound. (+)-APCI-MS: 490 (MH$^+$).

Example 102

[2-{2-(S)-[(1-Amino-isoquinolin-6-ylmethyl)-carbamoyl]-pyrrolidine-1-yl}-1-(R)-(4-methoxybenzyl)-2-oxo-ethylamino]-acetic acid ethyl ester hydrochloride (102h)

102a. (D)-4-Methoxy-phenylalanine benzyl ester hydrochloride (D)-4-Methoxy-phenylalanine hydrochloride (7.0 g), p-toluenesulphonic acid (6.9 g) and benzyl alcohol (15.0 ml) in 100 mL of toluene were refluxed for 4 h using a Dean-Stark trap, the toluene distilled off and the residue redissolved in ethyl acetate followed by extraction with 2 N NaOH. Then HCl in diethyl ether was added and the precipitated material collected by filtration. Yield: 7.2 g (75%); white solid; m.p. 207–211° C.; (+)-APCI-MS: 286 (MH$^+$).

102b. N-Ethoxycarbonylmethyl-2-(R)-amino-3-(4-methoxyphenyl)-propionic acid benzyl ester (D)-4-Methoxy-phenylalanine benzylester hydrochloride (1.7 g) was dissolved in 7 mL of dry N,N-dimethyl formamide. Bromoacetic acid ethyl ester (1.7 mL) and triethylamine (2.6 mL) were added in succession and the reaction mixture was allowed to stir for 16 h at room temperature. The mixture was poured on ice and extracted with ethyl acetate. The solvent was removed in vacuo and the residue was purified by silica chromatography (isohexane/ethyl acetate 1/1) to give 1.75 g (78%) of the title compound as a light yellow oil. (+)-APCI-MS: 372 (MH$^+$).

102c. N-Ethoxycarbonylmethyl-N-tert.-butoxycarbonyl-2-(R)-amino-3-(4-methoxyphenyl)-propionic acid benzyl ester (N-Ethoxycarbonylmethyl-2-(R)-amino-3-(4-methoxyphenyl)-propionic acid benzyl ester (1.7 g) was dissolved in 7 mL of water and a solution of BOC anhydride (1.22 g) in 7 mL of dioxane was added. The mixture was allowed to stir for 16 h while pH 9.5 was maintained by continous addition of the appropriate amounts of 0.1 N NaOH. The dioxane was distilled off followed by extraction with ethyl acetate, removal of the solvent in vacuo and purification of the remaining residue by silica chromatography (isohexane/ethyl acetate 1/1). Yield: 1.50 g (68%); colorless oil; (−)-APCI-MS: 470 ([M-H]$^−$).

102d. N-Ethoxycarbonylmethyl-N-tert.-butoxycarbonyl-2-(R)-amino-3-(4-methoxyphenyl)-propionic acid N-Ethoxycarbonylmethyl-N-tert.-butoxycarbonyl-2-(R)-amino-3-(4-methoxyphenyl)-propionic acid benzyl ester (1.50 g) were dissolved in 40 mL of methanol and hydrogenated for 4 h at room temperature using 0.3 g palladium on charcoal (10%) as catalyst. Filtration followed by concentration in vacuo affords 1.05 g (87%) of the title compound as a colorless oil. (−)-APCI-MS: 381 ([M-H]$^−$).

102e. {[2-{2-(S)-[Benzyloxy-carbonyl]-pyrrolidine-1-yl}-1-(R)-(4-methoxybenzyl)-2-oxo-ethyl]-tert.-butoxycarbonyl-amino}-acetic acid ethyl ester A mixture of (L)-proline benzyl ester hydrochloride (0.49 g), N-Ethoxycarbonylmethyl-N-tert.-butoxycarbonyl-2-(R)-amino-3-(4-methoxyphenyl)-propionic acid (0.760 g), N-methyl morpholine (0.93 mL) and 0.65 g of 2-(1H-benzotriazole-1-yl)-1,1,3,3-tetramethyluronium tetrafluoroborate (TBTU) in 10 mL of dry N,N-dimethyl formamide was stirred for 16 h at ambient temperature. The volatiles were pumped off and water was added followed by extraction with ethyl acetate and concentration of the organic layer., The remaining residue was purified by silica chromatography (isohexane/ethyl acetate 1/2). Yield: 0.99 g (86%); colorless oil; (+)-APCI-MS: 569 (MH$^+$).

102f. {[2-{2-(S)-Carboxy-pyrrolidine-1yl}1-(R)-(4-methoxybenzyl)-2-oxo-ethyl]-tert.-butoxycarbonyl-amino}-acetic acid ethyl ester 0.78 g of {[2-{2-(S)-[Benzyloxy-carbonyl]-pyrrolidine-1-yl}-1-(R)-(4-methoxybenzyl)-2-oxo-ethyl]-tert.-butoxycarbonyl-amino}-acetic acid ethyl ester were dissolved in 50 mL of methanol and hydrogenated for 3 h at room temperature using 0.4 g palladium on charcoal (10%) as catalyst. Filtration followed by concentration in vacuo affords 0.58 g (89%) of the title compound as a colorless oil. (−)-APCI-MS: 477 ([M-H]$^−$).

102g. {[2-{2-(S)-[(1-Amino-isoquinolin-6-ylmethyl)-carbamoyl]-pyrrolidine-1-yl}-1-(R)-(4-methoxybenzyl)-2-oxo-ethyl]-tert.-butoxycarbonyl-amino}-acetic acid ethyl ester A mixture of {[2-{2-(S)-Carboxy-pyrrolidine-1-yl}-1-(R)-(4-methoxybenzyl)-2-oxo-ethyl]-tert.-butoxycarbonyl-amino}-acetic acid ethyl ester (0.240 g), 6-aminomethyl-isoquinolin-1-ylamine (0.092 g), N-methyl morpholine (0.170 mL) and 0.160 g of 2-(1H-benzotriazole-1-yl)-1,1,3,3-tetramethyluronium tetrafluoroborate (TBTU) in 8 mL of dry N,N-dimethyl formamide was stirred for 3 h at ambient temperature. Removal of the solvent in vacuo followed by purification of the remaining residue by silica chromatography (dichloromethane/methanol 80/20) gave 0.310 g (100%) of the title compound as a light yellow solid. (+)-APCI-MS: 634 (MH$^+$).

102h. [2-{2-(S)-[(1-Amino-isoquinolin-6-ylmethyl)-carbamoyl]-pyrrolidine-1-yl}-1-(R)-(4-methoxybenzyl)-2-oxo-ethylamino]-acetic acid ethyl ester hydrochloride 0.150 g of {[2-{2-(S)-[(1-Amino-isoquinolin-6-ylmethyl)-carbamoyl]-pyrrolidine-1-yl}-1-(R)-(4-methoxybenzyl)-2-oxo-ethyl]-tert.-butoxycarbonyl-amino}-acetic acid ethyl ester were treated with 5 mL of HCl in dioxane (5M solution) and the mixture was stirred for 3 h at ambient temperature. The solvent was distilled off and the remaining white solid was washed with diethyl ether and dried. Yield 0.100 g (80%); (+)-APCI-MS: 534 (MH$^+$).

Example 103

N-(7-amino-thieno[2,3c]pyridin-2-ylmethyl) 1-(propyloxycarbonylmethylamino-2(R)-cyclohexylmethyl-acetyl)-prolinamide hydrochloride 103a. 7-azido-thieno[2,3c]pyridin To a stirred solution of 2 g of 7-chloro-thieno[2,3c] pyridine (U.S. Pat. No. 3,663,559) in 25 mL of dimethylsulfoxide was added 15.6 g of sodium azide and the reaction mixture was heated at 135° C. for 18 hours. After this period the reaction mixture was allowed to cool to room temperature and ethyl acetate and aqueous 1N sodium hydroxide were added. The ethyl acetate layer was separated, washed with aqueous 1N sodium hydroxide (twice) and brine, dried over magnesium sulphate and concentrated to give 1.65 g of 7-azido-thieno[2,3c]pyridine.

MS ESI$^+$: 177 (M+H)

103b. 7-amino-thieno[2,3c]pyridin

To a stirred solution of 2.1 g of 7-azido-thieno[2,3c] pyridine in 250 mL of ethanol was added 1 mL of hydrochloric acid (37%) and 13.4 g of tin(II) chloride dihydrate. The reaction mixture was heated at reflux temperature for two hours and then concentrated. To the residue was added ethyl acetate and a saturated aqueous sodium hydrogen carbonate solution. After stirring for 30 minutes the mixture was filtered. The ethyl acetate layer of the filtrate was separated, washed with a saturated aqueous sodium hydrogen carbonate solution and brine, dried over magnesium sulphate and concentrated to give 1.65 g of 7-amino-thieno [2,3c]pyridine.

TLC: Rf=0.5, dichloromethane/methanol=9/1 v/v on silica.

103c. N-[2-(azidomethyl)thieno[2,3c]pyridin-7-yl] benzamide

The procedures described in examples 1e, 1f, 1g and 73a were used to convert 7-amino-thieno[2,3c]pyridine into N-[2-(azidomethyl)thieno[2,3c]pyridin-7-yl]benzamide. Yield: 40%.

MS ESI+: 310 (M+H)

103d. 7-amino-2-(aminomethyl)thieno[2,3c]pyridine

To a stirred solution of 0.5 g of N-[2-(azidomethyl)thieno[2,3c]pyridin-7-yl]benzamide in 16 mL of ethyl acetate and 24 mL of ethanol was added 3 mL of hydrochloric acid (37%) and 3.6 g of tin(II) chloride dihydrate. The reaction mixture was heated at reflux temperature for 8 hours and an additional 1 mL of hydrochloric acid (37%) and 1 g of tin(II) chloride dihydrate were added. After heating for 17 hours an additional 1 g of tin(II) chloride dihydrate was added and the reaction mixture was heated at reflux temperature for another 6 hours. Then the reaction mixture was concentrated. To the residue were added ethyl acetate and water and after stirring for 10 minutes the mixture was filtered. The filtrate was extracted twice with 2N hydrochloric acid The combined hydrochloric acid extracts were made basic (pH 10) using aqueous sodium hydroxide and four times extracted with dichloromethane. The combine dichloromethane extracts were dried over magnesium sulphate and concentrated to give 0.2 g of the title compound.

MS ESI+: 180 (M+H)

103e. N-(7-amino-thieno[2,3c]pyridin-2-ylmethyl)1-(propyloxycarbonylmethylamino-2(R-cyclohexylmethyl-acetyl)-prolinamide hydrochloride A TBTU coupling (procedure described in example 73) of 7-amino-2-(aminomethyl)thieno[2,3c]pyridine and N-Boc-N-(1-propyloxycarbonylmethyl)-D-Cha-Pro-OH and subsequently TFA deprotection gave the TFA salt of the title compound. This TFA salt was dissolved in dichloromethane, washed with aqueous sodium hydrogencarbonate, dried over magnesium sulphate and concentrated to give the free base. This free base was dissolved in t-butanol/water, hydrochloric acid was added and lyophilisation afforded the title compound. Yield: 47%, MS ESI+: 530 (M+H).

Example 104

(2-{2-(S)-[(1-Amino-isoquinolin-6-ylmethyl)-carbamoyl]-pyrrolidine-1-yl}-2-oxo-1-(R)-phenyl-ethyl)-carbamic acid methyl ester (104d)

104a. (R)-Methoxy-carbonylamino-phenyl-acetic acid

Starting with 4.0 g of (D)-phenylglycine gave 2.0 g (35%) of the title compound as a white solid using the procedures described in example 91a. M.p. 122–125° C.; (−)-APCI-MS: 208 ([M-H]−).

104b. 1-[(R)-Methoxycarbonylamino-phenyl-acetyl]-pyrrolidine-2-(S)-carboxylic acid benzyl ester Reaction of 1.0 g of (R)-methoxycarbonylamino7phenyl-acetic acid and 1.16 g of (L)-proline benzyl ester hydrochloride according to the procedure described in example 91b gave 0.59 g (31%) of the title compound as a white solid and 0.28 g (15%) of 1-[(S)-methoxycarbonylamino-phenyl-acetyl]-pyrrolidine-2-(S)-carboxylic acid benzyl ester (+)-APCI-MS: 397 (MH+).

104c. 1-[(R)-Methoxycarbonylamino-phenyl-acetyl]-pyrrolidine-2-(S)-carboxylic acid 1.5 g of 1-[(R)-methoxycarbonylamino-phenyl-acetyl]-pyrrolidine-2-(S)-carboxylic acid benzyl ester were dissolved in a mixture of 15 mL of methanol and 15 ML of tetrahydrofuran and hydrogenated for 3 h at room temperature using 0.4 g palladium on charcoal (10%) as catalyst. Filtration followed by concentration in vacuo affords 0.45 g (100%) of the title compound as a white solid. (+)-APCI-MS: 307 (MH+).

104d. (2-{2-(S)-[(1-Amino-isoquinolin-6-ylmethyl)-carbamoyl]-pyrrolidine-1-yl}-2-oxo-1-(R)-phenyl-ethyl)-carbamic acid methyl ester Using the procedure described for example 91d 0.36 g of 1-[(R)-methoxycarbonylamino-phenyl-acetyl]-pyrrolidine-2-(S)-carboxylic acid was converted into 0.40 g (74%) of the title compound. (+)-APCI-MS: 462 (MH+).

Example 105

(2-{2-(S)-[(1-Amino-isoquinolin-6-ylmethyl)-carbamoyl]-pyrrolidine-1-yl}-2-oxo-1-(S)-phenyl-ethyl)-carbamic acid methyl ester (105b)

105a. 1-[(S)-Methoxycarbonylamino-phenyl-acetyl]-2-pyrrolidine-2-(S)-carboxylic acid 0.28 g of 1-[(S)-methoxycarbonylamino-phenyl-acetyl]-pyrrolidine-2-(S)-carboxylic acid benzyl ester were dissolved in a mixture of 15 mL of methanol and 15 mL of tetrahydrofuran and hydrogenated for 3 h at room temperature using 0.2 g palladium on charcoal (10%) as catalyst. Filtration followed by concentration in vacuo affords 0.21 g (100%) of the title compound as a white solid. (+)-APCI-MS: 307 (MH+).

105b. (2-{2-(S)-[(1-Amino-isoquinolin-6-ylmethyl)-carbamoyl]-pyrrolidine-1-yl}-2-oxo-1-(S)-phenyl-ethyl)-carbamic acid methyl ester Using the procedure described for example 91d 0.110 g of 1-[(S)-methoxycarbonylamino-phenyl-acetyl]-pyrrolidine-2-(S)-carboxylic acid was converted into 0.58 g (36%) of the title compound. (+)-APCI-MS: 462 (MH+).

Example 106

(2-{2-(S)-[(1-Amino-isoquinolin-6-ylmethyl)-carbamoyl]-pyrrolidine-1-yl}-1-(R)-cyclohexyl-2-oxo-ethyl)-carbamic acid methyl ester (106d)

106a. (R)-Methoxy-carbonylamino-cyclohexyl-acetic acid

A mixture of (D)-cyclohexylglycine (6.0 g) in 76.3 mL of 1 N NaOH and 80 mL of dichloromethane was cooled in an ice bath, 3.1 mL of methyl chloroformate were added dropwise and the resulting mixture was stirred for 16 h at room temperature. After adding aqueous NaOH (pH 10) the organic layer was discarded. KHSO$_4$ was added (pH 3) and the aqueous solution was extracted with ethyl acetate. Evaporation of the solvent in vacuo gave 2.5 g (30%) of the title compound as a colorless oil. (−)-APCI-MS; 214 ([M-H]−).

106b. 1-[(R)-Methoxycarbonylamino-cyclohexyl-acetyl]-pyrrolidine-2-(S)-carboxylic acid benzyl ester Reaction of 1.24 g of (R)-methoxycarbonylamino-cyclohexyl-acetic acid and 1.40 g of (L)-proline benzyl ester hydrochloride using the procedure described for example 91b gave 1.17 g (50%) of the title compound as a colorless oil. (+)-APCI-MS: 403 (MH$^+$).

106c. 1-[(R)-methoxycarbonylamino-cyclohexyl-acetyl]-pyrrolidine-2-(S)-carboxylic acid 1.17 g 1-[(R)-methoxycarbonylamino-cyclohexyl-acetyl]-pyrrolidine-2-(S)-carboxylic acid benzyl ester were dissolved in 90 mL of methanol and hydrogenated for 3 h at room temperature using 0.8 g palladium on charcoal (10%) as catalyst. Filtration followed by concentration in vacuo affords 0.80 g (89%) of the title compound as a colorless oil. (−)-APCI-MS: 311 ([M-H]$^-$).

106d. (2-{2-(S)-[(1-Amino-isoquinolin-6-ylmethyl)-carbamoyl]-pyrrolidine-1-yl}-2-oxo-1-(R)-cyclohexyl-ethyl)-carbamic acid methyl ester A mixture of 1-[(R)-methoxycarbonylamino-cyclohexyl-acetyl]-pyrrolidine-2-(S)-carboxylic acid (0.410 g), 6-aminomethyl-isoquinolin-1-ylamine (0.227 g), N-methyl morpholine (0.58 mL) and 0.423 g of 2-(1H-benzotriazole-1-yl)-1,1,3,3-tetramethyluronium tetrafluoroborate (TBTU) in 10 mL of dry N,N-dimethyl formamide was stirred for 3 h at ambient temperature. The mixture was concentrated and the remaining residue was purified by HPLC (RP-18; H$_2$O/CH$_3$OH 95/5→0/100) to give 0.350 g (58%) of the title compound as a white solid. (+)-APCI-MS: 468 (MH$^+$).

Example 107

1-(2-(R)-Methanesulfonylamino-3-phenyl-propionyl)-pyrrolidine-2-(S)-carboxylic acid (1-amino-isoquinolin-6-ylmethyl)-amide (107f)

107a. (D)-Phenylalanine methyl ester hydrochloride (D)-Phenylalanine (25.0 g) was dissolved in 450 mL of methanol and 22 mL thionyl chloride were slowly added at −20° C. The mixture was refluxed for 1 h, followed by evaporation of the volatiles to give 31.2 g (97%) of the title compound as a white solid. M.p. 155–163° C.

107b. 2-(R)-Methanesulfonylamino-3-phenyl-propionic acid methyl ester

To a mixture of (D)-phenylalanine methyl ester hydrochloride (1.10 g) and 2.6 mL of ethyl diisopropylamine in 20 mL of dichloromethane was added a solution of methanesulfonic anhydride (0.87 g) in 20 mL of dichloromethane and the resulting mixture was stirred for 1 h. Extraction with 2 N HCl followed by removal of the dichloromethane in vacuo gave 1.70 g of the title compound as a yellow oil.

107c. 2-(R)-Methanesulfonylamino-3-phenyl-propionic acid

A mixture of 2-(R)-methanesulfonylamino-3-phenyl-propionic acid methyl ester (0.90 g) and 0.10 g of LiOH in 10 mL of methanol and 1 mL of water was stirred for 16 h at ambient temperature. KHSO$_4$ was added, the volatiles were pumped off followed by addition of water, extraction with dichloromethane and removal of the solvent. Yield: 0.70 g (83%) of the title compound as a colorless oil. (−)-APCI-MS: 242 ([M-H]$^-$).

107d. 1-(2-(R)-Methanesulfonylamino-3-phenyl-propionyl)-pyrrolidine-2-(S)-carboxylic acid benzyl ester reaction of 0.65 g of 2-(R)-methanesulfonylamino-3-phenyl-propionic acid and 0.66 g of (L)-proline benzyl ester hydrochloride using the procedure described for example xib yielded 0.88 g (75%) of the title compound as a yellow oil. (+)-APCI-MS: 431 (MH$^+$).

107e. 1-(2-(R)-Methanesulfonylamino-3-phenyl-propionyl)-pyrrolidine-2-(S)-carboxylic acid Hydrogenation of 0.87 g of 1-(2-(R)-methanesulfonylamino-3-phenyl-propionyl)-pyrrolidine-2-(S)-carboxylic acid benzyl] ester according to the procedure described in example 97e afforded 0.60 g (88%) of the title compound as a light yellow solid. (−)-APCI-MS: 339 ([M-H]$^-$).

107f. 1-(2-(R)-Methanesulfonylamino-3-phenyl-propionyl)-pyrrolidine-2-(S)-carboxylic acid (1-amino-isoquinolin-6-ylmethyl)-amide Using the procedure described in example 97f 0.140 g of 1-(2-(R)-methanesulfonylamino-3-phenyl-propionyl)-pyrrolidine-2-(S)-carboxylic acid was converted into 0.1 80 g (90%) of the title compound. (+)-APCI-MS: 496 (MH$^+$).

Example 108

1-(2-(R)-Acetylamino-3-phenyl-propionyl)-pyrrolidine-2-(S)-carboxylic acid (1-amino-isoquinolin-6-ylmethyl)-amide (108c)

108a. 1-(2-(R)-Acetylamino-3-phenyl-propionyl)-pyrrolidine-2-(S)-carboxylic acid benzyl ester Reaction of 0.42 g of (D)-N-acetyl-phenylalanine and of 0.49 g (L)-proline benzyl ester hydrochloride according to the procedure described for example 91b afforded 0.79 g (100%) of the title compound as a yellow oil. (+)-APCI-MS: 395 (MH$^+$).

108b. 1-(2-(R)-Acetylamino-3-phenyl-propionyl)-pyrrolidine-2-(S)-carboxylic acid Hydrogenation of 0.75 g of 1-(2-(R)-acetylamino-3-phenyl-propionyl)-pyrrolidine-2-(S)-carboxylic acid benzyl ester using the procedure described in example 97e afforded 0.56 g (96%) of the title compound as a yellow solid. (+)-APCI-MS: 305 (MH$^+$).

108c. 1-(2-(R)-Acetylamino-3-phenyl-propionyl)-pyrrolidine-2-(S)-carboxylic acid (1-amino-isoquinolin-6-ylmethyl)-amide Using the procedure described for example 97f 0.125 g of 1-(2-(R)-acetylamino-3-phenyl)-propionyl)-pyrrolidine-2-(S)-carboxylic acid was converted into 0.90 g (47%) of the title compound. (+)-APCI-MS: 460 (MH$^+$).

Example 109

1-[2-(R)-(3-Ethyl-ureido)-3-(4-methoxy-phenyl)-propionyl]-pyrrolidine-2-(S)-carboxylic acid (1-amino-isoquinolin-6-ylmethyl)-amide (109h)

109a. N-tert.-Butoxycarbonyl-2-(R)-amino-3-(4-methoxyphenyl)-propionic acid benzyl ester)

(D)-4-Methoxy-phenylalanine benzylester hydrochloride (4.3 g) was dissolved in 20 mL of water and a solution of di-tert-butyl dicarbonate (3.5 g) in 20 MmL of dioxane was added. The mixture was allowed to stir for 16 h while pH 9.5 was maintained by continous addition of the appropriate amounts of 0.5 N NaOH. The dioxane was distilled off followed by extraction with dichloromethane and removal of the solvent to give 5,2 g (100%) of the title compound as a colorless oil.

109b. N-tert.-Butoxycarbonyl-2-(R)-amino-3-(4-methoxyphenyl)-propionic acid

Hydrogenation of 5.4 g of N-tert.-butoxycarbonyl-2-(R)-amino-3-(4-methoxyphenyl)-propionic acid benzyl ester according to the procedure described in example 97e afforded 3.6 g (90%) of the title compound as a yellow oil. (−)-APCI-MS: 294 ([M-H]−).

109c. 1-[(N-tert.-Butoxycarbonyl-2-(R)-amino-3-(4-methoxyphenyl)-propionyl]-pyrrolidine-2-(S)-carboxylic acid benzyl ester Reaction of 3.5 g of N-tert.-Butoxycarbonyl-2-(R)-amino-3-(4-methoxyphenyl)-propionic acid and 2.9 g of (L)-proline benzyl ester hydrochloride according to the procedure described for example 91b gave 3.0 g (52%) of the title compound as a yellow oil. (+)-APCI-MS: 505 (MNa+).

109d. 1-[2-(R)-Amino-3-(4-methoxyphenyl)-propionyl]-pyrrolidine-2-(S)-carboxylic acid benzyl ester hydrochloride 1-[(N-tert.-butoxycarbonyl)-2-(R)-amino-3-(4-methoxyphenyl)-propionyl]-pyrrolidine-2-(S)-carboxylic acid benzyl ester (2.8 g) were treated with 50 mL of HCl in dioxane (5M solution) and the mixture was stirred for 4 h at ambient temperature. The solvent was distilled off and the remaining white solid was washed with diethyl ether and dried. Yield: 2.3 g (96%); (+)-APCI-MS: 383 (MH+).

109e. 1-[2-(R)-Isocyanato-3-(4-methoxyphenyl)-propionyl]-pyrrolidine-2-(S)-carboxylic acid benzyl ester 1-[2-(R)-Amino-3-(4-methoxyphenyl)-propionyl]-pyrrolidine-2-(S)-carboxylic acid benzyl ester hydrochloride (2.8 g) was dissolved in 30 mL of dichloromethane followed by addition of 30 mL of $NaHCO_3$ solution (1M) under vigorous stirring. Triphosgene (0.6 g) in 6 mL of dichloromethane was added at 0° C. and the mixture was kept stirring for 0.25 h. The organic layer was separated and the solvent removed in vacuo to yield 1.20 g (98%) of the title compound as a yellow oil. (+)-APCI-MS: 409 (MH+).

109f. 1-[2-(R)-(3-Ethyl-ureido)-3-(4-methoxyphenyl)-propionyl]-pyrrolidine-2-(S)-carboxylic acid benzyl ester 1-[2-(R)-Isocyanato-3-(4-methoxyphenyl)-propionyl]-pyrrolidine-2-(S)-carboxylic acid benzyl ester (0.60 g) was dissolved under nitrogen in 20 mL of dichloromethane and ethyl amine was allowed to pass through at-20° C. for 5 minutes. The mixture was kept stirring for 16 h. The volatiles were pumped off and the remaining residue was purified by silica chromatography (dichloromethane/methanol 80/20) to give 0.29 g (42%) of the title compound as a colorless oil. (+)-APCI-MS: 454(MH−).

109g. 1-[2-(R)-(3-Ethyl-ureido)-3-(4-methoxyphenyl)-propionyl]-pyrrolidine-2-(S)-carboxylic acid Hydrogenation of 0.290 g of 1-[2-(R)-(3-ethyl-ureido)-3-(4-methoxyphenyl)-propionyl]-pyrrolidine-2-(S)-carboxylic acid benzyl ester using the procedure described in example 97e afforded 0.190 g (82%) of the title compound as a white solid. (−)-APCI-MS: 262 ([M-H]−).

109h. 1-[2-(R)-(3-Ethyl-ureido)-3-(4-methoxy-phenyl)-propionyl]-pyrrolidine-2-(S)-carboxylic acid (1-amino-isoquinolin-6-ylmethyl)-amide Using the procedure described for example 97f 0.190 g of 1-[2-(R)-(3-ethyl-ureido)-3-(4-methoxyphenyl)-propionyl]-pyrrolidine-2-(S)-carboxylic acid was converted into 0.180 g (69%) of the title compound. (+)-APCI-MS: 519(MH+).

Example 110

N-(1-amino-isoquinolin-6-ylmethyl) 1-(2-acetylamino-4-methyl-6-dimethyl-heptanoyl)-prolinamide (110d)

110a N-(1-Amino-isoquinolin-6-ylmethyl)-prolinamide 5.00 g of 1-Amino-6-aminomethyl-isoquinoline and 6.20 g Boc-L-proline were dissolved in 88 mL DMF. 10.6 g of TBTU was added followed by a dropwise addition of N-methylmorpholine. Stirring was continued for 1 h at ambient temperature and the solvent was removed i.vac. The residue was extracted with 5% aqueous NaHCO3 solution and with ethyl acetate. The organic layer was separated and dried (NaSO4). The solvent was removed to give 10.7 g (quant.) of N-(1-Amino-isoquinolin-6-ylmethyl)-1-tert.butoxycarbonyl-prolinamide as an oil. Without purification, the compound was dissolved in 50 mL dichloromethane and 25.0 mL trifluoroacetic acid was added. Stirring was continued for 16 h and the solvent was removed i.vac. The residue was dissolved in methanol, the solvent was removed i. vac. And the residue was triturated with diethyl ether. The crystalline material was collected to give 12.9 g (89%) of N-(1-amino-isoquinolin-6-ylmethyl)-prolinamide. M.p. 140–142° C..

110b. N-(1-Amino-isoquinolin-6-ylmethyl)-1-tert.butoxycarbonyl-azetidin-2(S)-carboxamide 2.00 g 1-Tert.butoxycarbonyl-azetidin-2(S)-carboxylic acid, 1.70 g 1-amino-6-aminomethyl-isoquinolin, 3.50 g TBTU were dissolved in 40 mL DMF. 3.55 mL N-methylmorpholine was added slowly with stirring. The solution was applied to a reversed-phase chromatography column (lenght 100 mm, diameter 14 mm, Merck Lichroprep RP-18, 15–25 μ). Elution was started with 25 mL of methanol/water containing 0.3% acetic acid (10 90), then a linear gradient to pure methanol over a period of 75 mL was applied followed by 50 mL of pure methanol. Fraktions of 5 mL each were sampled. The solvent was evaporated to give 3.4 g of the tile compound. MS: 357

110c. N-(-Amino-isoquinolin-6-ylmethyl)-azetidin-2(S)-carboxamide 10 mL Trifluoroacetic acid was added to a solution of 2.4 g of N-(1-amino-isoquinolin-6-ylmethyl)-1-tert.butoxycarbonyl-azetidin-2(S)-carboxamide in 5.0 mL dichloromethane. The solvent was removed i.vac to give 2.1 g of the title compound as trifluoroacetate salt. MS: 371.

110c. N-(1-amino-isoquinolin-6-ylmethyl) 1-(2-acetylamino-4-methyl-6-dimethyl-heptanoyl)-prolinamide 125 mg of N-(1-amino-isoquinolin-6-ylmethyl)-prolinamide was dissolved in 2 mL DMF, 60 mg of 2-acetylamino-4-methyl-6-dimethyl-heptanoic acid, 80 mg of TBTU and 75 mg of N-methylmorpholine were added. The solution was stirred for 1 h at ambient temperature. The solution was applied to a reversed-phase chromatography column (lenght 100 mm, diameter 14 mm; Merck Lichroprep RP-18, 15–25 μ). Elution was started with 25 mL of methanol/water containing 0.3% acetic acid (10:90), then a linear gradient to pure methanol over a period of 75 mL was applied followed by 50 mL of pure methanol. Fraktions of 5 mL each were sampled. The compound was detected in fractions 10–12 by mass spektra. The solvent was removed i.vac. to give 105 mg (87%) of the title compound as amorphous solid. MS: 482.

Example 111

The following compounds were prepared analogously to Example 110:

111a. N-(1-amino-isoquinolin-6-ylmethyl) 1-(2-acetylamino-2-(3,4-ethylenedioxy-phenyl)-acetyl)-prolinamide Yield 38%. MS: 504.

111b. N-(1-amino-isoquinolin-6-ylmethyl) 1-(2-acetylamino-2-(3-methoxy-phenyl)-acetyl)-prolinamide Yield 27%. MS: 476

111c. N-(1-amino-isoquinolin-6-ylmethyl) 1-(2-acetylamino-2-(2-methoxy-phenyl)-acetyl)-prolinamide Yield 78%. MS: 476

111d. N-(1-amino-isoquinolin-6-ylmethyl) 1-(2-acetylamino-2-(4-fluoro-phenyl)-acetyl)-prolinamide Yield 54%. MS: 464

111e. N-(1-amino-isoquinolin-6-ylmethyl) 1-(2-acetylamino-2-(thiophen-3-yl)-acetyl)-prolinamide Yield 86%. MS: 452.

111f. N-(1-amino-isoquinolin-6-ylmethyl) 1-(2-acetylamino-2-(naphthalene-2-yl)-acetyl)-prolinamide Yield 51%. MS: 496.

111g. N-(1-amino-isoquinolin-6-ylmethyl) 1-(2-acetylamino-2-(4-methoxycarbonyl-phenyl-acetyl)-prolinamide Yield 39%. MS: 504.

111h. N-(1-amino-isoquinolin-6-ylmethyl) 1-(2-acetylamino-2-(4-cyano-phenyl)-acetyl)-prolinamide Yield 21%. MS: 471.

111i. N-(1-amino-isoquinolin-6-ylmethyl) 1-(2-acetylamino-2-(4-trifluoromethyl-phenyl)-acetyl)-prolinamide Yield 29%. MS: 514.

111j. N-(1-amino-isoquinolin-6-ylmethyl) 1-(2-acetylamino-2-(2-chloro-phenyl)-acetyl)-prolinamide Yield 78%. MS: 481.

111k. N-(1-amino-isoquinolin-6-ylmethyl) 1-(2-acetylamino-2-(3-chloro-phenyl)-acetyl)-prolinamide Yield 34%. MS: 481.

111l. N-(1-amino-isoquinolin-6-ylmethyl) 1-(2-acetylamino-2-(4-chloro-phenyl)-acetyl)-prolinamide Yield 40%. MS: 481.

111m. N-(1-amino-isoquinolin-6-ylmethyl) 1-(2-acetyl-methyl-amino-2-cyclohexyl-acetyl)-prolinamide Yield 71%. MS: 466.

111n. N-(1-amino-isoquinolin-6-ylmethyl) 1-(2-acetylamino-2-cyclohexyl-acetyl)-prolinamide Yield 64%. MS: 452.

111o. N-(1-amino-isoquinolin-6-ylmethyl) 1-(2-acetoxy-2-(4-trifluormethyl-phenyl)-acetyl)-prolinamide Yield 57%. MS: 515.

111p. N-(1-amino-isoquinolin-6-ylmethyl) 1-(2-(2-methoxyphenyl)-sulfonylamino-2(R)-phenyl-acetyl)-prolinamide Yield 68%. MS: 574.

111q. N-(1-amino-isoquinolin-6-ylmethyl) 1-(2-benzylcarbonylamino-2(R)-phenyl-acetyl)-prolinamide Yield 54%. MS: 522.

111r. N-(1-amino-isoquinolin-6-ylmethyl) 1-(2-formylamino-2(R)-phenyl-acetyl)-prolinamide Yield 95%. MS: 432.

111s. N-(1-amino-isoquinolin-6-ylmethyl) 1-(2-benzylsulfonylamino-2(R)-phenyl-acetyl)-prolinamide Yield 57%. MS: 558.

111t. N-(1-amino-isoquinolin-6-ylmethyl) 1-(2-methylsulfonylamino-2(R)-phenyl-acetyl)-prolinamide Yield 67%. MS: 482.

111u. N-(1-amino-isoquinolin-6-ylmethyl) 1-(2-ethylsulfonylamino-2(R)-phenyl-acetyl)-prolinamide Yield 59%. MS: 496.

111v. N-(1-amino-isoquinolin-6-ylmethyl) 1-(2-acetylamino-2-(4-bromo-phenyl)-acetyl)-prolinamide Yield 63%. MS: 526.

111w. N-(1-amino-isoquinolin-6-ylmethyl) 1-(9-hydroxy-fluorenyl-9-yl)-carbonyl-prolinamide Yield 24%. MS: 479.

111x. N-(1-amino-isoquinolin-6-ylmethyl) 1-(2-acetoxy-2-(4-chlorophenyl)-acetyl)-prolinamide Yield 62%. MS: 481.

111y. N-(1-amino-isoquinolin-6-ylmethyl) 1-(2-acetoxy-2-(4-methoxyphenyl)-acetyl)-prolinamide Yield 63%. MS: 477.

111z. N-(1-amino-isoquinolin-6-ylmethyl) 1-(2-phenylsulfonylamino-2(R)-phenyl-acetyl)-prolinamide Yield 89%. MS: 544.

111aa. N-(1-amino-isoquinolin-6-ylmethyl) 1-(acetoxy-2(R)-cyclohexyl-acetyl)-prolinamide Yield 79%. MS: 453.

111ab. N-(1-amino-isoquinolin-6-ylmethyl) 1-(methoxycarbonylmethylamino-2(R)-cyclohexylmethyl-acetyl)-prolinamide Yield 16%. MS: 496.

111ac. N-(1-amino-isoquinolin-6-ylmethyl) 1-(propyloxycarbonylmethylamino-2(R)-cyclohexylmethyl-acetyl)-prolinamide Yield 30%. MS: 524.

111ad. N-(1-amino-isoquinolin-6-ylmethyl) 1-(2-ethoxycarbonylmethylamino-2(R)-cyclohexylmethyl-acetyl)-prolinamide Yield 60%. MS: 510.

111ae. [(2-{2(S)-[(1-Amino-isoquinolin-6-ylmethyl)-carbamoyl]-pyrrolidin-1-yl}-1(R)-cyclohexylmethyl-2-oxo-ethyl-tert-butoxycarbonylmethyl-amino]-acetic acid tert-butyl ester Yield 25%. MS: 652.

111af. [(2-{2(S)-[(1-Amino-isoquinolin-6-ylmethyl)-carbamoyl]-pyrrolidin-1-yl}-1(R -cyclohexylmethyl-2-oxo-ethyl)-methyl-amino]-acetic acid tert-butyl ester Yield 20%. MS: 552.

111ag. 1-((R)-Phenyl-propionylamino-acetyl)-pyrrolidine-2(S)-carboxylic acid (1-amino-isoquinolin-6-ylmethyl)-amide Yield 63%. MS: 460.

111ah. 1-((R)-Acetylamino-phenyl-acetyl)-pyrrolidine-2(S)-carboxylic acid (1-amino-isoquinolin-6-ylmethyl)-amide Yield 61%. MS: 446.

111ai. 1-((R)-Benzoylamino-phenyl-acetyl)-pyrrolidine-2(S)-carboxylic acid (1-amino-isoquinolin-6-ylmethyl)-amide Yield 40%. MS: 508.

111aj. (2-{2(S)-[(1-Amino-isoquinolin-6-ylmethyl)-carbamoyl]-pyrrolidin-1-yl}-2-oxo-1(R)-phenyl-ethyl)-carbamic acid tert-butyl ester Yield 68%. MS: 504.

111ak. 1-(3.3-Diphenyl-propionyl)-pyrrolidine-2(S)-carboxylic acid (1-amino-isoquinolin-6-ylmethyl)-amide Yield 69%. MS: 479.

111al. 1-{2(S)-[(1-Amino-isoquinolin-6-ylmethyl)-carbamoyl]-pyrrolidine-1-carbonyl}-octahydro-isoquinoline-2-carboxylic acid methyl ester Yield 74%. MS: 494.

111am. Acetic acid 2-{2(S)-[(1-amino-isoquinolin-6-ylmethyl)-carbamoyl]-pyrrolidin-1-yl}-2-oxo-1(R)-phenyl-ethyl ester Yield 69%. MS: 447.

111an. [2-{2(S)-[(1-Amino-isoquinolin-6-ylmethyl)-carbamoyl]-pyrrolidin-1-yl}-1(R)-(4-fluoro-benzyl)-2-oxo-ethyl]-carbamic acid tert-butyl ester Yield 83%. MS: 536.

111ao. [2-{2(S)-[(1-Amino-isoquinolin-6-ylmethyl)-carbamoyl]-pyrrolidin-1-yl}-1(R)-(4-methoxy-benzyl)-2-oxo-ethyl]-carbamic acid tert-butyl ester Yield 76%. MS: 548.

111ap. (2-{2(S)-[(1-Amino-isoquinolin-6-ylmethyl)-carbamoyl]-pyrrolidin-1-yl}-1(R)-benzyl-2-oxo-ethyl)-carbamic acid tert-butyl ester Yield 81%. MS: 518.

111aq. (2-{2(S)-[(1-Amino-isoquinolin-6-ylmethyl)-carbamoyl]-pyrrolidin-1yl}-1(R)-benzyl-2-oxo-ethyl)-carbamic acid benzyl ester Yield 82%. MS: 552.

111ar. Acetic acid 2-{2(S)-[(1-amino-isoquinolin-6-ylmethyl)-carbamoyl]-azetidin-1-yl}-2-oxo-1(R)-phenyl-ethyl ester Yield 23%. MS: 433.

111as. [2-{2(S)-[(1-amino-isoquinolin-6-ylmethyl)-carbamoyl]-pyrrolidin-1-yl}-1(R)-4-methoxy-benzyl)-2-oxo-ethylamino]-acetic acid Yield 91%. MS: 506.

111at. 1-(3-Cyclohexyl-2(R)-ethanesulfonylamino-propionyl)-pyrrolidine-2(S)-carboxylic acid (1-amino-isoquinolin-6-ylmethyl)-amide Yield 50%. MS: 516.

111av. (2-{2(S)-[(1-Amino-isoquinolin-6-ylmethyl)-carbamoyl]-azetidin-1-yl}-2-oxo-1(R)-phenyl-ethyl)-carbamic acid ethyl ester Yield 43%. MS: 462

Example 112

N-(1-amino-isoquinolin-6-ylmethyl) 1-(2-hydroxycarbonylmethylamino-2(R)-cyclohexylmethyl-acetyl)-prolinamide To a solution of 135 mg of N-(1-amino-isoquinolin-6-ylmethyl)-1-(propyloxycarbonylmethyl amino-2(R)-cyclohexylmethyl-acetyl)-prolinamide in 4.0 mL dimethoxyethane was added 2.0 mL of 2 M aqueous lithium hydroxide solution was added and stirring was continued for 3 h at ambient temperature. The solvent was removed i.vac., methanol was added and the compound was purified by reversed-phase column chromatography as described in example 110c. Yield: 100 mg (81%). MS: 482.

Example 113

The following compounds were prepared using the procedure described in example 112:

113a. N-(1-amino-isoquinolin-6-ylmethyl) 1-(2-hydroxy-2(R)-cyclohexyl-acetyl)-prolinamide Yield (84%) MS: 411.

113b. 1-((R)-Hydroxy-phenyl-acetyl)-pyrrolidine-2(S)-carboxylic acid (1-amino-isoquinolin-6-ylmethyl)-amide Yield 93%. MS: 404.

Example 114

1-((R)-Amino-phenyl-acetyl)-pyrrolidine-2(S)-carboxylic acid (1-amino-isoquinolin-6-ylmethyl)-amide Trifluoroacetic acid (3.0 mL) was added to 150 mg of (2-{2(S)-[(1-amino-isoquinolin-6-ylmethyl)-carbamoyl]-pyrrolidin-1-yl}-2-oxo-1(R)-phenyl-ethyl)-carbamic acid tert-butyl ester (prepared according to the procedures described in example 110) in 3.0 mL dichloromethane. Stirring was continued for 2 h at ambient temperature. The solvent was removed i.vac, the residue was dissolved in methanol and applied to a reversed-phase chromatography column (lenght 100 mm, diameter 14 mm; Merck Lichroprep RP-18, 15–25μ). Elution was started with 25 mL of methanol/water containing 0.3% acetic acid (10:90), then a linear gradient to pure methanol over a period of 75 mL was applied followed by 50 mL of pure methanol. Fractions of 5 mL each were sampled, The solvent was removed to give 75 mg (62%) of the title compound. MS: 404.

Example 115

The following compounds were prepared using the procedure described in example 114:

115a. 1-[2(R)-Amino-3-(4-fluoro-phenyl)-propionyl]-pyrrolidine-2(S)-carboxylic acid (1-amino-isoquinolin-6-ylmethyl)-amide Yield 99%. MS: 436.

115b. 1-[2(R)-Amino-3-(4-methoxy-phenyl-propionyl]-pyrrolidine-2(S)-carboxylic acid (1-amino-isoquinolin-6-ylmethyl)-amide Yield 90%. MS: 446.

115c. 1-(2(R)-Amino-3-phenyl-propionyl)-pyrrolidine-2(S)-carboxylic acid (1-amino-isoquinolin-6-ylmethyl)-amide Yield 94%. MS: 418.

115d. [2-{2(S)-[(1-Amino-isoquinolin-6-ylmethyl)-carbamoyl]-pyrrolidin-1-yl}-1(R)-(4-chloro-benzyl-2-oxo-ethylamino]-acetic acid Yield 84%. MS: 510.

115e. (2-{2-[(1-Amino-isoquinolin-6-ylmethyl)-carbamoyl]-pyrrolidin-1-yl}-2-oxo-1-phenyl-ethylamino)-acetic acid Yield 95%. MS: 462.

115f. (2-{2-[(1-Amino-isoquinolin-6-ylmethyl)-carbamoyl]-pyrrolidin-1-yl-}-1-cyclohexyl-2-oxo-ethylamino)-acetic acid Yield 80%. MS: 468.

115g. (2-{2(S)-[(1-Amino-isoquinolin-6-ylmethyl)-carbamoyl]-azetidin-1-yl}-1(R)-cyclohexyl-2-oxo-ethylamino)-acetic acid Yield 49%. MS: 454.

115h. 1-[2-Amino-3(R)-(4-chloro-phenyl)-propionyl]-pyrrolidine-2(S)-carboxylic acid (1-amino-isoquinolin-6-ylmethyl)-amide Yield 36%. MS: 452.

115i. [2-{2(S)-[(1-Amino-isoquinolin-6-ylmethyl)-carbamoyl]-pyrrolidin-1-yl-}-1(R)-(4-fluoro-benzyl)-2-oxo-ethylamino]-acetic acid Yield 25%. MS: 494.

Example 116

(2-{2(S)-[(1-Amino-isoquinolin-6-ylmethyl)-carbamoyl]-pyrrolidin-1-yl}-1(R)-benzyl-2-oxo-ethyl)-carbamic acid benzyl ester 12.5 g (10 mmol) of the aminomethyl-polystyrene resine (Bachem) in 100 mL dry THF was shaken for 1 h, 4.6 g of 4-aminosulfonyl-butyric acid, 4.5 mL of diisopropylcarbodiimid and 3.8 g of hydroxybenzotriazole were added and shaken at ambient temperature for 16 h. The resin was filtered, washed with THF, DMF, methanol and ether, and dried at 50° C. to give 13.7 g of dry resin.

This resin was shaken in 100 mL THF for 1 h at ambient temperature. To a solution of 3.2 g of N-Boc-proline in 30 mL dry THF was added 2.5 g of carbonyldiimidazole and stirred for 30 min, then refluxed for 30 min, and cooled to ambient temperature. This solution was added to the slurry of the resin in THF, followed after 10 min by 2.7 mL of DBU. Shaking was continued for 16 h at ambient temperature, the resin was filtered, washed with acetic acid, DMF, methanol and ether, and dried i.vac. at 50° C. for 3 h to give 13.3 g of dry resin. The resin was shaken in 150 mL dichloromethane for 1 h at ambient temperature. It was filtered, 50 mL of trifluoroacetic acid and 2.5 mL water was added, shaken for 45 min at ambient temperature, filtered, washed with dry dichloromethane and methanol, and dried i.vac. at 50° C. for 16 h.

150 mg of this dried resin was shaken with 2.4 mL of a 1 N solution of N-methyl-morpholine in DMF for 20 min, filtered, shaken with 2.4 mL DMF, and filtered. 0.4 mL of a 1 M solution of Z-(R)-phenylalanine in DMF was added, followed by 1.0 mL of a solution of a 0.4 M solution of TBTU in DMF and by 1.0 mL of a 1 M solution of NMM in DMF. The resin was shaken for 3.5 h at 40° C., filtered and washed three times with 2.4 mL each of DMF. Again, 0.4 mL of a 1 M solution of Z-(R)-phenylalanine in DMF was added, followed by 1.0 mL of a solution of a 0.3 M solution of TBTU in DMF and by 1.0 mL of a 1 M solution of NMM in DMF. The resin was shaken for 3.5 h at 40° C., filtered and washed three times with 2.4 mL each of DMF, three times with 2.4 mL each of dichloromethane, once with 3.0 mL methanol, and twice with 2.4 mL each of DMF.

1.4 mL Of a 0.25 M solution of DIPEA in DMF followed by 1.6 mL of a 1M solution of iodoacetonitrilc in DMF was added, and the resin was shaken at 40° C. for 4.5 h. The resin was filtered, washed three times with 2.4 mL each of DMF. Then, 1.4 mL of a 0.25 M solution of DIPEA in DMF followed by 1.6 mL of a 1M solution of iodoacetonitrile in DMF was added, and the resin was shaken at 40° C. for 4.5 h, filtered, washed three times with 2.4 mL each of DMF, three times with 2.4 mL each of dichloromethane, once with 3.0 mL methanol, and five times with 2.4 mL each of dichloromethane.

2.0 mL of a 0.05 M solution of 6-(aminomethyl)-isoquinoline-1-ylamine in dichloromethane followed by 1.0 mL dichloromethane was added to the resin and shaken for 4 h at ambient temperature. The solvent was collected by filtration and the resin was washed with 2.0 mL dichloromethane and 2.0 mL methanol. The organic phases were combined. The presence of the desired compound was detected by mass spectrum, and its purity was determined by TLC. The solvent was removed i.vac. to give (2-{2(S)-[(1-amino-isoquinolin-6-ylmethyl)-carbamoyl]-pyrrolidin-1-yl}-1(R)-benzyl-2-oxo-ethyl)-carbamic acid benzyl ester

MS: 552.

Example 117

The following compounds were prepared using the procedure described in example 116:

117a. 1-{1(S)-[(4-Amino-thieno[3,2-c]pyridin-2-ylmethyl)-carbamoyl]-2-naphthalen-1-yl-ethylcarbamoyl}-octahydro-isoquinoline-2-carboxylic acid methyl ester

MS: 600

117b. 1-{2(S)-[(4-Amino-thieno[3,2-c]pyridin-2-ylmethyl)-carbamoyl]-pyrrolidine-1-carbonyl}-octahydro-isoquinoline-2-carboxylic acid methyl ester

MS: 500

117c. (2-{2(S)-[(Amino-isoquinolin-6-ylmethyl)-carbamoyl]-pyrrolidin-1-yl-}1(R)-cyclohexylmethyl-2-oxo-ethyl)-carbamic acid benzyl ester

MS: 558

117d. (2-{2(S)-[(4-Amino-thieno[3,2-c]pyridin-2-ylmethyl)-carbamoyl]-pyrrolidin-1-yl}-1(R)-benzyl-2-oxo-ethyl)-carbamic acid benzyl ester

MS: 558

117e. (2-{2(S)-[(1-Amino-isoquinolin-6-ylmethyl)-carbamoyl]-azetidin-1-yl}-1-(R)-benzyl-2-oxo-ethyl)-carbamic acid benzyl ester

MS: 538

117f. (2-{2(S)-[(1-Amino-isoquinolin-6-ylmethyl)-carbamoyl]-piperidin-1-yl}-1(R)-benzyl-2-oxo-ethyl)-carbamic acid benzyl ester

MS: 560

117g. (2-{2(S)-[(1-Amino-isoquinolin-7-ylmethyl)-carbamoyl]-pyrrolidin-1-yl}-1-(R)-benzyl-2-oxo-ethyl)-carbamic acid benzyl ester

MS: 552

117h. (2-{2(S)-[(1-Amino-isoquinolin-7-ylmethyl)-carbamoyl]-pyrrolidin-1-yl}-1(R)-cyclohexylmethyl-2-oxo-ethyl)-carbamic acid benzyl ester

MS: 558

117i. (2-{2(S)-[(1-Amino-isoquinolin-6-ylmethyl)-carbamoyl]-azetidin-1-yl}-1(R)-cyclohexylmethyl-2-oxo-ethyl)-carbamic acid benzyl ester

MS: 544

117j. (2-{2(S)-[(1-Amino-isoquinolin-7-ylmethyl)-carbamoyl]-azetidin-1-yl}-1(R)-cyclohexylmethyl-2-oxo-ethyl)-carbamic acid benzyl ester

MS: 544

117k. [2-{2(S)-[(1-Amino-isoquinolin-6-ylmethyl)-carbamoyl]-piperdin-1-yl}-1(R)-(4-methoxy-benzyl)-2-oxo-ethyl]-carbamic acid tert-butyl ester

MS: 562

117l. 1-{2(S)-[(1-Amino-isoquinolin-6-ylmethyl)-carbamoyl]-azetidine-1-carbonyl}-octahydro-isoquinoline-2-carboxylic acid methyl ester

MS: 480

117m. 1-{2(S)-[(1-Amino-isoquinolin-7-ylmethyl)-carbamoyl]-pyrrolidine-carbonyl}-octahydro-isoquinoline-2-carboxylic acid methyl ester

MS: 494

117n. 1-{2(S)-[(1-Amino-isoquinolin-6-ylmethyl)-carbamoyl]-piperidine-1-carbonyl}-octahydro-isoquinoline-2-carboxylic acid methyl ester

MS: 508

117o. (2-{2(S)-[(1-Amino-isoquinolin-6-ylmethyl-carbamoyl]-piperidine-1-yl}-2-oxo-1(R)-phenyl-ethyl)-carbamic acid tert-butyl ester

MS: 518

117p. 1-{1(S)-[(1-Amino-isoquinolin-6-ylmethyl)-carbamoyl]-2-naphthalen-1-yl-ethylcarbamoyl}-octahydro-isoquinoline-2-carboxylic acid methyl ester

MS: 594

117q. 1(R)-(Benzoylamino-phenyl-acetyl)-azetidine-2(S)-carboxylic acid (1-amino-isoquinolin-6-ylmethyl)-amide

MS: 494

117r. 1(R)-(Benzoylamino-phenyl-acetyl)-pyrrolidine-2(S)-carboxylic acid (1-amino-isoquinolin-7-ylmethyl)-amide

MS: 508

117s. N-(4-Amino-thieno[3,2-c]pyridin-2-ylmethyl)-2(S)-(3,3-diphenyl-propionylamino)-3-naphthalen-1-yl-propionamide

MS: 585

117t. 1(R)-(Acetylamino-phenyl-acetyl)-pyrrolidine-2(S)-carboxylic acid (1-amino-isoquinolin-7-ylmethyl)-amide

MS: 446

117v. N-(1-Amino-isoquinolin-6-ylmethyl)-3-naphthalen-1-yl-2(S)-(2-phenoxy-acetylamino)-propionamide

MS: 505

117w. 1(R)-(Phenyl-propionylamino-acetyl)-pyrrolidine-2(S)-carboxylic acid (1-amino-isoquinolin-7-ylmethyl)-amide

MS: 460

117x. 1-[(R)-(2,2-Dimethyl-propionylamino)-phenyl-acetyl]-pyrrolidine-2(S )-carboxylic acid (1-amino-isoquinolin-6-ylmethyl)-amide

MS: 488

117y. 1-[(R)-(2,2-Dimethyl-propionylamino)-phenyl-acetyl]-pyrrolidine-2(S)-carboxylic acid (1-amino-isoquinolin-7-ylmethyl)-amide

MS: 488

117z. (1-{1(S)-[(4-Amino-thieno[3,2]-pyridin-2-ylmethyl)-carbamoyl]-2-naphthalen-1-yl-ethylcarbamoyl}-2(R)-naphthalen-1-yl-ethyl)-carbamic acid tert-butyl ester

MS: 674

117aa. (1-{1(S)-[(1-Amino-isoquinolin-6-ylmethyl)-carbamoyl]-2-naphthalen-1-yl-ethylcarbamoyl}-2(R)-naphthalen-1-yl-ethyl)-carbamic acid tert-butyl ester

MS: 668

117ab. (3(R)-{2(S)-[(1-Amino-isoquinolin-6-ylmethyl)-carbamoyl]-pyrrolidine-1-carbonyl}-3,4-dihydro-1H-isoquinolin-2-yl)-acetic acid tert-butyl ester

MS: 544

117ac. Acetic acid 2-{2(S)-[(4-amino-furo[3,2-c]pyridin-2-ylmethyl)-carbamoyl]-azetidin-1-yl}-2-oxo-1(S)-phenyl-ethyl ester

MS: 423

117ad. Acetic acid 2-{2(S)-[(4-amino-furo[3,2-c]pyridin-2-ylmethyl)-carbamoyl]-pyrrolidin-1-yl}-2-oxo-1(S)-phenyl-ethyl ester

MS: 437

117ae. Acetic acid 2-{2(S)-[(4-amino-furo[3,2-c]pyridin-2-ylmethyl)-carbamoyl]-piperidin-1-yl}-2-oxo-1(S)-phenyl-ethyl ester

MS: 451

117af. 1-Phenoxyacetyl-pyrrolidine-2(S)-carboxylic acid (1-amino-isoquinolin-6-ylmethyl)-amide

MS: 405

117ag. Acetic acid 2-{2(S)-[(1-amino-isoquinolin-6-ylmethyl)-carbamoyl]-pyrrolidin-1-yl}-2-oxo-1(S)-phenyl-ethyl ester

MS: 447

117ah. Acetic acid 2-{2(S)-[(1-amino-isoquinolin-6-ylmethyl)carbamoyl]piperidin-1-yl-2-oxo-1(S)-phenyl-ethyl ester

MS: 461

117ai. 1-(3,3-Diphenyl-propionyl)-azetidine-2(S)-carboxylic acid (1-amino-isoquinolin-6-ylmethyl)-amide

MS: 465

117aj. 1(R)-(Methoxy-phenyl-acetyl)-pyrrolidine-2(S)-carboxylic acid (1-amino-isoquinolin-6-ylmethyl)-amide

MS: 419

117ak. 1-((S)-Methoxy-phenyl-acetyl)-pyrrolidine-2(S)-carboxylic acid (1-amino-isoquinolin-6-ylmethyl)-amide

MS: 419

117al. 1-((R)-Methoxy-phenyl-acetyl)-pyrrolidine-2(S)-carboxylic acid (4-amino-thieno[3,2-c]pyridin-2-ylmethyl)-amide

MS: 425

117am. 1-((S)-Methoxy-phenyl-acetyl)-pyrrolidine-2(S)-carboxylic acid (4-amino-thieno[3,2-c]pyridin-2-ylmethyl)-amide

MS: 425

117an. Acetic acid 9-{2(S)-[(1-amino-isoquinolin-6-ylmethyl)-carbamoyl]-pyrrolidine 1-carbonyl}-9H-fluoren-9-yl ester

MS: 521

117ao. Acetic acid 9-{2(S)-[(1-amino-isoquinolin-6-ylmethyl)-carbamoyl]-azetidine-1-carbonyl}-9H-fluoren-9-yl ester

MS: 507

117ap. 1-(3,3-Diphenyl-propionyl)-pyrrolidine-2(S)-carboxylic acid (1-amino-isoquinolin-7-ylmethyl)-amide

MS: 479

117aq. 1-(3,3-Diphenyl-propionyl)-pyrrolidine-2(S)-carboxylic acid (4-amino-thieno[3,2-c]pyridin-2-ylmethyl)-amide

MS: 485

117ar. 1-[(9H-Fluoren-9-yl)-acetyl]-pyrrolidine-2(S)-carboxylic acid (1-amino-isoquinolin-6-ylmethyl)-amide

MS: 477

117as. [2-{2(S)-[(1-Amino-isoquinolin-6-ylmethyl)-carbamoyl]-pyrrolidin-1-yl}-1(R)-(4-chloro-benzyl)-2-oxo-ethyl]-carbamic acid tert-butyl ester

MS: 553

Example 118

The procedure described in example 116 was repeated. After the products had been isolated, the Boc-protecting groups were removed by treating the residues with 1 mL of 50% trifluoroacetic acid in dichloromethane and stirring for 20 min at ambient temperature. The solvent was removed in vacuo and the presence of the desired compound was detected by mass spectrum, and its purity was determined by TLC.

118a. 1-(2(R)-Amino-3-naphthalen-1-yl-propionyl)-pyrrolidine-2(S)-carboxylic acid (4-amino-furo[3,2-c]pyridin-2-ylmethyl)-amide

MS: 458

118b. 1-(2(R)-Amino-3-naphthalen-1-yl-propionyl)-azetidine-2(S)-carboxylic acid (4-amino-furo[3,2-c]pyridin-2-ylmethyl)-amide

MS: 444

118c. 1-(2(R)-Amino-3-naphthalen-1-yl-propionyl)-azetidine-2(S)-carboxylic acid (1-amino-isoquinolin-6-ylmethyl)-amide

MS: 454

118d. (2-{2(S)-[(4-Amino-furo[3,2-c]pyridin-2-ylmethyl)-carbamoyl]-pyrrolidin-1-yl}-1(R)-cyclohexyl-2-oxo-ethylamino)-acetic acid

MS: 458

118e. (2-{2(S)-[(4-Amino-furo[3,2-c]pyridin-2-ylmethyl)-carbamoyl]-azetidin-1-yl}-cyclohexyl-2-oxo-ethylamino)-acetic acid

MS: 444

118f. 1-(2(S)-Benzylamino-propionyl)-pyrrolidine-2(S)-carboxylic acid (1-amino-isoquinolin-6-ylmethyl)-amide 118g. (2-{2(S)-[(4-Amino-furo[3,2-c]pyridin-2-ylmethyl)-carbamoyl]-pyrrolidin-1-yl}-2-oxo-1(R)-phenyl-ethylamino)-acetic acid

MS: 452

118h. (2-{2(S)-[(4-Amino-furo[3,2-c]pyridin-2-ylmethyl)-carbamoyl]-azetidin-1-yl}-2-oxo-1(R)-phenyl-ethylamino)-acetic acid

MS: 438

118i. 1-(2(R)-Benzylamino-propionyl)-pyrrolidine-2(S)-carboxylic acid (1-amino-isoquinolin-6-ylmethyl)-amide.

MS: 432

118j. (2-{2(S)-[(1-Amino-isoquinolin-6-ylmethyl)-carbamoyl]-azetidin-1-yl}-2-oxo-1(R)-phenyl-ethylamino)-acetic acid

MS: 448

118k. (2-{(2(S)-[(4-Amino-furo[3,2-c]pyridin-2-ylmethyl)-carbamoyl]-pyrrolidin-1-yl}-1(R)-benzyl-2-oxo-ethylamino)-acetic acid

MS: 466

118l. (2-{2(S)-[(4-Amino-furo[3,2-c]pyridin-2-ylmethyl)-carbamoyl]-azetidin-1-yl}-1(R)-benzyl-2-oxo-ethylamino)-acetic acid

MS: 452

118m. (2-{2(S)-[(1-Amino-isoquinolin-6-ylmethyl)-carbamoyl]-pyrrolidin-1-yl}-1(R)-benzyl-2-oxo-ethylamino)-acetic acid

MS: 476

118n. (2-{2(S )-[(1-Amino-isoquinolin-6-ylmethyl)-carbamoyl]-azetidin-1-yl-1(R)-benzyl-2-oxo-ethylamino)-acetic acid 118o. (2-{2(S)-[(1-Amino-isoquinolin-7-ylmethyl)-carbamoyl]-pyrrolidin-1-yl}-1(R)-benzyl-2-oxo-ethylamino)-acetic acid OBM 14.1688

MS: 476

118p. [2-{2(S)-[(1-Amino-isoquinolin-6-ylmethyl)-carbamoyl]-azetidin-1-yl}-1(R)-(4-fluoro-benzyl)-2-oxo-ethylamino]-acetic acid

MS: 480

118q. (2-{2(S)-[(4-Amino-thieno[3,2-c]pyridin-2-ylmethyl)-carbamoyl]-azetidin-1-yl}-1(R)-cyclohexyl-2-oxo-ethylamino)-acetic acid

MS: 460

118r. [2-{2(S)-[(4-Amino-thieno[3,2-c]pyridin-2-ylmethyl)-carbamoyl]-azetidin-1-yl}-1(R)-(4-fluoro-benzyl)-2-oxo-ethylamino]-acetic acid

MS: 486

118s. [2-{2(S)-[(4-Amino-thieno[3,2-c]pyridin-2-ylmethyl)-carbamoyl]-pyrrolidin-1-yl}-1(R)-4-fluoro-benzyl)-2-oxo-ethylamino]-acetic acid

MS: 500

118t. (2-{2(S)-[(1-Amino-isoquinolin-6-ylmethyl)-carbamoyl]-pyrrolidin-1-yl}-1(R)-naphthalen-1-ylmethyl-2-oxo-ethylamino)-acetic acid 118u. (2-{2(S)-[(4-Amino-thieno[3,2-c]pyridin-2-ylmethyl)-carbamoyl]-azetidin-1-yl}-1(R)-cyclohexyl-2-oxo-ethylamino)-acetic acid tert-butyl ester

MS: 526

118v. (2-{2(S)-[(4-Amino-thieno[3,2-c]pyridin-2-ylmethyl)-carbamoyl]-pyrrolidin-1-yl}-2-oxo-1(R)-phenyl-ethylamino)-acetic acid tert-butyl ester

MS: 524

118w. (2-{2(S)-[(4-Amino-thieno[3,2-c]pyridin-2-ylmethyl)-carbamoyl]-1-azetidin-1-yl}-2-oxo-1(R)-phenyl-ethylamino)-acetic acid tert-butyl ester

MS: 510

118x. (2-{2(S)-[(4-Amino-thieno[3,2-c]pyridin-2-ylmethyl)-carbamoyl]-pyrrolidin-1-yl}-1(R)-cyclohexyl-2-oxo-ethylamino)-acetic acid tert-butyl ester

MS: 530

118y. (2-{2(S)-[(1-Amino-isoquinolin-6-ylmethyl)-carbamoyl]-pyrrolidin-1-yl}-1(R)-naphthalen-2-ylmethyl-2-oxo-ethylamino)-acetic acid

MS: 526

118z. (2-{2(S)-[(1-Amino-isoquinolin-7-ylmethyl)-carbamoyl]-pyrrolidin-1-yl}-1(R)-cyclohexyl-2-oxo-ethylamino)-acetic acid

MS: 468

118aa. [2-{2(S)-[(1-Amino-isoquinolin-6-ylmethyl)-carbamoyl]-azetidin-1-yl}-1(R)-(4-chloro-benzyl)-2-oxo-ethylamino]-acetic acid

MS: 497

118ab. [2-{2(S)-[(1-Amino-isoquinolin-7-ylmethyl)-carbamoyl]-pyrrolidin-1-yl}-1(R)-(4-chloro-benzyl)-2-oxo-ethylamino]-acetic acid

MS: 511

118ac. [2-{2(S)-[(1-Amino-isoquinolin-6-ylmethyl)-carbamoyl]-azetidin-1-yl}1(R)-(4-methoxy-benzyl)-2-oxo-ethylamino]-acetic acid

MS: 492

118ad. [2-{2(S)-[(1-Amino-isoquinolin-7-ylmethyl)-carbamoyl]-pyrrolidin-1-yl}-1(R)-(4-methoxy-benzyl)-2-oxo-ethylamino]-acetic acid

MS: 506

118ae. 1-Phenylaminoacetyl-azetidine-2(S)-carboxylic acid (4-amino-furo[3,2-c]pyridin-2-ylmethyl)-amide

MS: 380

118af. 1-Phenylaminoacetyl-azetidine-2(S)-carboxylic acid (1-amino-isoquinolin-6-ylmethyl)-amide 118ag. 1-Phenylaminoacetyl-pyrrolidine-2(S)-carboxylic acid (1-amino-isoquinolin-6-ylmethyl)-amide

MS: 404

118ah. 1-Phenylaminoacetyl-piperidine-2(S)-carboxylic acid (1-amino-isoquinolin-6-ylmethyl)-amide

MS: 418

118ai. 1-Phenethylaminoacetyl-azetidine-2(S)-carboxylic acid (4-amino-furo[3,2-c]pyridin-2-ylmethyl)-amide

MS. 408

118aj. 1-Phenethylaminoacetyl-azetidine-2(S)-carboxylic acid (1-amino-isoquinolin-6-ylmethyl)-amide

MS: 418

118ak. 1-Phenethylaminoacetyl-pyrrolidine-2(S)-carboxylic acid (1-amino-isoquinolin-6-ylmethyl)-amide

MS: 432

118al. 1-Phenethylaminoacetyl-piperidine-2(S)-carboxylic acid (1-amino-isoquinolin-6-ylmethyl)-amide

MS: 446

118am. 1-Benzylaminoacetyl-azetidine-2(S)-carboxylic acid (1-amino-isoquinolin-6-ylmethyl)-amide

MS: 404

118an. 1-Benzylaminoacetyl-pyrrolidine-2(S)-carboxylic acid (1-amino-isoquinolin-6-ylmethyl)-amide

MS: 418

118ao. 1-Benzylaminoacetyl-piperidine-2(S)-carboxylic acid (1-amino-isoquinolin-6-ylmethyl-amide

MS: 432

118ap. 1-Cyclopentylaminoacetyl-pyrrolidine-2(S)-carboxylic acid (1-amino-isoquinolin-6-ylmethyl)-amide

MS. 396

118aq. N-(1-Amino-isoquinolin-6-ylmethyl)-2(S)-(2-cyclohexylamino-acetylamino-3-naphthalen-1-yl-propionamide

MS: 510

118ar. N-(4-Amino-thieno[3,2-c]pyridin-2-ylmethyl)-2(S)-(2-cyclohexylamino-acetylamino)-3-naphthalen-1-yl-propionamide

MS: 516

118as. 2(S)-Amino-N-{1-[(1-amino-isoquinolin-6-ylmethyl)-carbamoyl]-2-naphthalen-1-yl-ethyl}-4-phenyl-butyramide

MS: 532

118at. 2(R)-Amino-N-{1(S)-[(4-amino-thieno[3,2-c]pyridin-2-ylmethyl)-carbamoyl]-2-naphthalen-1-yl-ethyl}-4-phenyl-butyramide

MS: 538

Example 119

The general procedure described in example 116 was repeated. After cleavage of the product from the resin, the organic phases were combined. Half of the solution was used to isolate the N-Boc-protected compounds, the other half was used to deprotect the compounds. The presence of the desired compounds was detected by mass spectrum, and their purities were determined by TLC. The solvents were removed in vacuo to give the following pairs of compounds:

119a1. 3(R)-{2(S)-[(1-Amino-isoquinolin-6-ylmethyl)-carbamoyl]-azetidine-1-carbonyl}-3,4-dihydro-1H-isoquinoline-2-carboxylic acid tert-butyl ester MS: 516 and 119a2. 1-(1,2,3,4-Tetrahydro-isoquinoline-3(R)-carbonyl)-azetidine-2(S)-carboxylic acid (1-amino-isoquinolin-6-ylmethyl)-amide

MS: 416

119b1. 3(R)-{2(S)-[(1-Amino-isoquinolin-6-ylmethyl)-carbamoyl]-pyrrolidine-1-carbonyl}-3,4-dihydro-1H-isoquinoline-2-carboxylic acid tert-butyl ester MS: 530 and 119b2. 1-(1,2,3,4-Tetrahydro-isoquinoline-3(R)-carbonyl)-pyrrolidine-2(S)-carboxylic acid (1-amino-isoquinolin-6-ylmethyl)-amide

MS: 430

119c1. [2-{2(S)-[(1-Amino-isoquinolin-6-ylmethyl)-carbamoyl]-pyrrolidin-1-yl}-1(R)-(1H-indol-3-ylmethyl)-2-oxo-ethyl]-carbamic acid tert-butyl ester MS: 557 and 119c2. 1-[2(R)-Amino-3-(1H-indol-3-yl)-propionyl]-pyrrolidine-2(S)-carboxylic acid (1-amino-isoquinolin-6-ylmethyl)-amide

MS: 457

119d1. [2-{2(S)-[(4-Amino-thieno[3,2-c]pyridin-2-methyl)-carbamoyl]-pyrrolidin-1-yl}-1(R)-(1H-indol-3-ylmethyl)-2-oxo-ethyl]-carbamic acid tert-butyl ester MS: 563 and 119d2. 1-[2(R)-Amino-3-(1H-indol-3-yl)-propionyl]-pyrrolidine-2(S)-carboxylic acid (4-amino-thieno[3,2-c]pyridin-2-ylmethyl)-amide

MS: 463

119e1. [2-{2(S)-[(4-Amino-thieno[3,2-c]pyridin-2-ylmethyl)-carbamoyl]-pyrrolidin-1-yl}-1(R)-(1-formyl-1H-indol-3-ylmethyl)-2-oxo-ethyl]-carbamic acid tert-butyl ester MS: 591 and 119e2. 1-[2(R)-Amino-3-(1-formyl-1H-indol-3-yl)-propionyl]-pyrrolidine-2(S)-carboxylic acid (4-amino-thieno[3,2-c]pyridin-2-ylmethyl)-amide 119f1. (2-{2(S)-[(4-Amino-thieno[3,2-c]pyridin-2-ylmethyl)-carbamoyl]-pyrrolidin-1-yl}-2-oxo-1(R)-phenyl-ethyl)-carbamic acid tert-butyl ester MS: 510 and 119f2. 1-((R)-Amino-phenyl-acetyl)-pyrrolidine-2(S)-carboxylic acid (4-amino-thieno[3,2-c]pyridin-2-ylmethyl)-amide

MS: 410

119g1. [2-{2(S)-[(4-Amino-thieno[3,2-c]pyridin-2-ylmethyl)-carbamoyl]-pyrrolidin-1-yl}-1(R)-(4-methoxy-benzyl)-2-oxo-ethyl]-carbamic acid tert-butyl ester MS: 554 and 119g2. 1-[2(R)-Amino-3-(4-methoxy-phenyl)-propionyl]-pyrrolidine-2(S)-carboxylic acid (4-amino-thieno[3,2-c]pyridin-2-ylmethyl)-amide

MS: 454

119h1. [2-2(S)-[(4-Amino-furo[3,2-c]pyridin-2-ylmethyl)-carbamoyl]-pyrrolidin-1-yl}-1(R)-(4-methoxy-benzyl)-2-oxo-ethyl]-carbamic acid tert-butyl ester MS: 538 and 119h2. 1-[2(R)-Amino-3-(4-methoxy-phenyl)-propionyl]-pyrrolidine-2(S)-carboxylic acid (4-amino-furo[3,2-c]pyridin-2-ylmethyl)-amide

MS: 438

119i1. [2-{2(S)-[(4-Amino-thieno[3,2-c]pyridin-2-ylmethyl)-carbamoyl]-pyrrolidin-1-yl}-1(R)-(4-fluoro-benzyl)-2-oxo-ethyl]-carbamic acid tert-butyl ester MS: 542 and 119i2. 1-[2(R)-Amino-3-(4-fluoro-phenyl)-propionyl]-pyrrolidine-2(S)-carboxylic acid (4-amino-thieno[3,2-c]pyridin-2-ylmethyl)-amide

MS: 442

119j1. [2-{2(S)-[(4-Amino-thieno[3,2-c]pyridin-2-ylmethyl)-carbamoyl]-pyrrolidin-1-yl}-1(R)-(4-chloro-benzyl)-2-oxo-ethyl]-carbamic acid tert-butyl ester MS: 559 and 119j2. 1-[2(R)-Amino-3-(4-chloro-phenyl)-propionyl]-pyrrolidine-2(S)-carboxylic acid (4-amino-thieno[3,2-c]pyridin-2-ylmethyl)-amide

MS: 459

119k1. (3-{2(S)-[(1-Amino-isoquinolin-6-ylmethyl)-carbamoyl]-pyrrolidin-1-yl}-1(R)-naphthalen-1-ylmethyl-2-oxo-ethyl)-carbamic acid tert-butyl ester MS: 568 and 119k2. 1-(2(R)-Amino-3-naphthalen-1-yl-2-oxo-propyl)-pyrrolidine-2(S)-carboxylic acid (1-amino-isoquinolin-6-ylmethyl)-amide

MS: 482

119l1. (1(R)-{2(S)-[(1-Amino-isoquinolin-6-ylmethyl)-carbamoyl]-pyrrolidine-1-carbonyl}-3-phenyl-propyl)-carbamic acid tert-butyl ester MS: 532 and 119l2. 1-(2(R)-Amino-4-phenyl-butyryl)-
pyrrolidine-2(S)-carboxylic acid (1-amino-
isoquinolin-6-ylmethyl)-amide

MS: 432

119m1. (2-{2(S)-[(1-Amino-isoquinolin-7-
ylmethyl)-carbamoyl]-pyrrolidin-1-yl}-1(R)-benzyl-
2-oxo-ethyl)-carbamic acid tert-butyl ester MS: 518 and 119m2. 1-(2(R)-Amino-3-phenyl-propionyl)-
pyrrolidine-2(S)-carboxylic acid (1-amino-
isoquinolin-7-ylmethyl)-amide

MS: 418

119n1. [2-{2(S)-[(1-Amino-isoquinolin-6-ylmethyl)-
carbamoyl]-azetidin-1-yl}-1(R)-(4-methoxy-benzyl)-
2-oxo-ethyl]-carbamic acid tert-butyl ester MS: 534 and 119n2. 1-[2(R)-Amino-3-(4-methoxy-phenyl)-
propionyl]-azetidine-2(S)-carboxylic acid (1-amino-
isoquinolin-6-ylmethyl)-amide

MS: 434

119o1. [2-{2(S)-[(1-Amino-isoquinolin-7-ylmethyl)-
carbamoyl]-azetidin-1-yl}-1(R)-(4-methoxy-benzyl)-
2-oxo-ethyl]-carbamic acid tert-butyl ester MS: 534 and 119o2. 1-[2(R)-Amino-3-(4-methoxy-phenyl)-
propionyl]-azetidine-2(S)-carboxylic acid (1-amino-
isoquinolin-7-ylmethyl)-amide

MS: 434

119p1. [2-1 2(S)-[(1-Amino-isoquinolin-7-
ylmethyl)-carbamoyl]-pyrrolidin-yl}-1(R)-(4-
methoxy-benzyl)-2-oxo-ethyl]-carbamic acid tert-
butyl ester MS: 548 and 119p2. 1-[2(R)-Amino-3-(4-methoxy-phenyl)-
propionyl]-pyrrolidine-2(S)-carboxylic acid (1-
amino-isoquinolin-7-ylmethyl)-amide

MS: 448

119q1. (2-{2(S)-[(1-Amino-isoquinolin-6-ylmethyl)-
carbamoyl]-azetidin-1-yl}-2-oxo-1(R)-phenyl-
ethyl)-carbamic acid tert-butyl ester MS: 490 and 119q2. 1-((R)-Amino-phenyl-acetyl)-azetidine-2(S)-
carboxylic acid (1-amino-isoquinolin-6-ylmethyl)-
amide

MS: 390

119r1. (2-{2(S)-[(1-Amino-isoquinolin-7-ylmethyl)-
carbamoyl]-pyrrolidin-1-yl}-2-oxo-1(R)-phenyl-
ethyl)-carbamic acid tert-butyl ester MS: 504 and 119r2. 1-((R)-Amino-phenyl-acetyl-pyrrolidine-2
(S)-carboxylic acid (1-amino-isoquinolin-7-
ylmethyl)-amide

MS: 404

119s1. (2-{2(S)-[(4-Amino-thieno[3,2-c]pyridin-2-
ylmethyl)-carbamoyl]-pyrrolidin-1-yl}-2-oxy-ethyl)-
phenyl-carbamic acid tert-butyl ester MS: 510 and 119s2. 1-Phenylaminoacetyl-pyrrolidine-2(S)-
carboxylic acid (4-amino-thieno[3,2-c]pyridin-2-
ylmethyl)-amide

MS: 410

119t1. (2-{2(S)-[4-Amino-thieno[3,2-c]pyridin-2-
ylmethyl)-carbamoyl]-pyrrolidin-1-yl}-2-oxo-ethyl)-
benzyl-carbamic acid tert-butyl ester MS: 524 and 119t2. 1-Benzylaminoacetyl-pyrrolidine-2(S)-
carboxylic acid (4-amino-thieno[3,2-c]pyridin-2-
ylmethyl)-amide

MS: 424

119u1. (2-{2(S)-[(4-Amino-thieno[3,2-c]pyridin-2-
ylmethyl)-carbamoyl]-pyrrolidin-1-yl}-2-oxo-ethyl)-
phenethyl-carbamic acid tert-butyl ester MS: 538 and 119u2. 1-Phenethylaminoacetyl-pyrrolidine-2(S)-
carboxylic acid (4-amino-thieno[3,2-c]pyridin-2-
ylmethyl)-amide

MS: 438

Example 120

The following compounds were prepared using the procedures described in example 73.

120a. N-(1-amino-isoquinolin-6-ylmethyl) 1-((2-
(hydroxycarbonylmethylamino)-2-
(cyclooctylmethyl)-acetyl)-prolinamide
hydrochloride Using 306 mg of 1-((2-((butyloxycarbonyl)
(butyloxycarbonylmethyl)amino)-2-(cyclooctylmethyl)-
acetyl)-proline (prepared according to WO 97/31939
example 7) and 104 mg of 1-amino-6-(aminomethyl)
isoquinoline gave 62 mg of the title compound. MS ESI+:
510 (M+H).

120b. N-(1-amino-isoquinolin-6-ylmethyl) 1-(2(R)-
(hydroxycarbonylmethylamino)-1-oxo-hexyl)-
prolinamide trifluoroacetate The use of 420 mg of 1-((2-((butyloxycarbonyl)
(butyloxycarbonylmethyl)amino)-(2(R)-
(hydroxycarbonylmethylamino)-1-oxo-hexyl)-proline
(prepared according to WO 97/31939 example 48) and 165
mg of 1-amino-6-(aminomethyl)isoquinoline gave 330 mg
of the title compound. MS ESI+: 442 (M+H).

120c. N-(1-amino-isoquinolin-6-ylmethyl)-4-cis-
ethyl-1-((2-(hydroxycarbonylmethylamino)-2(R)-
(cyclohexylmethyl)-acetyl)-prolinamide
trifluoroacetate Starting with 345 mg of 1-((2-((butyloxycarbonyl)
(butyloxycarbonylmethyl)amino)-2-(cyclohexylmethyl)- acetyl)-4-cis-ethyl-proline (prepared according to WO 97/31939 example 52) and 122 mg of 1-amino-6-(aminomethyl)isoquinoline gave 412 mg of the title compound.

MS ESI+: 510(M+H).

120d. N-(1-amino-isoquinolin-6-ylmethyl) 1-cyclopentyl-1-(2-((2-propyl)oxycarbonyl-methylamino)-2(R)-cyclohexylmethyl-acetyl) glycinamide hydrochloride The use of 397 mg of 1-cyclopentyl-1-(2-((2-propyl)oxycarbonylmethylamino)-2(R)-cyclohexylmethyl-acetyl) glycine and 138 mg of 1-amino-6-(aminomethyl)isoquinoline gave 301 mg of the title product.

MS ESI+: 552(M+H).

Example 121

N-(1-amino-isoquinolin-6-ylmethyl) 1-(2-((2-propyl)oxycarbonylmethylamino)-2(R)-cyclohexylmethyl-acetyl)-prolinamide To a stirred solution of 96 mg of N-(1-amino-isoquinolin-6-ylmethyl) 1-(2-hydroxycarbonylmethylamino-2(R)-cyclohexylmethyl-acetyl)-prolinamide in 6 mL of 2-propanol was added 0.03 mL of thionyl chloride and the reaction mixture was heated at reflux temperature for two days. After this period the reaction mixture was concentrated, ethyl acetate added, washed with aqueous 5% sodium hydrogencarbonate and brine, dried over sodium sulphate and concentrated. The residue was dissolved in a t-butanol/water 1/1 (v/v) mixture lyophilisation yielded 56 mg of the title compound. MS ESI+: 524 (M+H).

Example 122

The following compounds were prepared using the procedures described in example 121.

122a. N-(1-amino-isoquinolin-6-ylmethyl) 1-(2-((1-butyl)oxycarbonylmethylamino)-2(R)-cyclohexylmethyl-acetyl)-prolinamide Yield: 47%, MS ESI+: 538 (M+H).

122b. N-(1-amino-isoquinolin-6-ylmethyl) 1-(2-((2-methoxyethyl)oxycarbonylmethylamino)-2(R)-cyclohexylmethyl-acetyl)-prolinamide Yield: 70%, MS ESI+: 540 (M+H).

122c. N-(1-amino-isoquinolin-6-ylmethyl) 1-(2-(benzyloxycarbonylmethylamino)-2(R)-cyclohexylmethyl-acetyl)-prolinamide Yield: 32%, MS ESI+: 572 (M+H).

122d. N-(1-amino-isoquinolin-6-ylmethyl) 1-(2(R)-(propyloxycarbonylmethylamino)-1-oxo-hexyl)-prolinamide hydrochloride Hydrochloric acid was added to the t-butanol/water solution of the free base and lyophilistation afforded the title compound: Yield: 73%, MS ESI+: 484(M+H).

122e. N-(1-amino-isoquinolin-6-ylmethyl)-4-cis-ethyl-1-((2-(propyloxycarbonylmethylamino)-2(R)-(cyclohexylmethyl)-acetyl)-prolinamide Yield: 51%, MS ESI+: 552 (M+H).

122f. N-(1-amino-isoquinolin-6-ylmethyl)-1-((2-(propyloxycarbonylmethylamino)-2(R)-((4-methyoxyphenyl)methyl)-acetyl)-prolinamide Yield: 90%, MS ESI+: 548 (M+H).

Example 123

N-(1-amino-isoquinolin-6-ylmethyl) 1-(2-((morpholin-4-yl)carbonylmethylamino)-2(R)-cyclohexylmethyl-acetyl)-prolinamide trifluoroacetate 123a. N-Boc-N-((morpholin-4-yl)carbonylmethyl)-D-Cha-OH Using the procedures described in example 73 2.0 g of H-D-Cha-OMe.HCl and 2.07 g of 4-(bromoacetyl) morpholine (J. Med. Chem, 35, 1685 (1992)) gave 1.77 g of the title compound.

Rf=0.22 in ethyl acetate/heptanes=6/4 (v/v) on silica.

123b. N-Boc-N-((morpholin-4-yl)carbonylmethyl)-D-Cha-Pro-OH

To a stirred solution of 0.86 g of N-Boc-N-((morpholin-4-yl)carbonylmethyl)-D-Cha-OH in 8 mL of N,N-dimethylformamide at 0° C. were successively added 0.45 g of 1-hydroxy benzotriazole (HOBT) and 0.51 g of dicyclohexyl carbodiimide (DCC). After 30 minutes a mixture of 0.58 g of proline benzylester hydrochloride and 0.13 mL of triethyl amine in 8 mL of N,N-dimethylformamide was added. The reaction mixture was allowed to come to room temperature and an additional 0.05 mL of triethylamine was added. After 16 hours 0.36 g of DCC and 0.20 mL of triethylamine were added and stirred for 3 days at room temperature. The mixture was cooled to −20° C. and dicyclohexylurea was removed by filtration. The filtrate was evaporated to dryness. The residue was dissolved in ethyl acetate and washed successively with 5% sodium hydrogencarbonate, water, 2% citric acid and brine, dried over sodium sulphate and concentrated in vacuo. The residue was chromatographed on silica gel eluting with dichloromethane/methanol 3/1 v/v as eluent to yield 1.02 g of N-Boc-N-((morpholin-4-yl)carbonylmethyl)-D-Cha-Pro-OBzl. This benzyl ester was dissolved in 10 mL of methanol, 125 mg of 10% palladium on charcoal was added and the mixture was hydrogenated at atmospheric pressure at room temperature for 2 hours. The palladium catalyst was removed by filtration and the solvent removed by evaporation at reduced pressure to yield 0.86 g of the title compound.

MS ESI−: 494 (M-H)−.

1 23c. N-(1-amino-isoquinolin-6-ylmethyl) 1-(2-((morpholin-4-yl)carbonylmethylamino)-2(R)-cyclohexylmethyl-acetyl)-prolinamide trifluoroacetate This compound was prepared using the procedures described in example 73, A TBTU-coupling of 150 mg of N-Boc-N-((morpholin-4-yl)carbonylmethyl)-D-Cha-Pro-OH and 58 mg 1-amino-6-(aminomethyl)isoquinoline and deprotection using trifluoroacetic acid yielded 186 mg of the title compound.

MS ESI+: 551 (M+H).

Example 124

The following compounds were prepared using the procedures described in example 1k.

124a. N-(1-amino-isoquinolin-6-ylmethyl) 1-(2-((dimethylamino[]carbonylmethylamino)-2(R)-cyclohexylmethyl-acetyl)-prolinamide hydrochloride DCC/HOBt coupling of 193 mg of N-(1-amino-isoquinolin-6-ylmethyl) 1-(2-hydroxycarbonylmethylamino-2(R)-cyclohexylmethyl-acetyl)-prolinamide and 65 mg of dimethylamine hydrochloride yielded 40 mg of the title compound. MS ESI+: 509 (M+H).

124b. N-(-amino-isoquinolin-6-ylmethyl) 1-(2-(azetidin-1-ylcarbonylmethylamino)-2(R)-cyclohexylmethyl-acetyl)-prolinamide hydrochloride DCC/HOBt coupling of 193 mg of N-(1-amino-isoquinolin-6-ylmethyl) 1-(2-hydroxycarbonylmethylamino-2(R)-cyclohexylmethyl-acetyl)-prolinamide and 42 mg of azetidine hydrochloride yielded 40 mg of the title compound. MS ESI+: 521 (M+H).

Example 125

(4-(4-((1-aminoisoquinolin-7-yl)methylaminocarbonyl)benzoyl)-piperazin-1-yl) acetate Bromoacetate was coupled to the resin via an ester linkage. Piperazine was introduced followed by a peptide coupling with terephthalic acid. Then 1-amino-7-(aminomethyl)isoquinline was coupled and finally the product was cleaved off and lyphilisation gave the title compound.

MS (IonSpray): 447.5

Example 126

The following compounds wer prepared using the procedure described in example 125.

126a. (4-(3-((1-aminoisoquinolin-7-yl)methylaminocarbonyl)benzoyl)-piperazin-1-yl) acetate, MS (IonSpray): 447.5

126b. (4-(2-((-aminoisoquinolin-7-yl)methylaminocarbonyl)cyclohexylcarbonyl)-piperazin-1-yl)acetate, MS (IonSpray): 453.6

126c. (4-(4-((1-aminoisoquinolin-7-yl)methylamino) 1,4-dioxo-2-buten-1-yl)-piperazin-1-yl)acetate, MS (IonSpray): 397.5

126d. ((3-(4-((1-aminoisoquinolin-7-yl)methylaminocarbonyl)benzoyl)(methyl)amino)propyl)(methyl)amino)acetate, MS (IonSpray): 449.5

Other compounds of the invention which may be prepared following the procedures as set out in the specification are shown in Tables Ia, Ib, Ib, Ic, Id, Ie, If, Ig, Ig, Ih, Ij, Ik, and II TABLE Ia

X = CH=CH, O, S

TABLE Ib

X = CH=CH, O, S

TABLE Ic

R = OCH(CH$_3$)$_2$
N(CH$_3$)$_2$
NH(C( CH$_3$)$_3$)

O(CH$_2$)$_p$—N(morpholine)

p = 2, 3, 4

TABLE Id
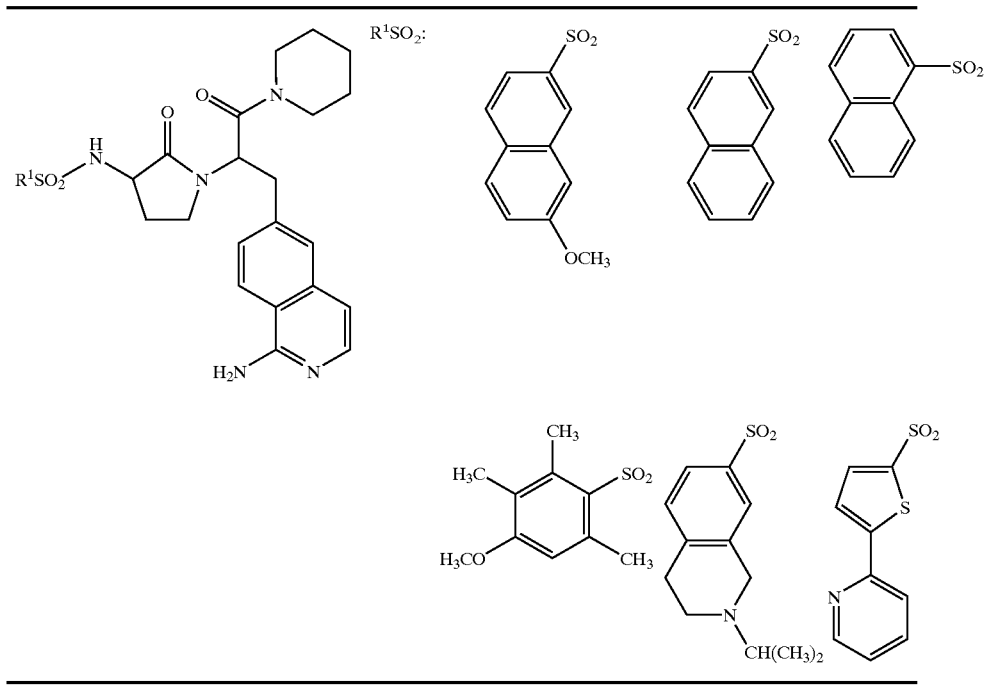
TABLE Ie
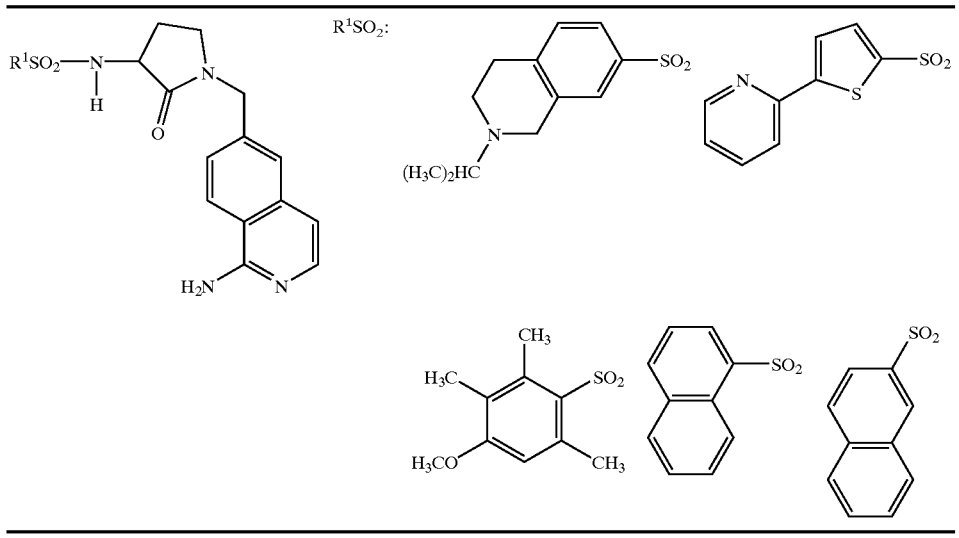
TABLE If
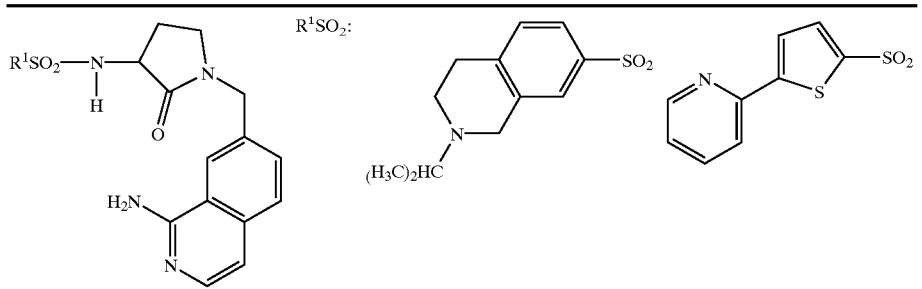

TABLE If-continued
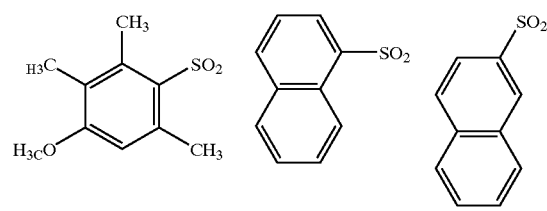
TABLE Ig
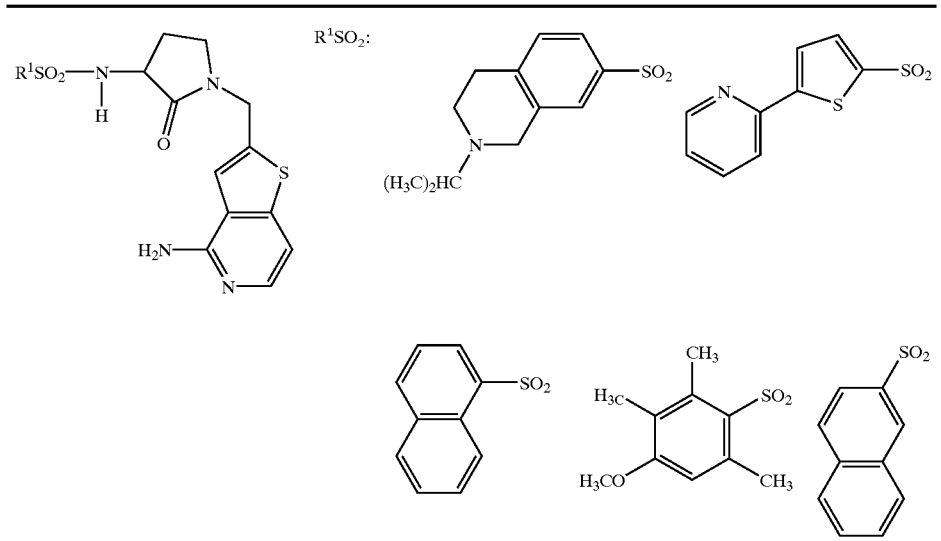
TABLE Ih
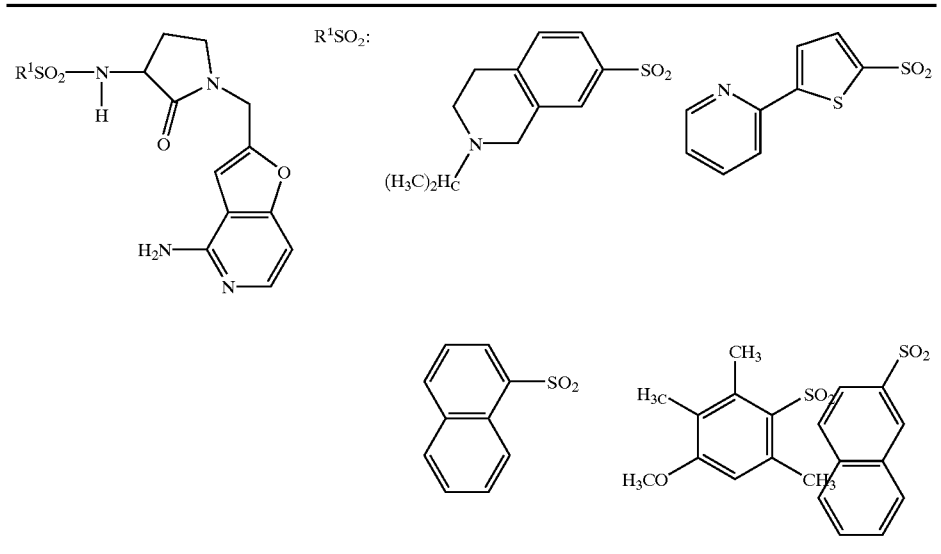

TABLE Ii
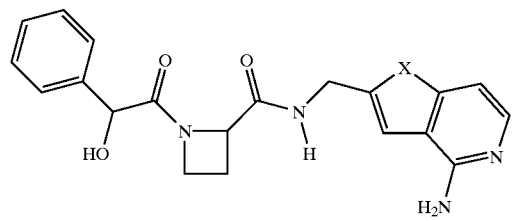
TABLE Ii-continued
X = CH=CH, O, S
TABLE Ij
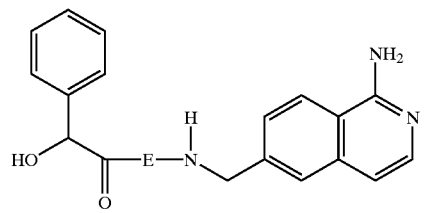
E: 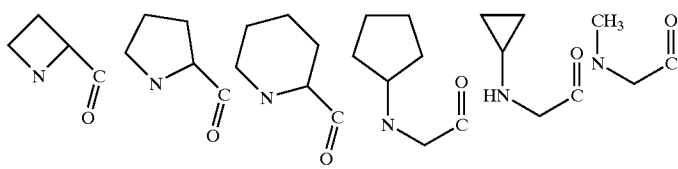
TABLE Il
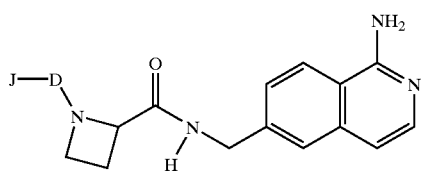
J-D: 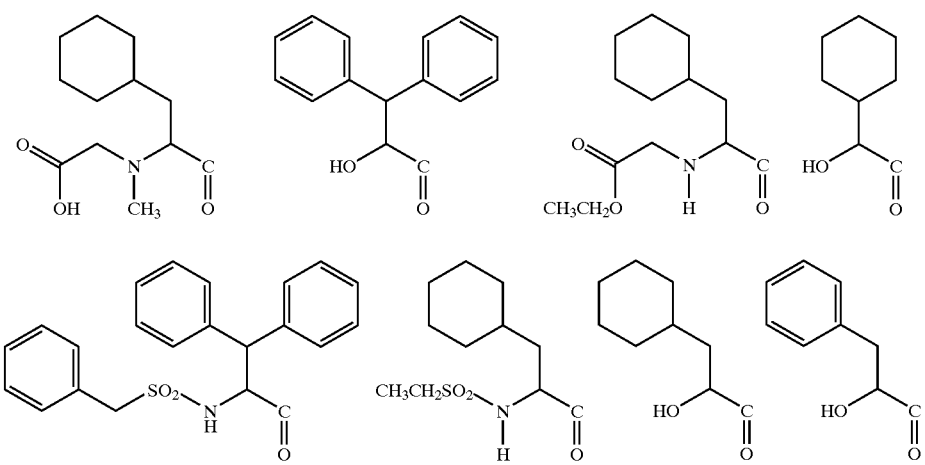

Also the following compounds may be prepared according the procedures as previously described:

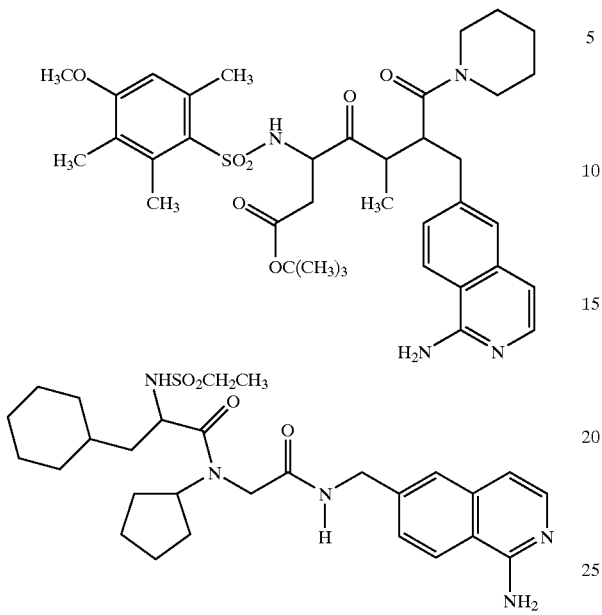

The biological activities of the compounds of the present invention were determined by the following test methods.

I. Anti-thrombin Assay

Thrombin (Factor IIa) is a factor in the coagulation cascade. The anti-thrombin activity of compounds of the present invention was assessed by measuring spectrophotometrically the rate of hydrolysis of the chromogenic substrate s-2238 exterted by thrombin. This assay for anti-thrombin activity in a buffer system was used to assess the $IC_{50}$-value of a test compound.

Test medium: Tromethamine-NaCl-polyethylene glycol 6000 (TNP) buffer
Reference compound: 12581 (Kabi)
Vehicle:
  TNP buffer.
  Solubilisation can be assisted with dimethylsulphoxide, methanol, ethanol, acetonitrile or tert.-butyl alcohol which are without adverse effects in concentrations up to 2.5% in the final reaction mixture.
Technique
  Reagents*
    1. Tromethamine-NaCl (TN) buffer
       Composition of the buffer:

| Tromothamine (Tris) | 6.057 g | (50 mmol) |
| NaCl | 5.844 g | (100 mmol) |
| Water to | 1 l | |

The pH of the solution is adjusted to 7.4 at 37° C. with HCl (10 mmol·l$^{-1}$)

2. TNP buffer
   Polyethylene glycol 6000 is dissolved in TN buffer to give a concentration of 3 g·l$^{-1}$
3. S-2238 solution
   One vial S-2238 (25 mg; Kabi Diagnostica, Sweden) is dissolved in 20 ml TN buffer to give a concentration of 1.25 mg·ml$^{-1}$ (2 mmol·l$^{-1}$)

4. Thrombin solution
   Human thrombin (16 000 nKat·vial$^{-1}$; Centraal Laboratorium voor Bloedtransfusie, Amsterdam, The Netherlands) is dissolved in TNP buffer to give a stock solution of 835 nKat·ml$^{-1}$.
   Immediately before use this solution is diluted with TNP buffer to give a concentration of 3.34 nKat·ml$^{-1}$.
Preparation of test and reference compound solutions
   The test and reference compounds are dissolved in Milli-Q water to give stock concentrations of $10^{-2}$ mol·l$^{-2}$. Each concentration is stepwise diluted with the vehicle to give concentrations of $10^{-3}$, $10^{-4}$ and $10^{-5}$ mol·l$^{-1}$. The dilutions, including the stock solution, are used in the assay (final concentrations in the reaction mixture: $3·10^{-3}$; $10^{-3}$; $3·10^{-4}$; $10^{-4}$; $3·10^{-5}$; $10^{-5}$; $3·10^{-6}$ and $10^{-6}$ mol·l$^{-1}$, respectively).
Procedure
   At room temperature 0.075 ml and 0.025 ml test compound or reference compound solutions or vehicle are alternately pipetted into the wells of a microtiter plate and these solutions are diluted with 0.115 ml and 0.0165 ml TNP buffer, respectively. An aliquot of 0.030 ml S-2238 solution is added to each well and the plate is pre-heated and pre-incubated with shaking in an incubator (Amersham) for 10 min. at 37° C. Following pre-incubation the hydrolysis of S-2238 is started by addition of 0.030 ml thrombin solution to each well. The plate is incubated (with shaking for 30 s) at 37° C. Starting after 1 min of incubation, the absorbance of each sample at 405 nm is measured every 2 min. for a period of 90 min. using a kinetic microtiter plate reader (Twinreader plus, Flow Laboratories).
   All data are collected in an IBM personal computer using LOTUS-MEASURE. For each compound concentration (expressed in mol·l$^{-1}$ action mixture) and for the blank the absorbance is plotted versus the action time in min.

*All ingredients used are of analytical grade
For aqueous solutions ultrapure water (Milli-Q quality) is used.

Evaluation of responses: For each final concentration the maximum absorbance was calculated from the assay plot. The $IC_{50}$-value (final concentration, expressed in $\mu$mol·l$^{-1}$, causing 50% inhibition of the maximum absorbance of the blank) was calculated using the logit transformation analysis according to Hafner et al. (Arzneim.-Forsch./Drug Res. 1977, 27(II): 1871–3).

| Antithrombin activity: | |
| --- | --- |
| Example | $IC_{50}$ ($\mu$mol·l$^{-1}$) |
| 5 | 28 |
| 7 | 6.8 |
| 8 | 0.082 |
| 10 | 1.1 |
| 18 | 0.53 |
| 30 | 35 |
| 32 | 1.44 |

II. Anti-factor Xa Assay
Activated Factor X (Xa) is a factor in the coagulation cascade. The anti-Xa activity of compounds of the present invention was assessed. by measuring spectrophotometrically the rate of hydrolysis of the chromogenic substrate s-2222 exterted by Xa. This assay for anti-Xa activity in a buffer system was used to assess the $IC_{50}$-value of the test compound.

In general the followed procedure and test conditions were analogous to those of the anti-thrombin assay as described above. Differences are indicated below,
Reference compound: benzamidine
Vehicle:
  TNP buffer.
  Solubilisation can be assisted with dimethylsulphoxide, methanol, ethanol, acetonitrile or tert.-butyl alcohol which are without adverse effects in concentrations up to 1% (for DMSO) and 2.5% (for the other solvents) in the final reaction mixture.
Technique
  Reagents*
    3. S-2222 solution
      One vial S-2222 (15 mg; Kabi Diagnostica, Sweden) is dissolved in 10 ml water to give a concentration of 1.5 mg·ml$^{-1}$ (2 mmol·l$^{-1}$).
    4. Xa solution
      Bovine Factor Xa Human (71 nKat·vial$^{-1}$; Kabi Diagnostica) is dissolved in 10 ml TNP buffer and then further diluted with 30 ml TNP buffer to give a concentration of 1.77 nKat·ml$^{-1}$. The dilution has to be freshly prepared.
Procedure
  Instead of the S-2238 solution (in anti-thrombin assay), the above S-2222 solution is added to each well in this assay.

| Anti-factor Xa activity | |
|---|---|
| Example | $IC_{50}$ ($\mu$mol·l$^{-1}$) |
| 1 | 48 |
| 3 | 29 |
| 14 | 41 |
| 24 | 14 |
| 26 | 14 |

*All ingredients used are of analytical grade
For aqueous solutions ultrapure water (Milli-Q quality) is used.

III. Caco-2 Permeability

Caco-2 cells were obtained from the American Type Culture Collection and were used in passage nrs 25 to 35. Cells were maintained at 37° C. in 75 cm$^2$ culture flasks (Nunc) in Dulbecco's Modified Eagle's Medium (DMEM) supplemented with 1% of non-essential amino acid solution (100×), 10% of heat-inactivated fetal bovine serum, penicillin (100 U/ml) and streptomycin (100 μg/ml) in an atmosphere of 95% of air and 5% of $CO_2$. The pH of the medium was 7.4. For experiments cells were grown on Transwell-COL™ collagen treated cell culture filter inserts (Costar, Cambridge, Mass., USA) with a surface area of 0.33 cm$^2$. The seeding density was 6.3×10$^5$ cells/cm$^2$. Culture medium was added on each side of the filter. The growth of the cells and degree of confluency was checked every 2–3 days microscopically. Confluent monolayers were used on day 23–24 after seeding, at which time the transepithelial electrical resistance of the monolayers was at a stable value of approximately 260 Ω·cm$^2$. Permeability experiments were performed with compound concentrations of 0.1 mM or 1 mM in the apical compartment in Hanks' Balanced Salt Solution with or without 0.5% (w/v) of bovine serum albumin. At 1, 2 and 3 hours after addition of compound to the cells the filters were placed into fresh acceptor compartments. In this way three one-hour samples were obtained. Compound concentration was determined in samples from acceptor compartments and donor compartment by HPLC or by measuring anti-thrombin activity. Permeability experiments of each compound were performed with 4 different filters. Results shown in the Table are means of the permeability between 2 and 3 hours after the start of the experiment of at least 2 filters.

In the following Table the apparent Caco-2 permeability ($P_{app}$) is given in nm/s for compounds of the present invention compared to the prior art compounds NAPAP and "Pefa 1286"*.

| Compound | Caco-2 $P_{app}$ (nm/s) |
|---|---|
| NAPAP | 4 |
| "Pefa 1286"* | 1.1 |
| ex. 2 | 19 |
| ex. 4 | 25 |
| ex. 5 | 37 |
| ex. 11 | 148 |
| ex. 13 | 118 |
| ex. 14 | 10 |
| ex. 18 | 121 |

*Pefa 1286 is the compound 1-[3-[3-(aminoiminomethyl)phenyl]-2-[(2-naphthalenyl-sulfonyl)amino]-1-oxopropyl]-4-(methylsulfonyl)piperazine (L-form) from WO 94/18185

Conclusion: The apparent permeability of compounds of the present invention is significantly higher than that of the prior art compounds NAPAP and Pefa 1286. Compounds of the present invention will therefore be considerably better absorbed in the gastrointestinal tract.

What is claimed is:
1. A GpIIb/IIIa antagonist of formula (L), wherein formula (L) is

Q-[spacer]-COOH    (L)

wherein Q is represented by formula

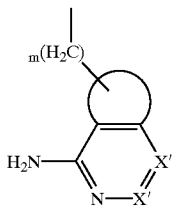

wherein the substructure

is a structure selected from

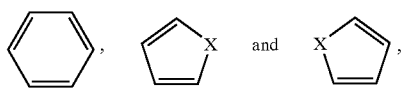

wherein
X is O or S;
X' being independently CH or N; and
m is 0, 1, 2 or 3;
wherein the group Q is bound through an oxygen atom or an unsubstituted or substituted nitrogen or carbon atom;
the distance between the amino substituted carbon atom of the group Q and the carbon atom of the carboxylate moiety has a length of 12–18 Å; the spacer is any suitable chemical moiety; and the carboxylate group may be esterified.

2. The GpIIb/IIIa antagonist of claim 1, wherein Q has the formula

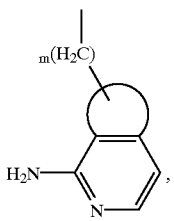

m is 0, 1, 2 or 3.

3. The GpIIb/IIIa antagonist of claim 1 having the formula (L), wherein the compound has the formula (La)

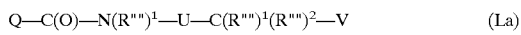 (La)

wherein
Q has the previously defined meaning;
$(R'''')^1$ is independently H or (1–4C)alkyl;
U is a bond or $CH(R'''')^1$,
$(R'''')^2$ is (1–12C)alkyl, (2–12C)alkenyl, (2–12C)alkynyl, (3–8C)cycloalkyl, (6–14C)aryl, (7–15C)aralkyl or (8–16)aralkenyl, which may be unsubstituted or substituted with (1–6C)alkyl, (3–8C)cycloalkyl, (1–6C)alkoxy, OH, COOH, $CF_3$ or halogen; and
V is a 5-, 6-, or 7-membered saturated, unsaturated or aromatic ring which may contain one or more heteroatoms selected from O, N or S and which ring is substituted with one or two substituents selected from $—(CH_2)_v—COO(R'''')^1$ and $—O—(CH_2)_v—COO(R'''')^1$, v being 1, 2, 3 or 4.

4. The GpIIb/IIIa antagonist of claim 3, wherein m is 0; U is a bond; $(R'''')^2$ is (1–4C)alkyl, phenyl or benzyl, which may be unsubstituted or substituted with OH or halogen and V is phenyl, piperidinyl, piperazinyl or thiazolyl, substituted with one substituent selected from $—CH_2—COO(R'''')^1$ and $—O—CH_2—COO(R'''')^1$.

5. The GpIIb/IIIa antagonist of claim 1 having the formula (L), wherein the compound has the formula (Lb)

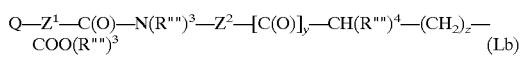 (Lb)

wherein
Q has the previously defined meaning:
$Z^1$ is a bond, C=C or C≡C;
$(R'''')^3$ is H or (1–4C)alkyl;
$Z^2$ is selected from

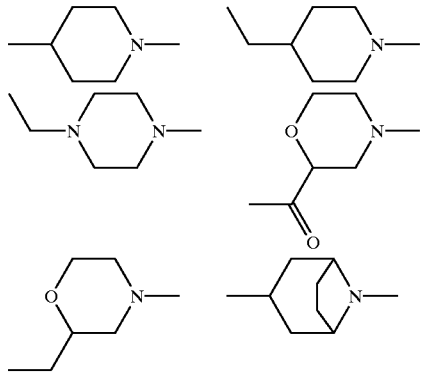

$(R'''')^4$ is H, (1–12C)alkyl, (2–12C)alkenyl, (2–12C)alkynyl, (3–8C)cycloalkyl, (6–14C)aryl, (7–15C)aralkyl or (8–16)aralkenyl, which may be unsubstituted or substituted with (1–6C)alkyl, (3–8C)cycloalkyl, (1–6C)alkoxy, OH, COOH, $CF_3$ or halogen;
y is 0 or 1; and
z is 0 or 1.

6. The GpIIb/IIIa antagonist of claim 3, wherein
$Z^1$ is C=C;
$Z^2$ is

$(R'''')^4$ is H;
y is 1; and
z is 0.

7. The GpIIb/IIIa antagonist of claim 1 having the formula (L), wherein the compound has the formula (Lc)

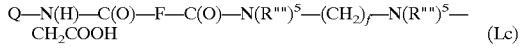 (Lc)

wherein
Q has the previously defined meaning;
$(R'''')^5$ is independently H, (1–4C)alkyl or benzyl or both $(R'''')^5$ groups are an ethylene bridge to form a 6- or 7-membered ring together with $N—(CH_2)_u—N$ to which they are bound;
F is C=C, or 1,2-, 1,3- or 1,4-phenylene, or 1,2-(4–5C) heteroarylene, 2,3-naphthylene or 1,2(5–7C) cycloalkylene, which groups may be unsubstituted or substituted With (1–4C)alkyl; and
f is 2 or 3.

8. A pharmaceutical composition, comprising:
the GpIIb/IIIa antagonist of claim 1 and
a pharmaceutically acceptable auxiliary.

9. A method of treating or preventing thrombosis or thrombosis-related diseases in a patient in need thereof, comprising:
administering to the patient an effective amount of the Group IIb/IIIa antagonist according to claim 1.

* * * * *